US012629057B2

(12) United States Patent
Lamrani et al.

(10) Patent No.: US 12,629,057 B2
(45) Date of Patent: May 19, 2026

(54) SYSTEM FOR COLLECTING AND UTILIZING HEALTH DATA

(71) Applicant: Menicon Co., Ltd., Nagoya (JP)

(72) Inventors: Mouad Lamrani, Geneva (CH);
Stephen D. Newman, Singapore (SG);
Sami Antero Lakka, Lempaala (FI)

(73) Assignee: Menicon Co., Ltd., Nagoya (JP)

( * ) Notice: Subject to any disclaimer, the term of this patent is extended or adjusted under 35 U.S.C. 154(b) by 395 days.

(21) Appl. No.: 16/979,480

(22) PCT Filed: Mar. 13, 2019

(86) PCT No.: PCT/IB2019/000250
§ 371 (c)(1),
(2) Date: Sep. 9, 2020

(87) PCT Pub. No.: WO2019/175669
PCT Pub. Date: Sep. 19, 2019

(65) Prior Publication Data
US 2021/0007643 A1     Jan. 14, 2021

Related U.S. Application Data

(60) Provisional application No. 62/642,926, filed on Mar. 14, 2018, provisional application No. 62/642,897, (Continued)

(51) Int. Cl.
*A61B 5/145* (2006.01)
*A45C 11/00* (2006.01)
(Continued)

(52) U.S. Cl.
CPC ........ *A61B 5/14532* (2013.01); *A45C 11/005* (2013.01); *A45C 15/00* (2013.01);
(Continued)

(58) Field of Classification Search
CPC ........ G16H 50/30; G16H 10/40; A45C 15/00; A45C 11/005; A61B 5/14532;
(Continued)

(56) References Cited

U.S. PATENT DOCUMENTS

| | | | |
|---|---|---|---|
| 3,545,260 A | 12/1970 | Lichtenstein et al. | |
| 3,585,849 A | 6/1971 | Grolman | |

(Continued)

FOREIGN PATENT DOCUMENTS

| | | | |
|---|---|---|---|
| CN | 104662416 A | 5/2015 | |
| EP | 1650567 A1 | 4/2006 | |

(Continued)

OTHER PUBLICATIONS

Kim HJ, et al. Deficits in color detection in patients with Alzheimer disease. PLoS One. Jan. 4, 2022; 17(1):e0262226. [serialonline], [retrieved on Sep. 6, 2024]. Retrieved from the Internet (Year: 2022) <URL: https://www.ncbi.nlm.nih.gov/pmc/articles/PMC8726485/#:~:text=K%2Dmeans%20cluster%20analysis%20and,may%20adequately%20detect%20Alzheimer's%20dementia. > <DOI: 10.1371/journal.pone.0262226 >.*

(Continued)

*Primary Examiner* — Alex M Valvis
*Assistant Examiner* — Jonathan M Haney
(74) *Attorney, Agent, or Firm* — Dorsey & Whitney LLP

(57) ABSTRACT

A system for collecting and utilizing health data can include collecting data relative to a patient's health and aggregating the data with other sources of data to define a database. The patient data can be collected using an electronic device, such as a smart contact lens or smart contact lens container. The data within the database can be manipulated, organized, or otherwise processed to determine trends, relationships, and other characteristics of the database. The characteristics of the database can be correlated to predict a health condition (Continued)

of the patient, generate a healthcare recommendation, or a combination thereof.

8 Claims, 56 Drawing Sheets

Related U.S. Application Data filed on Mar. 14, 2018, provisional application No. 62/642,875, filed on Mar. 14, 2018, provisional application No. 62/642,913, filed on Mar. 14, 2018, provisional application No. 62/642,860, filed on Mar. 14, 2018, provisional application No. 62/642,176, filed on Mar. 13, 2018.

(51) Int. Cl.

| | |
|---|---|
| A45C 15/00 | (2006.01) |
| A61B 3/10 | (2006.01) |
| A61B 3/16 | (2006.01) |
| A61B 5/00 | (2006.01) |
| A61B 10/00 | (2006.01) |
| G01N 33/543 | (2006.01) |
| G06N 20/00 | (2019.01) |
| G16H 10/40 | (2018.01) |
| G16H 50/30 | (2018.01) |

(52) U.S. Cl.
CPC ............... *A61B 3/101* (2013.01); *A61B 3/16* (2013.01); *A61B 5/0004* (2013.01); *A61B 5/14507* (2013.01); *A61B 5/14546* (2013.01); *A61B 5/411* (2013.01); *A61B 5/412* (2013.01); *A61B 5/4824* (2013.01); *A61B 5/6821* (2013.01); *A61B 5/6847* (2013.01); *A61B 5/7275* (2013.01); *A61B 10/0045* (2013.01); *G01N 33/54366* (2013.01); *G06N 20/00* (2019.01); *G16H 10/40* (2018.01); *G16H 50/30* (2018.01); *A61B 2010/0067* (2013.01)

(58) Field of Classification Search
CPC .............. A61B 5/0004; A61B 5/14507; A61B 5/14546; A61B 5/411; A61B 5/412; A61B 5/4824; A61B 5/6821; A61B 5/6847; A61B 5/7275; A61B 3/101; A61B 3/16; A61B 10/0045; A61B 2010/0067; G06N 20/00; G01N 33/54366; G02C 7/021; G02C 7/024; G02C 7/027; G02C 7/047
See application file for complete search history.

(56) References Cited

U.S. PATENT DOCUMENTS

| | | | |
|---|---|---|---|
| 3,724,263 | A | 4/1973 | Rose et al. |
| 4,305,399 | A | 12/1981 | Beale |
| 4,628,938 | A * | 12/1986 | Lee ........................... A61B 3/16 |
| | | | 600/405 |
| 4,771,792 | A | 9/1988 | Seale |
| 4,860,755 | A | 8/1989 | Erath |
| 4,922,913 | A | 5/1990 | Waters et al. |
| 4,944,303 | A | 7/1990 | Katsuragi |
| 4,947,849 | A | 8/1990 | Takahashi et al. |
| 4,951,671 | A | 8/1990 | Coan |
| 5,005,577 | A | 4/1991 | Frenkel |
| 5,076,274 | A | 12/1991 | Matsumoto |
| 5,109,852 | A | 5/1992 | Kaye et al. |
| 5,148,807 | A | 9/1992 | Hsu |
| 5,165,409 | A | 11/1992 | Coan |
| 5,179,953 | A | 1/1993 | Kursar |
| 5,183,044 | A | 2/1993 | Nishio et al. |
| 5,217,015 | A | 6/1993 | Kaye et al. |
| 5,251,627 | A | 10/1993 | Morris |
| 5,295,495 | A | 3/1994 | Maddess |
| 5,375,595 | A | 12/1994 | Sinha et al. |
| 6,060,256 | A | 5/2000 | Everhart et al. |
| 6,681,127 | B2 | 1/2004 | March |
| 7,429,465 | B2 | 9/2008 | Mueller et al. |
| 8,446,341 | B2 | 5/2013 | Amirparviz et al. |
| 8,870,370 | B1 | 10/2014 | Otis et al. |
| 8,914,089 | B2 | 12/2014 | Abreu |
| 9,730,638 | B2 * | 8/2017 | Haffner ................... A61B 3/16 |
| 10,399,291 | B2 * | 9/2019 | Hahn ................... A61K 39/395 |
| 10,606,100 | B2 * | 3/2020 | Schmeder .............. G02C 7/104 |
| 2001/0034500 | A1 | 10/2001 | March |
| 2004/0176977 | A1 * | 9/2004 | Broderick .............. G02C 7/046 |
| | | | 705/26.1 |
| 2004/0181172 | A1 | 9/2004 | Carney et al. |
| 2005/0065753 | A1 * | 3/2005 | Bigus .................. G06F 11/3447 |
| | | | 702/186 |
| 2005/0160009 | A1 | 7/2005 | Tanaka et al. |
| 2006/0224057 | A1 | 10/2006 | Burd et al. |
| 2007/0224275 | A1 | 9/2007 | Reid et al. |
| 2010/0131434 | A1 | 5/2010 | Magent et al. |
| 2010/0203103 | A1 | 8/2010 | Dana et al. |
| 2011/0029322 | A1 * | 2/2011 | Hindo ................... G06Q 10/10 |
| | | | 705/2 |
| 2011/0084834 | A1 * | 4/2011 | Sabeta ................. G06K 19/077 |
| | | | 340/540 |
| 2011/0117661 | A1 | 5/2011 | Daunert et al. |
| 2012/0138818 | A1 | 6/2012 | Pugh et al. |
| 2012/0245444 | A1 | 9/2012 | Otis et al. |
| 2013/0184554 | A1 | 7/2013 | Elsheikh et al. |
| 2014/0085083 | A1 | 3/2014 | Sabeta |
| 2014/0087452 | A1 | 3/2014 | Liu et al. |
| 2014/0088372 | A1 | 3/2014 | Saeedi et al. |
| 2014/0088381 | A1 | 3/2014 | Etzkorn et al. |
| 2014/0088881 | A1 * | 3/2014 | Saeedi .............. A61B 5/14532 |
| | | | 702/19 |
| 2014/0192312 | A1 | 7/2014 | Pletcher et al. |
| 2014/0194706 | A1 | 7/2014 | Liu et al. |
| 2015/0061837 | A1 | 3/2015 | Honoré et al. |
| 2015/0193588 | A1 | 7/2015 | Nemoto et al. |
| 2017/0020391 | A1 | 1/2017 | Flitsch et al. |
| 2017/0042480 | A1 | 2/2017 | Gandhi et al. |
| 2017/0049395 | A1 | 2/2017 | Cao |
| 2017/0085083 | A1 | 3/2017 | Berkcan et al. |
| 2017/0173262 | A1 | 6/2017 | Veltz |
| 2018/0046773 | A1 | 2/2018 | Tang et al. |
| 2018/0189452 | A1 * | 7/2018 | Serhani ................. G16H 40/67 |
| 2018/0267331 | A1 | 9/2018 | Abbasi et al. |
| 2021/0007643 | A1 | 1/2021 | Lamrani et al. |

FOREIGN PATENT DOCUMENTS

| | | |
|---|---|---|
| EP | 2280052 A1 | 2/2011 |
| EP | 3287167 A1 | 2/2018 |
| JP | H09105751 A | 4/1997 |
| JP | 2004513389 A | 4/2004 |
| JP | 2004212813 A | 7/2004 |
| JP | 6174232 B1 | 7/2017 |
| WO | 2014209657 A1 | 12/2014 |
| WO | 2015036432 A1 | 3/2015 |
| WO | 2015050174 A1 | 4/2015 |
| WO | 2015157855 A1 | 10/2015 |

OTHER PUBLICATIONS

He J, et al. Rapid measurement and machine learning classification of colour vision deficiency. Ophthalmic Physiol Opt. Nov. 2023; 43(6):1379-1390. [serialonline], [retrieved on Sep. 6, 2024]. Retrieved from the Internet (Year: 2023) <URL: https://pubmed.ncbi.nlm.nih. gov/37589437/#:~:text=Colour%20vision%20deficiencies% 20(CVDs)%20indicate%20potential%20genetic,a%20CVD%20but% 20do%20not%20quantify%20its > <DOI: 10.1111/opo.13210 >.*
Piro A, et. al. Color vision as a biological marker able to differentiate two phenotypically similar neurological diseases. Neurol Sci. May 2018; 39(5):951-952. [serialonline], [retrieved on Sep. 6,

(56)                    References Cited

OTHER PUBLICATIONS

2024] Retrieved from the Internet (Year: 2018) <URL: https://pubmed.ncbi.nlm.nih.gov/29242999/#:~:text=Color%20vision%20as%20a%20biological%20marker%20able%20to%20differentiate%20two%20phenotypically%20similar%20neurological%20diseases. > <DOI: 10.1007/s10072-017-3219-8 >.*
International Search Report and Written Opinion for PCT/JP2019/010062, dated Jun. 18, 2019.
Extended European Search Report for European Application No. 19767355.1 dated Dec. 7, 2021.
Office Action mailed May 17, 2022 in Japanese Patent App. No. 2020-546426.
Office Action mailed May 17, 2022 in Japanese Patent App. No. 2020-570348.
Extended European Search Report dated Nov. 8, 2021 for European Application No. 19767186.0.
Office Action dated Nov. 2, 2021 for Japanese Application No. 2020-546426.
International Search Report and Written Opinion for International Application No. PCT/IB2019/000237, dated Jul. 30, 2019.

International Search Report and Written Opinion for International Application No. PCT/IB2019/000239, dated Jul. 9, 2019.
International Search Report and Written Opinion for International Application No. PCT/IB2019/000240, dated Jul. 30, 2019.
Notice of Allowance dated Oct. 25, 2022 for Japanese Application No. 2020-546426.
Office Action mailed Sep. 14, 2021 in Japanese Patent App. No. 2020-570348.
International Search Report and Written Opinion for International Patent Application No. PCT/IB2019/00250, dated Jul. 23, 2019.
Kim, J., et al., Wearable Smart Sensor Systems Integrated on Soft Contact Lenses for Wireless Ocular Diagnostics, Nature Communications, Published Apr. 27, 2017, Article No. 14997, pp. 1-8.
Office Action mailed Jul. 24, 2023 for U.S. Appl. No. 16/980,196.
Office Action mailed Feb. 17, 2023 in Chinese Patent App. No. 201980018752.1 (with English translation).
Office Action mailed Feb. 3, 2023 in Chinese Patent App. No. 201980018492.8 (with English translation).
Final Office Action dated Jan. 9, 2024 for U.S. Appl. No. 16/980,196.

* cited by examiner

*900*

Provide a mold suitable for molding contact lenses    *905*

Mold at least one layer of contact lens    *910*

Insert sensor into partially cured contact lens    *915*

Finish formation and cure of contact lens    *920*

*1000*

Place contact lens into eye of a user with diabetes　*1005*

Observe glucose sensor　*1010*

Receive indication of glucose level　*1015*

1200

1230
1228
1226
1224
1222
1210

1220

1665

1525

1210

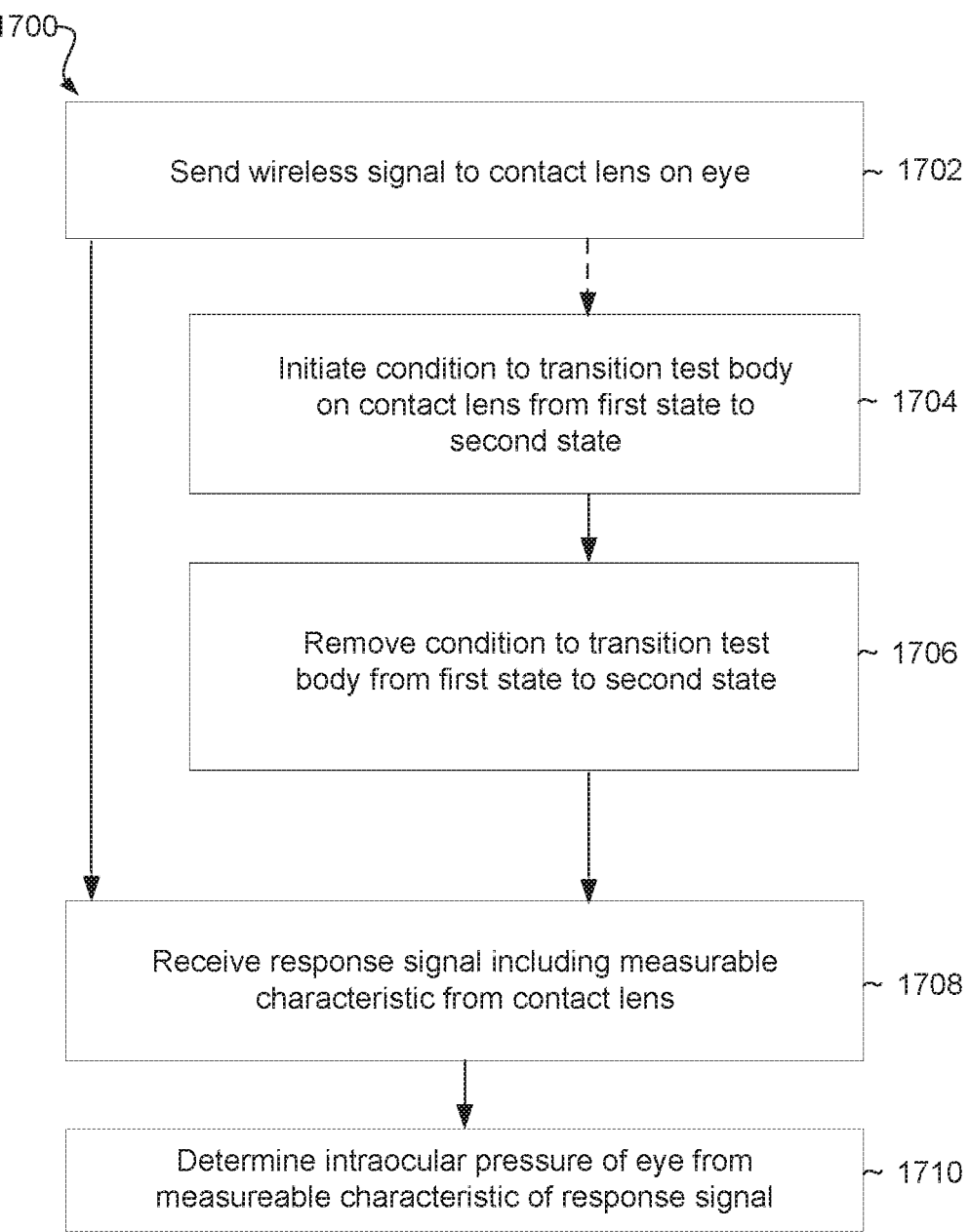

1700

Send wireless signal to contact lens on eye ~ 1702

Initiate condition to transition test body on contact lens from first state to second state ~ 1704

Remove condition to transition test body from first state to second state ~ 1706

Receive response signal including measurable characteristic from contact lens ~ 1708

Determine intraocular pressure of eye from measureable characteristic of response signal ~ 1710

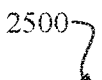

| 2502 Tear Chemistry | 2504 Database Indication | 2506 Possible Cause |
|---|---|---|
| 2508 — Normal lactoferrin and normal IgE | Normal lacrimal function and no allergic component | Evaporative dry eye |
| 2510 — Normal lactoferrin and high IgE | Normal lacrimal function and ocular allergy present | Ocular allergy and possible evaporative dry eye |
| 2512 — Low lactoferrin and normal IgE | Suppressed lacrimal function and no ocular allergy present | Aqueous deficient dry eye |
| 2514 — Low lactoferrin | Suppressed lacrimal function and contact lens desensitization | Hypoxia, bacterial conjunctivitis and/or contact lens dehydration |
| 2516 — High lactoferrin | Elevated tear proteins | Excess contact lens deposits |
| 2518 — High IgE | Ocular allergy present | Giant papillary conjunctivitis or inflammation |

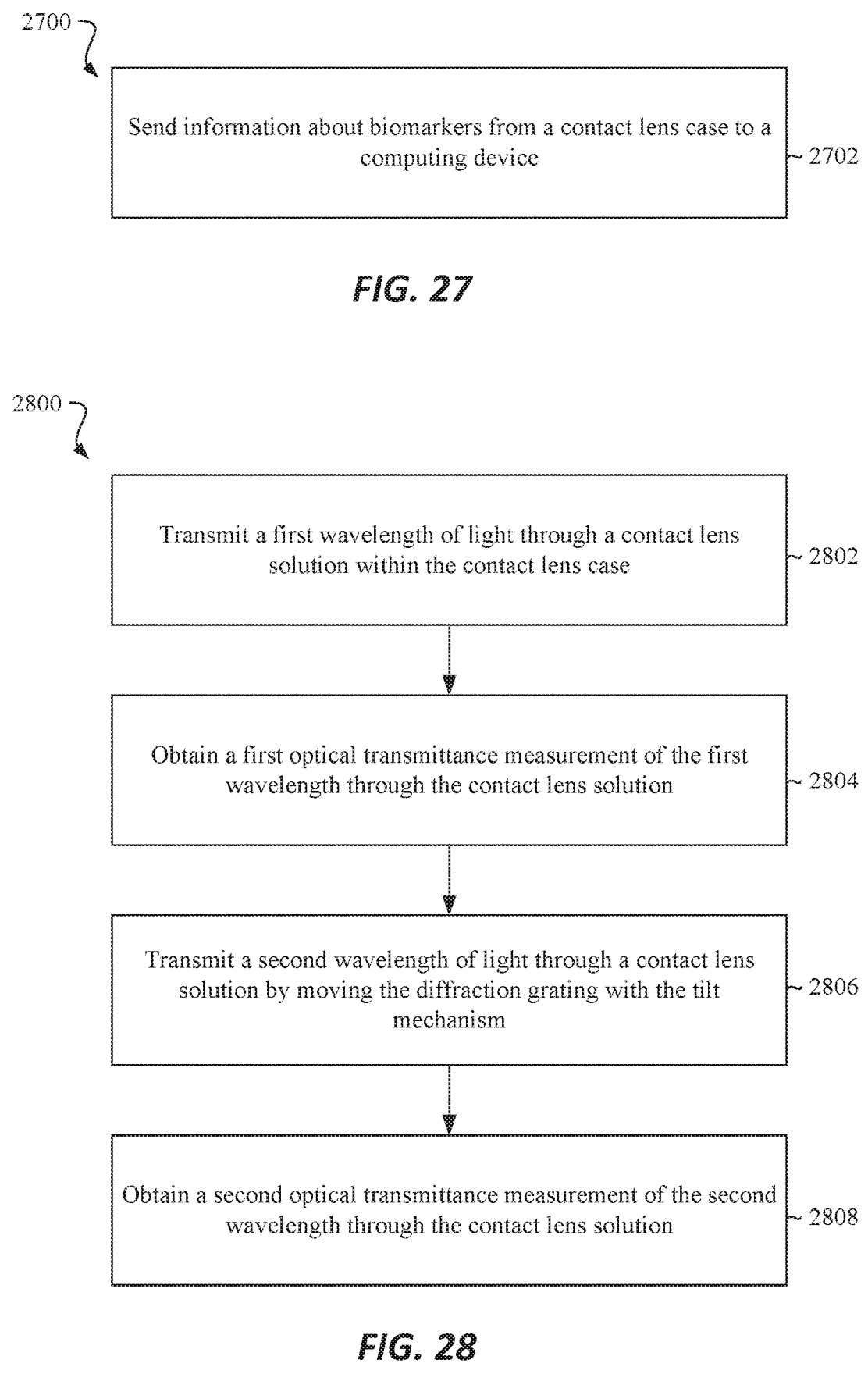

Send information about biomarkers from a contact lens case to a computing device ~ 2702

Transmit a first wavelength of light through a contact lens solution within the contact lens case ~ 2802

Obtain a first optical transmittance measurement of the first wavelength through the contact lens solution ~ 2804

Transmit a second wavelength of light through a contact lens solution by moving the diffraction grating with the tilt mechanism ~ 2806

Obtain a second optical transmittance measurement of the second wavelength through the contact lens solution ~ 2808

FIG. 28

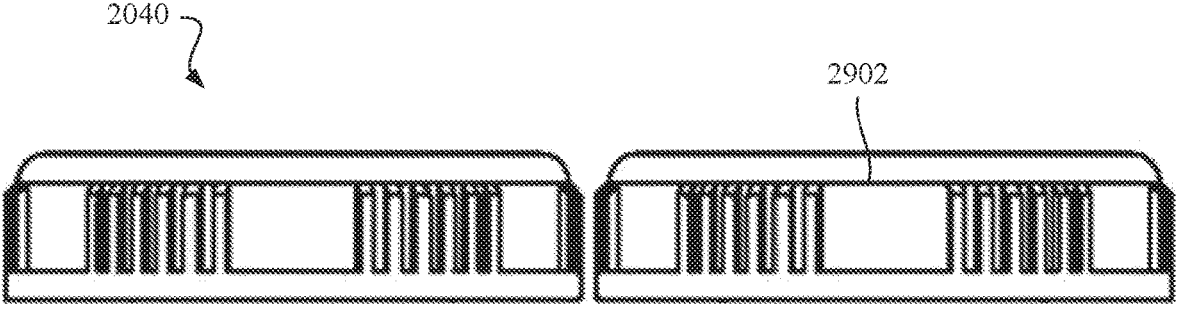
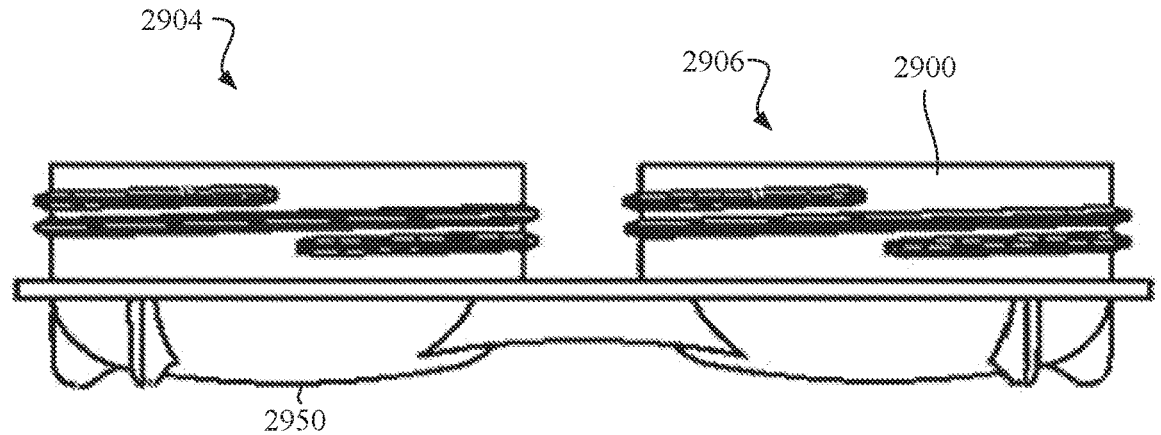
*FIG. 29*

2040

3400

Would you like to initiate a biomarker analysis?

Yes    No

2902

2900

4100

|  | 4102 | 4104 Database | 4106 |
|---|---|---|---|
|  | Tear Chemistry | Indication | Potential Cause |
| 4108 | Normal lactoferrin and normal IgE | Normal lacrimal function and no allergic component | Evaporative dry eye |
| 4110 | Normal lactoferrin and high IgE | Normal lacrimal function and ocular allergy present | Ocular allergy and possible evaporative dry eye |
| 4112 | Low lactoferrin and normal IgE | Suppressed lacrimal function and no ocular allergy present | Aqueous deficient dry eye |
| 4114 | Low lactoferrin | Suppressed lacrimal function and contact lens desensitization | Hypoxia, bacterial conjunctivitis and/or contact lens dehydration |
| 4116 | High lactoferrin | Elevated tear proteins | Excess contact lens deposits |
| 4118 | High IgE | Ocular allergy present | Giant papillary conjunctivitis or inflammation |

Obtain biomarkers from a contact lens previously worn by a user   ~ 4402

Analyze at least one biomarker to determine the health condition of the user   ~ 4404

Obtain a concentration level based on the analysis of the biomarker   ~ 4406

Compare the concentration level with a database that correlates concentration levels with health conditions   ~ 4408

4500 ⌐

4600 ⌐

4700

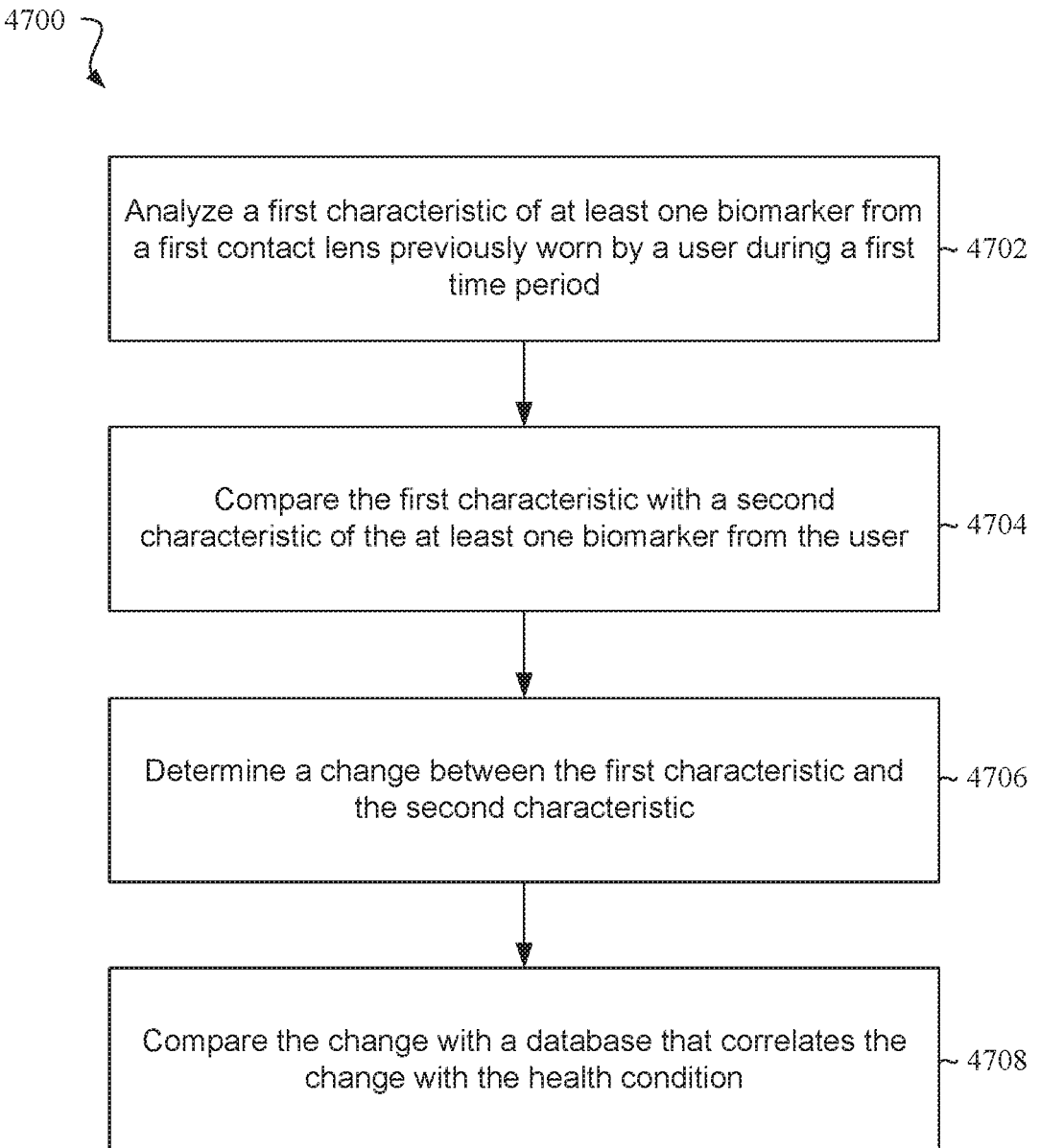

Analyze a first characteristic of at least one biomarker from a first contact lens previously worn by a user during a first time period ~ 4702

Compare the first characteristic with a second characteristic of the at least one biomarker from the user ~ 4704

Determine a change between the first characteristic and the second characteristic ~ 4706

Compare the change with a database that correlates the change with the health condition ~ 4708

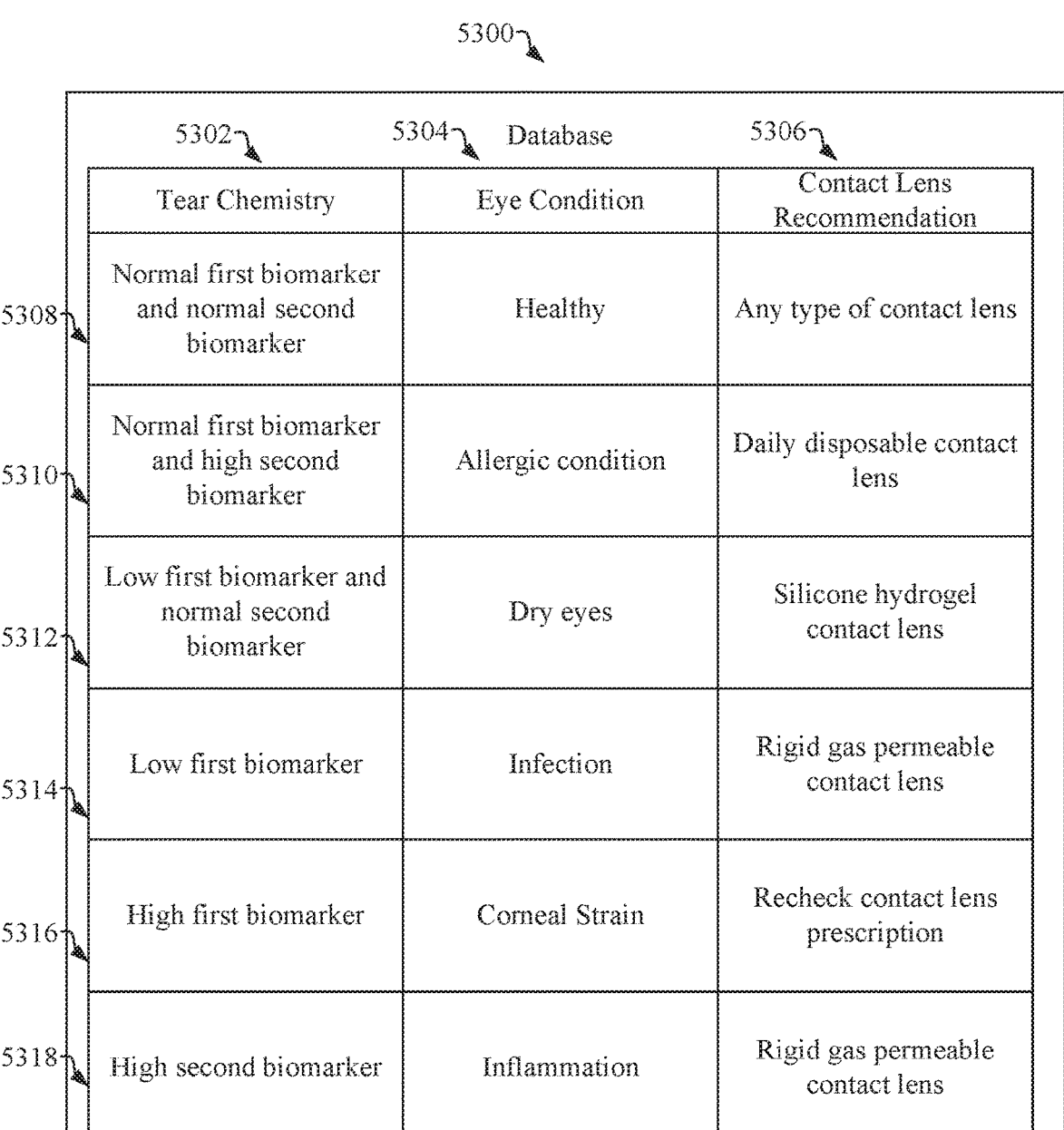

| 5302 | 5304 Database | 5306 |
|------|------|------|
| Tear Chemistry | Eye Condition | Contact Lens Recommendation |
| Normal first biomarker and normal second biomarker | Healthy | Any type of contact lens |
| Normal first biomarker and high second biomarker | Allergic condition | Daily disposable contact lens |
| Low first biomarker and normal second biomarker | Dry eyes | Silicone hydrogel contact lens |
| Low first biomarker | Infection | Rigid gas permeable contact lens |
| High first biomarker | Corneal Strain | Recheck contact lens prescription |
| High second biomarker | Inflammation | Rigid gas permeable contact lens |

Analyze a characteristic of at least one biomarker
contained on a contact lens ~ 5402

Compare the characteristic with a database that correlates ~ 5404
the characteristic with a contact lens recommendation

5500

5600

5700

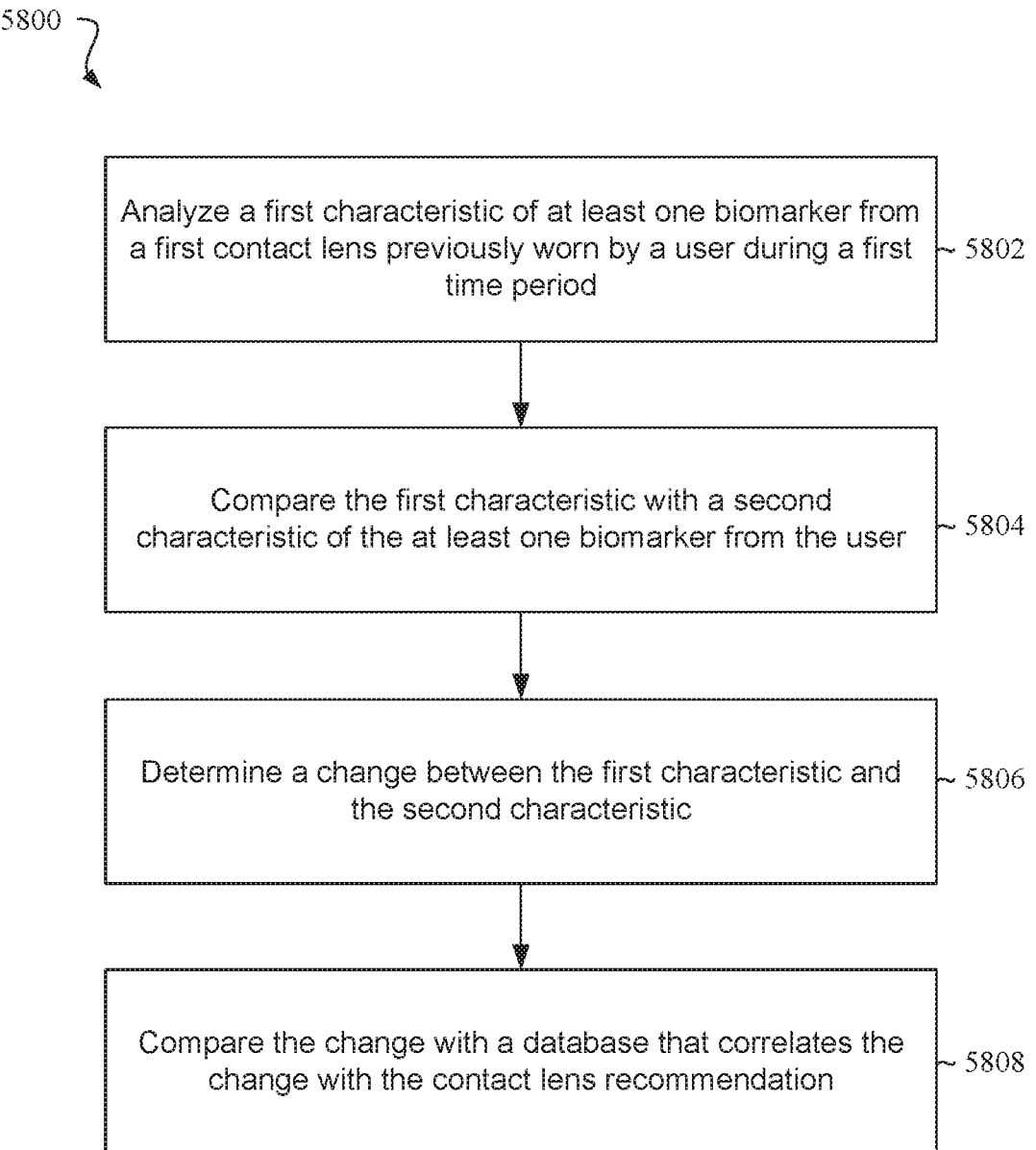

5800

Analyze a first characteristic of at least one biomarker from a first contact lens previously worn by a user during a first time period ~ 5802

Compare the first characteristic with a second characteristic of the at least one biomarker from the user ~ 5804

Determine a change between the first characteristic and the second characteristic ~ 5806

Compare the change with a database that correlates the change with the contact lens recommendation ~ 5808

*FIG. 58*

SYSTEM FOR COLLECTING AND UTILIZING HEALTH DATA

FIELD

The present disclosure relates to the field of health care, particularly to collecting and utilizing large quantities of patient data to predict health conditions and make recommendations.

BACKGROUND

Health care professionals have long been charged with diagnosing, monitoring, and treating individuals afflicted with disease. Early diagnosis and treatment often results in a higher likelihood of prolonged life expectancy or total recovery from the illness. Indeed, treatment for major diseases affecting the world populace, such as, diabetes, cancer, heart-disease, glaucoma, and so on are often more treatable if diagnosed early. Early diagnosis often requires regular healthcare screening and monitoring. Regular healthcare screenings, however, can be problematic for many people throughout the world. For example, bloodwork, biopsies, and other regular healthcare screenings can prove to be too costly. Similarly, modern medical equipment can be too expensive for a healthcare provider to procure. Even in regions possessing adequate medical equipment, regular access to the equipment can be withheld or otherwise difficult to schedule. Thus, a large number of individuals are forced to live without sufficient healthcare monitoring and therefore forfeit the benefits of early diagnosis.

SUMMARY

In one aspect of the present disclosure, a method for health monitoring can include collecting current user health data and receiving archived user health data from a database. The method can also include aggregating the user submitted health data with the archived user health data and analyzing the aggregated health data using a processor. The method can further include correlating the aggregated health data with a health condition indicator to predict a health condition of the user.

Analyzing the aggregated health data can comprise machine learning, artificial intelligence, and data mining. Collecting the current user health data from a user can include receiving user health data from a smart contact lens. The smart contact lens can be configured to measure intraocular eye pressure of the user. The smart contact lens can be configured to measure glucose levels or concentrations within the tear fluid of a user. Collecting current user health data can include using a smart contact lens container. The smart contact lens container can be configured to measure at least one biomarker characteristic of a biomarker within the smart contact lens container. The at least one biomarker characteristic can include identifying a type of biomarker or the concentration of a biomarker within the smart contact lens container. The method can also include generating a healthcare recommendation based on the correlation.

In another aspect of the present disclosure, a method for health monitoring can include collecting current user health data and receiving archived user health data from a database. The method can also include aggregating the user submitted health data with the archived user health data and analyzing the aggregated health data using a processor. The method can further include correlating the aggregated health data to generate a recommendation.

The recommendation can include recommending at least one of a medical examination, a contact lens, and a physician. The current user health data can include at least one of age, gender, weight, height, and place of domicile. Analyzing the aggregated health data can comprise machine learning, artificial intelligence, and data mining. Collecting current user health data can include using a smart contact lens. The smart contact lens can wirelessly communicate with another electronic device. Collecting current user health data can include using a smart contact lens container. The smart contact lens container can wirelessly communicate with another electronic device.

In yet another aspect of the present disclosure, a method of health monitoring can include collecting current user health data. Collecting current user health data can include detecting a glucose concentration within optical fluid using a smart contact lens. Collecting current user health data can include detecting an intraocular pressure of an eye using a smart contact lens. Detecting the intraocular pressure can include detecting relative intraocular pressure and absolute intraocular pressure. Collecting current user health data can include detecting a biomarker characteristic using a smart contact lens container. The method can include receiving archived user health data from a database and aggregating the current user health data with the archived user health data. The method can also include analyzing the aggregated health data using a processor. Analyzing the aggregated health data can include implementing data mining algorithms using a processor. The method can also include correlating the aggregated health data with a health condition indicator to generate a predicted health condition of the user.

The smart contact lens can be configured to transmit the current user health data after collecting the current user health data. Receiving the current user health data can include receiving the current user health data at an electronic device. Aggregating the current user health data with the archived user health data can include storing the current user health data within the database. The predicted health condition of the user can be received at a mobile device of the user. The glucose concentration can be detected using a glucose sensor positioned on a surface of the smart contact lens. The relative intraocular pressure can be detected using a variable capacitance sensor operably coupled to the smart contact lens. The absolute intraocular pressure can be detected using a tonometer operably coupled to the smart contact lens. The biomarker characteristic can be at least one of a type or concentration of a biomarker within the smart contact lens container.

BRIEF DESCRIPTION OF THE DRAWINGS

The accompanying drawings illustrate various embodiments of the present apparatus and are a part of the specification. The illustrated embodiments are merely examples of the present apparatus and do not limit the scope thereof.

FIG. 17 is a block diagram of an example system for wirelessly determining the intraocular pressure of an eye in accordance with the present disclosure.

FIG. 25 illustrates a block diagram of an example of a database, in accordance with the present disclosure.

FIG. 27 illustrates a block diagram of a method of determining a health condition, in accordance with the present disclosure.

FIG. 28 illustrates a block diagram of a method of determining a health condition, in accordance with the present disclosure.

FIG. 29 illustrates an example of a contact lens storage container, in accordance with the present disclosure.

FIG. 41 illustrates a block diagram of an example of a database, in accordance with the present disclosure.

FIG. 47 illustrates a block diagram of a method of an example of determining a health condition, in accordance with the present disclosure.

FIG. 53 is a block diagram of an example of a database in accordance with the present disclosure.

FIG. 58 is a block diagram of an example method for recommending a contact lens in accordance with the present disclosure.

Throughout the drawings, identical reference numbers designate similar, but not necessarily identical, elements.

DETAILED DESCRIPTION

The ability to diagnose and treat disease has long been tied to the current state of medical technology. Consequently, medical technology seems to be in a constant state of innovation. As does most technology, medical technology related to diagnosis acts to simplify a complex task while increasing the accuracy, dependability, and accessibility of the resulting diagnosis. Physicians often rely on bloodwork, biopsies, and other invasive forms of medical testing to formulate a diagnosis. These invasive forms of medical testing, however, can be too costly, too painful, or otherwise too burdensome for many individuals to regularly attain. For example, an individual's home can be located too far from the nearest healthcare center to regularly travel to the center. Likewise, the high cost of medical insurance can be too taxing for many individuals to obtain regular healthcare screenings.

Like modern medical technologies, technology related to data management also seems to be in a constant state of innovation. Recent developments in artificial intelligence, machine learning, and data mining represent substantial resources when applied to data management. Moreover, computing power relative to these developments has made large scale data processing more cost-effective and feasible than ever before.

A major aspect of the present disclosure relates to large scale data collection, processing, and utilization relative to the healthcare industry. More specifically, a holistic system is envisioned which allows large quantities of data to be collected, aggregated and analyzed to provide consistent healthcare monitoring to the populace. This system can include detecting health conditions and making healthcare related recommendations based on statistically relevant characteristics of the data. In some embodiments, a plurality of elements can communicate interchangeably to realize a system for collecting and utilizing health data. Health data can include current user health data (e.g., data collected from a user using, for example, a smart contact lens system or a smart contact lens container) and archived user health data (e.g., other data sources such as medical records, dental records, genealogical records, and so on).

Figure 1:
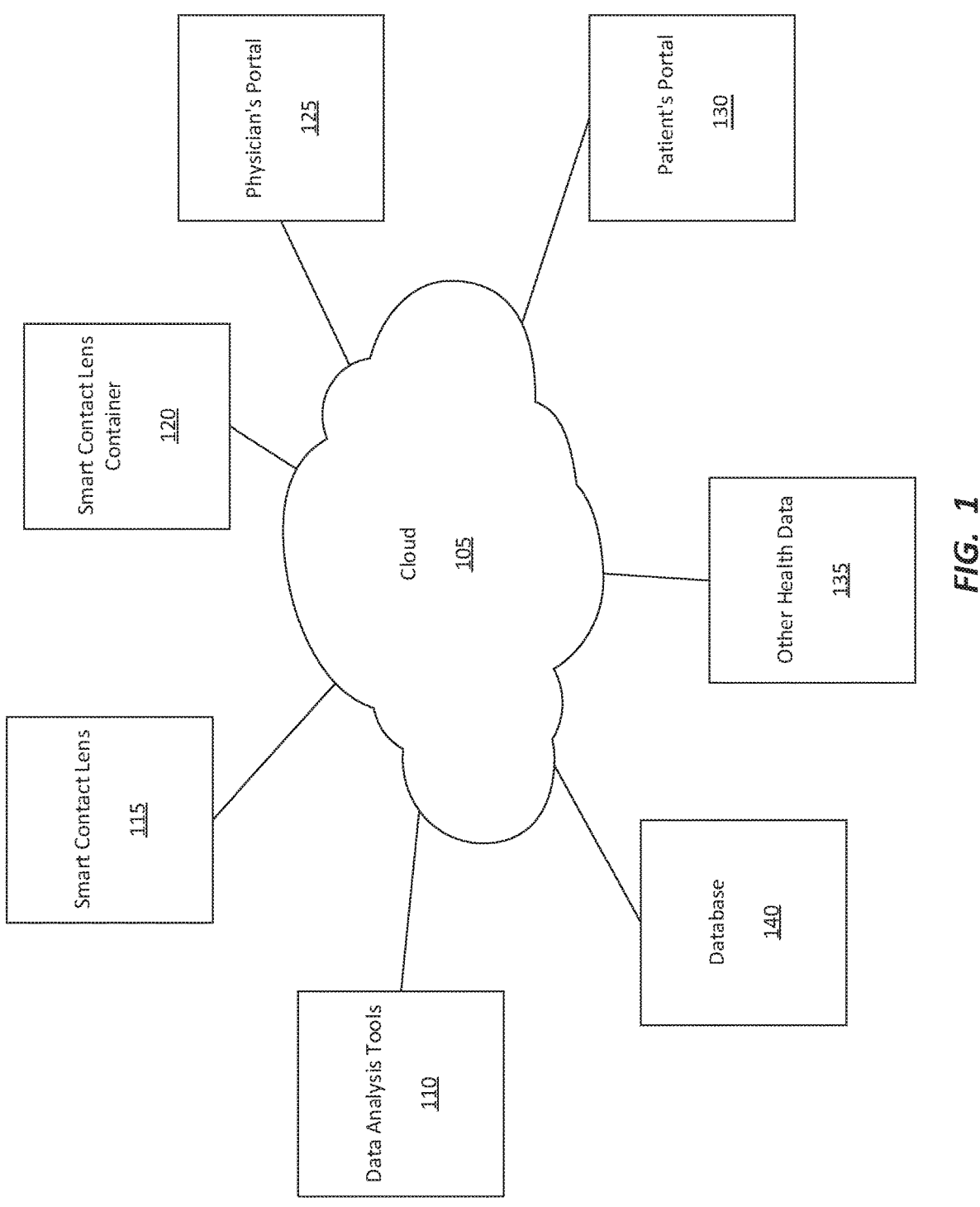
FIG. 1 illustrates a graphical representation of a system for collecting and utilizing health data in accordance with the present disclosure.

FIG. 1 depicts a graphical representation of an embodiment of a system for collecting and utilizing health data in accordance with the present disclosure. The system can include a plurality of elements communicably coupled to a cloud computing network 105. The plurality of elements include data analysis tools 110, a smart contact lens 115, a smart contact lens container 120, a physician's portal 125, a patient's portal 130, other health data 135, and a database 140. Each element is configured to communicate with the cloud computing network 105 and one or more of the other elements.

The cloud computing network 105 can include a network of data centers or server farms which provide a large amount computational power, software, and storage capacity on an as-needed basis. The cloud computing network 105 can include a plurality of nodes distributed throughout one or more data centers. Alternatively, or additionally, the cloud computing network 105 can utilize a plurality of virtual machines to process the data.

Data analysis tools 110 can represent modern data analytics, for example, data mining, machine learning, artificial intelligence, and so on. The data analysis tools 110 can also be configured to output or otherwise generate an output to a user, a physician, another medical professional, or another recipient. For example, the data analysis tools 110 can be configured to output a healthcare recommendation relative to correlations within the data. In another embodiment, the data analysis tools 110 can be configured to output a health condition prediction relative to correlations within the data.

Data Collection

The smart contact lens 115 can represent a contact lens which has been configured to measure or otherwise detect biomarker characteristics associated with the contact lens wearer. In some embodiments, the smart contact lens 115 can include a sensor or sensing component operably coupled to the contact lens. For example, a glucose sensor can be positioned on a surface of the contact lens and detect a concentration level of glucose within the tear fluid of the contact lens wearer at regular intervals. In other embodiments, the smart contact lens 115 can communicate the measured biomarker characteristics to another electronic device, for example, a wireless receiver or a mobile phone. The smart contact lens 115 can include other electronic components (e.g., a power supply, an antenna, a microcontroller, etc.) that enable the smart contact lens 115 to wirelessly communicate with other devices.

In other embodiments, the smart contact lens 115 can be configured to detect absolute and/or relative intraocular pressure of the contact lens wearer. For example, the smart contact lens 115 can be configured to detect the relative intraocular pressure of a user's eye by detecting changes in the mechanical strain of the contact lens using a variable capacitance sensor. In another embodiment, the smart contact lens can be configured to detect the absolute intraocular pressure of a user's eye by measuring the rebound of a surface of the user's eye using, for example, a tonometer system. The smart contact lens 115 can also communicate the intraocular pressure measurements to another electronic device, for example, a wireless receiver or a mobile phone. The smart contact lens 115 can include other electronic components (e.g., a power supply, an antenna, a microcontroller, etc.) that enable the smart contact lens 115 to wirelessly communicate with other devices.

The smart contact lens container 120 can represent any container configured to measure or detect biomarker characteristics of a user or a patient. For example, the smart contact lens container 120 can be an overnight contact lens storage container which houses an aqueous cleaning solution for contact lens maintenance. In this embodiment, the smart contact lens container 120 can include one or more sensors configured to measure biomarker characteristics within the smart contact lens container 120. The sensor can be a spectral analyzer including a light source and light receiver which measures various properties of light within the smart contact lens container 120. The smart contact lens container 120 can also be configured to communicate with one or more other electronic devices. For example, the smart contact lens container 120 can include a wireless transmitter, power supply, microcontroller, transceiver, or any other component that would enable communication between the smart contact lens container 120 and another electronic device.

The physician's portal 125 can represent an electronic device that enables a physician to input data, monitor data, request data, receive information, or otherwise communicate with other elements of the system. For example, a physician or other medical professional can utilize the physician's portal 125 to receive information relative to one of her patients, such as, a predicted health condition associated with the patient and based on the patient's health data. The predicted health condition can be the result of data processing undertaken by the data analysis tools 110.

The patient's portal 130 can represent an electronic device that enables a patient or user to input data, monitor data, request data, receive information, or otherwise communicate with other elements of the system. For example, a user or patient can utilize the patient's portal 125 to submit information or data relative to the patient's age, gender, height, weight, family health history, and so on. Data submitted by the patient can be stored, analyzed, and correlated within the database. The patient's portal 130 can also receive data relative to the patient's daily routine. For example, a patient can input the duration of time she has worn a particular smart contact lens or the duration of time in which her contact lens has been deposited within a smart contact lens container. The patient's portal 130 can also be configured to convey recommendations or other information to the patient relative to the patient's health data.

Other health data 135 or archived user health data can represent any information that can be influential in delivering accurate information to the patient or physician. For example, the city, state, province, or country in which the patient is domiciled, the patient's family medical history, the patient's genealogy, the patient's health records, the patient's exercise routine, the patient's diet, and any other data concerning the patient that is not currently being collected by a physician, a smart contact lens 115, or a smart contact lens container 120. In some embodiments, the other health data 135 can also be considered archived user health data previously collected and stored within the database 140.

The database 140 can represent a vast amount of data collected from thousands or millions of patients and stored, for example, within one or more data centers. The database 140 can undergo data processing techniques, for example, machine learning can be implemented to sort, process, organize, or otherwise utilize the data to generate predictions and recommendations to the patient, physician, or both. Other related data processing techniques, such as data mining, can also be used to discover patterns, statistical trends, correlations, or otherwise formulate predictions and recommendations relative to the data.

Smart Contact Lens System

According to one aspect of the present disclosure, the system for collecting and utilizing health data can incorporate a plurality of non-invasive devices which collect and monitor current user health data. Moreover, the system can compare or otherwise correlate the current user health data with archived user health data (e.g., health data associated with the surrounding populace). Aggregating current user health data with archived user health data can greatly increase the accuracy of correlations, statistical trends, and predictions derived from the data. Non-invasive devices capable of detecting and recording health data can be, for example, a smart contact lens system 115 and a smart contact lens container 120.

First Embodiment

The principles described in the current disclosure include a smart contact lens which incorporating a glucose sensor into a contact lens (e.g., one embodiment of a smart contact lens 115) to detect or otherwise determine when a threshold amount of glucose is present in optical fluids (e.g., tears), as described in U.S. Provisional Application No. 62/642,176 filed 13 Mar. 2018, the disclosure of which is incorporated herein, in its entirety, by this reference. This glucose sensing contact lens can also or alternatively detect, record, or otherwise measure glucose properties within a user's eye and transmit the measured values to an electronic device, computing device, database, or a combination thereof. The glucose sensor can be bonded or otherwise operably attached or incorporated into the contact lens. In some embodiments, the glucose sensor can transition between a first state and a second state based on a concentration of glucose within the optical fluids. For example, the first state can appear to an observer as a first color, transparency, or opacity and the second state can appear to an observer as a second color, transparency, or opacity. Thus, while the contact lens is worn within the user's eye, either the user or another person observing the user's eye can view the glucose sensor of the contact lens to quickly determine if the threshold amount of glucose is present in the user's system.

Figure 2:
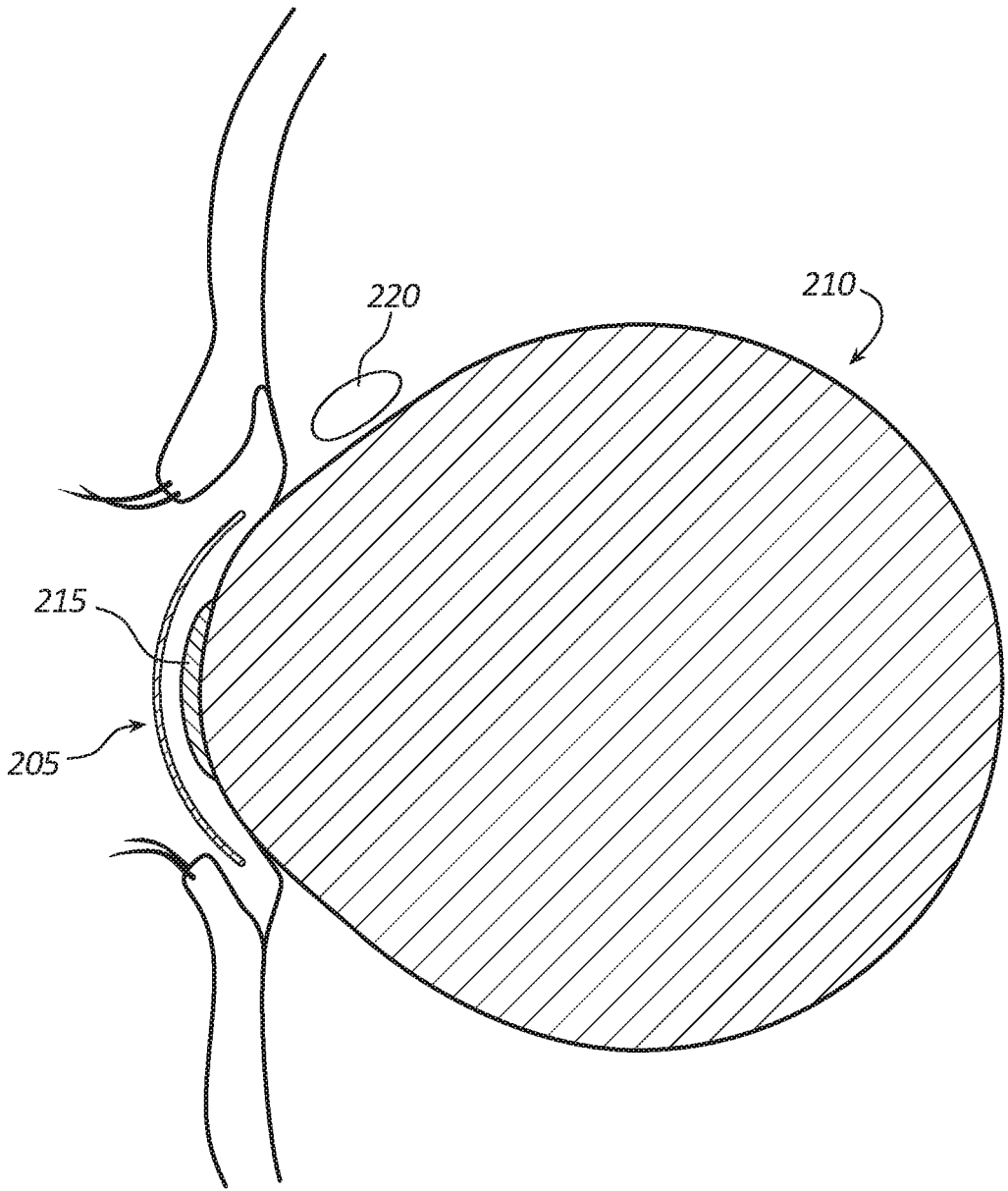
FIG. 2 illustrates a cross sectional view of an example of contact lens positioned on an eye in accordance with the present disclosure.

FIG. 2 depicts an example of a contact lens 205 according to the present disclosure. When a person closes an eyelid (e.g., by blinking or winking), the eyelid deposits optical fluid or tears onto the surface of the eye. This optical fluid is produced by the lacrimal gland 220 positioned above the eye 210. In some embodiments, a contact lens 205 of the present disclosure can sit atop the cornea 215 and contact optical fluid (e.g., tears) deposited by the eyelid. A glucose sensor (not shown) operably coupled to the contact lens 205 can measure the concentration of glucose within a user's tears. The glucose sensor (not shown) can dynamically transition between a first state and a second state relative to the concentration of glucose within the optical fluid.

The contact lens 205 can include a hard contact lens, hydrogel lens, silicone hydrogel lens, hydrogel lens, extended wear contacts, spherical contacts, toric contacts, multifocal contacts, monovision contacts, rigid gas permeable lens, toric lens, and the like. In some embodiments, the contact lens 205 can incorporate a colored portion to change the appearance of a user's iris.

Any monomer material suitable for use in manufacturing the contact lens 205 can be used. In some embodiments, the monomer is HEMA/GMA. While this example has been described with reference to specific types of monomers that can be used to make the contact lens 205, any appropriate type of monomer can be used to construct the contact lens 205. Further, in other examples, silicon, polymers, other types of constituents, or combinations thereof can be used with the monomers or in lieu of the monomers for constructing the contact lens 205.

In some embodiments, additional materials can be used with the monomer to make the contact lens 205. Any additives known in the art for improving various characteristics of the contact lens 205 can be used. Examples of additives that can be used in conjunction with the monomer include, but are not limited to, thickeners, dyes, buffers, other types of additives, or combinations thereof. The amount of additive used in conjunction with the monomer can vary based on a variety of factors, including optical properties of the contact lens 205 and the desired characteristics imparted by the additives. Generally speaking, the additives are used in quantities that are sufficiently small as to not significantly impact the mass of the resulting contact lens 205.

The contact lens 205 can be formed with any appropriate type of material. In some embodiments, the contact lens can be a hydrogel contact lens 205 or rigid gas permeable (RGP) contact lens 205. In some embodiments, the contact lens 205 can be a silicone hydrogel contact lens 205.

Other optical and structural properties of the contact lens 205 can be adjusted and/or fixed to produce a more comfortable and well performing contact lens 205. In some embodiments, the contact lens 205 includes a fixed base curve. In other words, the contact lens 205 can have the same volume of monomer and the same base curve across a wide range of powers. In some embodiments, the fixed base curve for the contact lens 205 across a range of powers is selected from within a range of from 7.50 to 9.10.

Figure 3:
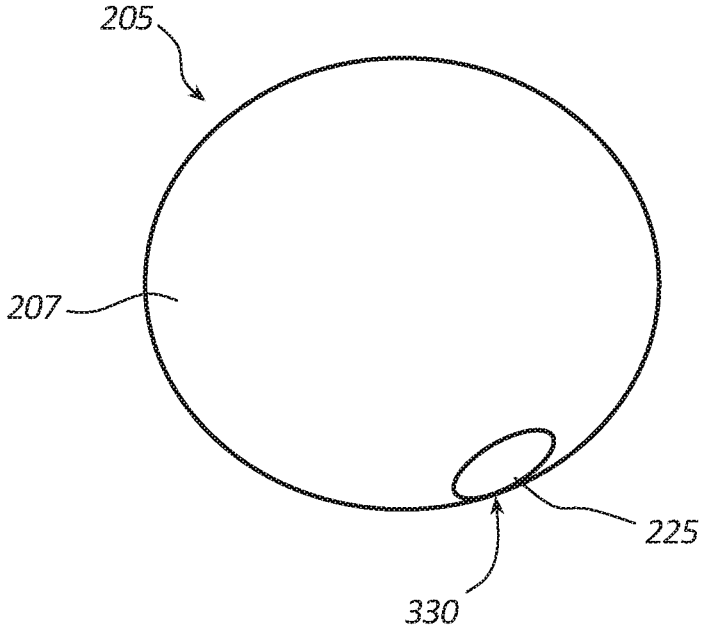
FIG. 3 illustrates an embodiment of a contact lens in accordance with the present disclosure.
Figure 4:
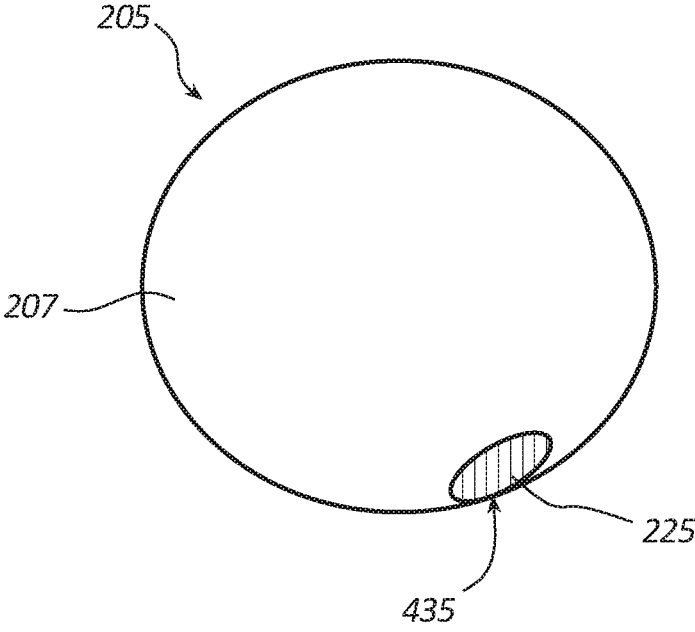
FIG. 4 illustrates an embodiment of a contact lens in accordance with the present disclosure.

FIGS. 3 and 4 depict examples of a contact lens 205 with glucose sensing capabilities. The contact lens 205 is shown with a glucose sensor 225 positioned on a periphery of the body 207 of the contact lens 205. The body 207 can include a rearward-facing surface and a forward-facing surface. The rearward-facing surface can have a substantially concave contour configured to contact the surface of the user's eye 210. The forward-facing surface can have a substantially convex contour. The glucose sensor 225 can be positioned at any location on the body 207 of the contact lens 205. In some embodiments, the glucose sensor 225 can be positioned on the forward-facing surface of the body 207 and away from a center of the body 207 of the contact lens 205 to prevent potential interference with a user's vision. In other embodiments, the glucose sensor 225 can be positioned on the forward-facing surface of the body 207 and near the center of the body 207 to blur a user's vision as an alert mechanism. In some embodiments, an outside periphery of the body 207 can form a circle. In other embodiments, the outside periphery of the body 207 can form an oval.

A characteristic of the glucose sensor 225 can change in the presence of glucose. For example, the color or opacity of the glucose sensor 225 can vary depending on the concentration of glucose within a user's optical fluid (e.g., tears). The glucose sensor 225 can be positioned on the rearward-facing surface of the body 207 of the contact lens 205 such that the glucose sensor 225 contacts tears on the cornea of an eye (e.g., FIG. 2, cornea 215 of the eye 210) in some embodiments. In other embodiments, the glucose sensor 225 can be operably coupled to the forward-facing surface of the body 207 such that the user's eyelid deposits tears onto the glucose sensor 225. A concentration of glucose can be present in the user's tears which can be indicative of an overall level of glucose present in the user's body and/or blood. If the amount of glucose present reaches a threshold, the user's health can be in danger. In some embodiments, the glucose sensor 225 can alter its appearance to visibly indicate when an excessive concentration of glucose is present.

For example, when a user places a new contact lens 205 over her cornea 215, the glucose sensor 225 can have a first state 330. An opacity of the first state 330 can be maintained or constant when a first concentration of glucose is present. For example the first concentration of glucose can include a range of glucose present in a person's system. The range can encompass what is considered a normal or healthy range for the general population or for a specific user or population of users. In some embodiments, the range of glucose can include an amount that corresponds to a blood glucose level of about 80-180 milligrams of glucose per deciliter of blood. This range can include a normal, fasting glucose level and can also incorporate a post-meal glucose level.

In some embodiments, the glucose sensor 225 can maintain the first state 330 when a healthy, acceptable range of glucose is present in a person's tears. In some embodiments, the first state 330 of the glucose sensor 225 can transition to a second state 435 when the glucose level has exceeded a threshold representing healthy glucose concentration. In further embodiments, the glucose sensor 225 can change to a second state 435 when the glucose level has been exceeded for a predetermined time period. For example, if the person's glucose level has surpassed a predetermined range for a predetermined duration of time, the state (e.g., appearance) of the glucose sensor 225 can change. Alternatively, if a person's glucose level has not surpassed a predetermined range for a predetermined period of time, the status of the glucose sensor 225 can remain unchanged. In other embodiments, the glucose sensor 225 can transition between a first state 330 and a second state 435 when a predetermined threshold of glucose is detected in the users system. For example, a single instance of a user's glucose concentration exceeding the predetermined threshold can cause the glucose sensor 225 to change appearance.

In one embodiment, the glucose sensor 225 can be a polymer which is prepared by ultra-violet initiated free radical reaction. For example, acrylamidophenyl boronic acid, ethylene acrylate and acrylic acid can be combined with a dimethyl sulfoxide solvent using methylenebisacrylamide as a cross-linker and 2,2-dimethoxy-2-phenylacetophenon as an initiator. The combination can be placed within a mold and undergo ultra-violet irradiation.

In another embodiment, the glucose sensor 225 can be a different polymer which is prepared by ultra-violet initiated free radical reaction. For example, acrylamidophenyl boronic acid, ethylene acrylate and dimethylacrylamide can be combined with a dimethyl sulfoxide solvent using methylenebisacrylamide as a cross-linker and 2,2-dimethoxy-2-phenylacetophenon as an initiator. The combination can be placed within a mold and undergo ultra-violet irradiation.

In some embodiments, the glucose sensor 225 can include a biosensor which can transition from the first state 330 to the second state 435 relative to a concentration of glucose present in a user's optical fluid. In some embodiments, the glucose sensor 225 can include an enzyme-free biosensor. The enzyme-free biosensor based glucose sensor 225 can be stable at room temperature and within the physiological conditions present in a user's eye. The biosensor can have a first appearance in the first state 330 and a second appearance in the second state 435.

For example, in some embodiments, the status of the glucose sensor 225 can have two settings of opacity: a first opacity associated with the first state 330 for a first glucose level or range and a second opacity for a second state 435 associated a second glucose level or range. The first opacity can include an opaque or mostly opaque region located within the glucose sensor 225 on the contact lens 205. The opaqueness can have a color associate with it. For example, the first opacity can include a white opaque region on the contact lens 205. The size and shape of the opaque region can vary based on size of the contact lens and other factors. A second opacity can be mostly and/or completely transparent.

In some embodiments, the glucose sensor 225 can include a material which changes opacity in the presence of glucose. In some examples, the material can change opacity by a chemical reaction with glucose in a user's optical fluid. In some examples, the material can change opacity by a chemical reaction or series of chemical reactions with glucose and/or another chemical in a user's optical fluid. In some embodiments, the glucose sensor 225 can be a boronic acid copolymer biomaterial. The glucose sensor 225 can react with glucose and change optical characteristics. In some embodiments, the glucose sensor 225 can include an enzyme-free material. It should be appreciated that the glucose sensor 225 can include any number of monomers such that the glucose sensor 225 can be classified as a homopolymer, copolymer, terpolymer, or the like.

In some embodiments, the glucose sensor 225 can change in color. For example, in a healthy glucose range, the glucose sensor 225 can have a first color. In a second, unhealthy, glucose range, the glucose sensor 225 can include a second color. In some embodiments, the glucose sensor 225 can transition slowly to the second color to indicate a rise in glucose. For example, the first color can include red and the second color can include blue. As the user's glucose level rises, the glucose sensor 225 can change to varying shades of purple as the red color fades and the blue color emerges. In further embodiments, the opacity and color of the glucose sensor 225 can change. For example, the first state 330 can have a first opacity and a first color, for example white, associated with it. As the glucose level rises to an unhealthy level, the opacity of the first state 330 can begin to fade and, at the same time, the color of the glucose sensor 225 can change. The initial color and end color or opacity can include any combination of colors or opacity. In some examples, the first and second colors and opacity are different enough to be easily distinguishable with the naked eye. In other examples, opacity sensors and/or color sensors are used to determine when the area changes its state.

In some embodiments, the concentration of glucose present in a user's system can be easily characterized by viewing the glucose sensor 225. For example, a user can look in a mirror and be able to visibly see if the first state 330 or second state 435 are present to quickly establish if the user has a healthy or unhealthy range of glucose in their system. Multiple observation methods can be utilized. For example, a third party can view the user's contact lens 205 and determine if the first or second state 330, 435 is present in the glucose sensor 225. A user can also use an image capturing device such as a mobile device or laptop to photograph their eye, with the contact lens 205, and visibly distinguish between the first and second states 330, 435. The user can view the image herself or can transmit the image to a third party for observation or recordation purposes.

Figure 5:
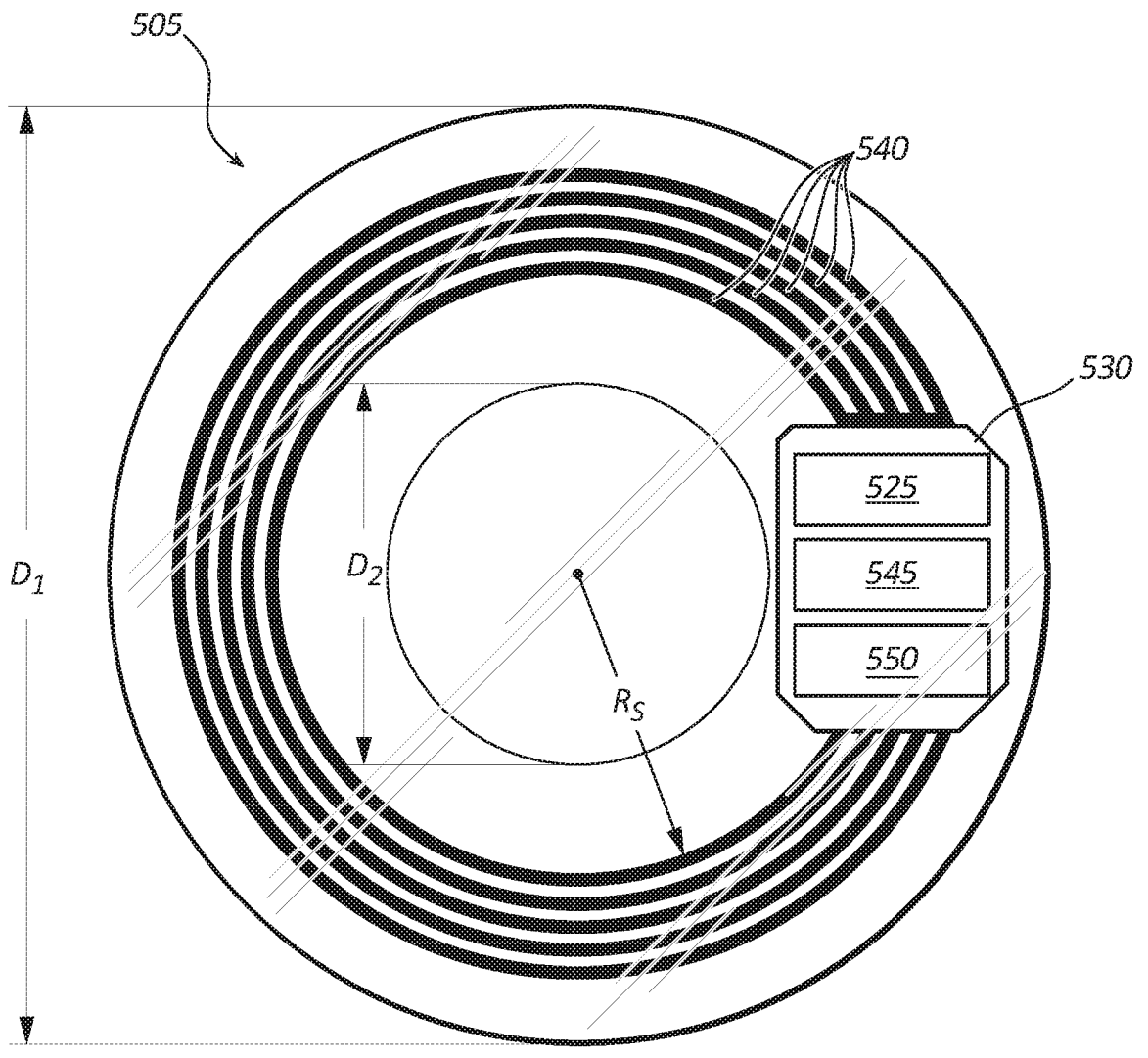
FIG. 5 illustrates an embodiment of a contact lens system in accordance with the present disclosure.

FIG. 5 depicts an example of a contact lens 505 for glucose sensing according to the present disclosure. The contact lens 505 can include a printed circuit board (PCB) 530 operably coupled with an antenna 540. The PCB 530 can include or be operably coupled with any number of electrical components to detect and transmit glucose concentrations on a surface of the contact lens 505. In one embodiment, the PCB 530 includes a glucose sensor 525, a transmitter power supply 545, and a wireless transmitter 550. The glucose sensor 525 can be configured to detect or otherwise measure a concentration of glucose on the surface of the contact lens 505. The glucose sensor 525 can be operably connected to the wireless transmitter 550. The wireless transmitter 550 is operably coupled to the antenna 540 and the transmitter power supply 545 to facilitate transmitting signals relative to glucose detection. In one embodiment, the antenna 540 can include multiple loops that span a periphery of the contact lens 505, as depicted in FIG. 5.

The position at which the PCB 530 and the antenna 540 are coupled to the contact lens 505 can vary. For example, the PCB 530 and the antenna 540 can be operably coupled to the forward-facing surface of the contact lens 505, in one embodiment. In another embodiment, the PCB 530 and the antenna 540 can be operably coupled to the rearward-facing surface of the contact lens 505. Moreover, the PCB 530 and the antenna 540 can also be coupled in varying positions relative to the line of sight of the contact lens wearer. For example, the antenna 540 can be positioned at a radius Rs from the center of the contact lens 505 as to avoid obstructing the wearer's vision. Similarly, the PCB 530 can be operably coupled outside of a dimension $D_2$ as to not obstruct the wearer's vision. Alternatively, a component of the contact lens 505 can be positioned near the center of the contact lens 505 as to obscure the vision of the wearer. For example, the glucose sensor 525 can be positioned at the center of the contact lens 505 and configured to change color or opacity to alert the wearer that a threshold glucose concentration has been exceeded.

The PCB 530 and the antenna 540 can be an RFID sensor-tag that has been incorporated onto or into the contact lens 505, in some embodiments. The RFID sensor-tag can include a sensor or multiple sensors which are sensitive to light and an RFID sensor. The RFID sensor-tag can also include a microcontroller unit configured to control operational aspects of the RFID sensor-tag (e.g., transmitting and receiving signals, power delivery and consumption, etc.). The RFID sensor-tag can also include an antenna (e.g., a multiple loop antenna). The RFID sensor-tag can be printed on a flexible polyimide substrate such as Kapton®. The RFID sensor-tag can be wirelessly powered using, for example, an RFID repeater device positioned near the contact lens 505. Moreover, the RFID repeater device can also be utilized to receive data or other signals transmitted by the RFID sensor-tag.

Figure 6:
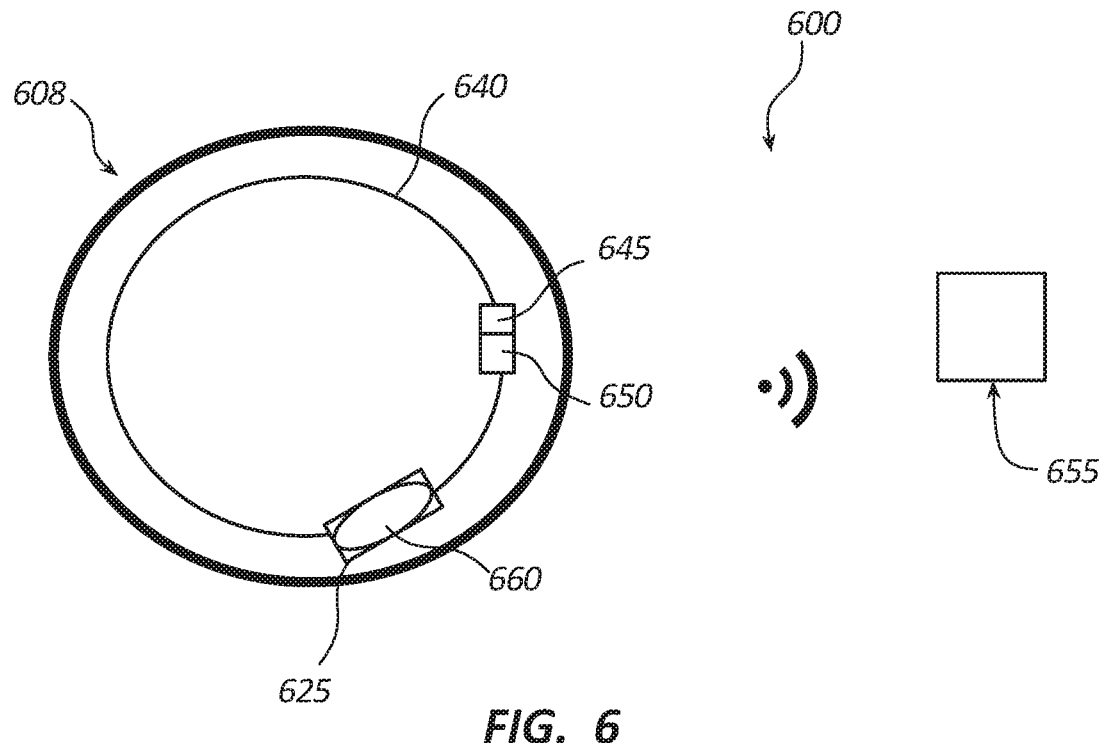
FIG. 6 illustrates an embodiment of a contact lens system in accordance with the present disclosure.

FIG. 6 depicts an example of a contact lens system 600 for glucose sensing according to the present disclosure. The contact lens system 600 can include a contact lens 608 and a wireless receiver 655. An example of contact lens 608 can include the contact lenses described with reference to FIGS. 2-5. In some embodiments, the contact lens 608 can include a glucose sensor 625, an antenna 640, a transmitter power supply 645, a wireless transmitter 650, and a glucose sensing area 660. The glucose sensor 625 can be identical to or similar to the glucose sensors described with reference to FIGS. 3-5. In some embodiments, a contact lens 608 can communicate wirelessly with the wireless receiver 655 by transmitting data to the wireless receiver 655 via the antenna 640.

Figure 7:
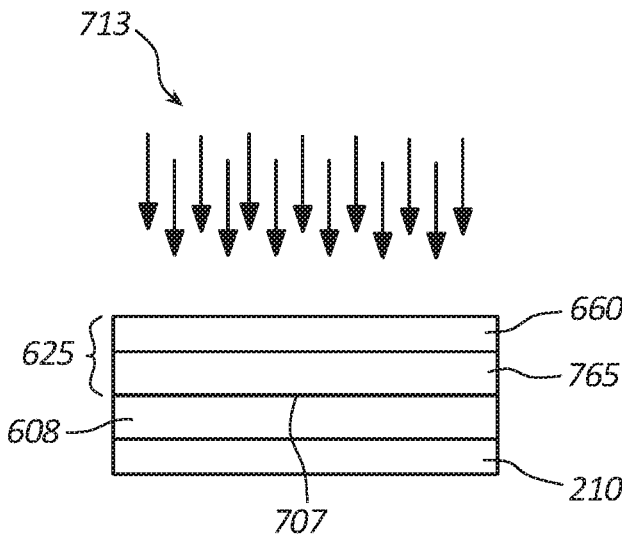
FIG. 7 illustrates a cross sectional view of an example of glucose sensor operably coupled to a contact lens in accordance with the present disclosure.

FIG. 7 depicts a cross sectional view of a glucose sensor 625 operably coupled to a contact lens 608, according to one embodiment of the present disclosure. The glucose sensor 625 can include a glucose sensing area 660 and an optical sensor 765. The glucose sensor 625 can be positioned on the contact lens 608 facing away from the eye 210 (e.g., operably coupled to the forward-facing 707 surface of the contact lens 608). The optical sensor 765 can be operably coupled to the glucose sensing area 660. For example, the optical sensor 765 can be positioned between the glucose sensing area 660 and the contact lens 608. The glucose sensing area 660 can have similar attributes as the glucose sensor described with reference to FIGS. 3-6. For example, the glucose sensing area 660 can transition between a first state and a second state. The first state and second state can be similar to the first state 330 and second state 435 as described with reference to FIGS. 3-4. The first state can have a first opacity, transparency, color or a combination thereof and the second state can have a second opacity, transparency, color or combination thereof relative to the concentration of glucose within the user's optical fluid. The glucose sensing area 660 can dynamically transition between the first and second state as the concentration of glucose within the user's tears vary.

The optical sensor 765 can initially be shielded or obscured from light 713 by the glucose sensing area 660 in a first state. As the glucose sensing area 660 transitions from the first state to the second state, the optical sensor 765 can gradually become partially or fully exposed to light 713. As the optical sensor 765 becomes exposed to light 713, the optical sensor 765 can begin to take measurements or otherwise collect data.

In the first state, the glucose sensing area 660 can be opaque to prevent light 713 from passing through the glucose sensor 625 and thereby prevent the optical sensor 765 from receiving light 713. When the glucose concentration in a user's tears reaches a predetermined threshold (e.g., an unhealthy concentration of glucose), the glucose sensing area 660 can transition to the second state. For example, the glucose sensing area 660 can be more transparent in the second state to allow light 713 to pass through the glucose sensor 625 and be received by the optical sensor 765.

In one embodiment, the optical sensor 765 can include a thin-film solar cell. The optical sensor 765 can include one or more thin layers of thin film of photovoltaic material on a substrate. The substrate can include a plastic. The optical sensor 765 can be a few nanometers thick up to a tens of micrometers thick. As the solar cell is exposed to light 713, the solar cell operating as the optical sensor 765, can begin to charge the transmitter power supply 645. As the transmitter power supply 645 becomes charged, the transmitter power supply 645 can power the antenna 640 and begin to transmit one or more signals, communications, or data to the wireless receiver 655. The transmission can include predetermined communications regarding a concentration of glucose in a user's optical fluid. In some embodiments, the transmission can be a simple communication relaying that the optical sensor 765 has been exposed to light 713. Thus, alerting the wearer that a threshold concentration of glucose has been reached or exceeded.

In some embodiments, the optical sensor 765 can additionally and/or alternatively include a photometer sensor or an ambient light sensor. The optical sensor 765 can measure light intensity or the optical intensity. The optical sensor 765 can measure illuminance, irradiance, light absorption, scattering of light, reflection of light, fluorescence, phosphorescence, luminescence, and the like. The optical sensor 765 can detect light using at least one of a photoresistor, photodiode, photomultipliers, or the like. In some embodiments, the optical sensor 765 can measure an amount of light after it has passed through a filter or monochromator. The use of a filter or monochromator can enable the optical sensor 765 to determine light intensity at defined wavelengths or to analyze a spectral distribution of the light.

In other embodiments, the optical sensor 765 can measure individual photons rather than incoming flux. Flux can include spectral flux or spectral power of the light that reaches the optical sensor 765. In some embodiments, the optical sensor 765 can include a reflectance photometer which can measure the reflectance of a surface as a function of wavelength.

In some embodiments, the optical sensor 765 can alternatively or additionally measure the absorption of light of a given wavelength. For example, the optical sensor 765 can measure the concentration of a colored substance in a solution. The optical sensor 765 can include an absorption photometer to measure ultraviolet and visible ranges of specific light wavelengths.

The optical sensor 765, as a photometer, can collect and feed data to the wireless transmitter 650. The wireless transmitter 650 can transmit data or other signals to the wireless receiver 655 through the antenna 640 powered by the transmitter power supply 645. For example, as the optical sensor 765 is exposed to light 713, the optical sensor 765 can begin measuring various optical attributes as discussed. When the optical measurements reach a predetermined threshold, the optical sensor 765 can feed data to the wireless transmitter 650. The wireless transmitter 650 can transmit the data to the wireless receiver 655. In one embodiment, as the glucose sensing area 660 transitions from a first state of opacity to a second state of opacity, the change in opacity can allow higher concentrations of light 713 to permeate the glucose sensing area 660 and thereby expose the optical sensor 765 to higher concentrations of light 713. Thus, the opacity of the glucose sensing area 660 can act as a temporary barrier which only allows light to pass when there is an unhealthy concentration of glucose within the user's optical fluid.

In some embodiments, the optical sensor 765 can act as a capacitor. For example, the optical sensor 765 can store a charge which can be released when the optical sensor 765 is exposed to light 713, for example, when the glucose sensing area 660 transitions from the first state to the second state. As the optical sensor 765, as a capacitor, is exposed to light 713, the capacitor can build up a charge and subsequently release the charge to power the transmitter power supply 645. Once the transmitter power supply 645 is powered, the antenna 640 can transmit data or other signal to the wireless receiver 655.

The transmitter power supply 645 can include a battery operably coupled to the contact lens 608. The battery can be rechargeable. The transmitter power supply 645 can initially have a stored charge or the transmitter power supply 645 can be charged by the optical sensor 765. The transmitter power supply 645 can include graphene. In some embodiments, the transmitter power supply 645 can be printed to a surface of the contact lens. The transmitter power supply 645 can be a graphene printed battery. In some embodiments, the transmitter power supply 645 can be fully printable, can include a planar architecture. In some embodiments, the transmitter power supply 645 can be flexible and have a long shelf-life. The transmitter power supply 645 can function in a moist environment. In some embodiments, the transmitter power supply 645 can have approximately one microampere per square millimeter capacity per unit area. The transmitter power supply 645 can include approximately twenty-five microampere per cubic centimeter capacity per unit volume.

In some embodiments, the transmitter power supply 645 can be capable of wirelessly charging. For example, the transmitter power supply 645 can receive power wirelessly from an electronic device (not shown) positioned near the transmitting power supply 645. In one embodiment, a repeater device having an RFID reader can be positioned near the contact lens 608 and configured to wirelessly transmit the power necessary to operate the transmitter power supply 645 and/or the glucose sensor 625.

Figure 8:
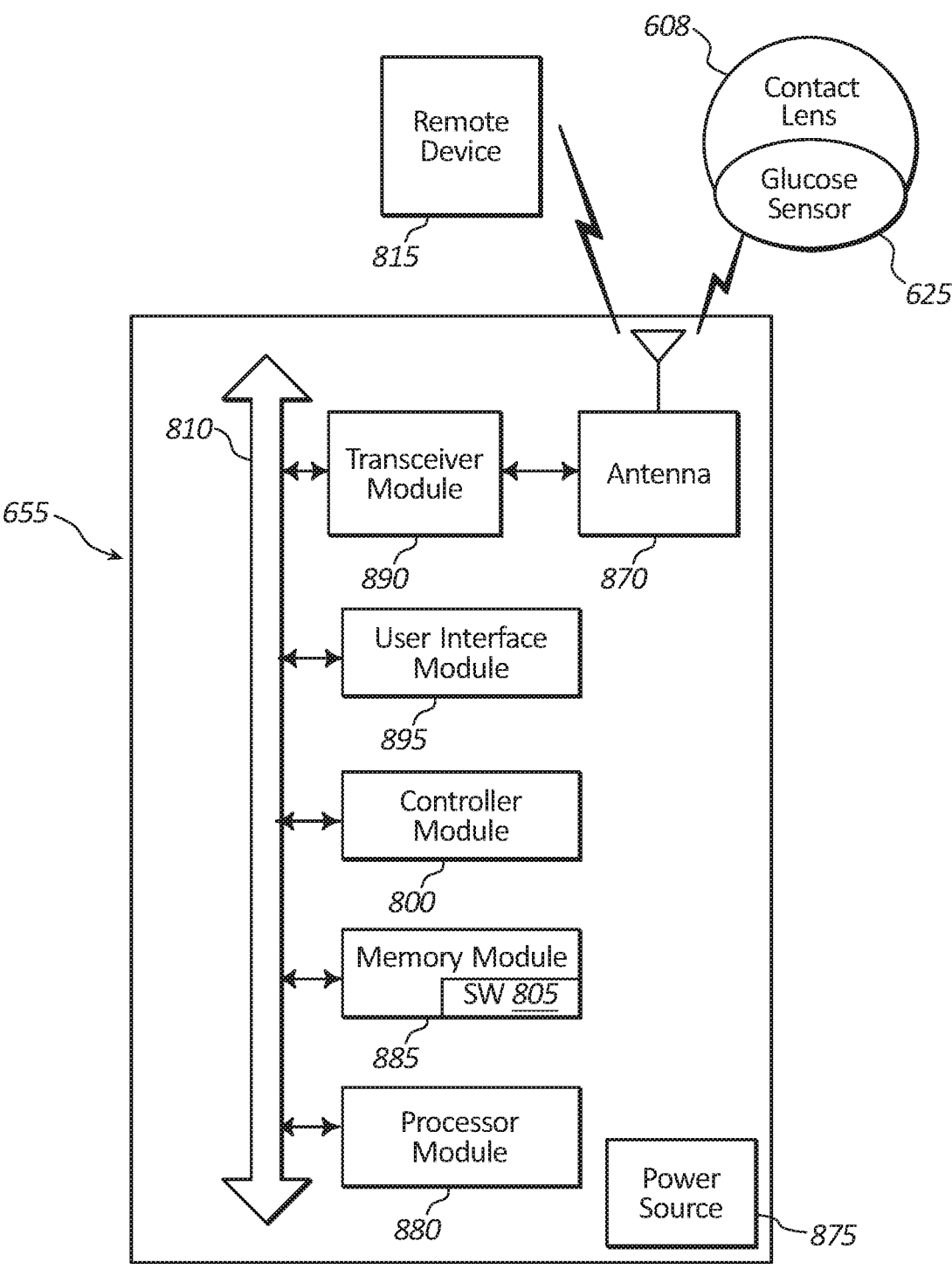
FIG. 8 illustrates a block diagram of an example wireless receiver in accordance with the present disclosure.

An embodiment of the wireless receiver 655 is shown in FIG. 8. The wireless receiver 655 can include a receiver power supply 875. The wireless receiver 655 can also include a processor module 880, and memory module 885 (including software/firmware code (SW) 805), a control module 800, a user interface module 895, a transceiver module 890, and one or more antennas 870 each of which can communicate—directly or indirectly—with one another (e.g., via one or more buses 810). The transceiver module 890 can communicate bi-directionally via the antenna 870 with the contact lens 608 (or a component on the contact lens 608). For example, the transceiver module 890 can receive data or other communication media from one or more contact lenses 608. In some embodiments, the transceiver module 890 can communicate bi-directionally with one or more contact lenses 608. In some embodiments, the transceiver module 890 can further communicate bi-directionally with a remote device 815. The remote device can include a mobile device, laptop, repeater device, or other device. The transceiver module 890 can modulate packets to send to the antennas 870 for transmission, and to demodulate packets received from the antenna 870. While the wireless receiver 655 can include a single antenna 870, the wireless receiver 655 can also have multiple antennas capable of concurrently transmitting or receiving multiple wireless transmissions.

In some embodiments, the wireless receiver 655 can be a repeater device positioned near the contact lens 608 (e.g., integrated into a pair of eyeglass frames). The repeater device can include an RFID reader, microcontroller, and transmitting antenna. Operation of the wireless receiver 655 can be controlled via a cloud server in wireless communication with a microcontroller within the wireless receiver 655. Moreover, transmission data received at the wireless receiver 655 from the contact lens 608 can be recorded on the cloud server.

The receiver power supply 875 can be operably coupled to each module within the wireless receiver 655 to provide electrical power. In some embodiments, the receiver power supply 875 can include a battery configured to accommodate mobile operation of the wireless receiver 655. In other embodiments, the receiver power supply can include a bridge circuit configured to convert a continuous supply of alternating current (i.e., AC) to direct current (i.e., DC) to power the hardware components of the wireless receiver 655. For example, the receiver power supply 875 can plug directly into an electrical outlet on the wall of a home or office.

In some embodiments, the wireless receiver 655 can connect to a remote device via a wired transmission. In some embodiments, one element of the wireless receiver 655 (e.g., antenna 870, transceiver module 890, etc.) can provide a connection using wireless techniques, including digital cellular telephone connection, Cellular Digital Packet Data (CDPD) connection, digital satellite data connection, and/or another connection. The signals associated with wireless receiver 655 can include wireless communication signals such as radio frequency, electromagnetics, local area network (LAN), wide area network (WAN), virtual private network (VPN), wireless network (using 802.11, for example), 345 MHz, Z-WAVE®, cellular network (using 3G and/or LTE, for example), and/or other signals. The one or more antennas 870 and/or transceiver module 890 can include or be related to, but are not limited to, WWAN (GSM, CDMA, and WCDMA), WLAN (including BLU-ETOOTH® and Wi-Fi), WMAN (WiMAX), antennas for mobile communications, antennas for Wireless Personal Area Network (WPAN) applications (including RFID and UWB). In some embodiments, the antenna 270 can include a plurality of antennae which can receive signals or information specific and/or exclusive to individual antennae.

The user interface module 895 can receive input from an operator (e.g., a physician) or a user of the wireless receiver 655. For example, the user or operator of the wireless receiver 655 can input periodic time intervals in which glucose data is collected, transmitted, or received. The user interface module 895 can also allow a user or operator to input or modify a minimum threshold of glucose concentration that must be reached before the user interface module 895 emits an alert. Additionally, a user or operator can input a minimum number of instances in which a glucose concentration threshold is exceeded before an alert is triggered. For example, an alert can be triggered when the threshold is met or exceeded five times within a two hour period. Similarly, a user or operator can input a time duration in which the glucose concentration is required to exceed the threshold before an alert is triggered. For example, an alert can be triggered when the measured glucose concentration exceeds a minimum threshold for at least thirty minutes.

In some embodiments, the user interface module 895 can include an audio device, such as an external speaker system, a visual display, and/or an input device. A speaker can provide an audible output when a glucose concentration has reached or exceeded a predetermined threshold. For example, once the glucose concentration reaches an unhealthy level as detected by a glucose sensor (e.g., glucose sensor 625), the wireless receiver 655 can receive a communication and can emit an audible alert to the user. In some embodiments, a visual display such as a screen or light can additionally or alternatively alert the user of a detected unhealthy glucose concentration.

One or more buses 810 can allow data communication between one or more modules of the wireless receiver 655 (e.g., processor module 880, memory module 885, control module 800, user interface module 895, etc.).

The memory module 885 can include random access memory (RAM), read only memory (ROM), flash RAM, and/or other types. The memory module 885 can store computer-readable information, computer-executable software/firmware code 805 including instructions that, when executed, cause the processor module 880 to perform various functions described in this disclosure (e.g., receiving an alert concerning glucose concentration, communicating an alert to the user, etc.). The processor module 880 can process data received by the antenna 870 and prepare data for transmission (e.g., encode, multiplex, and packetize data to be transmitted to the contact lens 608). The processor module 880 can compare data to the threshold concentration and actuate the user interface module 895 to emit an alert or alarm. The processor module 880 can also cause processed data to be stored within the memory module 885 as a time log for review by the user or a physician. The processor module 880 can make calculations based on the glucose concentration data (e.g., averages, medians, trends, etc.). The processor module 880 can process commands input into the user interface module 895 by a user.

The control module 800 can be configured to control operational aspects of the contact lens system. In some embodiments, the control module 800 can control the intervals in which glucose concentration data is collected and transmitted by the contact lens 608. The control module 800 can also control the interval in which transmissions from the contact lens 608 are received by the wireless receiver 655. In other embodiments, the control module 800 can control which types of data the contact lens is collecting (e.g., glucose concentration, illuminance, irradiance, light absorption, scattering of light, reflection of light, fluorescence, phosphorescence, luminescence, etc.). The control module 800 can also actuate or otherwise implement user or operator input received through the user interface module 895.

Figure 9:
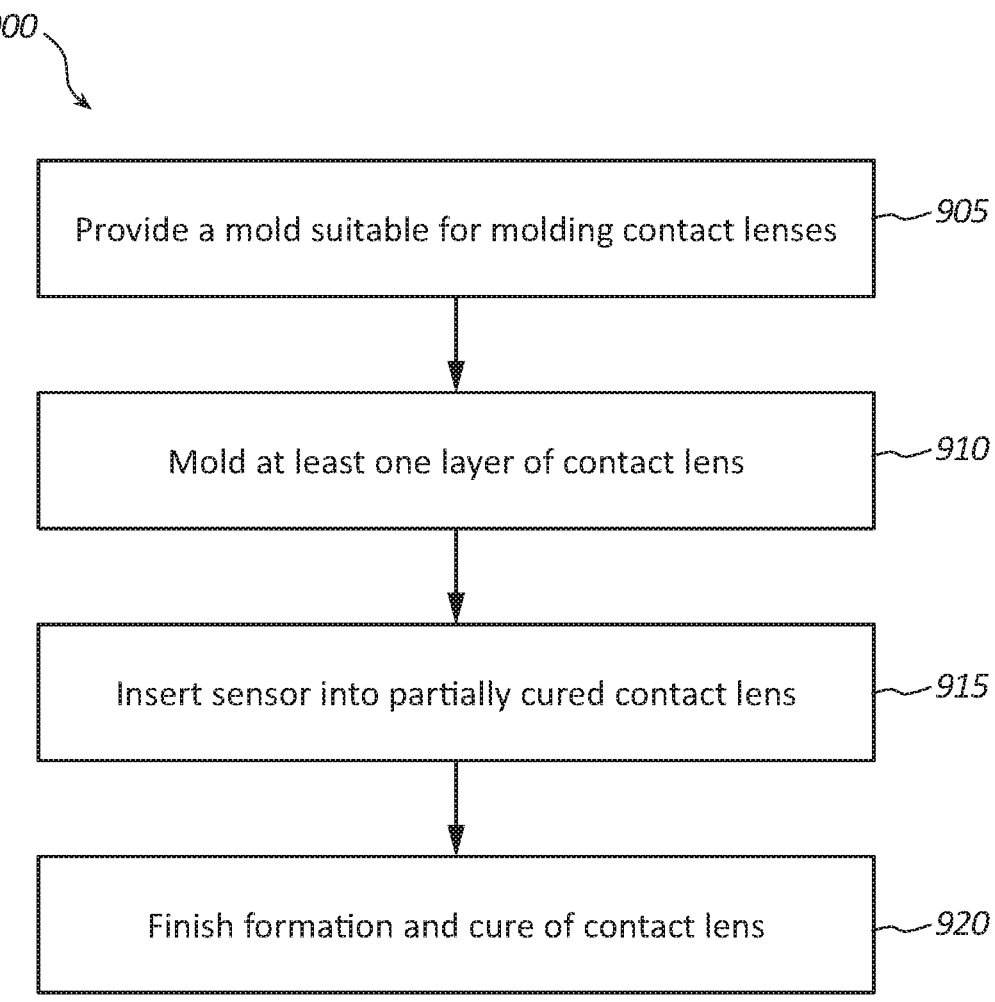
FIG. 9 illustrates a block diagram of an example of a method of using a glucose sensor in accordance with the present disclosure.

FIG. 9 illustrates an example of a method 900 of making a contact lens. In this example, the method 900 includes providing a mold suitable for molding contact lenses 905, molding various layers of the contact lens 910, inserting the sensor structure into the contact lens 915, and finish the formation and cure of the contact lens 920.

At block 905, a master mold is generated. The master mold has the profile of the ultimate contact lens being formed. The mold can include a low surface material such as PTFE. This can prevent adhesion to the mold. The mold can alternatively include other materials and then be coated with PTFE or other suitable low surface energy material. In some examples, the mold can include a metallic or ceramic material, or composites thereof. More particularly, the mold that is generated can be a female mold for cast molding, or, in the present example, the mold can be a mold configured for use in spin casting a contact lens. According to this exemplary embodiment, the surface of the spin casting mold includes the shape and features to be formed on the front surface of the ultimately formed contact lens.

At block 910, multiple layer of the contact lens can be formed. In the example where the lens is a spin casted lens, monomer can be deposited into the mold, and the mold can be rotated to distribute the monomer, while the monomer is partially cured, or cured to a gel state.

At block 915, the sensor is inserted into the body of the contact lens. According to one exemplary embodiment, the sensor can be pre-formed and inserted into the mold prior to the insertion and partial curing of the monomer, as described at block 910.

In an alternative embodiment, the sensor can be formed in a separate mold and inserted into the partially cured contact lens described in block 910. According to this exemplary embodiment, the sensor is formed in a mold mimicking the ultimate contact lens mold. The mimicking mold is coated with different layers of the sensor structure. For example the mold can be coated via printing, dipping, or spin coating the layers onto the mold. Upon completion, the sensor structure is formed atop the mold. In one example, the sensor structure is removed from the mold. For example, the sensor structure can be lifted from the mold using a separate tool that attaches to the sensor structure. The tool can include or include a tacky surface. For example, the tool can include a Sylgard® silicone gel or any other material suitable for use in removing structure from a mold. Once removed, the sensor structure can be pressed into the partially cured contact lens. For example, the sensor structure can be a separate entity and can be pressed against the partially cured contact lens for few seconds for a bond to form between the contact lens and the sensor structure. The bond can include polydimethylsiloxane (PDMS) and hydrogel or silicone hydrogel. If the sensor structure includes a first layer with PDMS, the PDMS layer can be tailored with alginate to enhance a bond between the sensor structure with PDMS and the hydrogel or silicone hydrogel.

Once the bond is formed, the formation and cure of the contact lens can be completed 520. According to one embodiment, additional monomer can be deposited in the mold encapsulating the sensor. For example the sensor structure can be coated with hydrogel, silicone hydrogel, or other suitable materials, or combinations thereof. The coating can surround and encapsulate the sensor structure onto the contact lens.

Figure 10:
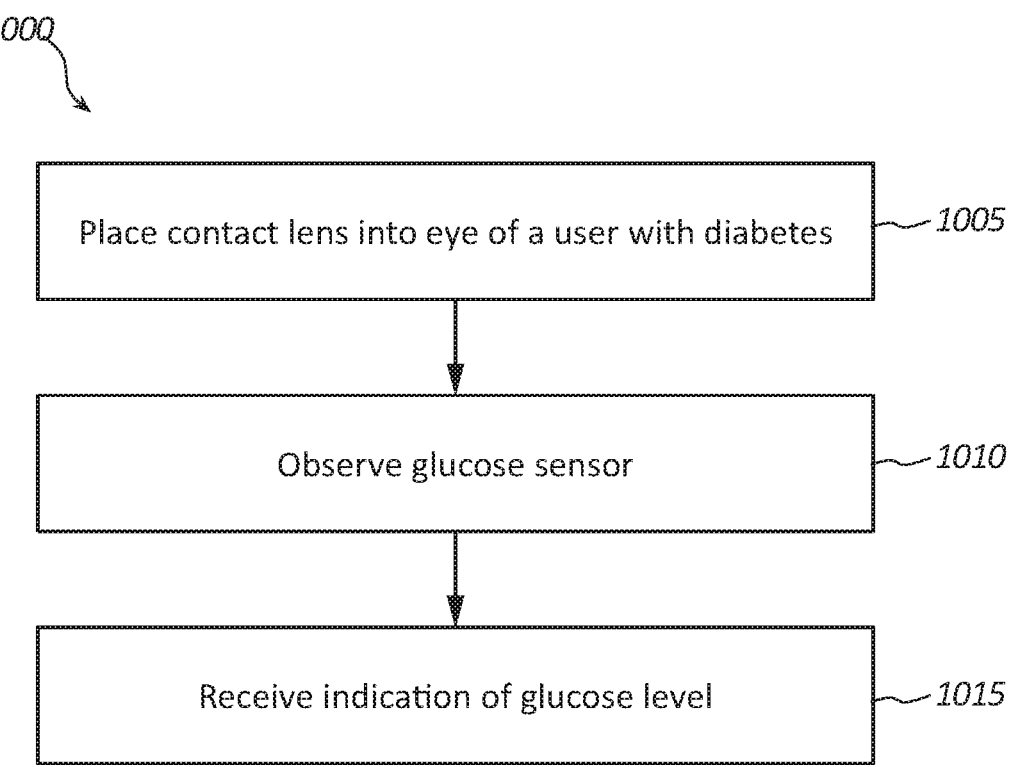
FIG. 10 illustrates a block diagram of an example of a method of using a glucose sensor in accordance with the present disclosure.

FIG. 10 illustrates an example of a method 1000 of using a contact lens. In this example, the method 1000 includes placing a contact lens onto an eye of a user with diabetes 1005, observing the glucose sensor 1010, and receiving an indication of a glucose level of the user 1015.

At block 1005, the contact lens is placed in the eye of a user. The use of the sensor can be most effective if the user has a confirmed example of diabetes or signs indicative of someone with diabetes. At block 1010, the glucose sensor is observed. The user can observe their own glucose sensor via a mirror, or picture (e.g. a selfie or other self-photograph, reflection, or other method of viewing one-self). At block 1015, the method 1000 can include receiving an indication of a glucose level. In some embodiments, the indication can include a change in the glucose sensor from the first state to the second state. For example, the glucose sensor can have a nonvisible first state which can transition to a visible second state. The transition between the first state and second state can indicate to the user or a third party that the glucose concentration has reached an unhealthy level. In other embodiments, a third party can view the glucose sensor and notify the user. In another embodiment, the glucose sensor can be a sensor and can automatically detect a level of glucose in the user's system. The glucose sensor can communicate to a remote device. The remote device can communicate an alert to user relating to the user's glucose concentration. In some embodiments, a lack of communication from the glucose sensor can indicate an acceptable glucose level in the user's system. Once the sensor structure begins to communicate with remote sensor, the user can be alerted to an unhealthy glucose concentration level in their system. In some embodiments, the user can also request the status of glucose concentration from the remote device.

Figure 11:
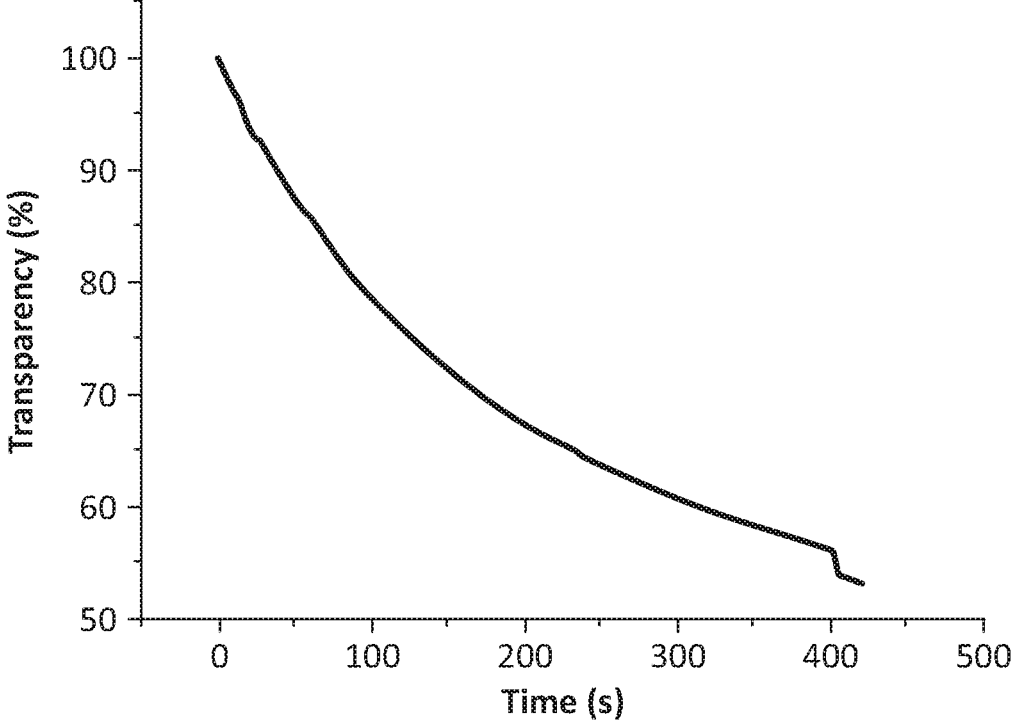
FIG. 11 illustrates a graphical representation of the transparency of a glucose sensor exposed to a concentration of glucose over a period of time, according to one embodiment.

In order to further clarify the specifics of the present disclosure, one embodiment of the present disclosure will be described in detail in reference to FIG. 11. A polymer glucose sensor was prepared utilizing ultra-violet initiated free radical reaction. The polymer glucose sensor was created by combining acrylamidophenyl boronic acid, ethylene acrylate and acrylic acid in a dimethyl sulfoxide solvent. Methylenebisacrylamidewas used as a cross-linker and 2,2-dimethoxy-2-phenylacetophenon was used as an initiator. The combination was then placed into a mold and underwent ultra-violet irradiation.

The polymer glucose sensor was submerged in a phosphate buffer solution (pH=7.4) containing 1M of D-glucose. The polymer glucose sensor was then positioned between a light source and a digital ambient light sensor (e.g., OPT3001 from Texas Instruments). The transparency of the polymer glucose sensor was then measured over a time interval of 420 seconds to create the graph depicted in FIG. 11. As shown in FIG. 11, the transparency of the polymer glucose sensor decreased by nearly 50% as the polymer glucose sensor remained submerged in the solution. This differential in transparency of the polymer glucose sensor can be utilized to visually or digitally communicate a concentration of glucose within the tear fluid of a contact lens wearer.

It should be noted that any of the features in the various examples and embodiments provided herein can be interchangeable and/or replaceable with any other example or embodiment. As such, the discussion of any component or element with respect to a particular example or embodiment is meant as illustrative only. In addition, it should be noted that the methods described above describe possible implementations, and that the operations and the steps can be rearranged or otherwise modified and that other implementations are possible. Furthermore, aspects from two or more of the methods can be combined.

Second Embodiment

The disclosures presented herein also describe various apparatuses, systems and methods for determining an intraocular pressure of an eye using a contact lens (e.g., one embodiment of a smart contact lens 115) worn on the eye, as described in U.S. application Ser. Nos. 62/642,913 and 62/642,926, both filed 14 Mar. 2018, the disclosure of which are incorporated herein, in its entirety, by this reference. As shall be described in greater detail in the embodiments disclosed herein, these apparatuses, systems, and methods can use a contact lens and a sensor utilizing at least one of a capacitance measurement, a deflection measurement, or a magnetic field measurement. These measurements can be correlated to at least one of an absolute intraocular pressure of the eye or a relative intraocular pressure of the eye.

For example, in some embodiments, the principles described herein include incorporating a variable capacitance sensor into a contact lens which can be worn on a user's eye. While the contact lens is worn on the user's eye, the relative intraocular pressure of the eye can be wirelessly measured and monitored by detecting changes in the mechanical strain of the contact lens via the variable capacitance sensor.

In some examples, the variable capacitance sensor can include one or more layers of transparent material and can be disposed on an outer surface of the contact lens. For example, the variable capacitance sensor can include a first conductive layer, a second conductive layer, and a dielectric layer disposed between the first and second conductive layers. One or more of the conductive layers can include a polymer, a metal, a microcomposite material, a nanocomposite material, any appropriate material, or combinations thereof. For example, the conductive layers can be transparent polymer layers and can include, for example, poly (3,4-ethylenedioxythiophene) polystyrene sulfonate. The dielectric layer can be a transparent polymer layer and can include, for example, polydimethylsiloxane. In some examples, one or more of these layers can be deposited on the contact lens by a number of deposition process, for example cast molding, printing, or spin coating. In some examples the layers can be deposited on a mold and can then be stamped onto the contact lens. In some examples, a diffusion or migration barrier is included between one or more layers to avoid material contamination between the layers. For example, a diffusion or migration barrier can be included between a conductive layer and dielectric layer to prevent the diffusion or migration of materials therebetween.

In some embodiments the variable capacitance sensor including first and second conductive layers with a dielectric layer disposed there between can function as a capacitor. For example, the variable capacitance sensor can be a parallel plate capacitor, with the first and second conductive layers serving as parallel plates. In this example the capacitance of the variable capacitance sensor is related to the separation distance between the first and second conductive layers, or, in other words, the thickness of the dielectric layer disposed there between. In some examples, as the contact lens, and variable capacitance sensor disposed thereon, is bent or stretched due to, for example, the expansion or retraction of an eye from changes in intraocular pressure, the dielectric layer can experience a corresponding change in thickness. This change in thickness, for example due to stretching of the dielectric material, can thereby result in a change in the capacitance of the capacitor including the variable capacitance sensor.

The variable capacitance sensor can further include an antenna structure. In some examples the antenna structure can be incorporated into the topmost conductive layer of the capacitor including the variable capacitance sensor. In some examples the antenna structure can be the topmost conductive layer of the capacitor including the variable capacitance sensor. Thus, in some examples, the variable capacitance sensor can be an electrical oscillator formed by the capacitor, the antenna, which has a constant inductance, and the natural resistance of the variable capacitance sensor. In some examples this electrical oscillator can have a natural frequency which is dependent on, or corresponds to the mechanical strain of the variable capacitance sensor. Thus, in some examples where the variable capacitance sensor is disposed on the contact lens, the mechanical strain of the contact lens, or how much the contact has been stretched by the eye, can be measured by detecting the natural frequency of the electrical oscillator including the variable capacitance sensor. In some examples, the contact lens and/or variable capacitance sensor can further include a temperature sensor. In some embodiments, data from the temperature sensor can be used to mathematically compensate for the natural thermal expansion of materials in the contact lens in order to obtain a more accurate reading.

In some examples, the natural frequency of the variable capacitance sensor can be wirelessly detected by an electronic device. For example, an electronic device can send a signal having a signal frequency to the contact lens such that the contact lens sends a response signal when the signal frequency matches the natural frequency of the electrical oscillator including the variable capacitance sensor. In this way, the mechanical strain of the contact lens, and thus relative intraocular pressure of the eye, can be wirelessly measured. Further, the contact lens may not include a battery or integrated circuit, thereby simplifying manufacturing and reducing costs. In some examples, the electronic device can has a wireless remote powering system and can use a far field electromagnetic coupling method to transmit power to the contact lens. In some examples, the electronic device can have a wireless remote powering system and can use an inductive coupling, or near field, method to transmit power to the contact lens. In some examples, communication between the contact lens and electronic device can occur via a half-duplex or full duplex scheme. That is, in some examples both power and data can be wirelessly transmitted between the contact lens and an electronic device via a single wireless connection. However, in some examples power can be transmitted by one method or connection and data can be transmitted by a second method or connection.

Additional principles described herein include incorporating a tonometer system including a test body into a contact lens that can be worn on a user's eye and utilizes a deflection measurement to determine at least one of an absolute or a relative intraocular eye pressure. In some embodiments, while the contact lens is worn on the user's eye a tonometer system can wirelessly measure the absolute intraocular pressure of the eye by measuring the rebound of the test body on the eye surface. In some examples, the rate of deceleration of the test body caused by the physical properties of the eye is detected and used to calculate the absolute intraocular pressure of the eye. In some examples, the rate of return of the eye and/or lens from an expanded state to a non-expanded state is measured and used to calculate the absolute intraocular pressure of the eye. The rate of deceleration of the test body and/or the rate of return of the contact lens or eye can be measured by a sensor which is situated on or incorporated into the contact lens and which can wirelessly transmit the relevant data to a secondary device, such as an electronic device. In some examples, the tonometer system can include the sensor. In some examples this sensor can be a variable capacitance sensor, and can measure the mechanical strain of the contact lens while on the eye.

In some examples, the contact lens can comprise lens material and a test body in contact with the lens material. The test body can be disposed on a surface of the lens material, or it can be incorporated into the lens material. In some embodiments, the test body can be positioned outside of the optic zone of the contact lens that is configured to correct the user's vision. In this type of example, the test body may not interfere with or obstruct a user's vision while wearing the contact lens. In some examples, a tonometer system can include a test body to exert force on the eye. In some examples, the test body can be a selectively expandable material which can exert a force on the eye when the expandable material is in an expanded state. That is, the expandable material can expand under certain conditions and can return to an initial state when those conditions are stopped or removed. For example, in some examples the selectively expandable material can be a magnetoresponsive elastomer. The magnetoresponsive elastomer material can expand in the presence of a magnetic field, and can return to an initial state when the magnetic field is removed.

In certain embodiments, the contact lens can further include a sensor, for example as a component of the tonometer system that can detect certain characteristics of the test body and/or contact lens to determine the absolute intraocular pressure of the eye. For example, the contact lens can include a sensor that can measure the amount of time it takes for the test body to return from an expanded state to the initial state. In some examples, the contact lens can include a sensor that can measure the deceleration of the test body caused by the eye as it enters the expanded state. The sensor can wirelessly communicate this information to a secondary device, such as an electronic device, which can manage sensor data in real time and calculate the absolute intraocular pressure of the eye, a relatively pressure of the eye, another parameter of the eye, or combinations thereof. In some examples, the sensor can be a transparent variable capacitance sensor that is capable of measuring the mechanical strain of the contact lens on the eye by correlating its changes in capacitance when the expandable material is expanded verses when the expandable material is in the initial state. As used herein, the term "absolute intraocular pressure" can refer to the total fluid pressure inside an eye, whereas the term "relative intraocular pressure" can refer to an amount of deviation or fluctuation from a baseline intraocular pressure value.

A contact lens including a test body can be manufactured by a variety of methods, including spin coating, dip coating, printing, stamping, or some combination thereof. In certain embodiments contact lens material can be provided and the test body can be deposited or formed on the lens material in a layer-by-layer deposition process. Thus, the test body can comprise one or more polymer layers which are deposited or formed on the lens material by printing, spin coating, and/or dip coating. However, in some other embodiments the contact lens can be manufactured by a stamping process, and the test body is deposited or formed on a mold, attached to a stamp or tool, and then deposited on the contact lens material. The stamping process can greatly reduce the processing or manufacturing time for the contact lens because the test body can be deposited or formed separately from the lens material, allowing for parallel processing lines. Once both the lens material and test body have been formed, they can be joined by stamping. In some examples, the contact lens body is formed through a spin casting process, and at least a portion of the circuitry for measuring the eye's intraocular pressure is manufactured separately and joined to the spin casted contact lens body.

In still other examples, additional principles described herein include incorporating a micromagnet or a micromagnet array as a test body into a contact lens that can be worn on a user's eye. These or other examples use a magnetic field measurement of the micromagnet or the micromagnet array to determine at least one of an absolute or a relative intraocular eye pressure. Similar to other embodiments, the contact lens can comprise lens material and a micromagnet test body in contact with the lens material. The micromagnet test body can be disposed on a surface of the lens material, or it can be incorporated into the lens material. In some embodiments, the micromagnet test body can be positioned outside of the optic zone of the contact lens that is configured to correct the user's vision. In this type of example, the micromagnet test body may not interfere with or obstruct a user's vision while wearing the contact lens. A gradiometer can be used to measure a measurement of the magnetic field around micromagnet test body, and correlate that measurement to at least one of an absolute or an intraocular eye pressure.

Figure 12A:
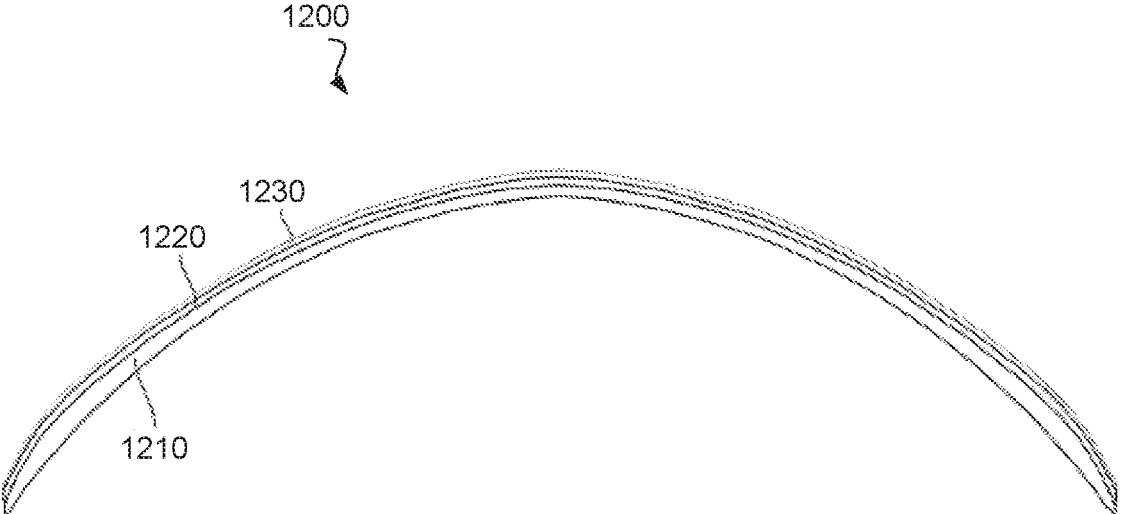
FIG. 12A is a cross sectional view of an example contact lens incorporating a variable capacitance sensor in accordance with the present disclosure.

FIG. 12A depicts an example of a contact lens 1200 including a lens material 1210 and a sensor 1220 disposed thereon. In some embodiments, the sensor can include a variable capacitance sensor 1220. The lens material 1210 can include any material suitable for use as a contact lens as is now know or can be developed in the future. That is, in some examples, the lens material 1210 can include a typical hydrogel contact lens as is known in the art. For example, in some embodiments the lens material 1210 can include a transparent polymer material, such as a hydrogel. In some examples the lens material 1210 can include a silicone hydrogel material. The contact lens material 1210 can include an optic area or zone positioned at the center of the contact lens 1200. The optic zone is typically about the same size as the pupil of the eye in low-light conditions, for example the optic zone can have a diameter of about 10 millimeters. The optic zone contains the corrective power of the contact lens 1200, if any corrective power is present.

Further, the contact lens 1200 can include an encapsulation layer 1230 disposed over the variable capacitance sensor 1220. The variable capacitance sensor 1220 and the encapsulation layer 1230 can have a combined thickness of between approximately 20 micrometers and approximately 50 micrometers, such as between approximately 20 micrometers and approximately 30 micrometers, between approximately 30 micrometers and approximately 40 micrometers, between approximately 40 micrometers and approximately 50 micrometers, less than approximately 50 micrometers, less than approximately 45 micrometers, less than approximately 40 micrometers, less than approximately 35 micrometers, less than approximately 30 micrometers, or less than less than approximately 25 micrometers.

In some embodiments and as shown in FIG. 1B, the variable capacitance sensor 1220 can contain at least a layer of conductive material 1224, also referred to as conductive layer 1224, and a layer of dielectric material 1226, also referred to as dielectric layer 1226, overlying the layer of conductive material 1224. In some examples the layer of dielectric material 1226 can be disposed directly on the layer of conductive material 1226. In some examples the variable capacitance sensor 1220 can include a first conductive layer 1224, a dielectric layer 1226 overlying the first conductive layer 1224, and a second conductive layer 1228 overlying the dielectric layer 1226. The second conductive layer 1228 can be disposed directly on the dielectric layer 1226.

The conductive layer or layers 1224, 1228 and the dielectric layer 1226 can cover or be disposed over a substantially similar area of the underlying lens material 1210. That is, the conductive layer or layers 1224, 1228 and the dielectric layer 1226 can have a substantially identical shape and/or border when viewed from above. In some examples the conductive layer or layers 1224, 1228 and the dielectric layer 1226 can have an approximately circular, elliptical, or ovular shape on the lens material 1210. However, in some other examples, the conductive layer or layers 1224, 1228 and the dielectric layer 1226 can include any shape and/or boundary as is suitable for use in the variable capacitance sensor 1220 as described herein, for example a conductive layer 1224, 1228 can have a half-moon shape. In some examples, a single conductive layers, for example conductive layer 1224 or 1228 can include two half-moon shapes separated from one another. The conductive and/or dielectric layers can be substantially continuous layers. In some examples the conductive and/or dielectric layers may not be substantially continuous and can include one or more separate areas of the same layer.

In some examples, the conductive material including the layer or layers of conductive material 1224, 1228, can be a transparent polymer material. The conductive material can include a polymer mixture of two or more ionomers. In some examples the conductive material can include a polymer or polymer mixture having aromatic cycles and/or double bonds. In some examples the conductive material can include a polymer or polymer mixture including nitrogen and/or sulfur. In some examples the conductive material can include a macromolecular salt. For example, in some embodiments the conductive material can include poly (3,4-ethylenedioxythiophene) polystyrene sulfonate (PEDOT:

PSS). In some examples the conductive material can include one or more additives, such as polyethylene glycol (PEG), for example to control or adjust the viscosity of the conductive material during processing.

In some other embodiments the conductive material can include a gel, such a hydrogel mixed with a suitable salt. For example, the conductive material can include a silicone hydrogel mixed with a salt to thereby form an ionic conductor. In some examples the salt can be sodium chloride (NaCl). In some examples where the conductive material include a hydrogel mixed with a salt the layer or layers forming the conductive material can advantageously have substantially the same or similar mechanical properties as the underlying lens material 1210.

In some examples the dielectric material including the dielectric layer 1226 can include a transparent polymer material. The dielectric material can be an elastomer. In some examples the dielectric material can include any transparent elastomer having a lower electrical and/or ionic conductivity than the conductive material. For example, in some examples the dielectric material can include polydimethylsiloxane (PDMS).

As used herein, the term 'conductive' refers to the ability of the layer or material to act as an electrical and/or ionic conductor while the term 'dielectric' refers to the ability of the layer or material to act as an electrical or ionic insulator. When used herein in conjunction with one another, the terms 'conductive' or 'conducting' refers to the fact that the 'conductive' material has a higher electrical and/or ionic conductivity than the 'dielectric' material.

In some embodiments the variable capacitance sensor 1220 can further include an additional layer of dielectric material 1222 disposed below the first conductive layer 1224. Thus, in some embodiments the first conductive layer 1224 of the variable capacitance sensor 1220 can be disposed directly on the lens material 1210, for example on the outer surface of the lens material 1210, however in some other embodiments the variable capacitance sensor 1220 can include a lower dielectric layer 1222 that is disposed directly on the lens material 1210. In some examples this lower dielectric layer 1222 can function as a substrate layer during manufacturing of the variable capacitance sensor 1220 as further described herein.

In some examples where the variable capacitance sensor 1220 can include two or more conductive layers 1224, 1228, each conductive layer can include the same conductive material, or each layer can include a different conductive material from any other conductive layer. Similarly, in examples where the variable capacitance sensor 1220 can include two or more dielectric layers 1222, 1226, each dielectric layer can include the same dielectric material, or each layer can include a different dielectric material from any other dielectric layer.

In some examples the contact lens 1200 can further include an encapsulation layer 1230 disposed over the variable capacitance sensor 1220. The encapsulation layer 1230 can be in direct contact with the variable capacitance sensor 1220. In some examples the encapsulation layer 1230 can include a polymer material, such as a hydrogel. In some examples the lens material 1210 can include a silicone hydrogel material and can be the same material as the lens material 1210. The encapsulation layer 1230 can have a thickness of from about 0.1 micrometers to about 20 micrometers, from about 0.5 micrometers to about 15 micrometers, or from about 1 micrometers to about 10 micrometers.

The variable capacitance sensor 1220 can have a thickness on the lens material 1210 of from about 10 micrometers to about 100 micrometers, or from about 20 micrometers to about 50 micrometers. It has been advantageously found that when the variable capacitance sensor 1220 has a thickness of less than about 100 micrometers, specifically less than about 50 micrometers, the variable capacitance sensor 1220 is able to function well in detecting the relative intraocular pressure of an eye, while the contact lens 1200 including the variable capacitance sensor 1220 perform in a substantially identical way with respect to user comfort and visions correction to a typical contact lens that does not include a sensor. In some examples the one or more conductive layers which include the variable capacitance sensor 1220 can each have a thickness of from about 0.1 micrometers to about 20 micrometers, from about 0.5 micrometers to about 15 micrometers, or from about 1 micrometer to about 10 micrometers. Similarly, the one or more dielectric layers 1222, 1226 which can include the variable capacitance sensor 1220, can have a thickness of from about 0.1 micrometers to about 20 micrometers, from about 0.5 micrometers to about 15 micrometers, or from about 1 micrometer to about 10 micrometers.

Figure 12B:
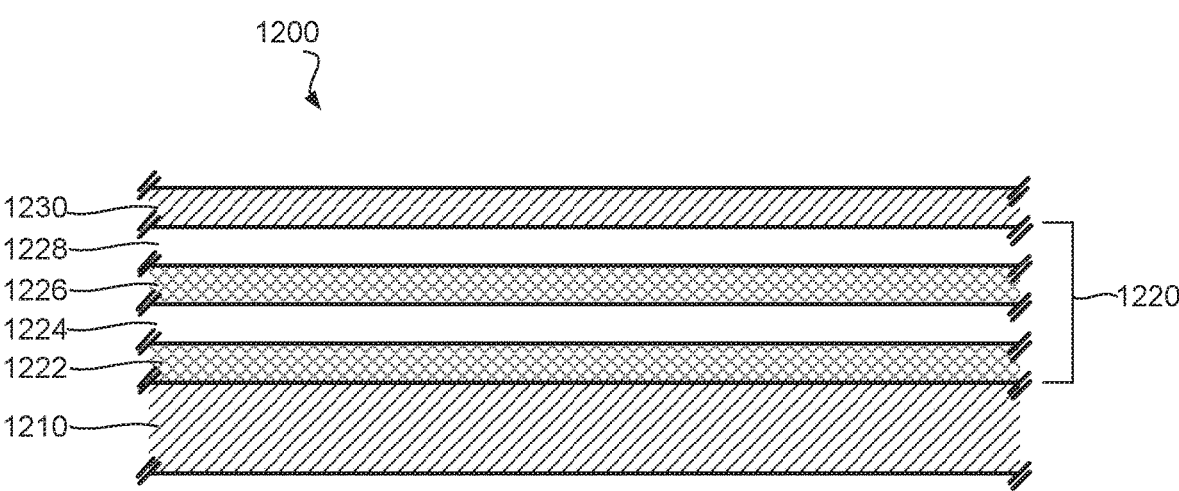
FIG. 12B is a cross sectional view of a central portion of an example contact lens incorporating a variable capacitance sensor in accordance with the present disclosure.
Figure 12C:
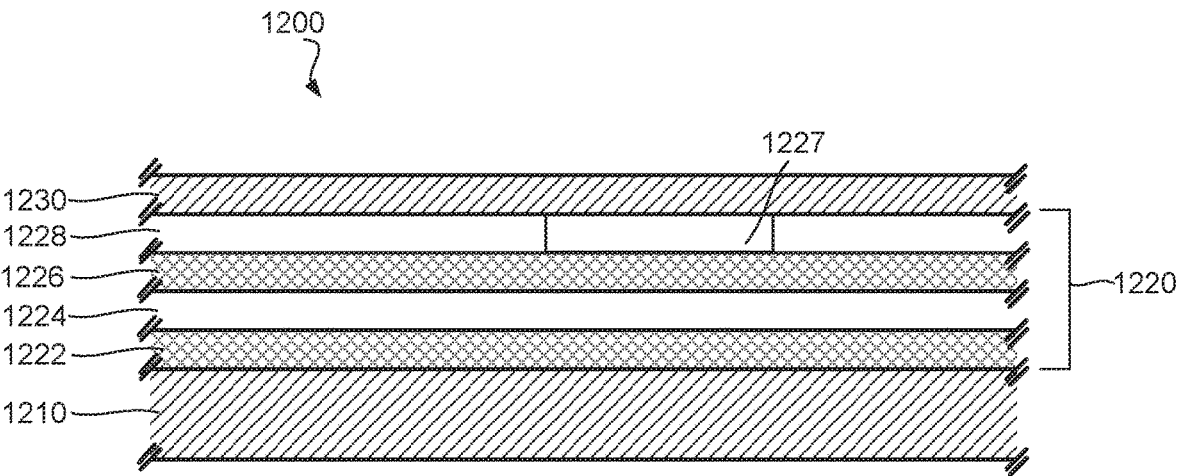
FIG. 12C is a cross section view of a central portion of an example contact lens incorporating a variable capacitance sensor and a micromagnet in accordance with the present disclosure.

Turning to FIG. 12C, in some embodiments, the contact lens 1200 also can include a micromagnet 1227. The micromagnet 1227 can be positioned between the lens material and the encapsulation layer 1230. According to some embodiments, the micromagnet 1227 described herein are positioned on the contact lens material 1210 outside of the optic zone. In some examples, the micromagnet 1227 can be positioned substantially adjacent to the optic zone, however in some other examples the micromagnet 1227 can be positioned near an edge of the lens material 1210, or any position therebetween.

In an example, the micromagnet 1227 is positioned between the encapsulation layer 1230 and the one or more dielectric layers 1222, 1226. For example, the micromagnet 1227 can be positioned between the dielectric layer 1226 and the encapsulation layer 1230. In another example, the micromagnet 1227 can be positioned between the conductive layer 1228 and the encapsulation layer 1230. In some embodiments, the micromagnet 1227 can be positioned on or embedded at least partially within at least one of the one or more dielectric layers 1222, 1226 or the one or more conductive layers 1228, 1224. For example, the micromagnet 1227 can be positioned on or embedded at least partially within the conductive layer 1228 or the dielectric layer 1226.

The micromagnet 1227 is actuated by a magnetic actuator positioned outside the eye. The magnetic actuator is configured to bias or otherwise push the micromagnet 1227 towards the eye to perform at least one of applanation or indentation of the eye. The micromagnet 1227 can include a rare earth magnet, such as a sintered samarium cobalt magnet or neodymium iron boron. In some embodiments, the micromagnet 1227 can include a coating to modify reflectance and enable time-of-flight proximity sensing. In some embodiments, the micromagnet 1227 can include a single magnet, such as a ferromagnetic disc. A single micromagnet disc can be molded into the contact lens 1200 and magnetized to a desired direction after polymerization of the contact lens 1200. Alternatively, a single micromagnet disc can be magnetized prior to the polymerization of the contact lens using an additional previously magnetized disc.

In some embodiments, the micromagnet 1227 can include a micromagnet array. The micromagnet array can be transparent, while the rigidity and the flexibility of the micromagnet are variable depending upon the particle granulometry and array density. The micromagnet 1227 also can include multiple layers of micromagnet arrays that are fabricated to transfer wireless power from the magnetic source to the contact lens 1200. The micromagnet array can be integrated into the contact lens 1200 during molding of the contact lens 1200.

Figure 13:
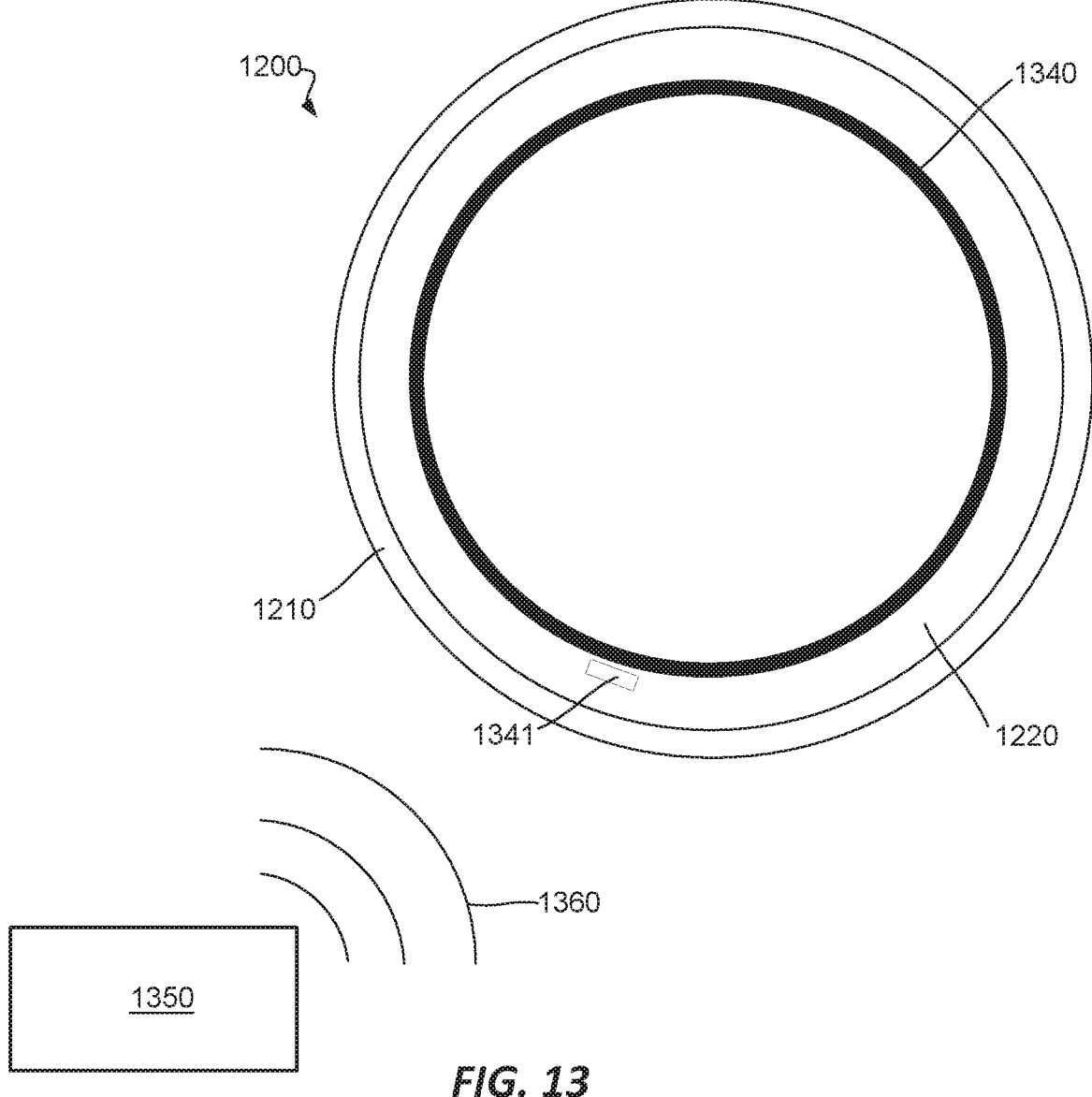
FIG. 13 is a top view of an example contact lens system including a contact lens incorporating a variable capacitance sensor and an antenna, and an electronic device in accordance with the present disclosure.

During applanation or indentation, as the magnetic actuator pushes the micromagnet 1227 towards the eye, the layers of the variable capacitance sensor 1220 will be mechanically compressed, thus changing the distance between the dielectric layers 1222, 1226 and the capacitance of the contact lens 1200. As illustrated in FIG. 13, in some examples the variable capacitance sensor 1220 also can include an application specific integrated circuit (ASIC) 1341. The ASIC 1341 is configured to measure the capacitance in the variable capacitance sensor 1220 before, during, and after applanation or indentation is performed using the magnetic actuator and the micromagnet 1227.

As described herein and illustrated in FIG. 13, in some examples the variable capacitance sensor 1220 can include an antenna structure 1340. The antenna structure 1340 can include a loop or coil structure as is well known in the art, however other antenna designs are expressly contemplated herein. For example, any antenna design capable of functioning as described herein and which can be incorporated into the variable capacitance sensor 1220 as described herein can be utilized as will be understood by the skilled artisan. In some examples the antenna structure 1340 can include conductive lines which include, for example, the coil or loop structure as shown. The conductive lines can include the conductive material used to form the conductive layers 1224, 1228 described herein and can have a line width of from about 25 micrometers to about 200 micrometers, or from about 50 micrometers to about 100 micrometers. Where the variable capacitance sensor 1220 includes a capacitor, the antenna structure 1340 can be electrically connected to each side of the capacitor to thereby form an electrical circuit. For example, where the variable capacitance sensor 1220 includes a parallel plate capacitor including two conductive layers 1224, 1228, the antenna structure 1340 can be electrically connected to each of the conductive layers 1224, 1228 to thereby form an electrical circuit.

In some examples, the antenna structure 1340 can be formed on the upper conductive layer 1228, for example, by printing conductive material in the form of the antenna structure 1340. In some examples the antenna structure 1340 can be formed by inkjet printing conductive material on the upper conductive layer 1228. The antenna structure 1340 can also be formed by a stencil process wherein conductive material is painted or applied into a stencil including the desired antenna structure 1340 which is disposed over the conductive layer 1228. Other methods of forming the antenna structure 1340 can be utilized as are known in the art or can be developed in the future. The antenna structure can have a thickness of from about 0.1 micrometers to about 20 micrometers, from about 0.5 micrometers to about 15 micrometers, or from about 1 micrometers to about 10 micrometers. In some examples the antenna structure 1340 can thus be incorporated into, or become a part of the upper conductive layer 1228 after it has been deposited or formed. However, in some other examples an additional layer including dielectric material (not shown) can be deposited or formed over the upper conductive layer 1228 and the antenna structure 1340 can be formed on this additional dielectric layer, for example by printing or a stencil process.

As described herein, in some examples the variable capacitance sensor 1220 can include a capacitor having two parallel conductive layers 1224, 1228 with a dielectric layer 1226 disposed there between. In these examples where the conductive layers 1224, 1228 act as the plates in a parallel plate capacitor, the capacitance (C) of the capacitor can be given by the equation:

$$C = \frac{e_0 e_r A}{d} \qquad \text{Equation 1}$$

Where $e_0$ is the permittivity of free space, a constant, $e_r$ is the relative permittivity of the dielectric layer 1226, A is the effective surface area of the plates of the capacitor, that is, conductive layers 1224, 1228, and d is the thickness of the dielectric layer 1226. When the contact lens 1200 is subjected to a mechanical strain, for example during relative changes in intraocular pressure while the lens 1200 is on the eye, the lens 1200 will expand or contract with the eye. This expansion or contraction will cause changes in the area of the conductive layers 1224, 1228(A) and in the thickness of the dielectric layer 1226(d), and thus will cause corresponding changes in the capacitance (C). For example, an increase in intraocular pressure will cause the eye and lens 1200 to expand, thereby causing an increase in the area of the conductive layers 1224, 1228(A) and a decrease in the thickness of the dielectric layer 1226(d). Similarly, a decrease in intraocular pressure will cause the eye and lens 1200 to contract, thereby causing a decrease in the area of the conductive layers 1224, 1228(A) and an increase in the thickness of the dielectric layer 1226(d). The corresponding changes to the capacitance (C) can ultimately be detected as described herein in order to determine the relative intraocular pressure of the eye.

However, rather than continuously measuring the area of thickness of the layers forming the capacitor, it was found that when a uniaxial force stretches the capacitor with a factor (A), as occurs during changes in intraocular pressure of the eye, the capacitance (C) scales as:

$$C = C_0 \lambda^4 \qquad \text{Equation 2}$$

Where $C_0$ is the original capacitance of the capacitor in an initial state. For example, the initial state can be an unstretched state, where the lens does not experience tensile forces. In some examples the initial state can be such that some tensile forces are exerted across at least a portion of the lens, for example when the lens is on an eye. By knowing the original capacitance ($C_0$) and measuring the capacitance (C) this scaling factor ($\lambda$) can be determined and, for example, transmitted to an external reader device in order to determine the relative intraocular pressure of the eye. This is possible because the scaling factor ($\lambda$) is proportional to the mechanical strain on the contact lens 1200 which is proportional to the intraocular pressure of the eye. In some examples, the scaling factor ($\lambda$) can be linearly related to the mechanical strain on the contact lens 1200, however in other examples the scaling factor ($\lambda$) can have a non-linear relationship with the mechanical strain on the contact lens.

Figure 14A:
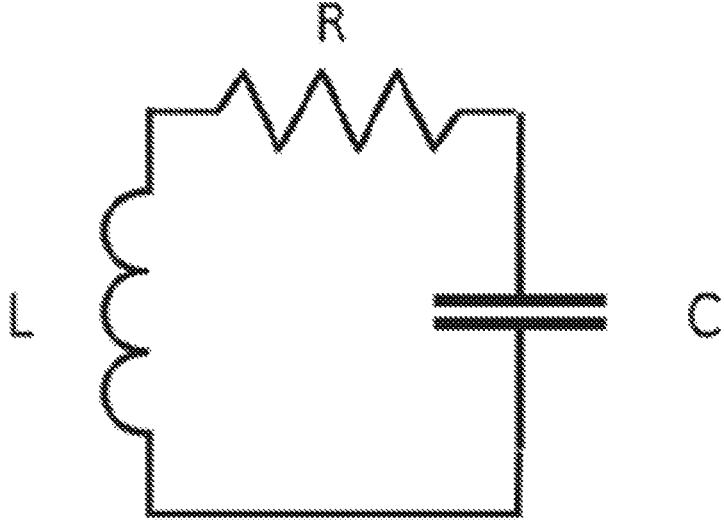
FIG. 14A illustrates an example circuit diagram of a variable capacitance sensor in accordance with the present disclosure.
Figure 14B:
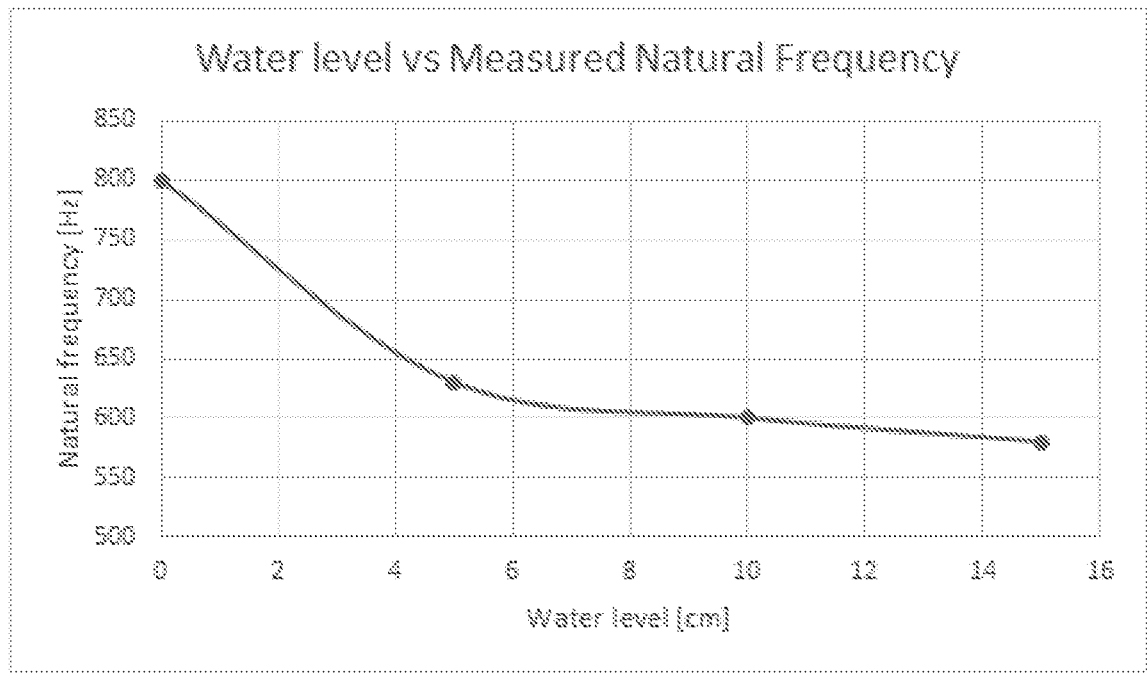
FIG. 14B is a graph comparing measured natural frequency relative to applied pressure.
Figure 14C:
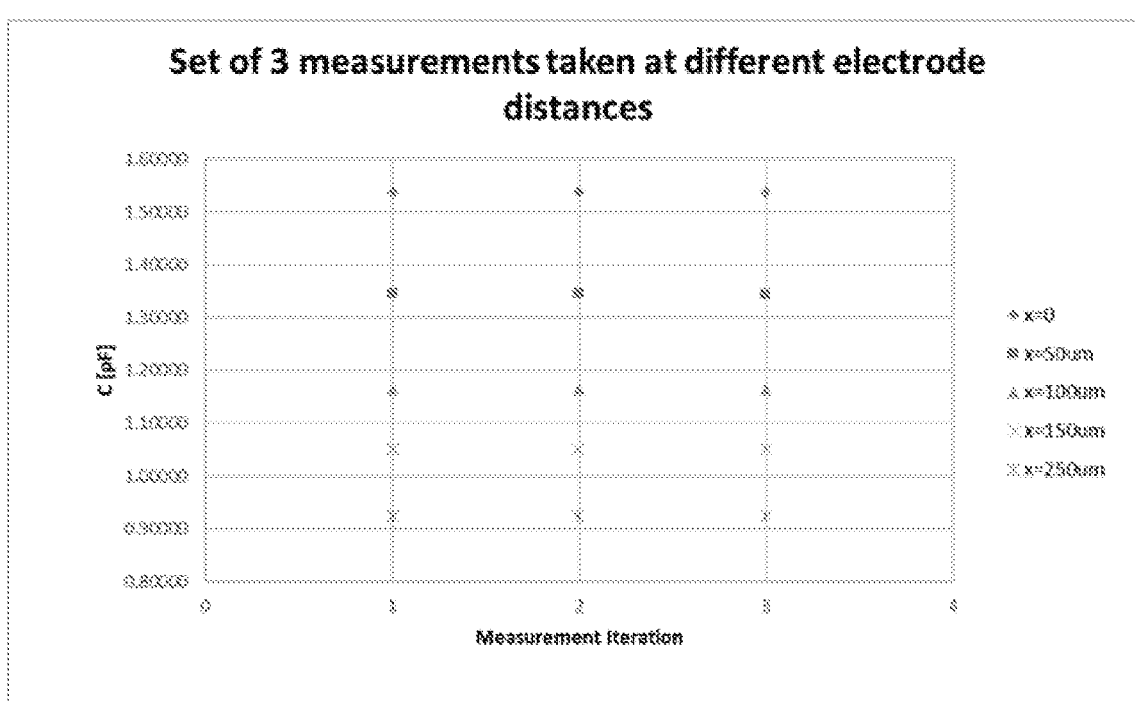
FIG. 14C-14G are graphs of test data used to determine intraocular pressure using capacitance.

In examples where the variable capacitance sensor 1220 includes an antenna structure 1340 electrically connected to the two conductive layers 1224, 1228 including the capacitor an electrical oscillator can be formed. The electrical oscillator is an LCR oscillator which can be conceptualized as an inductor, a capacitor, and a resistor connected in series. Here, the inductance (L) is constant and given by the structure of the antenna 1340, the capacitance (C) is described by Equation 1 and Equation 2, and the resistance (R) is determined by the conductivity of the conductive layers 1224, 1228. FIG. 14A illustrates an example circuit diagram of the LCR oscillator including variable capacitance sensor 1220 and antenna structure 1340. The natural frequency (f) of this oscillator is given by the equation:

$$f = \frac{1}{2\pi\sqrt{LC}} \qquad \text{Equation 3}$$

However utilizing Equation 2 to describe the capacitance (C) allows for the natural frequency (f) of oscillator to be written as:

$$f = \frac{1}{2\pi\lambda^2\sqrt{LC_0}} \qquad \text{Equation 4}$$

Accordingly, the scaling factor (A), and thus relative intraocular pressure of the eye, can be determined by measuring or detecting the natural frequency (f) of the electrical oscillator formed from the capacitor including the variable capacitance sensor 1220 and antenna structure 1340.

Referring again to FIG. 13, the natural frequency of such an electrical oscillator can be measured using the ASIC 1341 on the contact lens 1200. For example, as described above, the ASIC 1341 can measure the capacitance during before, during, and/or after the magnetic actuator and micromagnet 1227 perform applanation or indentation on the eye. Using the measured capacitance, the ASIC 1341 can then determine natural frequency. Alternatively, the capacitance measured by the ASIC 1341 can be transmitted via the antenna 1340 and a wireless signal 1360 to a separate electronic device 1350. The electronic device 1350 or some other electronic device can then determine the natural frequency using the capacitance measured by the ASIC 1341.

Alternatively, in some embodiments, the natural frequency of such an electrical oscillator can be measured from a separate electronic device 1350, such as a vector network analyzer (VNA). The electronic device 1350 can send a wireless signal 1360 to the contact lens 1200, which upon receipt of the wireless signal 1360 by the antenna structure 1340 can send a response signal to the electronic device 1350, as described further herein. The signal received by the electronic device 1350 can contain information such as the natural frequency (f) of the electrical oscillator in the contact lens 1200 which can then be used to determine the relative intraocular pressure of the eye. In some embodiments, utilizing a separate electronic reader device 1350 to determine the natural frequency (f) of the electrical oscillator allows for a wireless measurement of the relative intraocular pressure of the eye via the contact lens 1200 without the need for a power source, such as a battery, or an integrated circuit such as an ASIC on the lens 1200. Thus, in some examples the lens 1200 does not include a power source or an integrated circuit.

To test how natural frequency changed with application of pressure, small amounts of pressure were applied to a contact lens with graphite. Each water level of pressure was held for 1 minute, during which the natural frequency was measured. As demonstrated in FIG. 3B, it was observed that the natural frequency of the contact lens changed with varying amounts of pressure applied to the contact lens. Specifically, the measured natural frequency of the contact lens drops as the pressure applied to the contact lens increases. It is noted that the natural frequency was detected to be around 4.1395 GHz, and the y-axis of the graph shown in FIG. 3B present only the last three digits of the measurement. For example, with no pressure (a water level of 0 cm), the natural frequency was 4.139500800 GHz. At a water level pressure of 5 cm, the natural frequency dropped to between approximately 4.139500625 GHz and 4.139500640 GHz. At a water level pressure of 10 cm, the natural frequency dropped to approximately 4.139500600 GHz. At a water level pressure of 15 cm, the natural frequency of the contact lens dropped to between approximately 4.139500575 GHz and 4.139005590 GHz.

To demonstrate how capacitance between sensors in a contact lens can be used to determine intraocular eye pressure, a contact lens including an integrated single electrode was placed on a porcine eye in a laboratory. A half-moon configuration of a second internal electrode was mimicked using a first external half-moon sensing electrode and a second external half-moon sensing electrode, as illustrated in the cross-sectional view of FIG. 14H. A fluidic system including a pump was connected to the porcine eye to regulate intraocular eye pressures of the porcine eye, and the porcine eye was inserted into a support in the laboratory.

A first capacitance (CA) was measured between the first external half-moon sensing electrode and the integrated single electrode, and a second capacitance (CB) was measured between the second external half-moon sensing electrode and the integrated single electrode. Overall capacitance could be determined using $$\frac{1}{C_{AB}} = \frac{1}{C_A} + \frac{1}{C_B}$$

Changing the intraocular eye pressure of the porcine eye induced volume deformation of the globe of the porcine eye, which was reflected by a change in the distance x between the integrated single electrode and the two external half-moon sensing electrodes. It was observed that this change in distance also caused a change in total capacitance (C) value. Accordingly, $$C_{Total} \sim \frac{1}{x}$$

Data was acquired when the two half-moon electrodes were placed less than 1 mm from a single electrode, which at first was not integrated in any contact lens. As shown in the graph of FIG. 3C, a set of three measurements was taken at different electrode distances to validate measurements of the test setup. The different electrode distances included 0 micrometers, 50 micrometers, 100 micrometers, 150 micrometers, and 250 micrometers. Capacitance remained substantially unchanged during each of the three iterations at each respective distance, as shown in FIG. 3C.

Figure 14D:
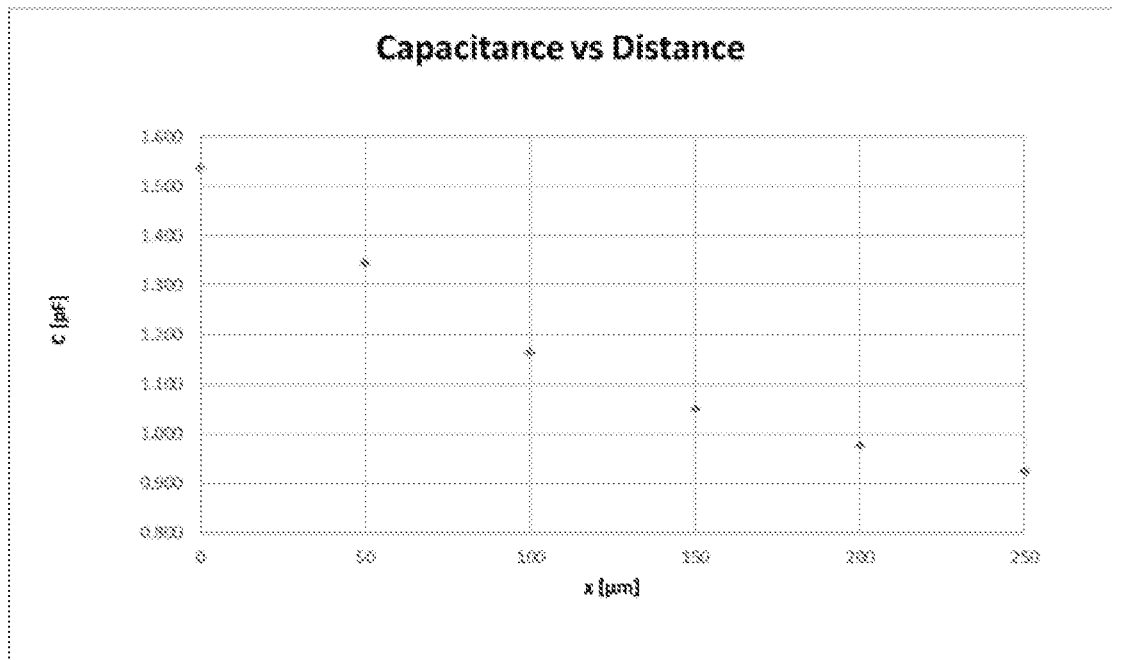

Total capacitance C also was measured as a function of distance x between the integrated single-electrode and the two external half-moon sensing electrodes, with the results shown in the graph of FIG. 14D. As demonstrated in the graph of FIG. 14D, capacitance decreased from between 1.500 and 1.600 pF at a distance of 0 micrometers to less than 1.000 pF at distances of 200 micrometers and 250 micrometers.

Figure 14E:
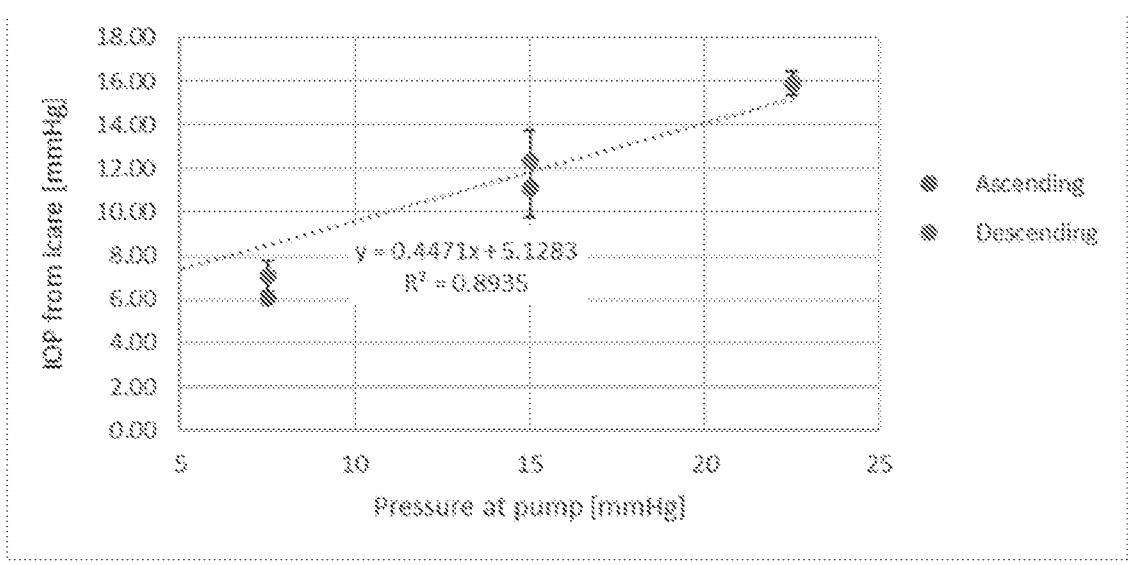
Figure 14F:
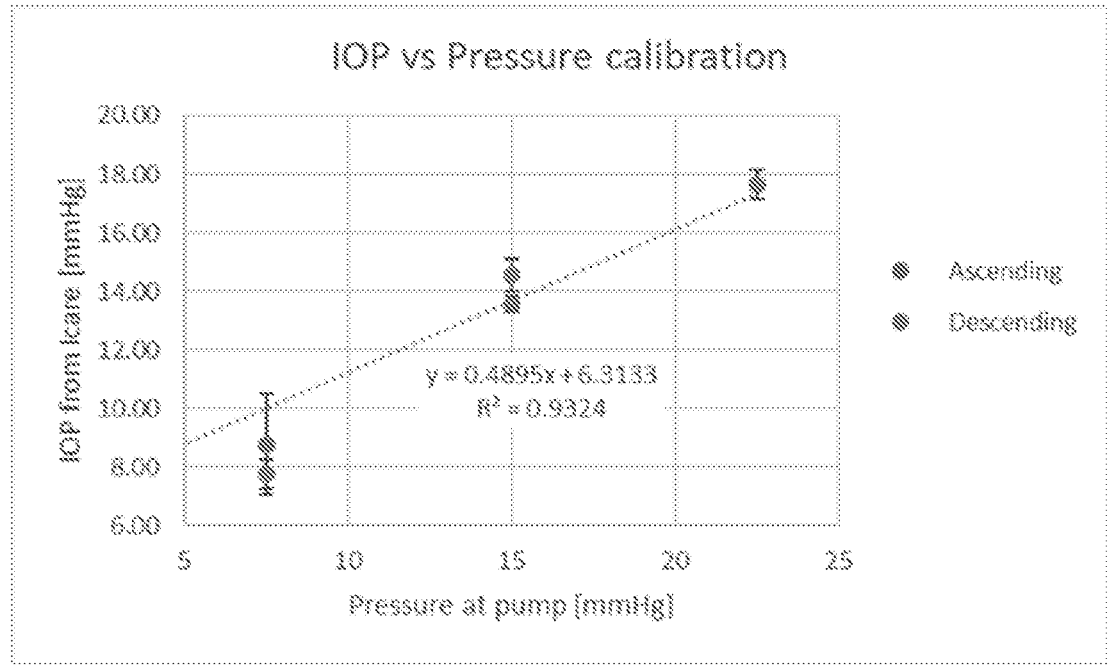
Figure 14G:
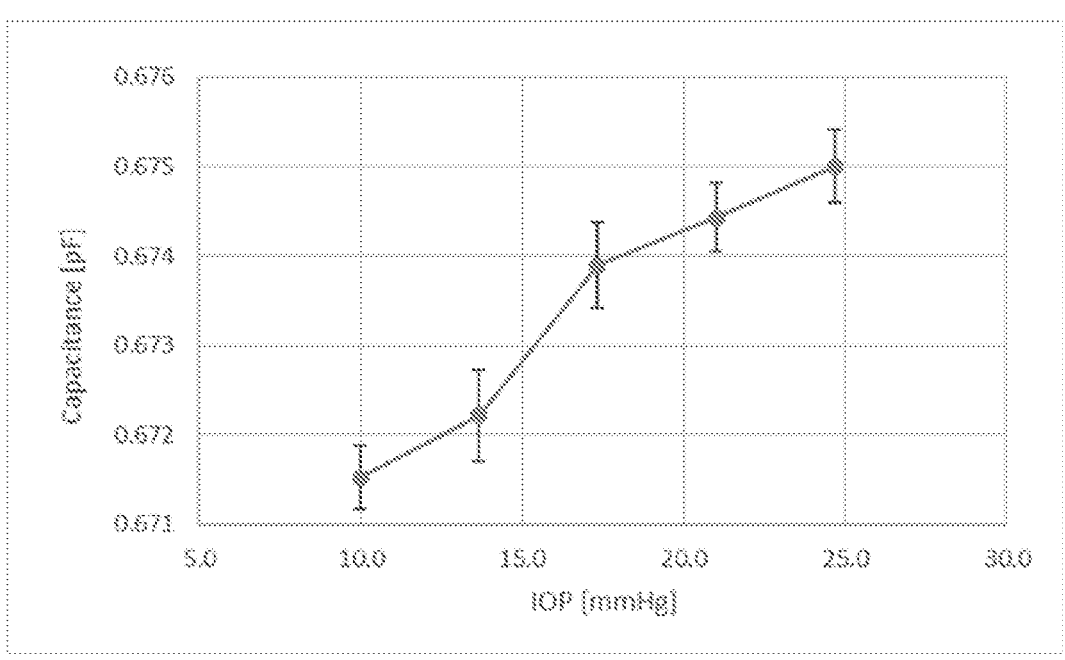
Figure 14H:
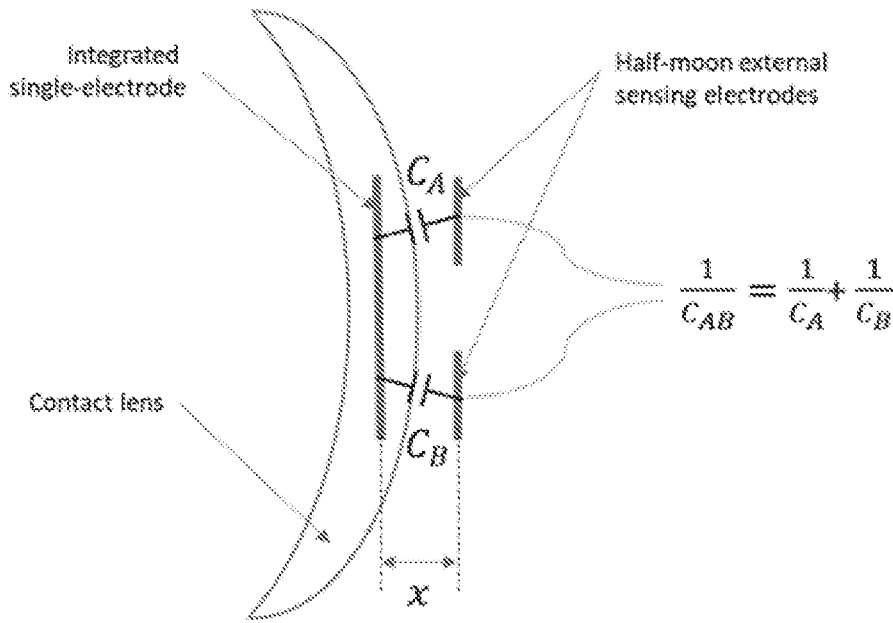
FIG. 14H is a cross sectional diagram of a contact lens used to measure capacitance at various eye pressures.

A reference sensor (ICARE tonometer) was used to calibrate actual intraocular eye pressure of the porcine eye with applied pressure from the pump of the fluidic system connected to the porcine eye. The ICARE tonometer measures deceleration and rebound time of a probe hitting the eye to calculate intraocular eye pressure of the eye. Calibration was performed on a first day (FIG. 14E) and on a second day (FIG. 14F) by determining intraocular eye pressure of the porcine eye with the ICARE tonometer at fluidic system pump pressures of 7.5 mmHg, 15 mmHg, and 22.5 mmHg.

Data from the two days of testing shown in FIGS. 3E and 3F was used to create a calibration curve for determining capacitance variation as a function of intraocular pressure of the eye, shown in FIG. 3G. Each point in FIG. 3G is an average of 200× raw capacitance values sampled at 4.6 Hz, and the error bars represent the standard deviation of these 200× values for each point. As demonstrated in FIG. 3G, then, measuring capacitance between two external electrodes and a third electrode in a contact lens can be useful in determining ocular hypertension and/or glaucoma, for example, in the eye of a wearer when an increase in the capacitance from (0.675 pF)to 0.675 pF, indicates an increase in the intraocular pressure of the eye from near 10 mmHg to near 25 mmHg.

Figure 15A:
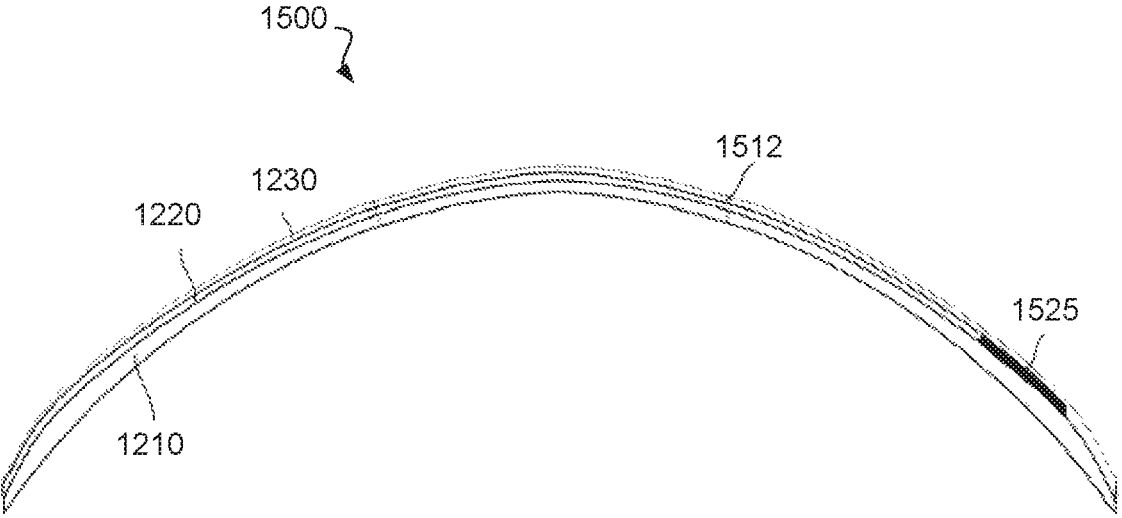
FIG. 15A illustrates a cross sectional view of an example contact lens incorporating a tonometer system in accordance with the present disclosure.
Figure 15B:
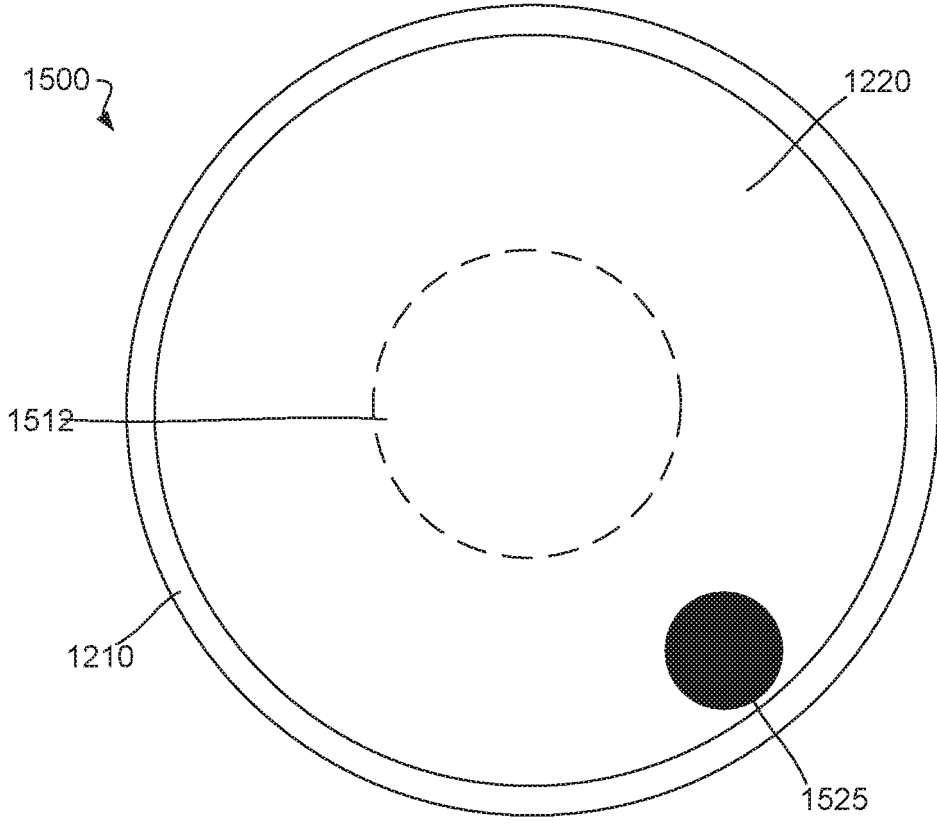
FIG. 15B illustrates a top view of an example contact lens incorporating a tonometer system in accordance with the present disclosure.

In many embodiments, a deflection measurement using a sensor in the contact lens can be used to determine at least one of an absolute or a relative intraocular eye pressure of an eye. FIGS. 15A and 15B depict an additional example of a contact lens 1500 comprising a lens material 1210, a sensor 1220, and an encapsulation layer 1230. The contact lens 1500 can be utilized to determine an absolute intraocular pressure of the eye of a wearer. The contact lens 1500 also can include a tonometer system including a test body 1525 disposed thereon. The test body 1525 can be disposed outside of the optic zone 1512 of the contact lens. The lens material 1210 can comprise any material suitable for use as a contact lens. That is, in some examples, the lens material 1210 can comprise a typical hydrogel contact lens. For example, in some embodiments the lens material 1210 can comprise a transparent polymer material, such as a hydrogel. In some examples the lens material 1210 can comprise a silicone hydrogel material.

In some embodiments, the test body 1525 can be disposed completely or partially within the optic zone 1512 of the contact lens 1500. In some of these examples, the test body 1525 can be transparent and may not distort or interfere with the user's vision, at least when in an initial state. In some examples, however, a test body 1525 positioned at least partially within the optic zone 1512 of the contact lens 1500 can interfere with or distort a user's vision when in an expanded state and/or the initial state.

The test body 1525 can selectively exert the force on the eye sufficient to obtain an intraocular pressure value via rebound tonometry. In some embodiments, the test body 1525 can be a selectively expandable material. That is, the test body 1525 can be a material that expands under a predetermined condition or set of conditions, and returns to its initial state when the condition or conditions are removed. In certain embodiments, the expandable material can be a polymer material, and in some examples the expandable material can be an elastomer. In some embodiments, the expandable material can be a hydrogel material.

In some examples, the expandable material can comprise a magnetoresponsive material that expands in the presence of a magnetic field and returns to the initial state when no longer in the presence of the magnetic field or within the presence of a magnetic field with a sufficient strength to expand the material. In these examples, the expandable magnetoresponsive material can include a polymer film including a plurality of molecular microchains which can be preferentially aligned with a magnetic field when the material is exposed to a magnetic field of sufficient strength. In some embodiments the expandable magnetoresponsive material can include aligned magnetic microchains throughout an entire thickness of the polymer film. In some embodiments, the aligned magnetic microchains can be formed upon the magnetophoretic transport and assembly of microparticles during polymer curing of the expandable magnetoresponsive material, for example during formation of the test body 1525.

In some embodiments, the expandable magnetoresponsive material can include a plurality of magnetic nanocrystals embedded in a polymer matrix, such as a polyvinyl alcohol (PVA) matrix. In some embodiments, the expandable magnetoresponsive material can include an elastomer, such as a silicon elastomer. In some examples, the elastomer can be a matrix in which magnetic microchains are dispersed. In some embodiments the magnetic microchains can be formed of particles having an average size of less than about 500 microns, less than about 250 microns, less than about 100 microns, less than about 50 microns, less than about 10 microns, or smaller. In some embodiments, the particles forming the magnetic microchains can be ferromagnetic particles, such as metallic ferromagnetic alloy particles. In some examples, these particles can include one or more of Nd, Fe, Pr, Co, B, Dy, Ga, or other elements. In some embodiments, the magnetic particles can be from about 1 wt % to about 50 wt % of the cured magnetoresponsive material. In some embodiments, magnetic microchains can be formed in an elastomeric matrix by applying an external magnetic field to the magnetoresponsive material while it is being cured or formed so that the magnetic particles are transported and aligned to form microchains having a substantially uniform orientation throughout the cured elastomeric matrix.

In some embodiments, when the expandable magnetoresponsive material is not exposed to a magnetic field of sufficient strength to expand the material, for example less than about 100 mT, less than about 10 mT, or less than about 1 mT or lower, the material can comprise a homogenous dispersion of microparticles or polymer blocks.

In some examples, the tonometer system and/or test body 1525 do not comprise separate mechanical moveable parts. That is, in some embodiments the tonometer system and/or test body 1525 may not comprise parts which move or slide with respect to one another. For example, in some examples a tonometer system and/or test body 1525 may not include a slideable or moveable central piece, such as a magnet and housing piece, such as a coil, through which the central piece can move. In some embodiments, the tonometer system and/or test body 1525 may not comprise a permanent magnet and/or an electromagnet.

The test body 1525 can have a diameter in an initial state of from about 1 millimeters to about 3 millimeters. In some examples the test body 1525 can have a diameter of about 2 millimeters. The test body 1525 can have a thickness of about from about 25 micrometers to about 200 micrometers, or from about 50 micrometers to about 100 micrometers. It has been advantageously found that a test body 1525 having a thickness of, for example, less than 100 micrometers allows for the ability to measure the absolute intraocular pressure of the eye without causing discomfort when the contact lens 1500 is on the eye. Although the test body 1220 is depicted in FIG. 15B as approximately circular in shape, other shapes are expressly contemplated. For example, in some embodiments the test body 1525 can be elliptical, rectangular, or irregular shape. In some examples, the test body 1525 can have a surface area of from about 1 square millimeter to about 10 square millimeters. In some examples, the test body 1525 can have a surface area of about 4 square millimeters. In some situations, the surface area of the tonometer can be less than 10 percent of the contact lens' surface area, more than 10 percent of the contact lens' surface area, more than 20 percent of the contact lens' surface area, more than 30 percent of the contact lens' surface area, more than 50 percent of the contact lens' surface area, more than another percentage of the contact lens' surface area, or combinations thereof.

The contact lens material 1210 can include an optic area or zone 1512 positioned at the center of the contact lens 1500. The optic zone 1512 is typically about the same size as the pupil of the eye in low-light conditions, for example the optic zone can have a diameter of about 10 millimeters. The optic zone 1512 contains the corrective power of the contact lens 1500, if any corrective power is present. According to some embodiments, the test body 1525 described herein is positioned on the contact lens material 1210 outside of the optic zone 1512. In some examples, the test body can be positioned substantially adjacent to the optic zone 1512, however in some other examples the tonometer can be positioned near an edge of the lens material 1210, or any position therebetween.

In some embodiments, the tonometer system of the contact lens 1500 can further comprise a sensor 1220. The sensor 1220 can be in contact with the lens material 1210. In some examples, the sensor 1220 can detect and/or wirelessly transmit information regarding the rate of change of the mechanical strain of the contact lens 1210 as the test body 1525 transitions from an expanded state to an initial state. In some examples, the sensor 1220 can detect and/or wirelessly transmit information regarding the deceleration of the test body 1525 caused by the eye as the expandable material enters the expanded state. The sensor 1220 can be, for example, a variable capacitance sensor. The sensor 1220 thus can include a parallel plate capacitor and an antenna structure. The parallel plate capacitor of the sensor 1220 can include at least a first transparent conductive layer and a second transparent conductive layer, with a dielectric layer disposed therebetween. The antenna connected to the sensor 1220 can be electrically connected to each of the conductive layers to thereby form an electrical oscillator. In some examples, the natural frequency of the electrical oscillator comprising the sensor 1220 can correspond to the amount of mechanical strain experienced by the contact lens 1500, for example due to the expansion of the test body 1525. Accordingly, a secondary electronic device, such as a vector network analyzer (VNA) can be used to detect the mechanical strain of the contact lens 1500 via the sensor 1220 in order to determine the rate of change of the mechanical strain and the absolute intraocular pressure of the eye.

In some examples, the contact lens 1500 can further comprise an encapsulation layer 1230 disposed over the test body 1525 and/or sensor 1220. The encapsulation layer 1230 can be in direct contact with the test body 1525. In some examples, the encapsulation layer 1230 can comprise a polymer material, such as a hydrogel. In some examples the encapsulation layer 1230 can comprise a silicone hydrogel material and can be the same material as the lens material 1210. The encapsulation layer 130 can have a thickness of from about 0.1 micrometers to about 20 micrometers, from about 0.5 micrometers to about 15 micrometers, or from about 1 micrometers to about 10 micrometers.

Figure 16A:
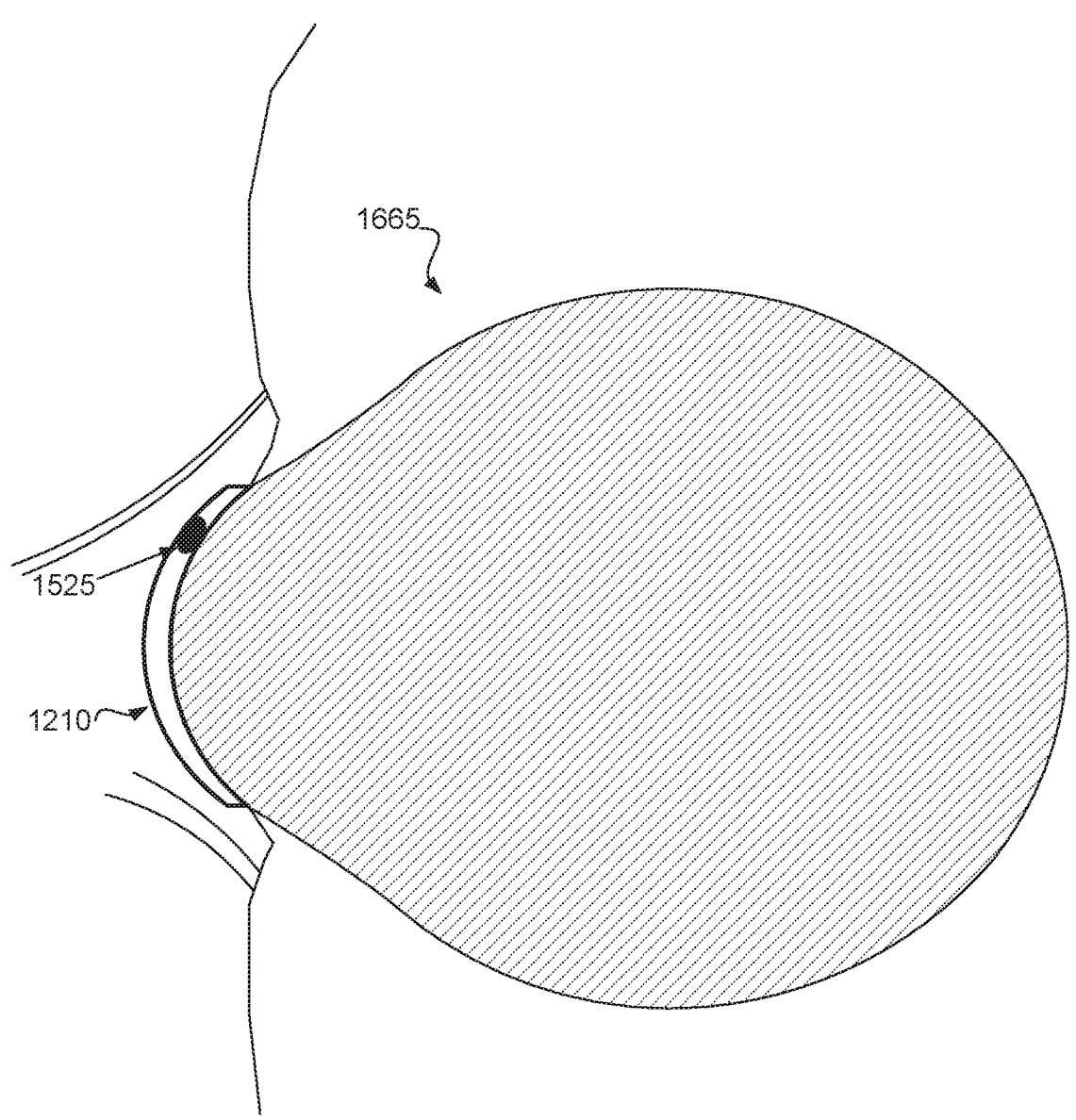
FIG. 16A illustrates a cross sectional view of an example contact lens including a test body in an initial position on an eye in accordance with the present disclosure.
Figure 16B:
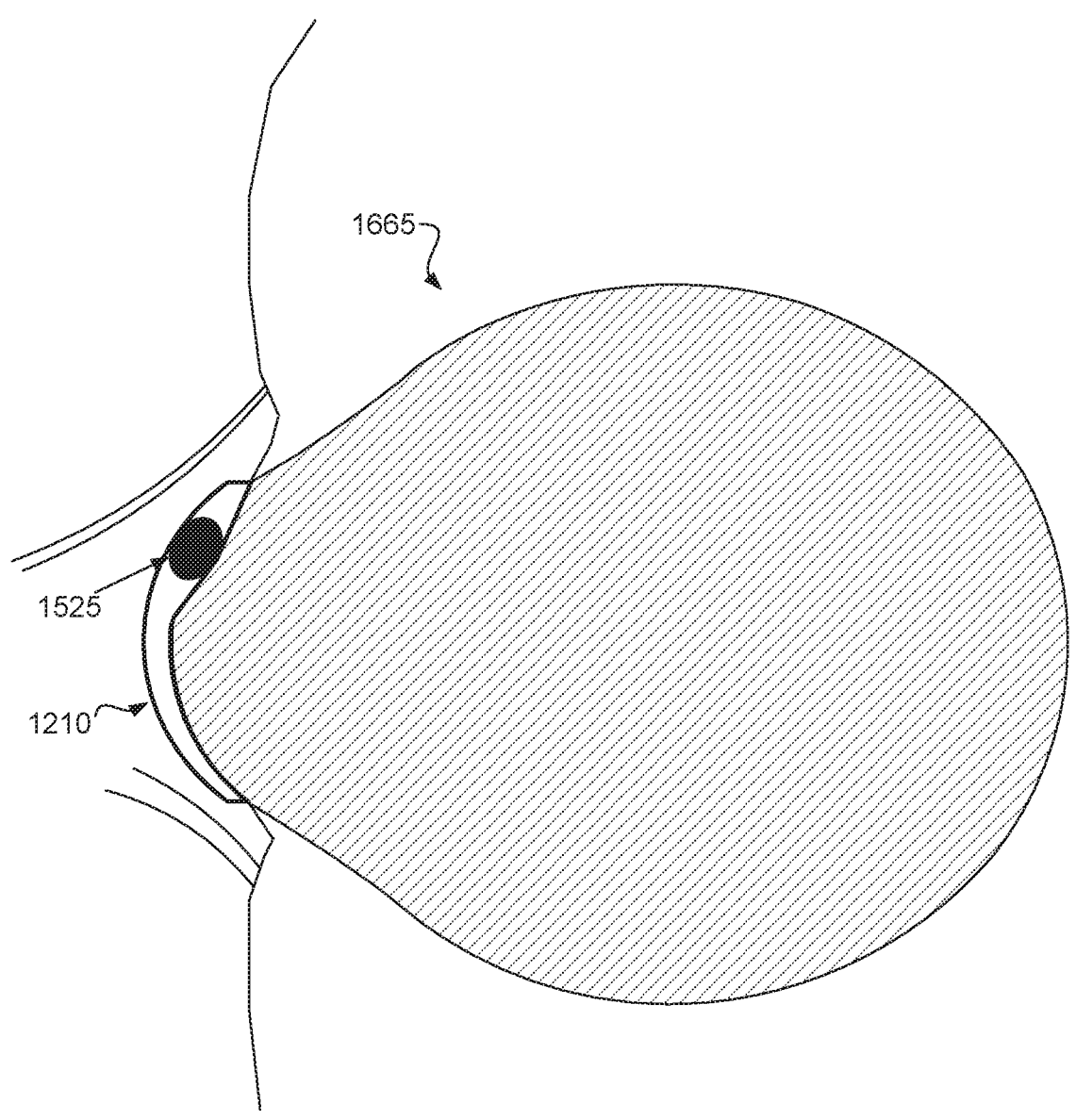
FIG. 16B cross sectional view of an example contact lens including a test body in an expanded position on an eye in accordance with the present disclosure.

FIG. 16A shows a cross sectional view of contact lens 1500, including test body 1525 in an initial state, positioned on the eye 1665 of a user. As described herein, the test body 1525 is positioned outside the optic zone 1512 of the eye. FIG. 16B shows the contact lens 1500 and test body 1525 positioned on the eye 1665 while the test body 1525 is, for example, exposed to a magnetic field sufficient to expand the expandable magnetoresponsive material which can comprise the test body 1525. As can be seen in FIG. 16B, and as described herein, when the test body 1525 is in an expanded state it can exert a pressure on the eye 1665 due to the expansion of the test body 1525. This expansion and associated force can cause a slight deformation in the eye 1665.

Figure 16C:
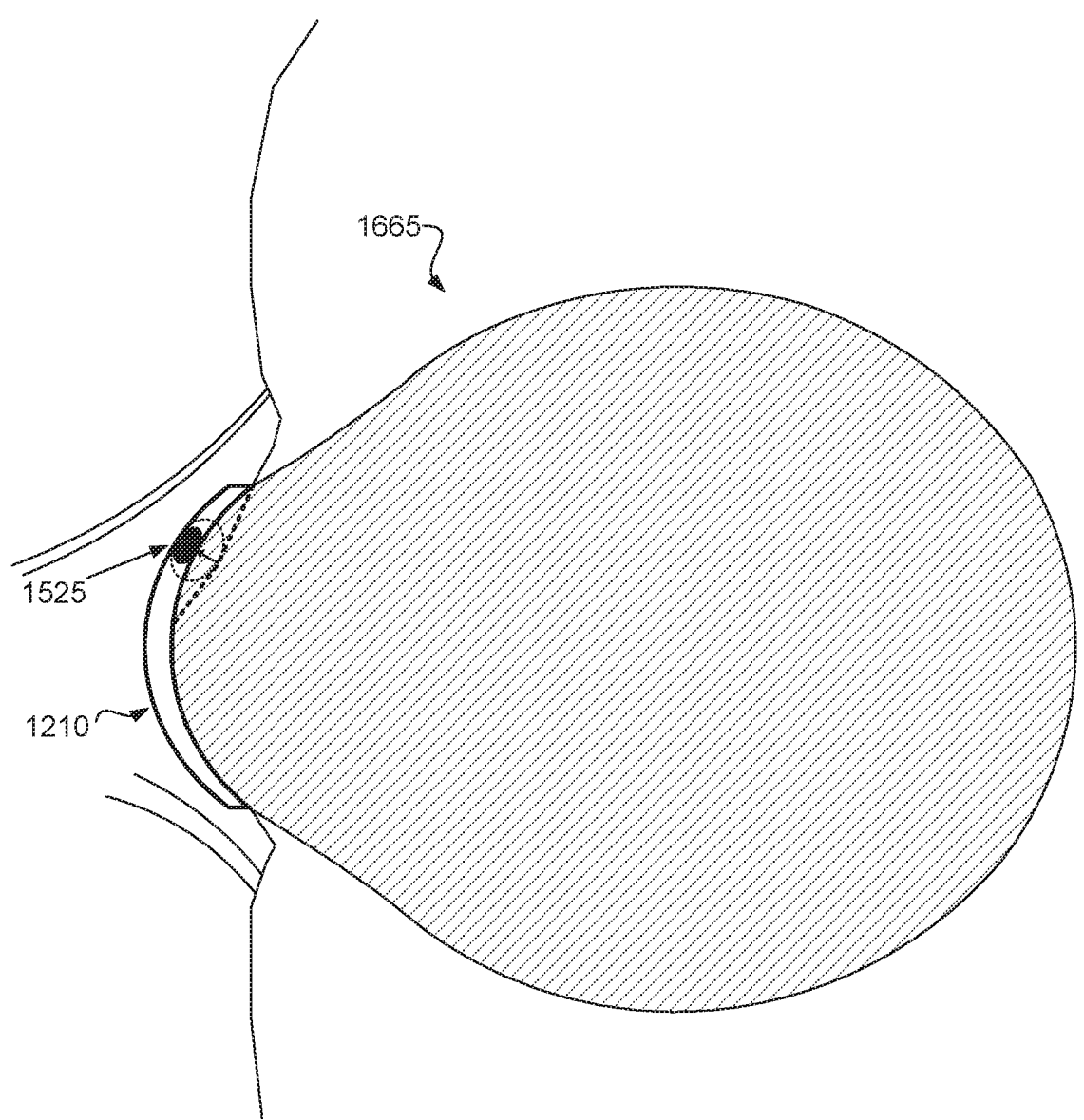
FIG. 16C illustrates a cross sectional view of an example contact lens including a test body transitioning from an expanded state to an initial state to measure the absolute intraocular pressure of an eye in accordance with the present disclosure.

When the test body 1525 is removed from, for example, a magnetic field and it can return to an initial state as the eye 1665 rebounds to its original shape, as illustrated in FIG. 16C. As described herein, the amount of time involved for the test body 1525 to transition back to the initial state, as shown in FIG. 16C, is measured by wirelessly detecting the change or rate of change in the mechanical strain experienced by the contact lens, which can then be used to determine the absolute intraocular pressure of the eye. It should be noted that the degree of expansion of the expandable material comprising the test body 1525 as depicted in FIGS. 16A-16C can be exaggerated in order to better aid in the understanding of the present disclosure.

In many embodiments, a magnetic field measurement using a sensor in the contact lens can be used to determine at least one of an absolute or a relative intraocular eye pressure of an eye. For example, in some embodiments, the test body 1525 includes a micromagnet. The micromagnet of the test body 1525 can include a rare earth magnet, such as a sintered samarium cobalt magnet or neodymium iron boron. In some embodiments, the micromagnet of the test body can include a single magnet, such as a ferromagnetic disc. A single micromagnet disc can be molded into the contact lens 1500 and magnetized to a desired direction after polymerization of the contact lens 1500. Alternatively, a single micromagnet disc can be magnetized prior to the polymerization of the contact lens using an additional previously magnetized disc.

In some embodiments, the micromagnet of the test body 1525 can include a micromagnet array. The micromagnet array can be transparent, while the rigidity and the flexibility of the micromagnet are variable depending upon the particle granulometry and array density. The micromagnet of the test body 1525 also can include multiple layers of micromagnet arrays that are fabricated to transfer wireless power from the magnetic source to the contact lens 1500. The micromagnet array can be integrated into the contact lens 1500 during molding of the contact lens 1500.

In some embodiments, the test body 1525 includes a contrast agent configured to enable time-of-flight proximity sensing. The contrast agent can include at least one of a coating of a radiation source layer, a dye, or a tag. Alternatively, a surface of the test body 1525, such as the micromagnet of the test body 1525, can optionally include a coating to modify reflectance and enable time-of-flight proximity. The surface of the test body 1525 also can include a selective specific transmitter time-of-flight system for position measurement. In these and other embodiments, the radiation source layer can be replaced by a radiation reflector material.

In some embodiments, an actuator outside the contact lens can be configured to bias or otherwise push the micromagnet of the test body 1525 towards the eye to perform at least one of applanation or indentation of the eye. For example, when the micromagnet of the test body 1525 is exposed to a magnetic field, the micromagnet of the test body 1525 pushes towards the eye 1665. Similar to the expandable magnetoresponsive material in FIG. 16B, the micromagnet of the test body 1525 can exert a pressure on the eye 1665. This force applied to the eye 1665 responsive to movement of the micromagnet of the test body 1525 can cause a slight deformation in the eye 1665.

Figure 16D:
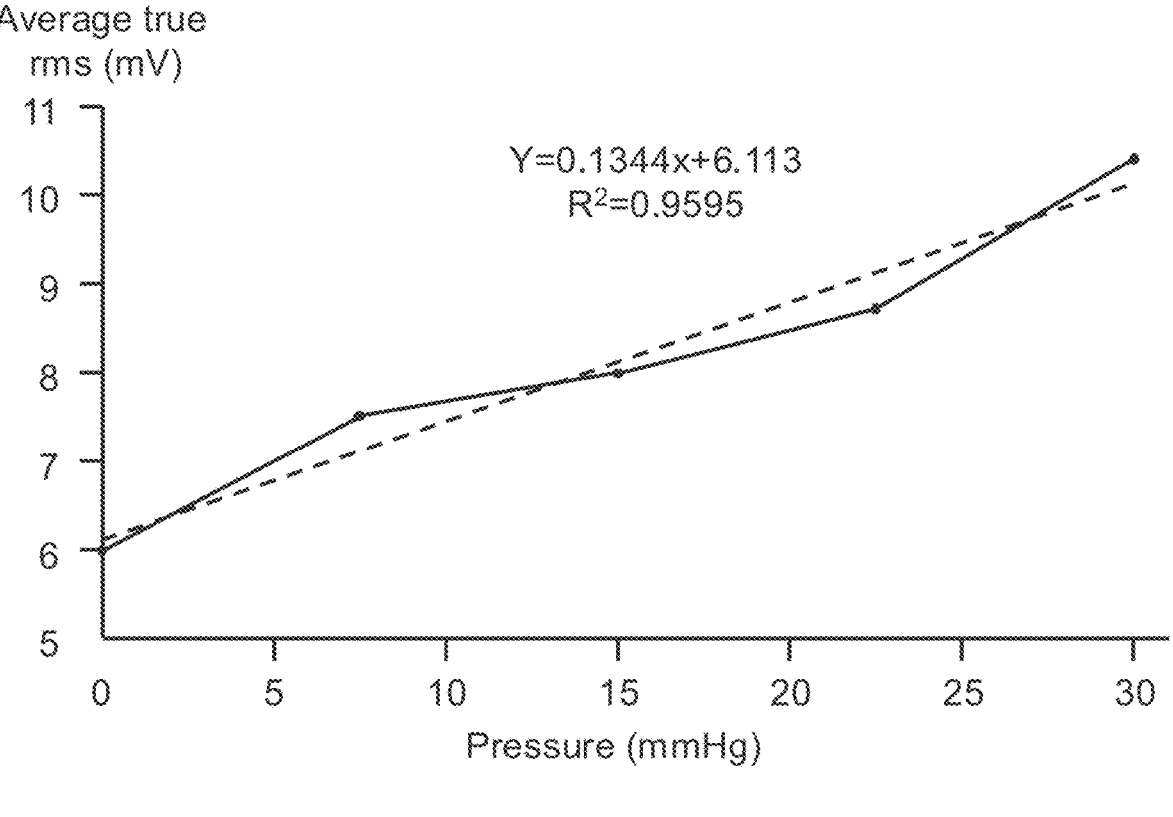
FIG. 16D is a graph of a calibration curve of a contact lens on a porcine eye.

In some embodiments, the sensor 1220 can measure the magnetic field of the test body 1525, using a magnetometer or a gradiometer sensor, resulting in a voltage that can be correlated to a pressure of the eye 1665. According to some examples, a contact lens including a micromagnet in the test body 1525 may not include a sensor 1220 in the contact lens, and instead use an external sensor in conjunction with the micromagnet in the test body 1525. For example, a gradiometer can determine the magnetic field gradient of the test body 1525, and determine a pressure on the eye 1665 correlated with the displacement of the micromagnet integrated in the contact lens. FIG. 16D provides a graph demonstrating a calibration curve of a contact lens on a porcine eye. The gradiometer measured an average true root mean square (rms) of 5.988 mV with 0 Mbar (0 mmHg) of pressure, an average rms of 7.513 mV with 10 Mbar (7.50062 mmHg) of pressure, an average rms of 7.995 mV with 20 Mbar (15.00124 mmHg) of pressure, an average rms of 8.729 mV with 30 Mbar (22.50186 mmHg) of pressure, and an average rms of 10.42 mV with 40 Mbar (30.00248 mmHg) of pressure.

FIG. 17 illustrates an example of a method 1700 of wirelessly determining the intraocular pressure of an eye. In this example, the method 1700 includes sending a wireless signal to the contact lens 1702, receiving a response signal from the contact lens 1708, and determining the intraocular pressure of the eye 1710. In some embodiments, the method 1700 can include additional activities between blocks 1702 and 1708. For example, after the wireless signal is sent to the contact lens, the method 1700 can include initiating a condition to transition a test body on the contact lens from a first state to a second state 1704 and removing the condition to transition to the test body on the contact lens from the first state to the second state 1706. The intraocular pressure of the eye determine in block 1706 can include at least one of a relative intraocular eye pressure or an absolute intraocular eye pressure.

At block 1702 a wireless signal is sent from an electronic device, such as a vector network analyzer, to the contact lens on the eye. The contact lens and electronic device can be contact lens 1200 and electronic device 1350 as described herein with respect to FIGS. 12A, 12B, and 13, and can include a variable capacitance sensor including an electrical oscillator as described herein. The wireless signal has a signal frequency. In some examples the electronic device can vary the signal frequency over a predetermined range, thus sending a plurality of wireless signals to the contact lens, each having a different signal frequency.

In some embodiments, the method 1700 also includes actuating a micromagnet in the contact lens with a magnetic actuator. Actuation of the micromagnet includes pushing or otherwise forcing the micromagnet towards the eye for at least one of applanation or indentation of the eye. During applanation or indentation, one or more layers of the sensors in the contact lens are mechanically compressed, altering the space between dielectric layers in the sensor in the contact lens. In some embodiments, the method 1700 also includes measuring, with an ASIC in the contact lens, the capacitance produced in the sensor when the one or more layers of the sensor are compressed.

In alternative embodiments, method 1700 can include initiating a condition to transition a test body on the contact lens from a first state to a second state 1704. In some embodiments, initiating the condition to transition the test body includes initiating a condition in order to transition a test body on a contact lens, for example a test body of a tonometer system, to an expanded state. Accordingly, a contact lens including a test body as described herein, for example with regard to FIGS. 15A-16C can be exposed to a condition such that the test body transitions from an initial state to an expanded state, to thereby exert a force on the eye as shown in FIGS. 16A-16C. For example, where the contact lens includes a tonometer system including a magnetoresponsive test body as described herein, the test body can be exposed to a magnetic field such that the test body transitions from an initial state to an expanded state, for example as shown in FIG. 16B. In some examples a secondary device, such as an electromagnetic device capable of generating a magnetic field can be positioned near the contact lens to transition the test body from an initial state to an expanded state. For example, a device included in the contact lens can generate the magnetic field. In some examples, the antenna, when it receives a signal carries an electric current that produces a magnetic field, which causes the expandable material to expand. In another example, the user can be provided with a device that generates the magnetic field. In yet another example, the magnetic field is generated by a hand-held device or another type of device. In some examples, the magnetic field is generated in a doctor's office or another type of location.

In some embodiments, initiating the condition to transition the test body includes initiating a condition in order to transition a test body on the contact lens to an expanded state whereby a micromagnet of the test body pushes against or otherwise exerts a force against the eye (such as applanation or indentation). For example, the test body can be exposed to a magnetic field such that the test body transitions from an initial state whereby the micromagnet of the test body is not exerting a force against the eye to an expanded state whereby the micromagnet of the test body is exerting a force against the eye. In some examples a secondary device, such as an electromagnetic device capable of generating a magnetic field can be positioned near the contact lens to transition the micromagnet of the test body from an initial state to an expanded state. For example, a device included in the contact lens can generate the magnetic field. In some examples, the antenna, when it receives a signal carries an electric current that produces a magnetic field, which causes the micromagnet to transition the test body to an expanded state. In another example, the user can be provided with a device that generates the magnetic field. In yet another example, the magnetic field is generated by a hand-held device or another type of device. In some examples, the magnetic field is generated in a doctor's office or another type of location.

In these alternative embodiments, method 1700 also can include removing the condition to transition to the test body on the contact lens from the first state to the second state 1706. Removing the condition to transition to the test body can include stopping the condition so that the test body transitions from the expanded state to the initial state 1704. In some examples, the contact lens can be removed from the magnetic field, or a device used to generate a magnetic field can be removed from the vicinity of the contact lens. In some examples where the magnetic field is generated by an electromagnetic device, the magnetic field can be turned off. In some embodiments when the condition, such as the magnetic field, is turned off or removed the test body can transition from an expanded state to an initial state as described herein.

In some embodiments, method 1700 can include wirelessly monitoring an amount of time involved for the test body to transition from an expanded state to an initial state. The transition time can be wirelessly monitored by, for example, the sensor 1220 as described herein with respect to FIGS. 15A and 15B. In some examples the amount of time involved for the test body to transition is measured by wirelessly detecting the change or rate of change in the mechanical strain experienced by the contact lens. In some examples this can be achieved with a variable capacitance sensor, as described herein. For example, in some examples a first mechanical strain can correspond to the expanded state of the magnetoresponsive test body and a second mechanical strain can correspond to the initial state of the magnetoresponsive test body, and the amount of time between detecting the first mechanical strain and detecting the second mechanical strain can be wirelessly recorded, for example by an electronic device in communication with the sensor. However, in some other examples the deceleration of the test body as the expandable material transitions from an initial state to an expanded state at block 608 can be wirelessly measured or detected. In some embodiments, the method 1700 also includes measuring, with an ASIC in the contact lens, the capacitance produced in the sensor when the one or more layers of the sensor are no longer compressed as the test body transitions from the expanded state to the initial state.

At block 1708, the electronic device receives a response signal including a measurable characteristic from the contact lens. The measurable characteristics received in the response signal can vary according to different embodiments described herein. In some embodiments, the response signal is sent or transmitted from the contact lens to the electronic device when the signal frequency of the wireless signal sent in block 1702 matches or corresponds to the natural frequency of the electrical oscillator. Further, the response signal sent from the contact lens includes a measurable characteristic, such as the frequency of the response signal itself, corresponding to the natural frequency of the electrical oscillator. In some embodiments, the response signal includes a measurable characteristic of a capacitance value measured by the ASIC in the contact lens. In some embodiments, the response signal include a measurable characteristic of the amount of time involved for the test body to transition from the expanded state to the initial state, or the rate of change of the mechanical strain of the contact lens is used to determine the absolute intraocular pressure of the eye. In some examples, where the amount of time for the test body to transition from the expanded state to the initial state can correspond to the absolute intraocular pressure of the eye. Similarly, in some examples the rate of change of the mechanical strain of the test body can correspond to the absolute intraocular pressure of the eye. In some embodiments, the response signal includes a measurable characteristic of a voltage of the magnetic field of the test body in at least one of the initial state or the expanded state. At block 1710 the measureable characteristics of the response signal are used to determine the intraocular pressure of the eye. The intraocular pressure determined by either relative intraocular pressure or absolute intraocular pressure. For example, the natural frequency of the electrical oscillator can be used to determine the relative intraocular pressure of the eye by utilizing, for example, Equation 4 as described herein. In some embodiments, the capacitance measured by the ASIC on the contact lens can be used to determine the relative intraocular pressure of the eye by utilizing, for example, a correlation between the eye pressure and the measured natural frequency. In some embodiment, the absolute intraocular pressure of the eye can be determined from the amount of time involved for the test body to transition from the expanded state to the initial state. In some embodiments, the absolute intraocular pressure of the eye can be determined from the voltage of the magnetic field of the test body in at least one of the initial state or expanded state.

Smart Contact Lens Container

According to another aspect of the present disclosure, constituents in tear fluid (e.g., biomarkers) can be analyzed (e.g., via a smart contact lens container 120) to determine a health condition of a user, as described in U.S. application Ser. No. 62/642,897 filed 14 Mar. 2018, the disclosure of which is incorporated herein, in its entirety, by this reference. These biomarkers can be collected on a contact lens worn by the user. Any appropriate type of contact lens can be used to collect the biomarkers. However, unaltered commercially available contact lenses from a wide variety of manufacturers for corrective vision are envisioned to be the contact lens that are used to collect the biomarkers. Biomarkers, such as proteins, generally start to bind to these contact lenses as soon as the contact lenses are placed over the user's eye. Without modifying the contact lens as they are provided by the manufacturers, the contact lens can bind to these proteins, electrolytes, and/or other biomarkers in the tear fluid.

Generally, a user removes the contact lenses after wearing them for a period of time. Often, before the user retires to bed, the user removes the contact lens and places the contact lens in a storage container for the night. The storage container can include a storage solution that disinfects the contact lens and also breaks down the build-up on the contact lens. The storage solution can be an aqueous solution that causes the build-up on the contact lens to dissolve into the solution. After a period of time, the storage solution can be replaced with fresh storage solution to reduce the concentration of tear fluid constituents in the fluid.

The storage solution can be analyzed to determine the type and/or concentration of biomarkers that dissolved off of the contact lens. In some examples, the solution can be analyzed without the contact lens in the solution. In other examples, the contact lens is removed from the solution before analyzing the biomarkers.

Any appropriate type of sensor can be used to identify the type and/or concentration of the biomarkers. In some instances, the sensor is incorporated into the contact lenses' storage container. In this example, the sensor can be an optical spectral analyzer that passes light through the cavity of the storage container holding the storage solution from a light source to a light receiver. The receiver can measure the amount the light's optical transmittance through the storage solution. In some examples, the spectral analyzer passes light through the storage solution at isolated predetermined wavelengths and measures the optical transmittance at each of the predetermined wavelength ranges. Each of the recorded transmittances can correlate to the presence of specific kinds of biomarkers and their concentrations.

In other examples, the sensor is incorporated into a hand-held device. In one example, the sensor can be incorporated into the user's mobile device, such as a smart phone and/or electric tablet. In one of these types of examples, the user can direct a beam of light into the storage solution and measure a reflection.

In some examples, the measurements are associated with an amount of time that the user wore the contact lens. For example, the user can interact with a user interface to the sensor to input how long the user wore the contacts lenses. In some examples, the user can be requested to input the number of hours that the user wore the contact lens. In other examples, the user can be requested to input the number of days that he or she wore the contact lenses, whether the user removed the contact lenses during the night, the time of when the storage solution was last replaced, other factors that can affect the concentration of biomarkers in the storage solution, or combinations thereof.

In some examples, the sensor can record the measurements to determine a measurement level of each of the desired biomarkers. In some examples, the sensor can record the measurements in real time. Further, the sensor can include local and/or cloud based logic to determine the type concentration, and/or other characteristics of the varying kinds of biomarkers. In some examples, the sensor can use learning algorithms, predictive models, data correlation models, clustering models, any other appropriate computational techniques, and combinations thereof. In some examples, the algorithms applied to data collected from the sensor can include support vector machines, neural networks, decision trees, gaussian mixture models, hidden markov methods, and wavelet analysis. The models used to learn from data can include but it is not limited to anomaly detection models, clustering models, classification models, regressions models or summarization models. In some examples, the sensor can include a database that stores the correlation between the identification/concentration of the biomarkers and a health condition of the user.

The measurements can be sent to a computing device that processes the information retrieved from the sensor. In some examples, at least some computations are performed by the sensor before sending data to a computing device where the computations are finished. In other examples, the sensor sends raw data to the computing device. In this example, all data processing, including data cleaning, data management, data mining, and any application specific issues, is performed remotely to the sensor. In some examples, information processing can include data preprocessing, for example in order to format or modify the data for use in subsequent processing. In some examples, data preprocessing can include formatting for matrix computations, data normalization, data synchronization and data filtering.

The determinations of the type of biomarkers, the characteristics of biomarkers, such as the concentration of the biomarkers, chemometric data such as ratio kinetics, peak, plateau, time constant, decay, and so forth can be compared to data points stored in a database. The database can be local to the computing device or the computing device can have remote access to the database. The data in the database can correlate the different types and concentrations of biomarkers with health conditions, such as eye health conditions, allergic conditions, other physiological conditions, or combinations thereof. In some examples, the data in the database can be used as input or training data to implement supervise machine learning techniques, or other statistical learning approaches to solve prediction inference, or other data mining problems related to health conditions, such as eye health conditions, allergic conditions, other physiological conditions, or combinations thereof.

In some examples, the database is in communication with multiple users and data sources. As data regarding the storage solution of a user is collected, data from each of the users can contribute to the information in the database. In some examples, data collection can automatically launch a data management system of the database. In some examples, the data management system or another process can incorporate additional data into the database, such as the health conditions of each of the users. As result, the correlations in the database can be built from reports from the users. In some examples, patient data can be used as predictors in a statistical machine learning process. In some examples where the database is built using thousands of users, the database's input can identify correlations between health conditions and specific levels of different types of biomarkers that are unknown to the scientific community. Thus, even before scientific studies can be conducted to find a correlation between a biomarker and a health condition, the database can send information related to the diagnosis of a disease, a disease severity assessment, a risk stratification, a therapeutic decision or request, a recommendation to the user to be tested for a specific type of condition, or combinations thereof.

These principles allow a super multivariate database to be built that correlates the health conditions of the users with varying parameters of the biomarkers. For example, the database can include supplementary user data such as age, gender, weight, height, and the like. These principles also allow the user to have a non-invasive procedure to measure the biomarkers. Further, in those examples where the user is already storing and cleaning his or her contact lens from time to time, the user can incurred little to no additional effort to measure the biomarkers and receive reports on at least some of his or her health conditions.

In some examples, the database can include correlations between a user's biomarker profile or other types of biomarker characteristics to determine a type of contact lens for the user. The biomarkers can indicate that the user has an allergic reaction to a particular type of contact lens, and the database can include information on other types of contact lenses that the user is likely to be non-allergic to. In other examples, the database can indicate that the user is allergic or the contact lens has another property that would suggest that another type of contact lens is better suited for the user, but the database may not provide alternative options to the user. However, the user is better off for knowing which of the contact lens types do not have a high likelihood of being comfortable for the user, so the user can avoid purchasing these types of contact lenses. In other examples, the system can look to a different source, other than the database, to find information on the types of contact lenses that are more likely to be well suited for the user.

Figure 18:
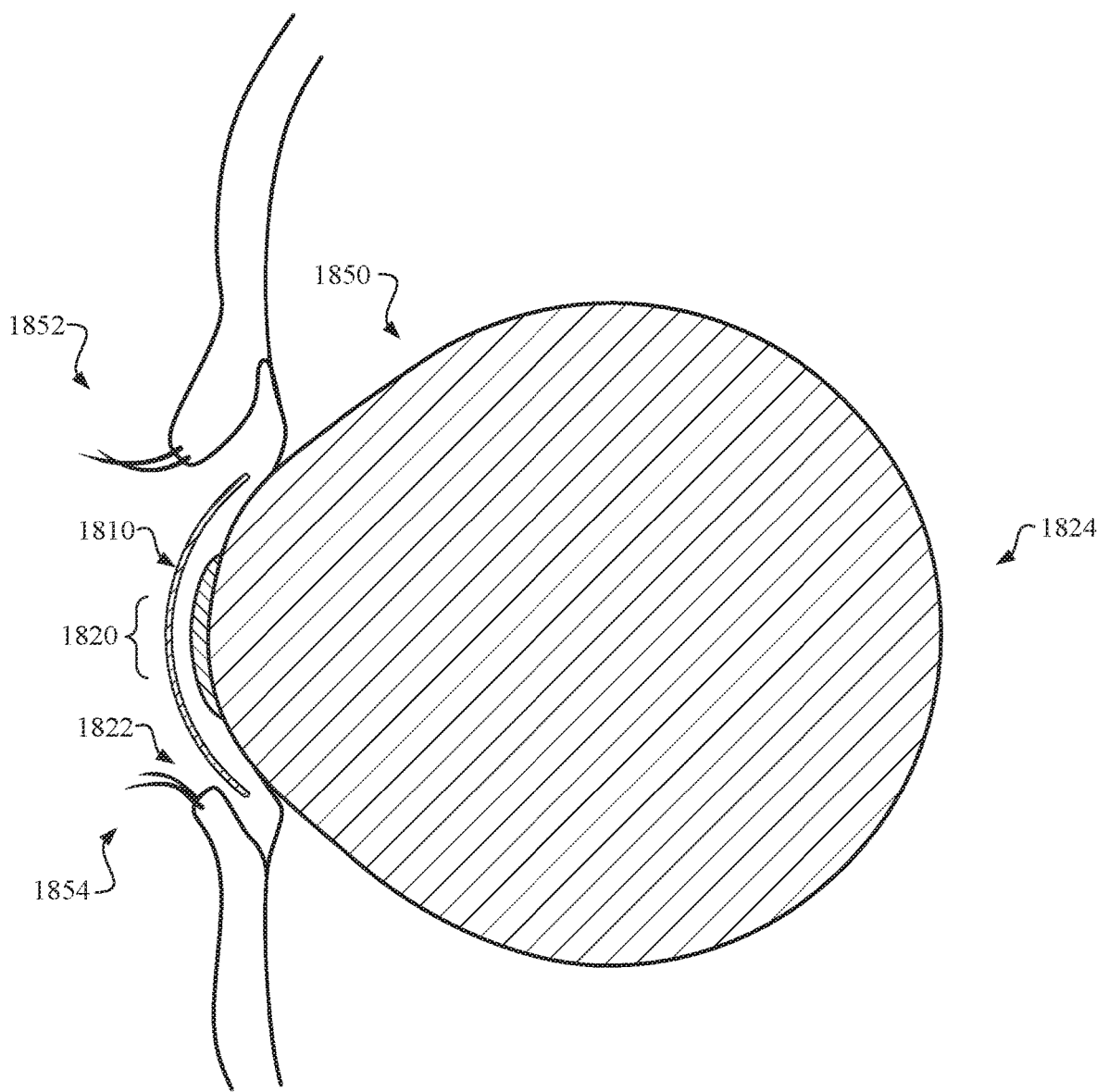
FIG. 18 illustrates an exemplary cross-sectional view of a contact lens positioned on an eye, in accordance with the present disclosure.

Referring now to the figures, FIG. 18 depicts an example of a contact lens 1810 situated on the outside of a human eye 1850. The contact lens 1810 spans the outside surface of the exposed portion of the eye 1850. An upper portion of the contact lens 1810 is adjacent a set of eyelashes 1852 of the upper eye lid. The contact lens 1810 can include a posterior side that is in contact with the cornea of the eye 1850, and an anterior side that is opposite of the posterior side. As the lid travels over the eye 1850, the eye lid moves across the anterior side of the contact lens 1810.

A user can wear the contact lens for vision correction purposes. In this type of example, the contact lens can include an optic zone 1820 and a peripheral zone 1822. The optic zone 1820 can include a region that focuses light to the center of the user's retina 1824. The peripheral zone 1822 can contact the eye over the sclera. While this example discloses using commercially available contact lenses configured for vision correction to be worn on the eye, other types of contact lenses can be used in accordance with the principles described in the present disclosure. For example, the contact lens may not include a curvature or features that correct vision.

The contact lens 1810 can be soft contact lenses, rigid gas permeable (RGP) contact lenses, orthokeratology contact lens, another type of contact lenses, or combinations thereof. The contact lens can be made of any appropriate type of material. A non-exhaustive list of materials that can be used to construct the contact lens include any appropriate silicone material and/or hydrogel material. Such material can be formed of polymers, such as tefilcon, tetrafilcon A, crofilcon, helfilcon A&B, mafilcon, polymacon, hioxifilcon B, lotrafilcon A, lotrafilcon B, galyfilcon A, senofilcon A, sifilcon A, comfilcon A, enfilcon A, lidofilcon B, surfilcon A, lidofilcon A, alfafilcon A, omafilcon A, vasurfilcon A, hioxifilcon A, hioxifilcon D, nelfilcon A, hilafilcon A, acofilcon A, bufilcon A, deltafilcon A, phemfilcon A, bufilcon A, perfilcon, etafilcon A, focofilcon A, ocufilcon B, ocufilcon C, ocufilcon D ocufilcon E, ocufilcon F, phemfilcon A, methafilcon A, methafilcon B, vilfilcon A, other types of polymers, monomers, or combinations thereof. These materials can include various combinations of monomers, polymers, and other materials to form the material that makes up the contact lens.

In one embodiment, the contact lens material is made of hydrogel polymers without any silicone. This can be desirable to increase the wettability of the contact lens. In another embodiment, the contact lens material is made of silicone hydrogel material.

The tear fluid in the ocular cavity can come into contact with the contact lens. In some examples, the entire surface area of the contact lens comes into contact with the tear fluid. The constituents of the tear fluid can include lipids, electrolytes, metabolites, proteins, antibodies, other types of compounds, or combinations thereof. These constituents can be biomarkers that can be indicative of a health condition of the user. The biomarkers can bind to the contact lens.

A non-exhaustive list of biomarkers from the tear fluid that can be of interest includes, but is not limited to, electrolytes, sodium, potassium, chloride, phenylalanine, uric acid, galactose, glucose, cysteine, homocysteine, calcium, ethanol, acetylcholine and acetylcholine analogs, ornithine, blood urea nitrogen, creatinine, metallic elements, iron, copper, magnesium, polypeptide hormones, thyroid stimulating hormone, growth hormone, insulin, luteinizing hormones, chorionogonadotrophic hormone, obesity hormones, leptin, serotonin, medications, dilantin, phenobarbital, propranolol, cocaine, heroin, ketamine, hormones, thyroid hormones, ACTH, estrogen, cortisol, progesterone, histamine, IgE, cytokines, lipids, cholesterol, apolipo protein $A_1$, proteins and enzymes, lactoferrin, lysozyme, tear-specific prealbumin or lipocalin, albumin, complement, coagulation factors, liver function enzymes, heart damage enzymes, ferritin, virus components, immunoglobulins such as IgM, IgG, proteases, protease inhibitors, lactate, ketone bodies, other types of biomarkers, or combinations thereof.

In some examples, a commercially available contact lens can have surface properties to allow the biomarkers to bind to the contact lens without any modifications. Conventionally, protein build-ups and other types of build-ups on contact lens are considered a problem on regular contact lens that do not have surface modifications to enhance a biomarker's ability to bind to the contact lens. In other examples, the contact lens can be modified to enhance the binding ability of the biomarkers or just for specific bio-markers. In those examples where the surface of the contact lens can be modified to enhance an ability to bind to the biomarkers, the binding enhancements can be made to any appropriate location on the contact lens, including, but not limited to, the peripheral zone, the optical zone, the anterior side of the contact lens, the posterior side of the contact lens, other areas of the contact lens, or combinations thereof.

Figure 19:
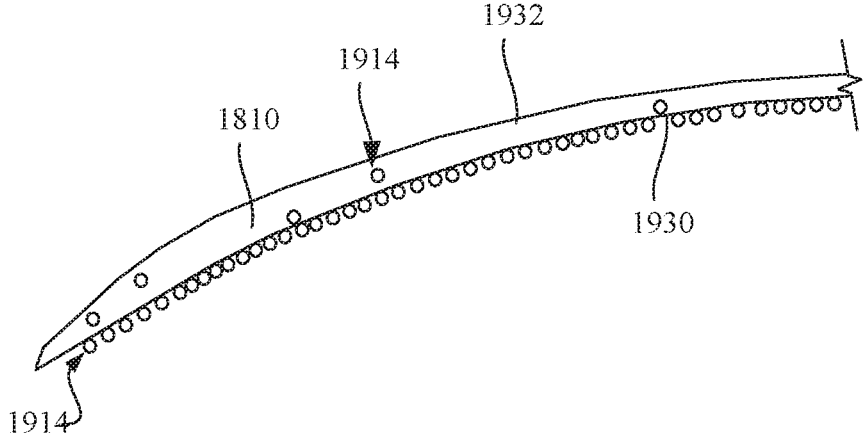
FIG. 19 illustrates an exemplary cross-sectional view of biomarkers adhered to a contact lens, in accordance with the present disclosure.

FIG. 19 depicts an example of biomarkers 1914 attached to the posterior surface 1930 of the contact lens. While this example depicts the biomarkers 1914 attached to the posterior surface 1930 of the contact lens 1810, the biomarkers 1914 can be attached to just the anterior surface 1932 or to both the anterior surface 1932 and posterior surface 1930 of the contact lens 1810. In some examples, the biomarkers 1914 can be adsorbed, absorbed, bonded, covalently bonded, ionically bonded, adhered, cohered, or otherwise connected to a surface of the contact lens 1810. In some examples, the biomarkers 1914 are incorporated into the thickness of the contact lens 1810.

When the contact lens 1810 is removed from the user's eye, the biomarkers 1914 can stay with the contact lens 1810 as depicted in FIG. 19. The amount of biomarkers 1914 that are attached to the contact lens 1810 can be related to the amount of time that the contact lens 1810 was on the eye. In some examples, the contact lens 1810 can be worn by the user during that day and removed at nighttime. Under these circumstances, biomarkers 1914 can cover a substantial amount of the contact's lens surface area. However, in other examples, the contact lens 1810 can be worn by the user for a smaller period of time.

In one specific instance, a patient can be provided with a contact lens 1810 for a period of minutes in a doctor's office to collect biomarkers 1914 for analysis. In other examples, a patient can be instructed to keep a contact lens 1810 in for a matter of hours or even longer than a day to collect the desired about of biomarkers 1914.

Figure 20:
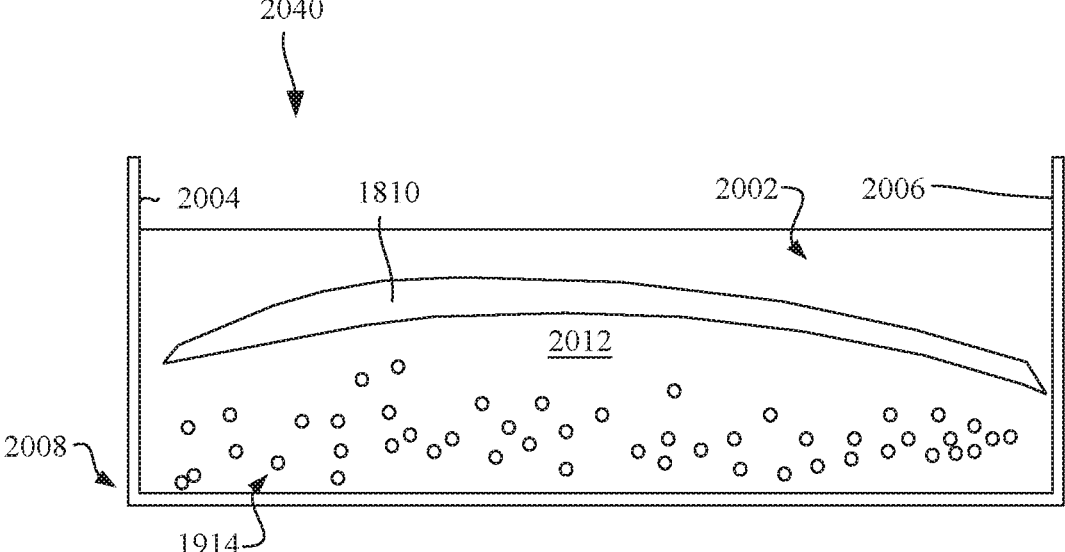
FIG. 20 illustrates a cross-sectional view of an example contact lens in solution, in accordance with the present disclosure.

FIG. 20 depicts an example of a contact lens 1810 in a storage container 2040 with an internal cavity 2002. The cavity 2002 is defined by a first wall 2004 and a second wall 2006 that are connected together at a lower surface 2008. A contact lens 1810 and a solution 2012 are also disposed within the cavity 2002.

The solution 2012 can include a cleansing agent, such as a hydrogen peroxide or another type of agent to clean the contact lens and kill bacteria, fungus, other types of germs, or combinations thereof. The solution 2012 can be an off-the-shelf type of storage solution that hydrates and cleans the contact lens. The storage solution 2012 can cause the biomarkers 1914 to dissolve into the solution 2012 thereby cleaning the contact lens 1810. The contact lens 1810 stays in the storage solution 2012 until the contact lens 1810 is later retrieved by the user for wearing. In some examples, the contact lens 1810 is immersed into the solution 2012 for a short period of time, such as a couple of minutes. In other examples, the contact lens 1810 can remain in the solution 2012 for multiple hours, such as overnight. With the biomarkers 1914 removed from the contact lens 1810, the biomarkers 1914 are in the solution 2012 where the biomarker types and their respective concentrations can be analyzed.

The biomarkers 1914 can be removed from the contact lens 1810 without adversely affecting the contact lens 1810. In those examples, the contact lens 1810 can be re-worn by the user. In some examples, the contact lens 1810 is removed from the solution 2012 so that the contact lens 1810 is not affected by the testing mechanism performed on the solution. In other examples, the contact lens 1810 remains in the solution 2012 while the solution 2012 is analyzed, but the analysis does not adversely affect the contact lens 1810 so that the contact lens 1810 can be re-worn by the user.

In some examples, the biomarkers 1914 can be analyzed in the storage container 2040. In other examples, the solution 2012 can be transferred to another type of device with a sensor for taking the measurements. In yet another example, a hand-held device can incorporate a sensor that can perform the analysis on the solution 2012.

Figure 21:
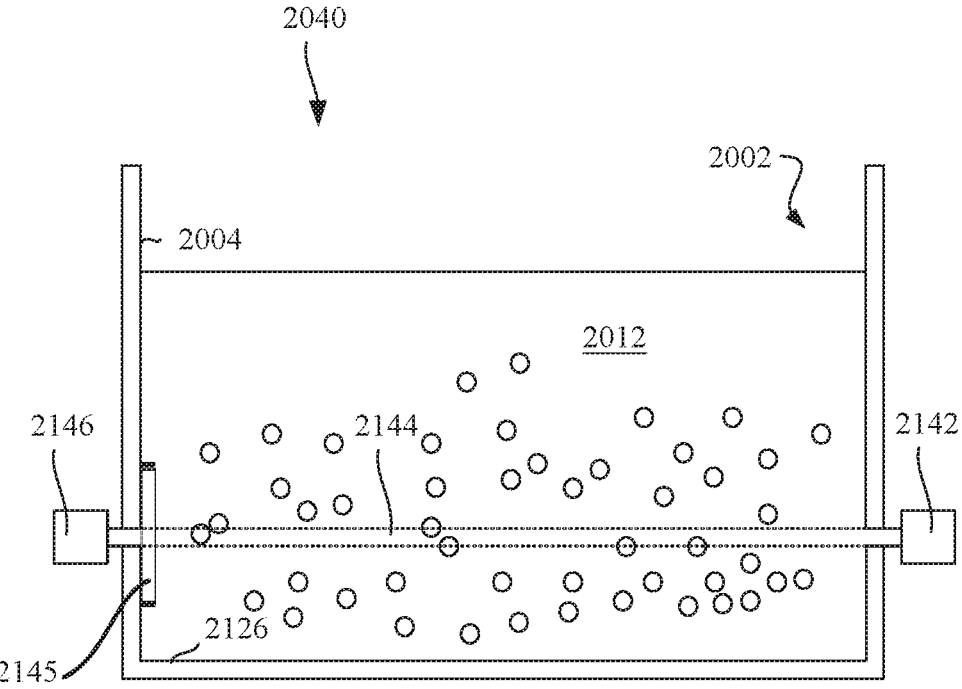
FIG. 21 illustrates a cross-sectional view of an example of running a test on the solution containing biomarkers from a contact lens, in accordance with the present disclosure.

One type of approach of analyzing the solution is depicted in FIG. 21. In this example, an optical spectral analyzer is a type of sensor that is incorporated into the storage container 2040. In the example of FIG. 21, a storage container 2040 for a contact lens 1810 includes a cavity 2002 that is defined by at least one wall 2004 that is connected by a floor 2126. In some examples, a single circular wall defines at least a portion of the cavity 2002. In other examples, multiple independent walls are joined together to define the cavity 2002.

A light transmitter 2142 is incorporated into a first side of the cavity. The light transmitter 2142 can transmit any appropriate type of light. In some examples, the light transmitter 2142 transmits an incandescent light, a fluorescent light, a halogen light, an infrared light, a visible light, an ultraviolet light, another type of light, or combinations thereof. The light transmitter 2142 can include a bulb, diode, or other source that can be turned on and off with a switch. The light transmitter 2142 can include one or multiple light sources. Light sources in the light transmitter 2142 can be configured to provide light at within a desired wavelength. For example, the light transmitter 2142 can include one or more light sources to transmit light having wavelengths in the ultraviolet region and the infrared region.

The light transmitter 2142 can be oriented to direct a beam 2144 of light through the solution 2012 to a light receiver 2146 or detector. As the beam 2144 of light is transmitted through the solution 2012, a portion of the light is absorbed by the solution 2012 depending on its contents. A solution with a different type of biomarker 1914 can have a different light transmittance through the solution 2012. Further, a solution 2012 with a different concentration of the same biomarker 1914 can also exhibit a different light transmittance.

In some examples, the light transmitter 2142 can have an ability to isolate a range of wavelengths to be transmitted independently through the solution 2012. The transmittance for each wavelength can be measured. Certain biomarkers in the solution 2012 may not affect the optical transmittance at a first wavelength, but can affect the optical transmittance at a second wavelength. Thus, by transmitting light at different wavelengths, a more refined measurement of the solution's composition can be measured. The measured transmittances at each wavelength can be compared to other solutions with known types and known amounts of biomarkers. Thus, the measured transmittance levels can be correlated to the types and concentration of the biomarkers 1914 in the solution 2012.

Other types of spectroscopic methods can be used to identify the types and concentration of the biomarkers in the solution. In some examples, measuring a frequency rather than a wavelength can be performed by the spectral analyzer. A non-exhaustive list of other types of spectroscopic mechanisms for analyzing the solution can include atomic absorption spectroscopy, attenuated total reflectance spectroscopy, electron paramagnetic spectroscopy, electron spectroscopy, Fourier transform spectroscopy, gamma-ray spectroscopy, infrared spectroscopy, laser spectroscopy, mass spectrometry multiplex or frequency-modulated spectroscopy, near-infrared (NIR) spectroscopy, Raman spectroscopy, ultraviolet spectroscopy, and x-ray spectroscopy.

The light receiver 2146 or detector also can correspond to the wavelength of light emitted by the light transmitter 2142. For example, a light transmitter 2142 transmitting infrared light can correspond to a light receiver configured to detect light at an infrared wavelength. In some embodiments, the light receiver 2146 is configured to detect light at multiple spectra, such as both ultraviolet and infrared. The light receiver 2146 can be configured to detect one or more of incandescent light, fluorescent light, halogen light, infrared light, visible light, ultraviolet light, another type of light, or combinations thereof.

While the example of FIG. 21 includes the light transmitter 2142 and the light receiver 2146 on different sides of the cavity walls, the light transmitter 2142 and the light receiver 2146 can be on the same side of the cavity 2002. In such an example, the light transmitter 2142 can cause a reflection of the light that was emitted from the light transmitter 2142 with the light receiver 2146.

In some embodiments, a microfluidic disposable strip 2145 also can be used in analyzing a solution 2012. The microfluidic disposable strip 2145 can be incorporated into or adhered to the body portion of the lens container. For example, in FIG. 21, a microfluidic disposable strip 2145 is positioned on the first wall 2004. In other embodiments, the microfluidic disposable strip 2145 can be positioned on the floor 2126, the second wall 2006, or elsewhere in body portion or the lid portion of the lens container. For example, a microfluidic disposable strip 2145 can be positioned anywhere on at least one of the body portion or the lid portion such the microfluidic disposable strip 2145 is at least partially immersed in lens solution in the cavity of the lens container. When the cavity 2002 is at least partially filled with a contact solution and the contact lens is in the standard position in the lens container, the microfluidic strip sensor 2145 continuously collects contact lens solution and solutes dissolved from worn contact lens.

Sensing of the microfluidic disposable strip can be performed using an immuno-based platform with colorimetric reading. For example, in some embodiments, the light transmitter 2142 and the light receiver 2146 include an ultraviolet spectrometer incorporated into the body portion of the lens container. The ultraviolet spectrometer can be used to quantitatively analyze a color change of a substrate on the microfluidic disposable strip 2145 to target specific antibodies on the microfluidic disposable strip 2145.

In some embodiments, sensing of the microfluidic disposable strip also can be performed in a fluorescent immuno-based platform associated with a fluorescent reader unit. The fluorescent immuno-based platform and fluorescent reader unit allow for prolonged measurement during contact lens immersion in contact lens solution in the lens container. Colorimetric evolution of the fluorescent sensing signal with time is directly related to the dissolution in the contact lens solution of biomarkers from the contact lens. These biomarkers can be related to ocular surface inflammation, such as one or more of cytokines, enzymes, immunoglobulins, peptides, and lipids. The time-dependent evolution of the fluorescent sensing signal can be sent in real time to a database and prediction platform for follow up. The database and prediction platform can send back analyses and prediction results to a user interface, such as incorporated user interface on the lens container or, at the request of the user, a user interface on a smartphone or tablet. The database also sends back analyses and prediction result when the contact lens is removed from the lens container or after a selected period of time.

The solution can be analyzed by the sensor automatically, responsive to user input, or both. For example, in some embodiments, the solution can be automatically analyzed by the sensor at predetermined intervals. The predetermined time intervals can begin once a contact lens and the solution have been deposited in the cavity and/or a lid portion of the lens container is secured to the body portion. Alternatively, the predetermined intervals can begin responsive to user input on the lens container or a device in communication with the sensor. In some embodiments, the solution can be analyzed only in response to user input, i.e. without automatic repeated intervals.

Figure 22:
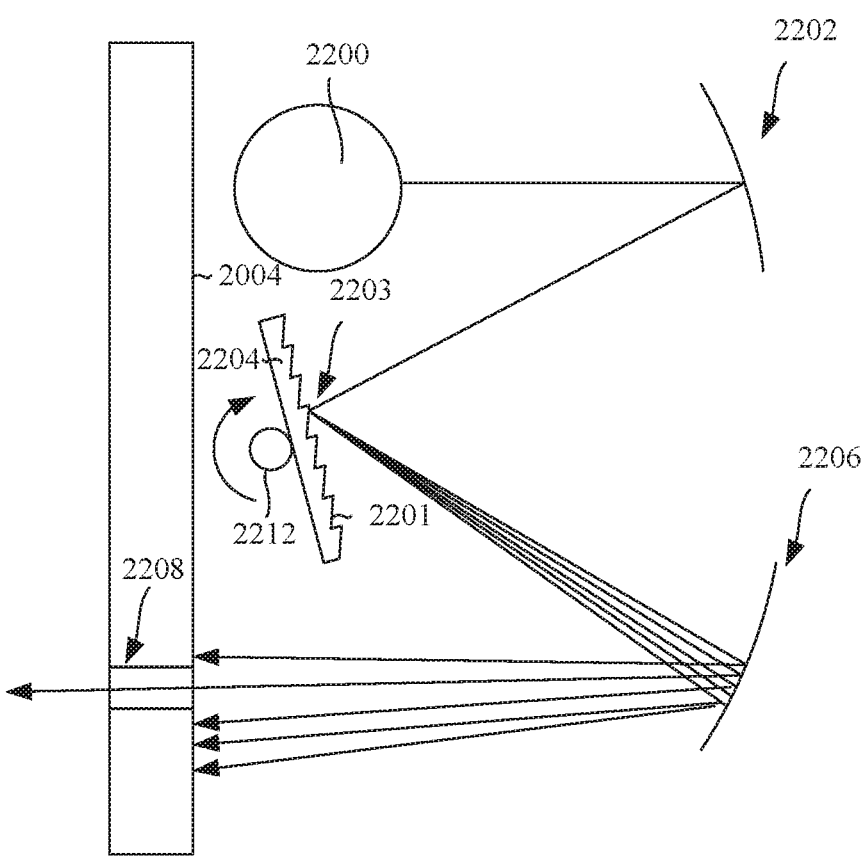
FIG. 22 illustrates a cross-sectional view of an example of a light transmitter, in accordance with the present disclosure.

FIG. 22 depicts an example of a light transmitter 2142. In this example, the light transmitter 2142 includes a light source 2200, a first mirror 2202, a diffraction grating 2204, a second mirror 2206, and a slit 2208 in the wall 2004 of the storage container 2040. In some examples, an optical window can be placed within the slit 2008. In some examples, these components of the light transmitter 2142 are located within the body portion of the storage container, the lid portion of the storage container, an attachment to the storage container 2040, or combinations thereof.

The light source 2200 can be any appropriate type of light source. In some examples, the light source is an incandescent light source, a fluorescent light source, a halogen light source, a light emitting diode light source, another type of light source, or combinations thereof. The light source can be encompassed within a blub, diode, or other source that can be turned on and off with a switch. In some examples, the light source can emit at least two different types of wavelengths. In some situations, the light source is an infrared light source, a visible light source, an ultraviolet light source, another type of light source, or combinations thereof.

The first mirror 2202 can be used to direct light from the light source 2200 to the diffraction grating 2204. In some examples, the first mirror 2202 is curved so that different wavelengths of light come into contact with the mirror at slightly different positions. With the wavelengths coming off the mirror at different positions, the wavelengths also come off the first mirror at slightly different angles, which assists in causing the wavelengths to separate.

The diffraction grating 2204 can be an optical component that splits light into several beams of different wavelengths in different directions. The directions of these beams depends on the spacing of the grating and the wavelength of the light. The diffraction grating 2204 can be a reflective grating or a transmissive grating. In the example of FIG. 22, the diffraction grating 2204 is a reflective grating that reflects the wavelengths in a way that causes the wavelengths to disperse. In this example, the diffraction grating 2204 has a plurality of ridges 2201 on its reflective surface 2203. The angle of each wavelength hits the reflective surface at a different location, and the angle of the diffraction grating separates the beams of different wavelengths farther apart. In other words, the diffraction grating 2204 is a dispersive element that causes the wavelengths to spread out even more. In other examples with transmissive gratings, the diffraction grating 2204 can be a prism that separates light into different wavelengths as the light passes through the thickness of the prism's material.

Figure 23:
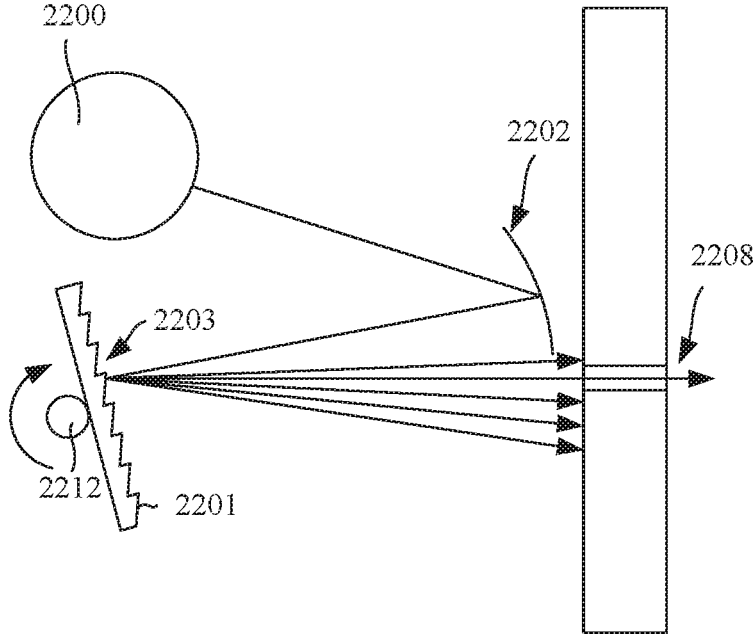
FIG. 23 illustrates a cross-sectional view of an example of a light transmitter, in accordance with the present disclosure.

In some examples, the diffraction grating 2204 is connected to a tilt mechanism 2212. In those examples, where the diffraction grating 2204 is connected to a tilt mechanism, the tilt mechanism 2212 can cause the diffraction grating 2204 to move to a different angle. This can cause the angle that the beams of different wavelengths come off of the diffraction grating 2204 to change. In some examples, a second mirror 2206 reflects the light beams off of the diffraction grating 2204 towards the slit 2208. In the example of FIG. 23, the diffraction grating 2204 directs the light directly to the slit 2208 without being directed through a second mirror.

The spacing of the light beams approaching the slit can be such that just a single beam of light can pass through the optical window at a time. Thus, just a single light beam is transmitted into the solution 2012 at a time. To cause another light beam of a different wavelength to be transmitted through the optical window, the tilt mechanism 2212 can cause the diffraction grating 2204 to move so that a different beam of a different wavelength is transmitted through the slit 2208.

While these examples have depicted light transmitters with specific components in specific arrangements, the light transmitters can include more or less components than those depicted and in different arrangements. Any appropriate type of light transmitter can be used in accordance with the principles described in the present disclosure.

Figure 24:
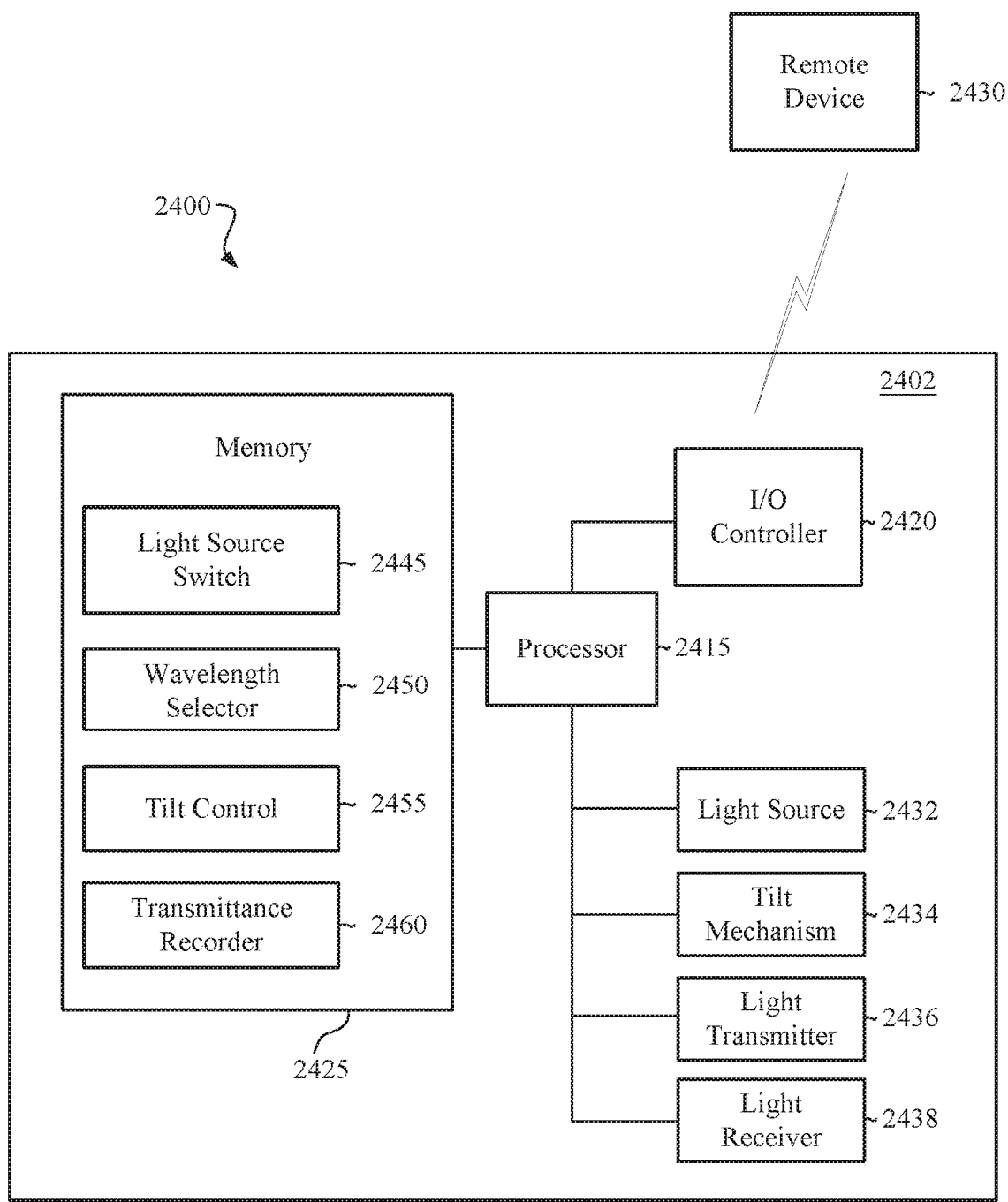
FIG. 24 illustrates a block diagram of an example of a health condition system, in accordance with the present disclosure.

FIG. 24 depicts a diagram of a health condition system 2400 incorporated into a contact lens container 2402. The system 2400 includes a processor 2415, an input-output (I/O) controller 2420, and memory 2425. The I/O controller 2420 can be in communication with a remote device 2430. The components of the system and the remote device 2430 can communicate wirelessly, through hard wired connections, or combinations thereof. In some examples, the contact lens container 2402 can include a transponder to communicate with the remove device 2430. Further, in some examples, the remove device 2430 can include a base station in communication with the transponder. In some examples, the remote device 2430 can be a data center. The memory 2425 of the system can include a light source switch 2445, wavelength selector 2450, a tilt control 2455, and a transmittance recorder 2460. The processor 2415 can also be in communication with a light source 2432, a tilt mechanism 2434, a light transmitter 2436, and a light receiver 2438.

The processor 2415 can include an intelligent hardware device, (e.g., a general-purpose processor, a digital signal processor (DSP), a central processing unit (CPU), a micro-controller, an application-specific integrated circuit (ASIC), a field-programmable gate array (FPGA), a programmable logic device, a discrete gate or transistor logic component, a discrete hardware component, or any combination thereof). In some examples, the processor 2415 can be configured to operate a memory array using a memory controller. In other examples, a memory controller can be integrated into the processor 2415. The processor 2415 can be configured to execute computer-readable instructions stored in a memory to perform various functions (e.g., functions or tasks supporting the evaluation of prescribed optical devices).

The I/O controller 2420 can represent or interact with a modem, a keyboard, a mouse, a touchscreen, or a similar device. In some examples, the I/O controller 2420 can be implemented as part of the processor. In some examples, a user can interact with the system via the I/O controller 2420 or via hardware components controlled by the I/O controller 2420. The I/O controller 2420 can be in communication with any appropriate input and any appropriate output.

The memory 2425 can include random access memory (RAM) and read only memory (ROM). The memory 2425 can store computer-readable, computer-executable software including instructions that, when executed, cause the processor to perform various functions described herein. In some examples, the memory 2425 can contain, among other things, a basic input/output system (BIOS) which can control basic hardware and/or software operation such as the interaction with peripheral components or devices.

The light source switch 2445 represents programmed instructions that cause the processor 2415 to switch the light source on or off. In some examples, the light source switch 2445 can block or unblock a light source 2432 that is continuously emitting light. The light source 2432 can automatically illuminate when a light portion is combined with the body portion of the contact lens container 2402. In other examples, the light source switch 2445 causes the light source 2432 to illuminate when instructed to do so. The instructions to illuminate can come from the user interface, a remote device, another type of device, or combinations thereof.

The wavelength selector 2450 represents programmed instructions that cause the processor 2415 to select a desired wavelength of light to be transmitted through the contact lens solution. In some examples, in response to the contact lens container being instructed to analyze the contact lens solution, the wavelength selector is programmed to automatically cause the processor to start from one end of the light spectrum to the other end. In this example, the wavelength selector can sequentially test each wavelength in a consistent manner. In other examples, the wavelength selector causes only certain types of wavelengths to be tested. In situations where the contact lens solution is being tested for only a particular type of characteristic or certain types of biomarkers, at least some of the wavelengths can be omitted from the analysis. In some examples, a certain wavelength can alter or adversely affect a particular biomarker making the biomarker difficult to identify later in the analysis. In these situations, certain wavelengths can be omitted from the analysis.

The tilt control 2455 represents programmed instructions that cause the processor 2415 to control the tilt mechanism that is connected to the diffraction grating. The angle at which the diffraction grating is positioned can determine which of the wavelengths is transmitted into the solution. In some examples, the wavelength selector communicates with the tilt control to cause the appropriate wavelength to be transmitted into the solution.

The transmittance recorder 2460 represents programmed instructions that cause the processor 2415 to record the transmittance of the beam transmitted into the solution. In some examples, multiple beams of different transmittances are separately transmitted into the solution, and the transmittance recorder can record a transmittance for each of the wavelengths. In some examples, the transmittance recorder is in communication with the receiver that receives the light beams. In some situations, the recorder collects the transmittance strength with time stamps and the wavelengths transmitted through the solution are also timestamped. In these situations, the wavelengths transmitted can be compared to the recorded transmittance strengths based on matching times.

Correlations between certain biomarkers and their respective concentrations can go unobserved on one-on-one analysis with each of the patients. However, with such a large sample size, correlations that have been previously unobserved can be detected, for example via data mining techniques used by the system. For example, an analysis can be run on all the biomarker characteristics of users with a specific health conditions. Such an analysis can reveal that a certain biomarkers that had not previously been linked to that health condition has a statistically significant normal concentration level, a statistically significant low concentration level, a statistically significant high concentration level, another statistically significant concentration level, a statistically insignificant type of concentration level, or combinations thereof that had not previously been observed. These correlations can help identify health conditions that can go otherwise unobserved in a patient. Even in those events where the user's health condition can be eventually diagnosed properly, comparing the obtained biomarker characteristics with the information stored in the database can result in a quicker diagnosis.

FIG. 25 depicts an example of a database 2500 that associates a characteristic of the tear chemistry, potential indications, and possible causes of the tear chemistry. In this example, the database 2500 includes a first column 2502 that represents the tear chemistry, a second column 2504 that represents the potential indications, and a third column 2506 that represents the possible causes of the tear chemistry. The database 2500 can include a first row 2508 that includes the correlation for a tear chemistry with a normal lactoferrin level and a normal IgE level, a second row 2510 that includes the correlation for a tear chemistry with a normal lactoferrin level and a high IgE level, a third row 2512 that includes the correlation for a tear chemistry with a low lactoferrin level and a normal IgE level, a fourth row 2514 that includes the correlation for a tear chemistry with a low lactoferrin level, a fifth row 2516 that includes the correlation for a tear chemistry with a high lactoferrin level, and a sixth row 2518 that includes the correlation for a tear chemistry with a high IgE level.

While the example of FIG. 25 depicts an example with the correlations of specific types of biomarkers, any appropriate type of correlation can be included in the database. In some instances, the characteristics correlated with a single biomarker can be included as depicted in rows 2514, 2516, 2518. In other instances, the characteristics correlated with a specific set of biomarkers can be included. For example, the health conditions correlated with two or more characteristics of different types of biomarkers can be included as depicted in rows 2508, 2510, 2512. Any appropriate number of biomarker characteristics can be included. For example, one, or alternatively, hundreds of characteristics can be collectively correlated to a specific type of health condition. Further, while the example of FIG. 25 includes specific types of biomarkers, the database can include any appropriate type of biomarker correlations.

Figure 26:
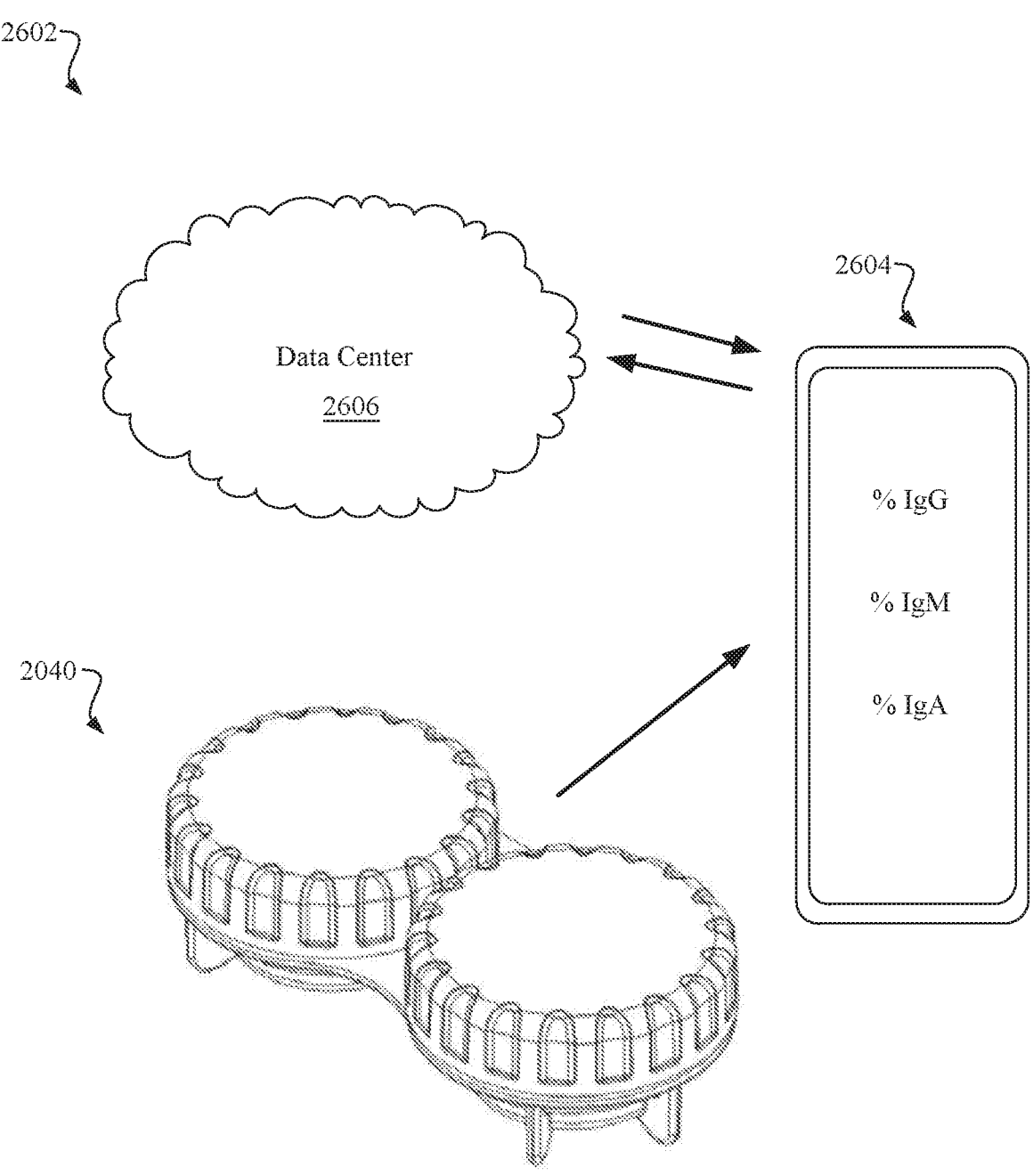
FIG. 26 illustrates a view of an example of a health condition system, in accordance with the present disclosure.

FIG. 26 depicts an example of a system 2602 of determining the health condition of a user. In this example, a storage solution can be contained within a contact lens container 2040. The contact lens container 2040 can be in wireless communication with a mobile device 2604. The mobile device 2604 can relay the recorded levels to the database in the data center 2606, which can send the correlations back to the mobile device 2604. The mobile device 2604 can present the results from the hand-held device and/or the correlations from the database in a user-interface of the mobile device 2604.

At least some of the processing of the measurements obtained from the return signals from the storage solution can occur at the contact lens container 2040, the mobile device 2604, and/or the data center 2606. In some examples, the mobile device 2604 includes a program that retrieves the correlations from the database and performs additional tasks. For example, the mobile device 2604 can retrieve information about the health condition from another source other than the database in response to receiving the health condition from the database. Another additional task that the mobile device 2604 can perform in response to receiving the health condition is to retrieve a health professional's contact information, consult a user's calendar to set up an appointment with the health professional, schedule an appointment with the health professional, perform another task, or combinations thereof.

FIG. 27 illustrates an example of a method 2700 of determining a health condition. In this example, the method 2700 includes sending 2702 information about biomarkers from a contact lens container to a computing device.

At block 2702, information about the biomarkers is sent from the contact lens container to a computing device. The information can be sent to any appropriate computing device. In some examples, the computing device is a laptop, a desktop, a mobile device, a smart phone, an electronic tablet, a digital device, a remote device, a networked device, another type of device, or combinations thereof.

In some examples, the biomarkers remain on the contact lens when the biomarkers are being analyzed. In other examples, the biomarkers are removed from the contact lens before the analysis. The characteristic can include a type of biomarker, a concentration of biomarker, a location of the biomarker on the contact lens, another type of characteristic, or combinations thereof. The characteristic can involve a single biomarker. In other examples, the characteristic includes the collective condition of multiple biomarkers.

FIG. 28 illustrates an example of a method 2800 of obtaining a biomarker characteristic. In this example, the method 2800 includes transmitting 2802 a first wavelength of light through a contact lens solution within the contact lens container, obtaining 2804 a first optical transmittance measurement of the first wavelength through the contact lens solution, transmitting 2806 a second wavelength of light through a contact lens solution by moving the diffraction grating with the tilt mechanism, and obtaining 2808 a second optical transmittance measurement of the second wavelength through the contact lens solution.

In some examples, the contact lens solution includes hyaluronan, sulfobetaine, poloxamine, boric acid, sodium borate, ascorbic acid, edetate disodium, sodium chloride, hydroxyalkyl phosphate, poloxamer, sodium phosphate buffer, polyoxyethylene polyoxypropylene block copolymer with ethylene diamine, and polyaminopropyl biguanide, or combinations thereof. The contact lens can include a disinfectant, a surfactant, an anti-fungal agent, an anti-bacterial agent, another type of agent, or combinations thereof.

The removal of the biomarkers from the contact lens into the solution can occur over any appropriate time period. In some examples, the biomarkers are in the solution for at least one minute, at least five minutes, at least 20 minutes, at least 45 minutes, at least an hour, at least two hours, at least 5 hours, at least 7 hours, at least one day, at least two days, another appropriate time period, or combinations thereof.

In some examples, the contact lens is free of surface cavities that are constructed to be binding sites for biomarkers or to draw in tear fluid into the contact lens. In some examples, the contact lens is free of surface treatments that target the binding of specific biomarkers to the contact lens.

In some situations, the storage solution includes binding agents that are configured to facilitate the bonding between a surface of the contact lens and a biomarker from the tear fluid. In other examples, no binding agents are introduced to the contact lens solution. The contact lens can include a surface where the biomarkers are as likely to bind to any surface of the contact lens as any other surface of the contact lens. In some examples, the biomarkers can attach to the optical zone of the contact lens, a peripheral zone of the contact lens, an edge of the contact lens, a posterior side of the contact lens, an anterior side of the contact lens, another area of the contact lens, or combinations thereof.

The contact lens can be made through any appropriate manufacturing method. In some examples, the contact lenses are molded into their shape. In other examples, the contact lenses are machined to their precise shape. In yet other examples, the contact lens are cast molded or spin cast. Spin cast contact lenses can make a continuous surface on the posterior side of the contact lens that matches a profile constructed to assist the user with his or her vision. The front side of the contact lens during a spin casting procedure can include a profile that matches a contact lens mold. The contact lens mold can include a continuous, curved surface without interruptions. In some examples, the spin cast contacts lens provide for a continuous surface that is substantially free of interruptions, such as micro-cavities. In some examples, having a continuous, interruption free surface on both the anterior side and the posterior side can prevent the collection of tear fluid in the contact lens. Avoiding the collection of tear fluid can prevent the contact lens from having an additional amount of weight. Further, when the contact lens is introduced into the solution, a substantial amount of tear fluid may not mix with the contact lens solution, which can skew the volume of fluid in being analyzed and affect the concentration analyses. In some examples where tear fluid is not collected, just the biomarkers can be carried with the contact lens into the solution. Thus, the analysis does not have to be adjusted to accommodate an increase in fluid. However, in some examples, the amount of fluid being analyzed may not require a precise amount of fluid. In one example, the contact lens container can include a fill line and the measurements performed by the sensor can be adequate enough if the solution is close to being at the fill line, but not required to be precisely at the fill line. Further, by not modifying the contact lens to have an enhanced ability to collect specific biomarkers, the concentrations of the biomarkers that bind to the contact lens can be more reflective of the actual concentration of that biomarker in the tear fluid. An enhanced ability to collect a particular biomarker or a wide variety of biomarkers can cause a disproportionate amount of that biomarker to bind to the contact lens, which can skew the measurement levels made when analyzing the solution and potentially lead to an inaccurate characterization of the biomarker's actual concentration.

FIG. 29-34 illustrate various contact lens containers, according to the present exemplary teachings. Each of the contact lens containers can include the elements disclosed in connection with FIG. 24, including a processor, memory, and I/O controller, and the like.

FIG. 29 depicts an example of a contact lens container 2040. In this example, the container 2040 includes a body portion 2900 and a lid portion 2902. The lid portion 2902 can interlock with the body portion 2900. In the illustrated example, the lid portion 2902 can threadably interlock with the body portion 2900.

Figure 30:
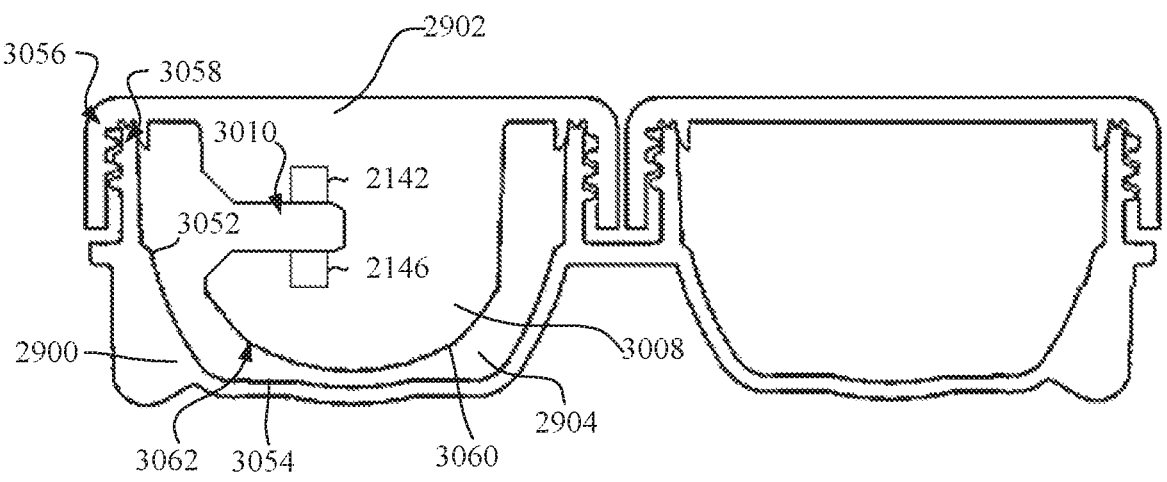
FIG. 30 illustrates an example of a contact lens storage container, in accordance with the present disclosure.

The body portion 2900 can have a substantially flat undersurface 2950 that provides stability to the container 2040 when resting on a support surface, such as a counter top or sink surface. In other examples, the body portion 2900 includes a plurality of legs that stabilize the body portion 2900 in an upright orientation. In the upright position, the contact lens container 2040 is oriented so that the storage solution pools in the bottom of the cavity and away from the threaded portions or other connection mechanisms that secure the lid portion 2902 to the body portion 2900. The body portion 2900 can also include an inner wall (FIG. 30, 3052) that is connected to a floor (FIG. 30, 3054). The inner wall 3052 and the floor 3054 collectively define the cavity. The cavity can be configured to receive a volume of contact lens storage solution. A contact lens can be inserted into the cavity into the storage solution for a desired period of time, such as overnight, until the user decides to reinsert the contact lens back into the user's eye.

The body portion 2900 can include a first cavity 2904 and a second cavity 2906. Since a user generally wears a separate contact lens in each of his eyes, the contact lens container 2040 can include the first cavity 2904 for the first contact lens and the second cavity 2906 for the second contact lens. A sensor can be incorporated into each of the cavities or just one of the cavities. In some examples, the biomarker profile of one of the user's eyes can be similar or the same to the biomarker profile of the other eye. In these examples, testing the biomarkers of one eye can be sufficient to understand the user's tear's chemistry. However, in other examples, testing each of the eye's tear fluid can help identify profiles that may not be realized when testing just a single eye.

Any appropriate type of storage solution can be used in connection with the principles disclosed herein. In some examples, the storage solution includes a disinfectant that kills bacteria, viruses, fungus, germs, enzymes, undesirable organisms, or combinations thereof that are on the contact lens. In some examples, the storage solution also prevents a protein build-up, a lipid build-up, a debris build-up, or other type of build-up on the contact lens. Further, the storage solution can include ingredients that improve wettability and comfort of silicon hydrogel contact lenses or other types of contact lens. In some examples, the storage solution includes a saline solution, a hydrogen peroxide solution, another type of solution, or combinations thereof.

The contact lens container 2040 can be formed through any appropriate mechanism. In some examples, the contact lens container 2040 is injection molded using synthetic resins, such as polypropylene (PP), polyethylene (PE), polystyrene (PS), polycarbonate (PC), polyethylene terephthalate (PET), acrylonitrile butadiene styrene copolymer (ABS), propylene ethylenic copolymer, or combinations thereof. In other examples, the contact lens container 2040 can be casted, machined, or otherwise formed. In some examples, the lid portion 2902 is made of the same materials as the body portion 2900.

In some examples, the body portion 2900 includes a first thread portion (FIG. 30, 3056), and the lid portion 2902 includes a second thread portion (FIG. 30, 3058). In some examples, the first thread portion 3056 is an outer thread portion, and the second thread portion 3058 is an inner thread portion. However, in other examples, the first thread portion 3056 is an inner thread portion, and the second thread portion 3058 is an outer thread portion. The first thread portion 3056 and the second thread portion 3058 can be threadably connected to one another. With the lid portion 2902 secured to the body portion 2900 through the threaded portions, the lid portion 2902 closes off the cavity.

While these examples have been described with reference to the contact lens container 2040 having the lid portion 2902 and the body portion 2900 connected through complementary threaded portions, the lid portion 2902 and the body portion 2900 can be connected through any appropriate mechanism. For example, the lid portion 2902 and the body portion 2900 can be secured together through a snap connection, a compression fit connection, a hinged connection, another type of connection, or combinations thereof. In some examples, the connection is water tight to prevent the storage solution from leaking out of the cavity when the contact lens container 2040 is oriented on its side or is oriented upside-down.

Figure 31:
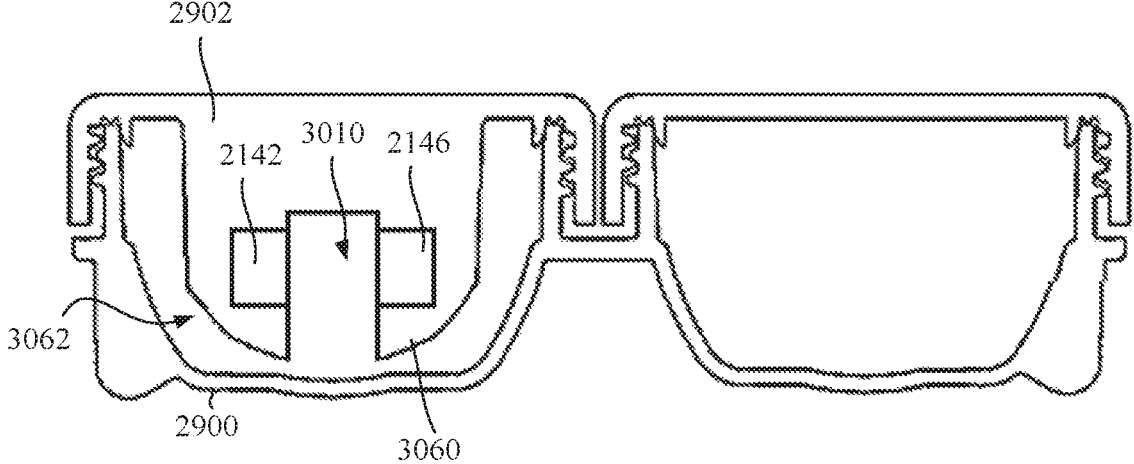
FIG. 31 illustrates an example of a contact lens storage container, in accordance with the present disclosure.

FIGS. 30 and 31 depict examples of a sensor incorporated into a lid portion 2902. In these examples, the lid portion 2902 includes a protrusion 3008 that protrudes into a volume of the first cavity 2904. The protrusion 3008 can have a cross-sectional thickness that is less than the cross-sectional thickness of the cavity thereby allowing fluid to move within the space between the surface of the cavity's walls and the surface of the protrusions 3008. The protrusions can also be sized to pin the contact lens to the bottom of the cavity or at least cause the contact lens to be located between the bottom of the cavity and a distal end of the protrusion 3008.

The protrusion 3008 can be connected to the lid portion 2902. The protrusion 3008 can extend farther away from the lid portion 2902 than the second threaded portion. The protrusion 3008 can include a distal end 3060, and the distal end 3060 can include a curved surface 3062.

In some examples, a center portion of the contact lens comes into contact with a central portion of the floor 3054 of the cavity. In those examples where a gap between the floor 3054 and the distal end 3060 of the protrusion 3008 are smaller than the sagittal depth of the contact lens, the protrusion 3008 and the floor 3054 can collective impose a compressive load on the contact lens that assists in keeping the contact lens up against the curved surface 3062. However, due to the curvature of the distal end 3060, the gap can progressively increase from the central portion of the floor 3054 towards the edge of the curved surface 3062. In such circumstances, the contact lens can otherwise be prone to dislodging from the curved surface 3062 if the contact lens were positioned off center on the curved surface 3062.

The protrusion 3008 can cause the contact lens to be located in a space within the cavity's volume that is away from a light beam that can be transmitted by the sensor. In other words, the protrusion 3008 can assist in locating the contact lens in a region of the cavity, so that the contact lens is less likely to interfere with the measurements taken in the contact lens solution.

A channel 3010 can be defined in the protrusion 3008 that is sized to allow a portion of the contact lens solution to enter within a volume defined by the channel 3010. The light transmitter 2142 and the light receiver 2146 can be located proximate to the channel 3010 so that they can test the contact lens solution that is located in the channel 3010. In the example of FIG. 30, the channel 3010 is defined in the side wall of the protrusion 3008, and in FIG. 31, the channel 3010 is formed in the distal end 3060 of the protrusion 3008. In the example of FIG. 31, to avoid trapping air within the channel 3010 as the protrusion 3008 comes into the contact lens solution, a vent hole (not shown) can connect the channel to the surface of the protrusion's wall.

Figure 32:
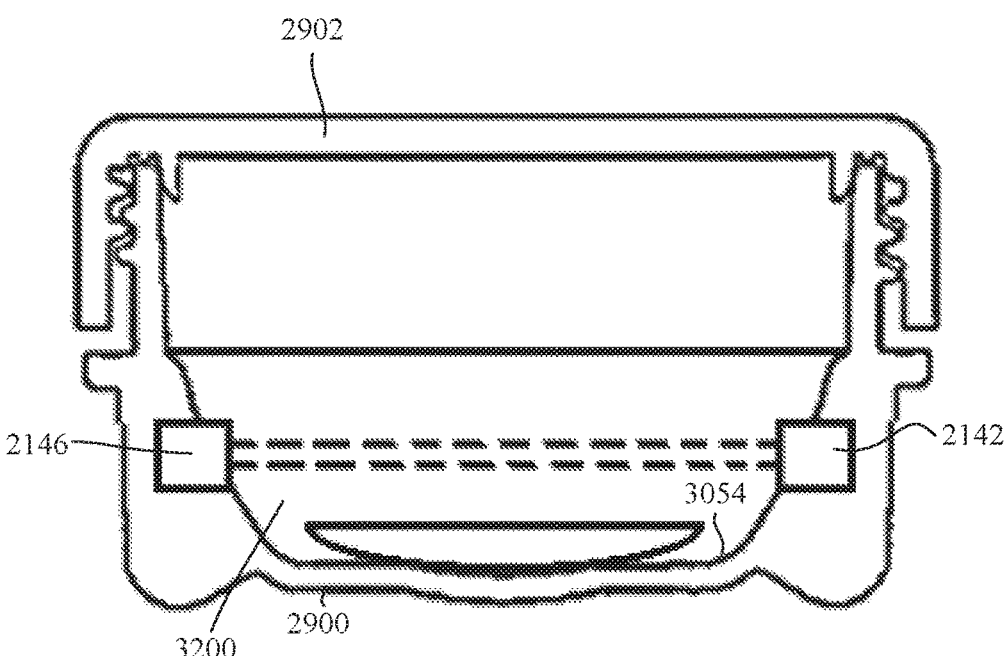
FIG. 32 illustrates an example of a contact lens storage container, in accordance with the present disclosure.

FIG. 32 depicts an example of a cavity 3200 within the body portion 2900 that has a light receiver and a light transmitter 2142 located at a distance from the floor 3054 of the cavity that is far enough away so that when the contact lens settles at the bottom of the cavity, the contact lens is located below a space where the light beam is transmitted.

Figure 33:
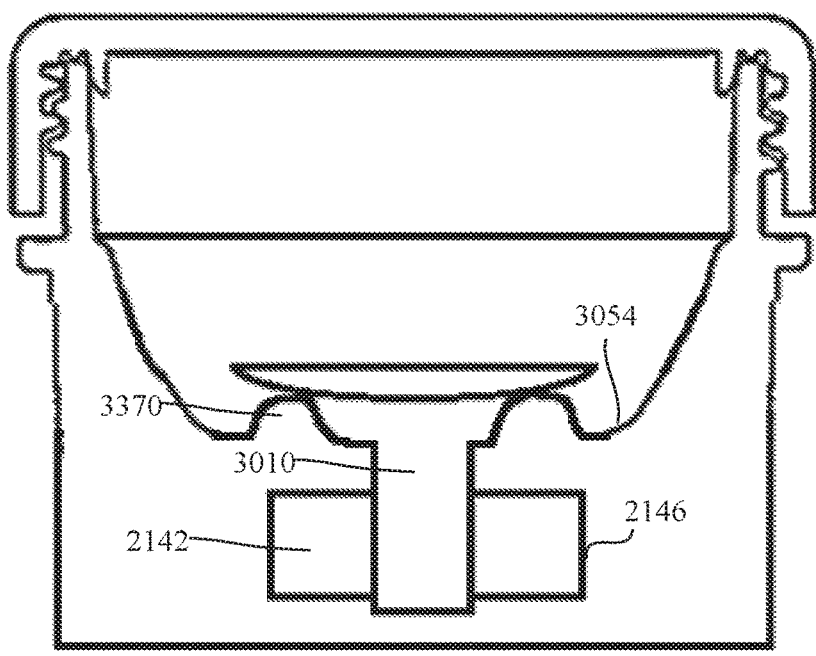
FIG. 33 illustrates an example of a contact lens storage container, in accordance with the present disclosure.

FIG. 33 depicts an example of the channel 3010 defined in the floor 3054 and the associated light transmitter 2142 and receiver 2146 are adjacent to the channel 3010 where the solution can be analyzed. In the illustrated examples, risers 3370 protrude from off of the floor 3054 to space the contact lens off of the floor 3054. The risers 3370 are spaced so that the storage solution can pass around the risers 3370. Thus, the risers 3370 prevent the contact lens from blocking the solution from entering into the channel 3010.

Figure 34:
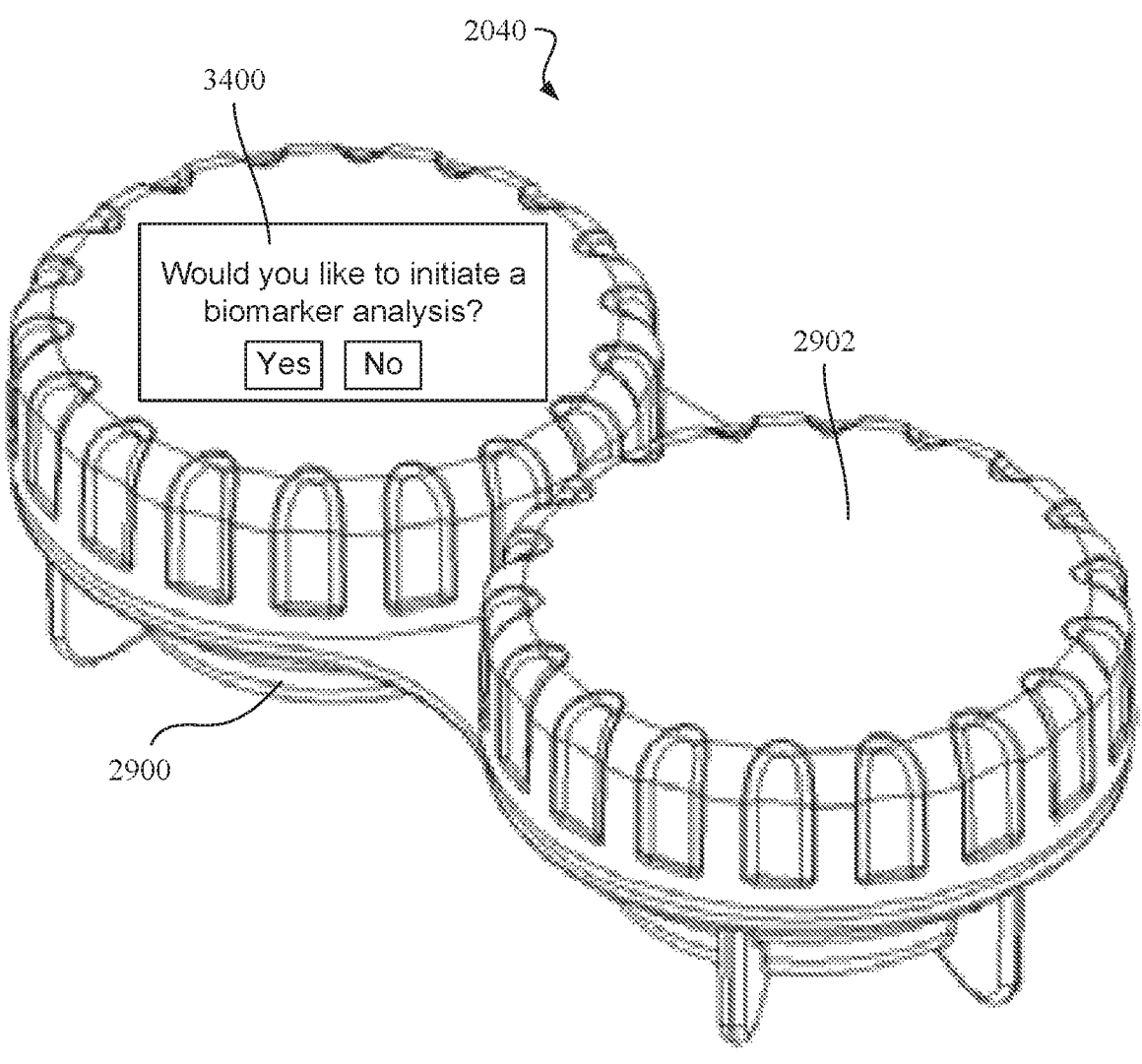
FIG. 34 illustrates an example of a contact lens storage container, in accordance with the present disclosure.

FIG. 34 depicts an example of a contact lens container 2040 with a user interface 3400. The user interface 3400 can be used to present messages to the user or present options to the user. The user can also use the user interface 3400 to give instructions to the contact lens container 2040. In other examples, the user interface is incorporated into a device that is in communication with the contact lens container 2040. For example, the contact lens container 2040 can be in wireless communication with a mobile device, and the user interface of the mobile device can operate as an interface between the container and the user. In other examples, the user interface can be hardwired to the container 2040. A non-exhaustive list of devices that can be in communication with the container and provide a user interface include, but are not limited to, a mobile device, a smart phone, an electronic tablet, a laptop, a desktop, a computing device, a networked device, another type of device, or combinations thereof.

While the example of FIG. 34 depicts the user incorporated into the lid portion 2902 of the container 2040, the user interface 3400 can be incorporated into any appropriate portion of the container 2040. For example, the user interface 3400 can be incorporated into the body portion 2900, the side of the container, the undersurface of the container, another portion of the container, or combinations thereof.

Examples of messages that can be presented to the user include the results of the analysis, an option to initiate the analysis, a request to change batteries, a request to replace the storage solution, a schedule of when the analysis is to be performed, an option to test for specific health conditions, a request to tighten the lid portion, a request to replace a light source or another component of the container, a request to insert the contact lens, a request for permission to send the results of a test to remote device, another type of message, or combinations thereof.

Examples of instructions that the user can communicate to the container through the user interface includes initiating a test, restricting the testing to specific types of conditions, limiting the range of wavelengths, setting a time to cause a test to be run, sending the test results to a remote device, to discontinue a test, to not perform a test, another type of instructions, or combinations thereof.

EXAMPLE

Example 1

In one example, one or more protein biomarkers previously deposited on a contact lens were detected using near-infrared spectroscopy. The sensor included a near-infrared spectrometer having a light transmitter and a light receiver incorporated into a body of a lens container. The light transmitter (or radiation source) is positioned in the body of the lens container to direct light substantially perpendicular to a contact lens when the contact lens is stored in the standard position in the lens container during overnight removal. The contact lens container lid portion is closed when the light transmitter is transmitting the light, thus containing the light within the lens container.

The light transmitter provides light having a wavelength in the region of 900 nm to 2500 nm. For example, the light transmitter can provide light having a wavelength in a narrower selected region of 1300 nm to 1600 nm, including a first overtone of water. The light transmitter can repeatedly emit a spectra in response to a user request. Additionally or alternatively, the light transmitter can be programmed to automatically repeat emission of a spectra of light from the light transmitter. For example, spectral analysis can be performed every hour after the contact lens is inserted into the lens container and the container lid portion is closed. Spectral analysis can be performed 1 hour after the contact lens is inserted into the lens container, 2 hours after the contact lens is inserted into the lens container, and/or after overnight incubation in the contact lens solution in the lens container. Spectral analysis can be initiated using a button or actuator on the lid portion. Spectral analysis also can be initiated wirelessly via a user interface on a smartphone or tablet. Results of the spectral analysis are temporarily stored in the memory unit and analyzed in the processing units incorporated into the body portion.

Once processed, the spectral results are sent wirelessly to a database. Special algorithms developed for ocular health condition prediction will analyze data of the spectral results and compare the spectral results with the health database of the patient. A database and computing platform send back an analysis and prediction results to a user interface such as the user interface on a smartphone or tablet.

Example 2

In another example, one or more biomarkers previously deposited on a contact lens are detected using a microfluidic disposable strip. The microfluidic disposable strip is incorporated into the body portion of the lens container. For example, the microfluidic disposable strip is incorporated into either the wall or into the floor defining the cavity of the lens container. When the cavity is at least partially filled with a contact solution and the contact lens is in the standard position in the lens container, the microfluidic strip sensor continuously collects contact lens solution and solutes dissolved from worn contact lens.

Sensing of the microfluidic disposable strip is performed in an immuno-based platform with colorimetric reading. An ultraviolet spectrometer incorporated into the body of the lens container can be used to quantitatively analyze a color change of a substrate on the microfluidic disposable strip to target specific antibodies on the microfluidic disposable strip.

Sensing of the microfluidic disposable strip also is performed in a fluorescent immuno-based platform associated with a fluorescent reader unit. The fluorescent immuno-based platform and fluorescent reader unit allow for prolonged measurement during contact lens immersion in contact lens solution in the lens container. Colorimetric evolution of the fluorescent sensing signal with time is directly related to the dissolution in the contact lens solution of biomarkers from the contact lens. These biomarkers can be related to ocular surface inflammation, such as one or more of cytokines, enzymes, immunoglobulins, peptides, and lipids. The time-dependent evolution of the fluorescent sensing signal is sent in real time to a database and prediction platform for follow up.

The database and prediction platform send back analyses and prediction results to a user interface, such as incorporated user interface on the lens container or, at the request of the user, a user interface on a smartphone or tablet. The database also sends back analyses and prediction result when the contact lens is removed from the lens container or after a selected period of time.

Example 3

In another example, various dilutions of glucose water were analyzed to demonstrate detection of exemplary particles in a solution. Sample solutions were prepared having the following concentrations: pure water, 1 gram glucose per liter of water, 5 grams glucose per liter of water, 10 grams glucose per liter of water, 50 grams glucose per liter of water, and 100 grams glucose per liter of water.

For each measurement, several drops of the sample solution were placed on a diamond crystal sample plate. Infrared absorbance at 400-4000 cm-1 of each of the samples was measured with a Thermo Scientific Nicolet 8700 FT-IR spectrometer, based on the following measurement conditions: attenuated total reflectance (ATR) reflection measurement method; diamond crystal sample plate; 256 seconds measurement time; approximately 1.9 cm-1 measurement interval; approximately 4 cm-1 resolution; and atmospherically and background corrected by ATR.

Figure 35:
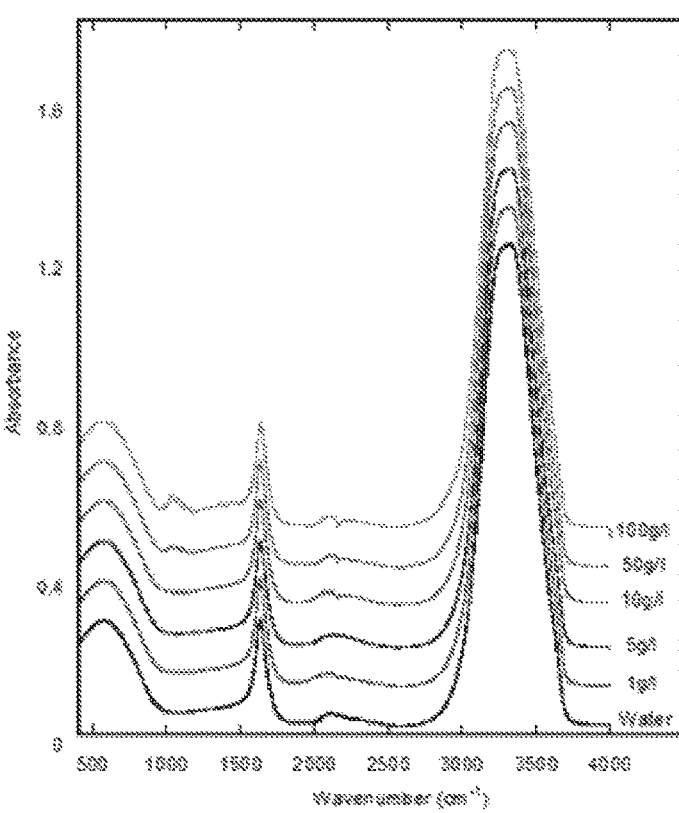
FIG. 35-37 illustrate infrared absorbance of glucose solution samples at various wavelengths, in accordance with the present disclosure.
Figure 36:
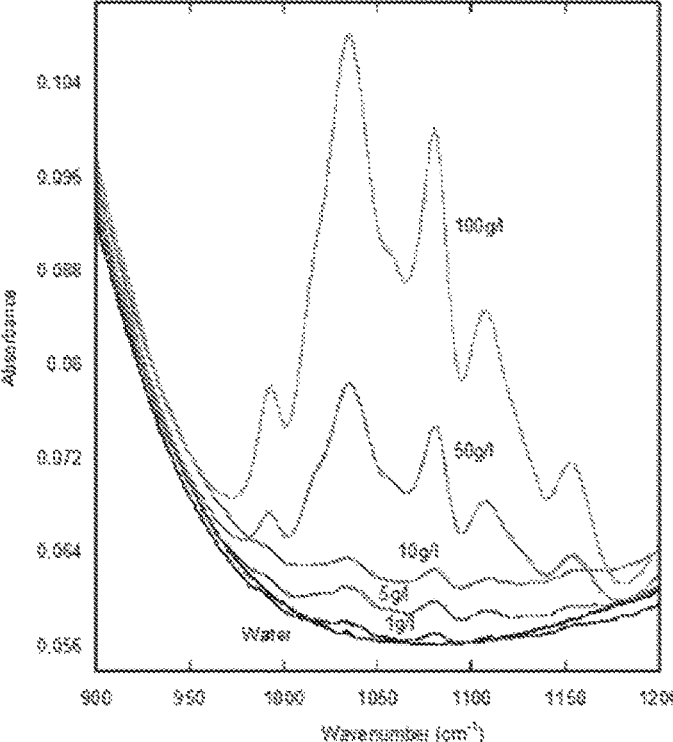
Figures 37, 38:
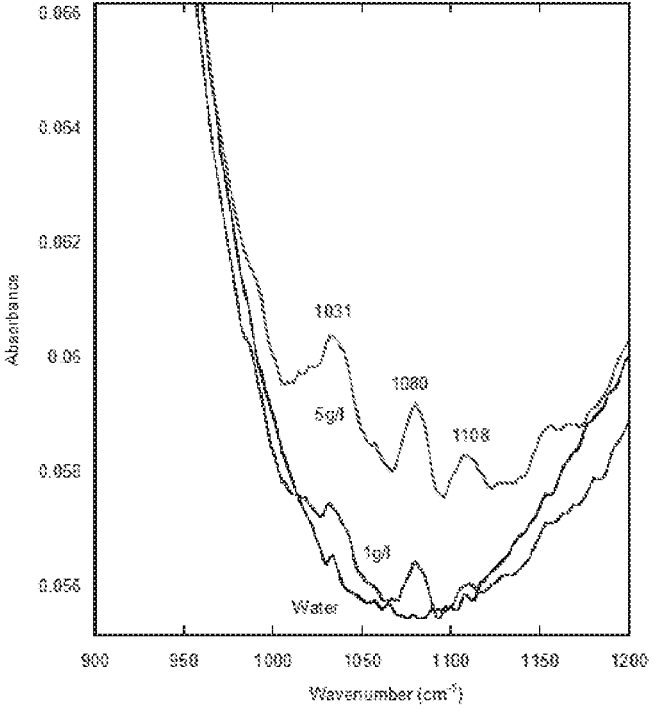
FIG. 38 illustrates a calibration curve of glucose, in accordance with the present disclosure.

FIG. 35 is a graph showing infrared absorbance from 400 to 4000 cm-1 of the six samples. In the graph of FIG. 35, a first region from approximately 900 to 1200 cm-1 and a second region from approximately 2000 to 2300 cm-1 demonstrate concentration-dependent regions among the six sample. The first region and the second region, then, are likely regions specific to the glucose molecule. FIG. 36 is a graph showing infrared absorbance in the first region referenced above, from 900 to 1200 cm-1, of the six samples. FIG. 36 demonstrates that the spectra change depends on the concentration of glucose. FIG. 37 is a more detailed graph showing infrared absorbance in the first region referenced above, from 900-1200 cm-1, of the lower concentration samples of pure water, 1 gram glucose per liter of water, and 5 grams glucose per liter of water. Peaks are shown in FIG. 37 at 1031 cm-1, 1080 cm-1, and 1108 cm-1. A calibration curve, then, can be set at 1080 cm-1 for estimation of glucose concentration in a sample. FIG. 38 shows a calibration curving using an absorbance of 1080 cm-1, which can be used to provide the concentration of a new sample when absorbance of the new sample is provided.

Data Analysis

According to another aspect of the present disclosure, the system for collecting and utilizing health data can categorize, analyze, manipulate, or otherwise process vast quantities of data. The data can be collected using a smart contact lens system, a smart contact lens container, public health records, patient health records, other record sources, or a combination thereof. The data can be organized as a database. The database can be configured on a computer readable storage medium (e.g., non-volatile random access memory) and maintained using a plurality of servers, for example, within a data center or server farm. In some embodiments, the data can be transferred from a data source to the database via a cloud computing network.

The data stored within the database can be analyzed, manipulated, or otherwise processed to deduce relationships, commonalities, patterns, correlations, or other underlying characteristics of the data. Data processing algorithms can be utilized to process the data. These algorithms can include learning algorithms, predictive models, data correlation models, clustering models, any other appropriate computational techniques, and combinations thereof. In some examples, the algorithms applied to the collected data can also include support vector machines, neural networks, decision trees, gaussian mixture models, hidden markov methods, and wavelet analysis. Similarly, models can be applied to the data. These models can include anomaly detection models, clustering models, classification models, regressions models or summarization models. Modern data mining processes, machine learning, and artificial intelligence can also be used to process the data.

Consequently, processing the data can result in the discovery of informative and meaningful relationships, trends, correlations, patterns, subsets, and clusters within the data. Such information can be used to provide information to a user or physician relative to the user's predicted health or a healthcare recommendation, as discussed in greater detail below.

System Utilization

According to another aspect of the present disclosure, the system for collecting and utilizing health data can output information relative to comparisons, correlations, trends, or other characteristics derived from the data. For example, the system can be utilized to detect or otherwise predict that a patient has contacted a particular disease (glaucoma, diabetes, etc.). Additionally or alternatively, the system can be configured to generate a recommendation to a patient or physician based on the comparisons, correlations, trends, or other characteristics derived from the data. For example, the system can generate a contact lens recommendation which includes a recommended material, style, manufacturer, and so on.

First Embodiment

The principles disclosed herein include a method of using the constituents within tear fluid as biomarkers that can be analyzed to determine a health condition of a user, as described in U.S. application Ser. No. 62/642,860 filed on 14 Mar. 2018, the disclosure of which is incorporated herein, in its entirety, by this reference. These biomarkers can be collected on a contact lens worn by the user. Any appropriate type of contact lens can be used to collect the biomarkers. However, unaltered commercially available contact lenses from a wide variety of manufacturers for corrective vision are envisioned to be the contact lens that are used to collect the biomarkers. Biomarkers, such as proteins, generally start to bind to these contact lenses as soon as the contact lenses are placed over the user's eye. Without modifying the contact lens as they are provided by the manufacturers, proteins, electrolytes, and/or other biomarkers in the tear fluid can bind to the contact lens.

Generally, a user removes the contact lenses after wearing them for a period of time. Often, before the user retires to bed, the user removes their contact lenses and places their contact lenses in a storage example for the night. The storage example can include a storage solution that disinfects the contact lenses and also breaks down any build-up on the contact lenses. The storage solution can be an aqueous solution that causes the build-up on the contact lenses to dissolve into the solution. After a period of time, the storage solution can be replaced with fresh storage solution to reduce the concentration of tear fluid constituents or other contaminants within the solution.

The storage solution can be analyzed to determine the type and/or concentration of biomarkers that dissolved into the solution from the contact lens. In some examples, the solution can be analyzed with the contact lens in the solution. In other examples, the contact lens can be removed from the solution before analyzing the biomarkers.

In some embodiments, a sensor or a sensing device can be used to collect analyte information from the solution. Any appropriate type of sensor can be used to identify the type, concentration, and/or characteristics of the biomarkers. In some instances, the sensor can be incorporated into the contact lenses' storage container. For example, the sensor can be a single electrode or an array of electrodes operably coupled to the storage container. Alternatively or additionally, the sensor can be an optical spectral analyzer that passes light from a light source, through a cavity within the storage container (e.g., a contact lens container housing a storage solution), and into a detector or light receiver. The detector or receiver can measure the optical transmittance of the light through the storage solution. In some embodiments, the spectral analyzer passes light through the storage solution at isolated predetermined wavelengths and measures the optical transmittance at each of the predetermined wavelength ranges. Each of the recorded transmittances can correlate to the presence of specific kinds of biomarkers and their concentrations. In one embodiment, the storage container can comprise the sensor, a processor, and a memory. The sensor can be configured to obtain information which indicates a characteristic of at least one biomarker derived from a contact lens used by a user and stored in the storage container. The processor can be configured to send the information to a computing device which ascertains a health condition of the user based on the information.

In other examples, the sensor can be incorporated into a hand-held device. In one embodiment, the sensor can be incorporated into the user's mobile device, such as a smart phone and/or electric tablet. Using a mobile phone or other electronic device, the user can direct a beam of light into the storage solution and measure a reflection with a sensor incorporated into the hand-held device.

In some embodiments, the measured values can be augmented with complementary information, such as an amount of time that the user wore the contact lens. For example, the user can interact with a user interface to input how long the user wore the contact lenses. In some examples, the user can be prompted to input the number of hours that the user wore the contact lenses. In other examples, the user can be prompted to input the number of days that she wore the contact lenses, whether the user removed the contact lenses during the night, the time of when the storage solution was last replaced, other factors that can affect the concentration of biomarkers in the storage solution, or combinations thereof.

In some embodiments, the sensor or other sensing device can record the measured values to determine a concentration or other measurable characteristic of one or more biomarkers. The recorded measurements (i.e., the measured values) can be a numerical value which fall within a predetermined range of numerical values correlated with particular biomarkers. In some examples, the sensor can record the measurements in real time. Further, the sensor can include local and/or cloud based logic to determine the type, concentration, and/or other characteristics of the varying kinds of biomarkers. In some examples, the sensor or sensing device including a sensor can use learning algorithms, predictive models, data correlation models, clustering models, any other appropriate computational techniques, and combinations thereof. In some examples, the sensor or sensing device including a sensor can include a database that stores the correlation between the identification/concentration of the biomarkers and a health condition of the user.

The measurements can be sent to a computing device that processes the information collected by the sensor. In some examples, at least some computations are performed by the sensor before sending data to a computing device where the computations are finished. In other examples, the sensor can send raw data to the computing device. In this example, all data processing, including data cleaning, data management, data mining, and any application specific issues, is performed remotely away from the sensor.

The determinations of the type of biomarkers, the characteristics of biomarkers, such as the concentration of the biomarkers, chemometric data such as ratio kinetics, peak, plateau, time constant, decay, and so forth can be compared to data points stored in a database. The database can be local to the computing device or the computing device can have remote access to the database. The data in the database can correlate the different types and concentrations of biomarkers with health conditions, such as eye health conditions, allergic conditions, other physiological conditions, or combinations thereof. In some examples, the data in the database can be used as input or training data to implement and supervise machine learning techniques, or other statistical learning approaches to solve prediction inference, or other data mining problems related to health conditions, such as eye health conditions, allergic conditions, other physiological conditions, or combinations thereof. In some embodiments, the database can also correlate the measured biomarkers characteristics to health conditions in subcategories based on at least one population demographic.

In some examples, the database is in communication with multiple users and data sources. As data relating to a user's biomarker characteristics is collected, this data and data from a plurality of other users can contribute to the information stored within the database. In some examples, data collection can automatically launch a data management system of the database. In some examples, the data management system or another process can incorporate additional data into the database, such as health conditions of each of the users. As a result, the correlations in the database can include reports from the users. The computing device can update the database based on the reports from the users. In some examples, patient data can be used as predictors in a statistical machine learning process. In some examples where the database is built using thousands of users, the database's input can identify correlations between health conditions and specific levels of different types of biomarkers that are unknown to the scientific community. Thus, even before scientific studies can be conducted to find a correlation between a biomarker and a health condition, the computing device can, with reference to the database, send information related to the diagnosis of a disease, a disease severity assessment, a risk stratification, a therapeutic decision or request, a recommendation to the user to be tested for a specific type of health condition, or combinations thereof. In other embodiments, the database can send information related to the diagnosis of a disease, a disease severity assessment, a risk stratification, a therapeutic decision or request, or test recommendations to a user specified physician.

These principles allow a vast database to be built that correlates the health conditions of the users with varying parameters of the biomarkers (i.e., biomarker characteristics). For example, the database can include supplementary user data such as age, gender, weight, height, and the like.

These principles also allow the user to have a non-invasive procedure to measure the biomarkers. Further, in those examples where the user is already storing and cleaning his or her contact lens from time to time, the user can incur little to no additional effort to measure the biomarkers and receive reports on at least some of his or her health conditions.

Referring now to the figures, as described above, FIG. 18 depicts an example of a contact lens 1810 situated on the outside of a human eye 1850. The contact lens 1810 spans a portion of the outside surface of the exposed portion of the eye 1850. An upper portion of the contact lens 1810 is adjacent a set of eyelashes 1852 of the upper eye lid. The contact lens 1810 can include a posterior side that is in contact with the cornea of the eye 1850, and an anterior side that is opposite of the posterior side. As the eye lid travels over the eye 1850, the eye lid can move across the anterior side of the contact lens 1810.

A user can wear the contact lens for vision correction purposes. In this type of example, the contact lens can include an optic zone 1820 and a peripheral zone 1822. The optic zone 1820 can include a region that focuses light to the center of the user's retina 1824. The peripheral zone 1822 can contact the eye near or over the sclera. While this example discloses using commercially available contact lenses configured for vision correction to be worn on the eye, other types of contact lenses can be used in accordance with the principles described in the present disclosure. For example, the contact lens may not include a curvature or other features that correct vision. Indeed, a physician can prescribe contact lenses for the sole purpose of collecting biomarkers within the patient's tear fluid, in one embodiment.

The contact lens 1810 can be soft contact lenses, rigid gas permeable (RGP) contact lenses, orthokeratology contact lens, another type of contact lenses, or combinations thereof. The contact lens can be made of any appropriate type of material. A non-exhaustive list of materials that can be used to construct the contact lens include any appropriate silicone material and/or hydrogel material. Such material can be formed of polymers, such as tefilcon, tetrafilcon A, crofilcon, helfilcon A&B, mafilcon, polymacon, hioxifilcon B, lotrafilcon A, lotrafilcon B, galyfilcon A, senofilcon A, sifilcon A, comfilcon A, enfilcon A, lidofilcon B, surfilcon A, lidofilcon A, alfafilcon A, omafilcon A, vasurfilcon A, hioxifilcon A, hioxifilcon D, nelfilcon A, hilafilcon A, acofilcon A, bufilcon A, deltafilcon A, phemfilcon A, bufilcon A, perfilcon, etafilcon A, focofilcon A, ocufilcon B, ocufilcon C, ocufilcon D ocufilcon E, ocufilcon F, phemfilcon A, methafilcon A, methafilcon B, vilfilcon A, other types of polymers, monomers, or combinations thereof. These materials can include various combinations of monomers, polymers, and other materials to form the material that makes up the contact lens.

In one embodiment, the contact lens material can be made of hydrogel polymers without any silicone. This can be desirable to increase the wettability of the contact lens. In another embodiment, the contact lens material can be made of silicone hydrogel material.

The tear fluid in the ocular cavity can come into contact with the contact lens. In some examples, the entire surface area of the contact lens comes into contact with the tear fluid. The constituents of the tear fluid can include lipids, electrolytes, metabolites, proteins, antibodies, other types of compounds, or combinations thereof. These constituents can be biomarkers that can be indicative of a health condition of the user. The biomarkers can bind to the contact lens.

A non-exhaustive list of biomarkers from the tear fluid that can be of interest includes, but is not limited to, electrolytes, sodium, potassium, chloride, phenylalanine, uric acid, galactose, glucose, cysteine, homocysteine, calcium, ethanol, acetylcholine and acetylcholine analogs, ornithine, blood urea nitrogen, creatinine, metallic elements, iron, copper, magnesium, polypeptide hormones, thyroid stimulating hormone, growth hormone, insulin, luteinizing hormones, chorionogonadotrophic hormone, obesity hormones, leptin, serotonin, medications, dilantin, phenobarbital, propranolol, cocaine, heroin, ketamine, hormones, thyroid hormones, ACTH, estrogen, cortisol, progesterone, histamine, IgE, cytokines, lipids, cholesterol, apolipo protein $A_1$, proteins and enzymes, lactoferrin, lysozyme, tear-specific prealbumin or lipocalin, albumin, complement, coagulation factors, liver function enzymes, heart damage enzymes, ferritin, virus components, immunoglobulins such as IgM, IgG, proteases, protease inhibitors, lactate, ketone bodies, other types of biomarkers, or combinations thereof.

In some examples, commercially available contact lenses can have surface properties to allow the biomarkers to bind to the contact lens without any modifications. Conventionally, protein build-up and other types of build-up is considered a problem on regular contact lenses that do not have surface modifications to enhance a biomarker's ability to bind to the contact lens. In other examples, the contact lens can be modified to enhance the binding ability of the biomarkers or just for specific biomarkers. In those examples where the surface of the contact lens can be modified to enhance an ability to bind to the biomarkers, the binding enhancements can be made to any appropriate location on the contact lens, including, but not limited to, the peripheral zone, the optical zone, the anterior side of the contact lens, the posterior side of the contact lens, other areas of the contact lens, or combinations thereof.

As described above, FIG. 19 depicts an example of biomarkers 1914 attached to the posterior surface 1930 of the contact lens. While this example depicts the biomarkers 1914 attached to the posterior surface 1930 of the contact lens, the biomarkers 1914 can be attached to just the anterior surface 1932 or to both the anterior surface 1932 and posterior surface 1930 of the contact lens 1810. In some embodiments, the biomarkers 1914 can be adsorbed, absorbed, bonded, covalently bonded, ionically bonded, adhered, cohered, or otherwise connected to a surface of the contact lens 1810. In some embodiments, the biomarkers 1914 are incorporated into the thickness of the contact lens 1810.

When the contact lens 1810 is removed from the user's eye, the biomarkers 1914 can stay with the contact lens 1810 as depicted in FIG. 19. The amount of biomarkers 1914 that are attached to the contact lens 1810 can be related to the amount of time that the contact lens 1810 was on the eye. In some examples, the contact lens 1810 can be worn by the user during that day and removed at night. Under these circumstances, biomarkers 1914 can cover a substantial amount of the contact lens' surface area. However, in other examples, the contact lens 1810 can be worn by the user for a smaller period of time. In one specific instance, a patient can be provided with a contact lens 1810 for a period of minutes in a doctor's office to collect biomarkers 1914 for analysis. In other examples, a patient can be instructed to keep a contact lens 1810 in for a matter of hours or some other duration of time to collect the desired amount of biomarkers 1914.

As described above, FIG. 20 depicts an example of a contact lens 1810 in a storage container 2040 with an internal cavity 2002. The cavity 2002 is defined by a first wall 2004 and a second wall 2006 that are connected together at a bottom surface 2008. A contact lens 1810 and a solution 2012 are also disposed within the cavity 2002.

The solution 2012 can include a cleansing agent, such as a hydrogen peroxide or another type of agent to clean the contact lens and kill bacteria, fungus, other types of germs, or combinations thereof. The solution 2012 can be an off-the-shelf type of storage solution that hydrates and cleans the contact lens. The storage solution 2012 can cause the biomarkers 1914 to dissolve into the solution 2012 thereby cleaning the contact lens 1810. The contact lens 1810 can remain in the storage solution 2012 until the contact lens 1810 is subsequently retrieved by the user. In some examples, the contact lens 1810 is immersed into the solution for a short period of time, such as a couple of minutes. In other examples, the contact lens 1810 can remain in the solution for multiple hours, such as overnight. With the biomarkers 1914 removed from the contact lens 1810, the biomarkers 1914 can be diluted into the solution 2012 where the biomarker types, their respective concentrations, or other biomarker characteristics can be measured or analyzed.

The biomarkers 1914 can be removed from the contact lens 1810 without adversely affecting the contact lens 1810. In those examples, the contact lens 1810 can be re-worn by the user. In some examples, the contact lens 1810 is removed from the solution 2012 so that the contact lens 1810 is not affected by the testing mechanism performed on the solution. In other examples, the contact lens 1810 remains in the solution 2012 while the solution 2012 is analyzed, but the analysis does not adversely affect the contact lens 110 so that the contact lens 1810 can be re-worn by the user.

In some examples, the biomarkers 1914 can be analyzed in the storage container 2040. In other examples, the solution 2012 can be transferred to another type of device with a sensor for taking the measurements. In yet another example, a hand-held device can incorporate a sensor that can perform the analysis on the solution.

Figure 39A:
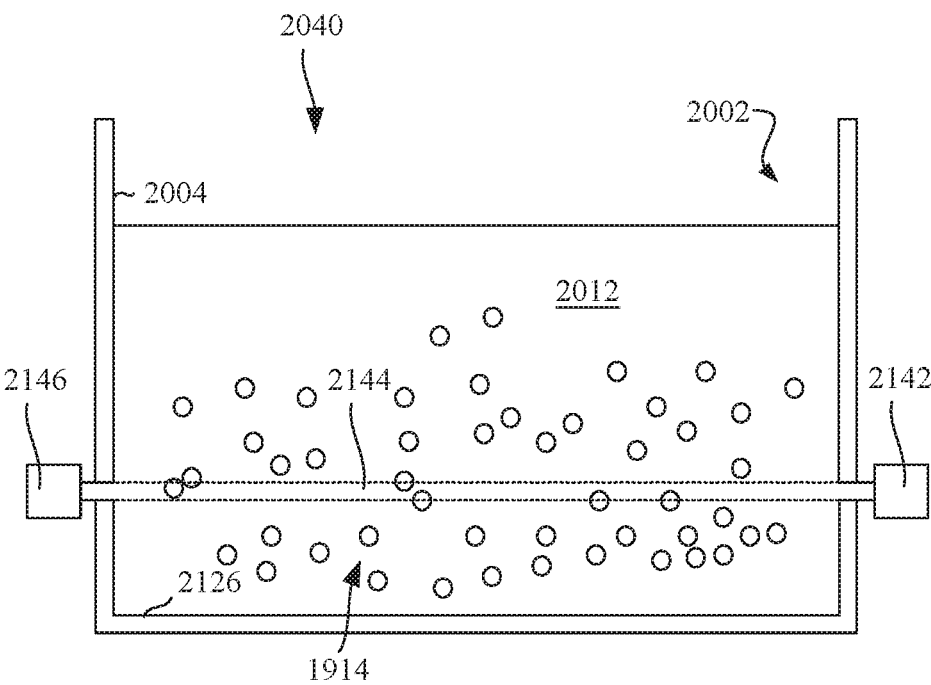
FIG. 39A illustrates a cross-sectional view of running a test on the solution containing biomarkers from a contact lens, according to one embodiment.

One approach of analyzing the solution is depicted in FIG. 39A. In some embodiments, an optical spectral analyzer can be incorporated into the storage solution container 2040. In the example of FIG. 39A, a storage container 2040 for a contact lens 1810 includes a cavity 2002 that is defined by at least one wall 2004 that is connected by a floor 2126. In some examples, a single circular wall defines at least a portion of the cavity 2002. In other examples, multiple independent walls are joined together to define the cavity 2002.

A light source 2142 can be incorporated into a first side of the cavity 2002. The light source 2142 can be oriented to direct a beam of light 2144 through the solution 2012 to a light receiver 2146. As the beam of light 2144 is transmitted through the solution 2012, a portion of the light can be absorbed by the solution, depending on its contents. A solution 2012 with a different type of biomarker 1914 can have a different or unique light transmittance through the solution 2012. Further, a solution 2012 with a different concentration of the same biomarker 1914 can also exhibit a different or unique light transmittance.

In some embodiments, the light source 2142 can isolate a range of wavelengths to be transmitted independently through the solution 2012. The transmittance for each wavelength can be measured. Certain biomarkers in the solution 2012 may not affect the optical transmittance at a first wavelength, but can affect the optical transmittance at a second wavelength. Thus, by transmitting light at different wavelengths, a more refined measurement of the solution's composition can be measured. The measured transmittances at each wavelength can be compared to the data of other solutions wherein the types and concentrations of the biomarkers are known. Thus, the measured transmittance levels can be correlated to the types and concentration of the biomarkers 1914 in the solution 2012.

Other types of spectroscopic methods can be used to analyze and identify the types and concentration of the biomarkers in the solution. In some examples, measuring a frequency rather than a wavelength can be performed by the light receiver 2146 (e.g., spectral analyzer). A non-exhaustive list of other types of spectroscopic mechanisms for analyzing the solution can include atomic absorption spectroscopy, attenuated total reflectance spectroscopy, electron paramagnetic spectroscopy, electron spectroscopy, Fourier transform spectroscopy, gamma-ray spectroscopy, infrared spectroscopy, laser spectroscopy, mass spectrometry multiplex or frequency-modulated spectroscopy, Raman spectroscopy, and x-ray spectroscopy.

While the example embodiment of FIG. 39A includes the light source 2142 and the light receiver 2146 on different sides of the cavity walls, the light source 2142 and the light receiver 2146 can be on the same side of the cavity 2002. In such an example, light emitted from the light source 2142 can be reflected within container and the reflection can be recorded or otherwise measured by the light receiver 2146 (e.g., a spectral analyzer).

Figure 42:
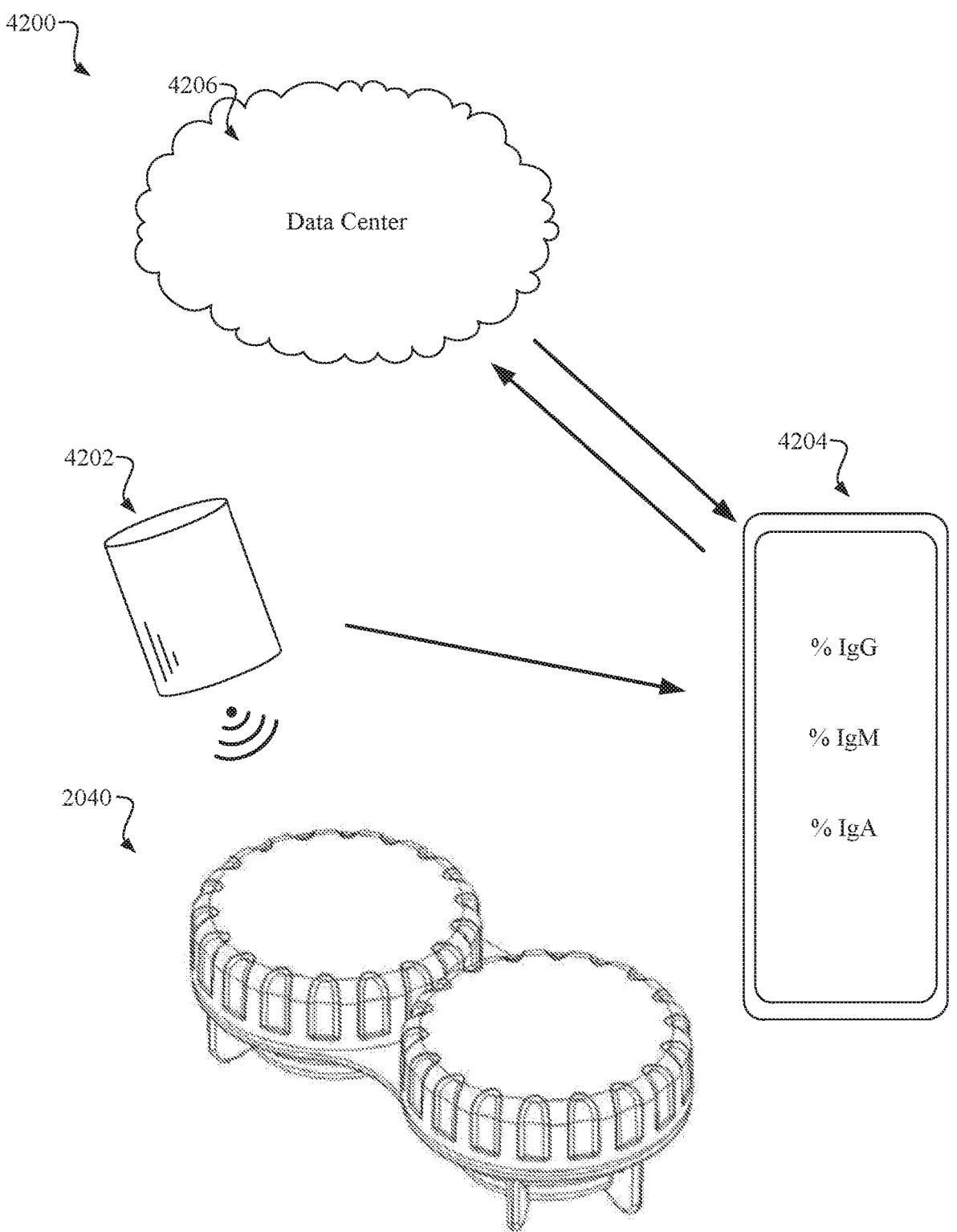
FIG. 42 illustrates a cross-sectional view of an example of a health condition system, in accordance with the present disclosure.

In some examples, the sensor can be part of a hand-held device 4202 depicted in FIG. 42. In this example, the hand-held device includes a sensor, such as an infrared spectrometer, that can measure a concentration of a biomarker within the solution. For example, the hand-held device can include an end that has an infrared source that sends infrared light into the solution when the user orients the hand-held device to appropriately direct the infrared light and instructs the hand-held device to send the light. The amount of the infrared light that is absorbed into the solution can be based, at least in part, on the concentration of the biomarker in the solution. Thus, the returning amount of the infrared light to the hand-held device can be measured with an infrared receiver incorporated into the hand-held device.

In yet other examples, the solution 2012 can be poured into another device for analysis. In one example, the solution 2012 can be poured into an immunodiffusion machine, a centrifuge, another type of device, or combinations thereof for measuring at least one property (e.g., a biomarker characteristic) of the solution 2012.

Figure 39B:
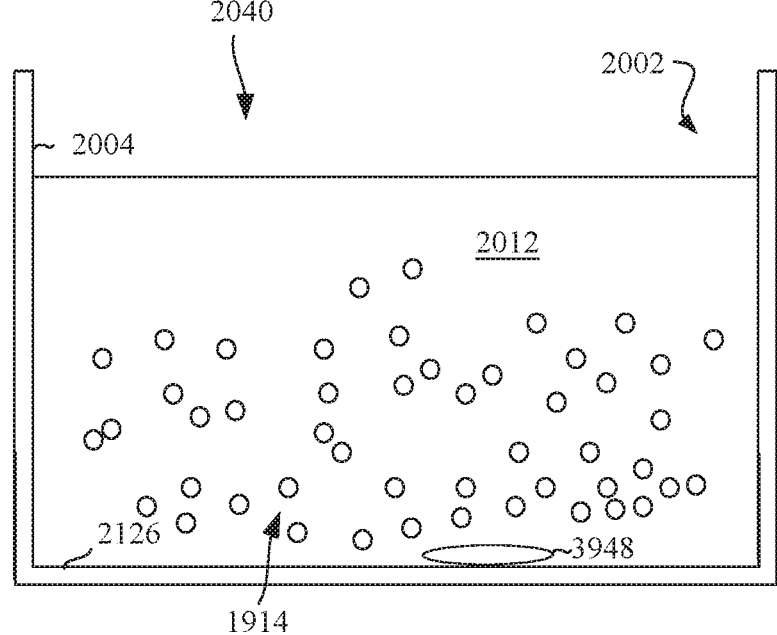
FIG. 39B illustrates a cross-sectional view of running a test on the solution containing biomarkers from a contact lens, according to another embodiment.

Another approach of analyzing the solution is depicted in FIG. 39B. In some embodiments, at least one electrode can be incorporated into the storage solution container 2040 to analyze the contents of the storage solution 2012 by chronoamperometry.

In the example of FIG. 39B, an electrical potential can be applied to an electrode 3948 over a predetermined time period to elicit a resultant current intensity. The current intensity can vary relative to the properties of the solution 2012. For example, the current intensity measured at the electrode 3948 can vary relative to the concentration of glucose within the solution 2012, in one embodiment. The current intensity of the electrode 3948 can be recorded and compared with a database to determine a health condition of the contact lens user.

The electrode 3948 can be incorporated into the floor 2126 of the container 2040. In some embodiments, a stepped potential or voltage can be applied to the electrode 3948 wherein the voltage applied to the electrode 3948 increases by predetermined steps over a period of time. In other embodiments, the potential or voltage applied to the electrode 3948 can be a constant potential over a period of time. A plurality of electrodes comprising an array of electrodes can be incorporated into the floor 2126 or any other surface of the container 2040. The electrode 3948 can be operably coupled to a power supply (not shown) configured to supply electrical power to the electrode 3948. The electrode 3948 can be operably coupled to a processing unit (not shown) configured to measure operational parameters of the electrode (e.g., voltage, current, time, etc.).

Figure 40:
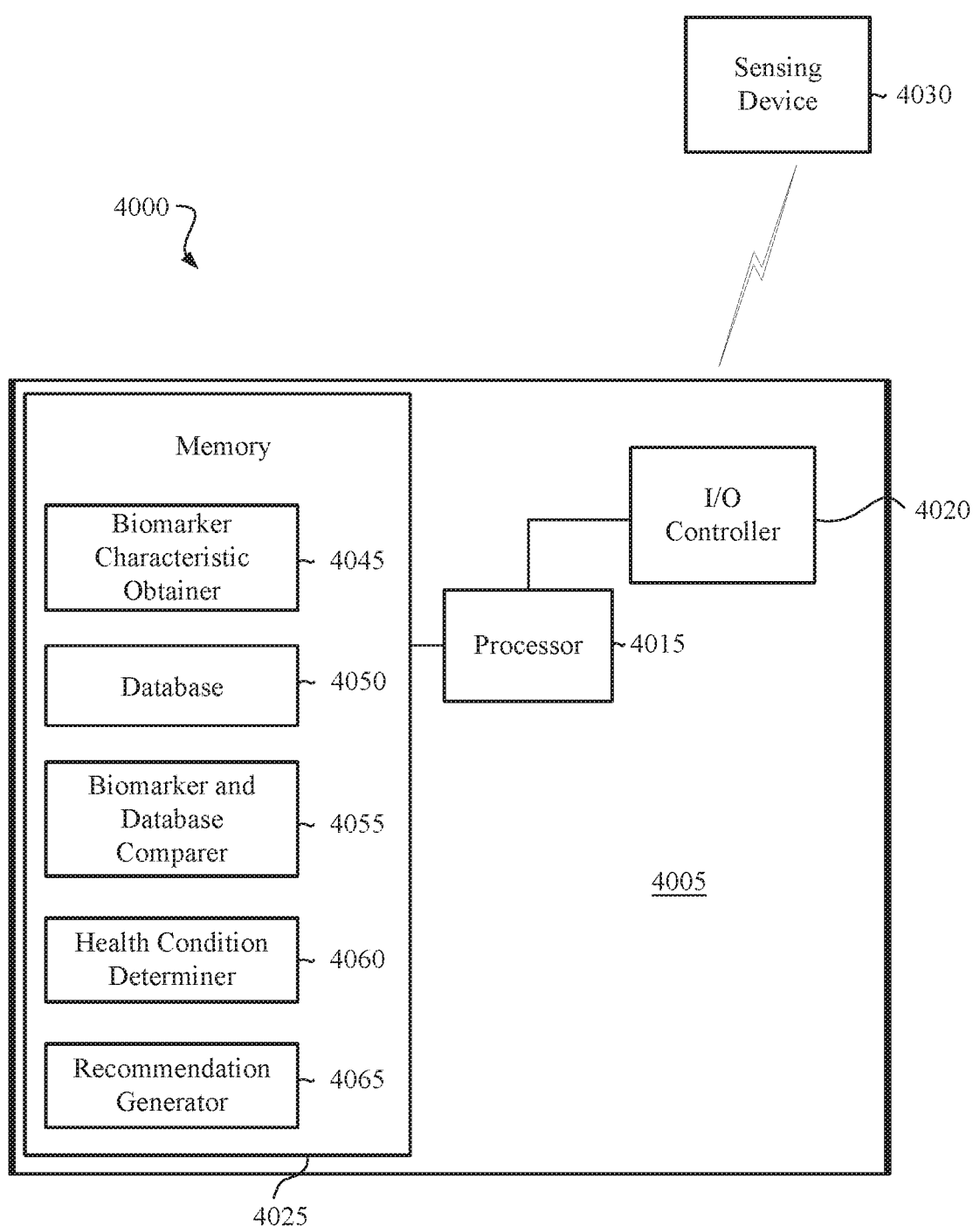
FIG. 40 illustrates a block diagram of an example of a health condition system, in accordance with the present disclosure.

FIG. 40 depicts a diagram of a health condition system 4000. The system 4000 includes a base station 4005 having a processor 4015, an input/output (I/O) controller 4020, and memory 4025. In some embodiments, the processor 4015 and the memory 4025 are subcomponents of a computing device, for example, the base station 4005 can be a computing device. The I/O controller 4020 can be in communication with a sensing device 4030, for example, through an antenna. In some examples, a sensor of the sensing device 4030 can be incorporated into the contact lens storage example, into a hand-held device, an independent machine configured to analyze the solution, another type of sensor, or combinations thereof. In some examples, the sensing device can include its own processor, memory, and/or I/O controller 4020. The components of the system and the sensing device 4030 can communicate wirelessly, through hard wired connections, or combinations thereof. The memory 4025 of the system can include a biomarker characteristic obtainer 4045, a database 4050, a biomarker and database comparer 4055, a health condition determiner 4060, and a recommendation generator 4065. In some embodiments, the system 4000 can further include a base station 4005 in communication with the memory 4025, the base station 4005 can be in communication with the processor 4015 and/or the sensing device 4030, for example via an antenna within the I/O controller 4020 or a transponder. In some embodiments, the sensing device 4030 is at least one electrode and/or optical spectral analyzer.

The processor 4015 can include an intelligent hardware device, (e.g., a general-purpose processor, a digital signal processor (DSP), a central processing unit (CPU), a microcontroller, an application-specific integrated circuit (ASIC), a field-programmable gate array (FPGA), a programmable logic device, a discrete gate or transistor logic component, a discrete hardware component, or any combination thereof). In some examples, the processor 4015 can be configured to operate a memory array using a memory controller. In other examples, a memory controller can be integrated into the processor 4015. The processor 4015 can be configured to execute computer-readable instructions stored in a memory to perform various functions (e.g., functions or tasks supporting the evaluation of the prescribed optical devices).

The I/O controller 4020 can include or interact with a modem, a keyboard, a mouse, a touchscreen, or a similar device. In some examples, the I/O controller 4020 can be implemented as part of the processor. In some examples, a user can interact with the system via the I/O controller 4020 or via hardware components controlled by the I/O controller 4020. The I/O controller 4020 can be in communication with any input and any output of the system 4000.

The memory 4025 can include random access memory (RAM) and read only memory (ROM). The memory 4025 can store computer-readable, computer-executable software including instructions that, when executed, cause the processor 4015 to perform various functions described herein. In some examples, the memory 4025 can include, among other elements, a basic input/output system (BIOS) which can control basic hardware and/or software operation such as the interaction with peripheral components or devices. The memory 4025 storing the software (e.g., a program) can be referred to as a "computer readable recording medium." The recording medium can be a "non-transitory tangible medium" such as, for example, a tape, a disk, a card, a semiconductor memory, a programmable logic circuit, or the like. The program can be supplied to the computer via any transmission medium (such as a communication network or a broadcast wave) that can transmit the program. In some embodiments, aspects of the present disclosure can also be achieved in the form of a computer data signal in which the various programs are embodied via electronic transmission and which is embedded in a carrier wave.

The biomarker characteristic obtainer 4045 can include programmed instructions that cause the processor 4015 to obtain a biomarker characteristic from the solution. In other words, the processor 4015 can execute the programmed instructions to function as the biomarker characteristic obtainer 4045. The biomarker characteristic can include a biomarker identification, a biomarker concentration, another type of characteristic, or combinations thereof. In some examples, the biomarker characteristic obtainer 4045 passively receives a signal containing information about the biomarker characteristic. In other examples, the biomarker characteristic obtainer 4045 actively requests information about the biomarker characteristic.

The database 4050 can include a data structure that holds information relating to the biomarker characteristics. The database 4050 can include information relating to the biomarker characteristics that have been recorded or measured in labs, for example by chemometric methods, obtained from at least one user, or combinations thereof. In some examples, the database can be initially populated with information from patients and/or users who have known health conditions and the biomarkers types and concentration levels in the tear fluid have been studied in labs or in other settings. Since some users with the same health condition can exhibit slightly different biomarker characteristics, the information from a plurality of users can be compiled. In some examples, thousands to millions of sample biomarker characteristics can be collected.

The biomarker and database comparer 4055 can represent or otherwise include programmed instructions that cause the processor 4015 to compare the obtained biomarker characteristic against the information stored in the database 4050. In other words, the processor 4015 can execute the programmed instructions to function as the biomarker and database comparer 4055. In some examples, the programmed instructions can include data mining algorithms to compare biomarker characteristics. The health condition determiner 4060 can represent or otherwise include programmed instructions that cause the processor 4015 to correlate a user's biomarker characteristics to similar biomarker characteristics stored within the database 4050 to determine or predict a health condition of the user. In other words, the processor 4015 can execute the programmed instructions to function as the health condition determiner 4060.

Correlations between certain biomarkers and their respective concentrations can go unobserved on one-on-one analysis with each of the patients. However, with a larger sample size, correlations that have been previously unobserved can be detected, for example via data mining techniques used by the system 4000. For example, the biomarker characteristics of users with a specific health conditions can be analyzed which can reveal that certain biomarkers that had not previously been linked to that health condition have a statistically significant normal concentration level, a statistically significant low concentration level, a statistically significant high concentration level, another statistically significant concentration level, a statistically insignificant type of concentration level, or combinations thereof that had not previously been observed. These correlations can help identify health conditions that can go otherwise unobserved in a patient. Even in those events where the user's health condition can be eventually diagnosed properly, comparing the obtained biomarker characteristics with the information stored in the database 4050 can result in a quicker diagnosis.

The recommendation generator 4065 can represent or otherwise include programmed instructions that cause the processor 4015 to generate a recommendation to the user. In other words, the processor 4015 can execute the programmed instructions to function as the recommendation generator 4065. The recommendation can include a confirmation test to confirm whether or not the user has that determined health condition. The confirmation test can be conducted by an external computing device commonly operated by the user (e.g., a mobile device). In those examples where a confirmation test is conducted, the results of the confirmation test can be sent to the database and/or computing device. The results can be used to assist the database and its associated analytics to improve the health condition determinations.

Another recommendation can prompt a user to receive treatment for the determined health condition. Another recommendation can prompt the user to visit a specific type of doctor. Another recommendation can include avoiding certain types of foods. Yet, another recommendation can include a health regime, a particular type of diet, another recommendation to perform a type of action, or combinations thereof.

FIG. 41 depicts an example of a database 4100 that associates a characteristic of the tear chemistry (e.g., constituents and their associated concentrations within a user's tear fluid), potential indications, and potential causes of the tear chemistry. In this example, the database 4100 includes a first column 4102 that represents the tear chemistry, a second column 4104 that represents the potential indications, and a third column 4106 that represents the potential causes of the tear chemistry. The database 4100 can include a first row 4108 that includes the correlation for a tear chemistry with a normal lactoferrin level and a normal IgE level, a second row 4110 that includes the correlation for a tear chemistry with a normal lactoferrin level and a high IgE level, a third row 4112 that includes the correlation for a tear chemistry with a low lactoferrin level and a normal IgE level, a fourth row 4114 that includes the correlation for a tear chemistry with a low lactoferrin level, a fifth row 4116 that includes the correlation for a tear chemistry with a high lactoferrin level, and a sixth row 4118 that includes the correlation for a tear chemistry with a high IgE level.

While the example of FIG. 41 depicts an example with the correlations of specific types of biomarkers, any appropriate type of correlation can be included in the database. In some instances, the characteristics correlated with a single biomarker can be included as depicted in rows 4114, 4116, 4118. In other instances, the characteristics correlated with a specific set of biomarkers can be included. For example, the health conditions correlated with two or more characteristics of different types of biomarkers can be included as depicted in rows 4108, 4110, 4112. Any appropriate number of biomarker characteristics can be included. For example, anywhere from one, three, to hundreds of characteristics can be collectively correlated to a specific type of health condition. Further, while the example of FIG. 41 includes specific types of biomarkers, the database can include any appropriate type of biomarker correlation. In the embodiment depicted in FIG. 41, whether a biomarker level is "Normal", "Low", or "High" can be determined by comparing the measured value of the biomarker with a predetermined threshold.

FIG. 42 depicts an example of a system 4200 of ascertaining or otherwise determining a health condition of a user. In this example, a storage solution (i.e., aqueous solution) can be contained within a contact lens container 2040. A hand-held device 4202 with a sensor can be used to take a measurement of at least one characteristic of the biomarkers in the solution. The hand-held device 4202 can send the biomarker characteristic to a mobile device 4204 (i.e., a computing device) that is in communication with a cloud based data center 4206 that stores the database (FIG. 41, 4100). The mobile device 4204 can relay the measured biomarker characteristics to the database in the data center 4206, which can send a correlation between the biomarker characteristics and a health condition back to the mobile device 4204. The mobile device 4204 can present the results from the hand-held device 4202 and/or the correlations from the database in a user-interface of the mobile device 4204.

At least some of the processing of the measurements obtained from the return signals from the storage solution can occur at the hand-held device 4202, the mobile device 4204, and/or the data center 4206. In some examples, the mobile device 4204 can include a program that retrieves the correlations from the database and performs additional tasks. For example, the mobile device 4204 can retrieve information about the health condition from another source other than the database in response to receiving the health condition from the database. The mobile device 4204 can also retrieve a health professional's contact information, consult a user's calendar to set up an appointment with the health professional, schedule an appointment with the health professional, perform another task, or combinations thereof.

Figure 43:
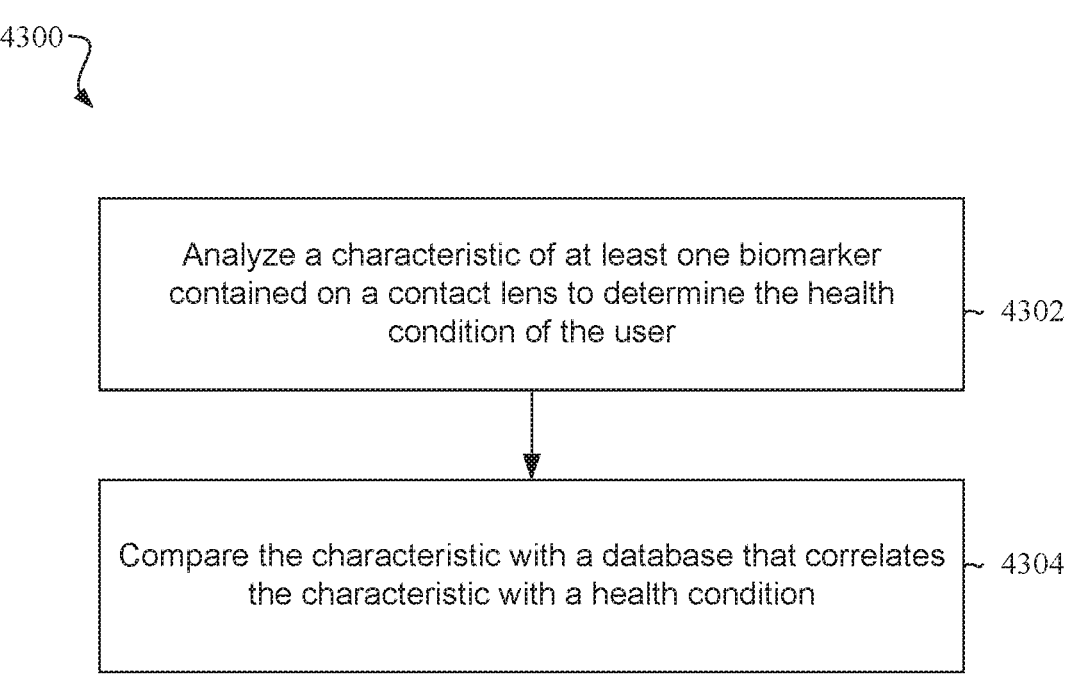
FIG. 43 illustrates a block diagram of a method of an example of determining a health condition, in accordance with the present disclosure.

FIG. 43 illustrates an example of a method 4300 of determining a health condition. In this example, the method 4300 includes analyzing 4302 a characteristic of at least one biomarker contained on a contact lens to determine the health condition of the user and comparing 4304 the characteristic with a database that correlates the characteristic with a health condition.

At block 4302, a characteristic of at least one biomarker is analyzed. This process can be performed by the sensing device 4030 or by the processor 4015 (e.g., the biomarker characteristic obtainer 4045) after the processor 4015 obtains or otherwise receives the measured values detected by a sensor within the sensing device 4030. As previously described, the biomarkers can be obtained from a contact lens. In some examples, the biomarkers can remain on the contact lens when the biomarkers are being analyzed or otherwise measured. In other examples, the biomarkers can be removed from the contact lens before the analysis. The biomarker characteristic can include a type of biomarker, a concentration of biomarker, a location of the biomarker on the contact lens, another type of characteristic, or combinations thereof. The biomarker characteristic can involve a single biomarker. In other examples, the biomarker characteristic can include the collective condition of multiple biomarkers.

At block 4304, the biomarker characteristic can be compared to a database that correlates the biomarker characteristic with a health condition (e.g., the database 4050 in FIG. 40). For example, the database can include the type and concentration of a single biomarker that is correlated with a specific health condition. This process can be performed by the processor 4015 (e.g., the biomarker and database comparer 4055). In another example, the database can correlate that a first type of biomarker having a specific concentration and a second type of biomarker having different specific concentration can be associated with a specific type of health condition.

Figure 44:
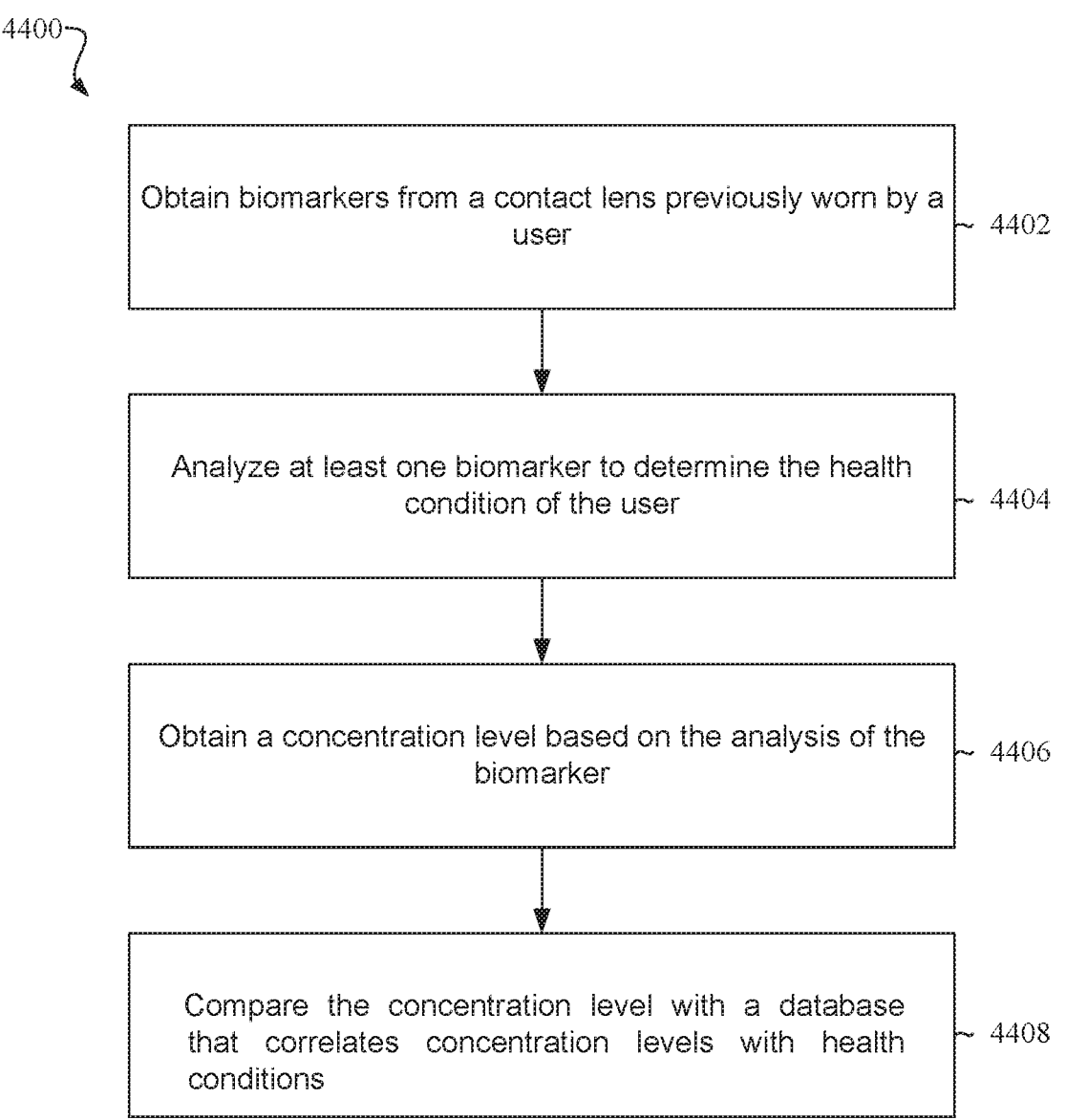
FIG. 44 illustrates a block diagram of a method of an example of determining a health condition, in accordance with the present disclosure.

FIG. 44 illustrates an example of a method 4400 of determining a health condition. In this example, the method 4400 includes obtaining 4402 biomarkers from a contact lens previously worn by a user, analyzing 4404 at least one biomarker to determine the health condition of the user, obtaining 4406 a concentration level based on the analysis of the biomarker, and comparing 4408 the concentration level with a database that correlates concentration levels with health conditions. The process blocks 4404 and 4406 can be performed by the same entity (e.g., a processor) as that of block 4302 in FIG. 43. The process block 4408 can be performed by the same entity (e.g., a processor) as that for block 4304 in FIG. 43.

At block 4402, the biomarkers can be obtained from the contact lens in any appropriate way. In some examples, the biomarkers can dissociate from the contact lens in a multipurpose contact lens storage solution. In another example, the biomarkers are obtained from the contact lens by wiping a material across the contact lens' surface. In yet other examples, the biomarkers can be removed from the contact lens by scratching the biomarkers off of the lens's surface. In some examples, obtaining the biomarkers from the contact lens results in a contact lens that can be re-worn by the user. In other examples, obtaining the biomarkers from the contact lens results in modifying the contact lens such that it cannot be re-worn by the user. The biomarker characteristic obtainer 4045 obtains from, for example, the sensing device 4030, information indicating characteristics of the biomarkers obtained as above.

Figure 45:
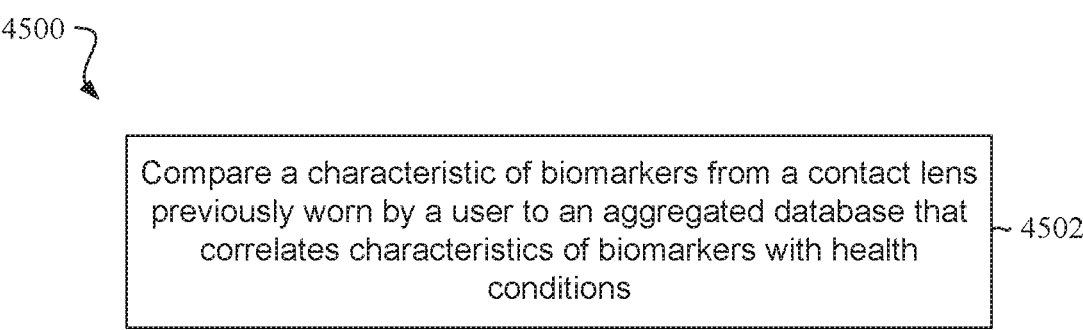
FIG. 45 illustrates a block diagram of a method of an example of determining a health condition, in accordance with the present disclosure.

FIG. 45 illustrates an example of a method 4500 of determining a health condition. In this example, the method 4500 includes comparing 4502 a characteristic of biomarkers from a contact lens previously worn by a user to an aggregated database that correlates characteristics of biomarkers with health conditions. The process block 4502 can be performed by the same entity as that for the block 4304 in FIG. 43.

The aggregated database can include the concentration levels associated with health conditions from multiple sources. In some examples, doctors, patients, other types of professionals, other types of sources, or combinations thereof can contribute information that can be populated into the database. In some examples, thousand and even millions of health conditions with their associated biomarker characteristics can be aggregated into the database.

Further, after the correlated health condition can be sent to the user, the user can have an option to confirm whether the health condition was accurate. For example, a user can place his or her contact lens in the storage example and receive a notification that he or she has or can have a health condition. As a result, the user can visit with a doctor, who performs a test to confirm whether the user has that health condition. In the event that the user has the health condition indicated by the database, the user can send a confirmation message to the database. The confirmation message can increase a confidence level of the correlation between the characteristic of the biomarker and the health condition. In the event that the test indicates that the user does not have the health condition indicated by the database, the user can send confirmation message to the database indicating that the user does not have the health condition. This confirmation message can cause a decrease in a confidence level of the correlation between the characteristic of the biomarker and the health condition. In the event that the user does not have the indicated health condition, the database can reassess the correlation drawn and determine whether the correlation drawn is based on proper assumptions. In some examples, the message indicating that the user does not have the indicated health condition can include that the user has a different health condition that was not identified by the database previously. The database can correlate the different health condition with the user's determined biomarker characteristics.

Figure 46:
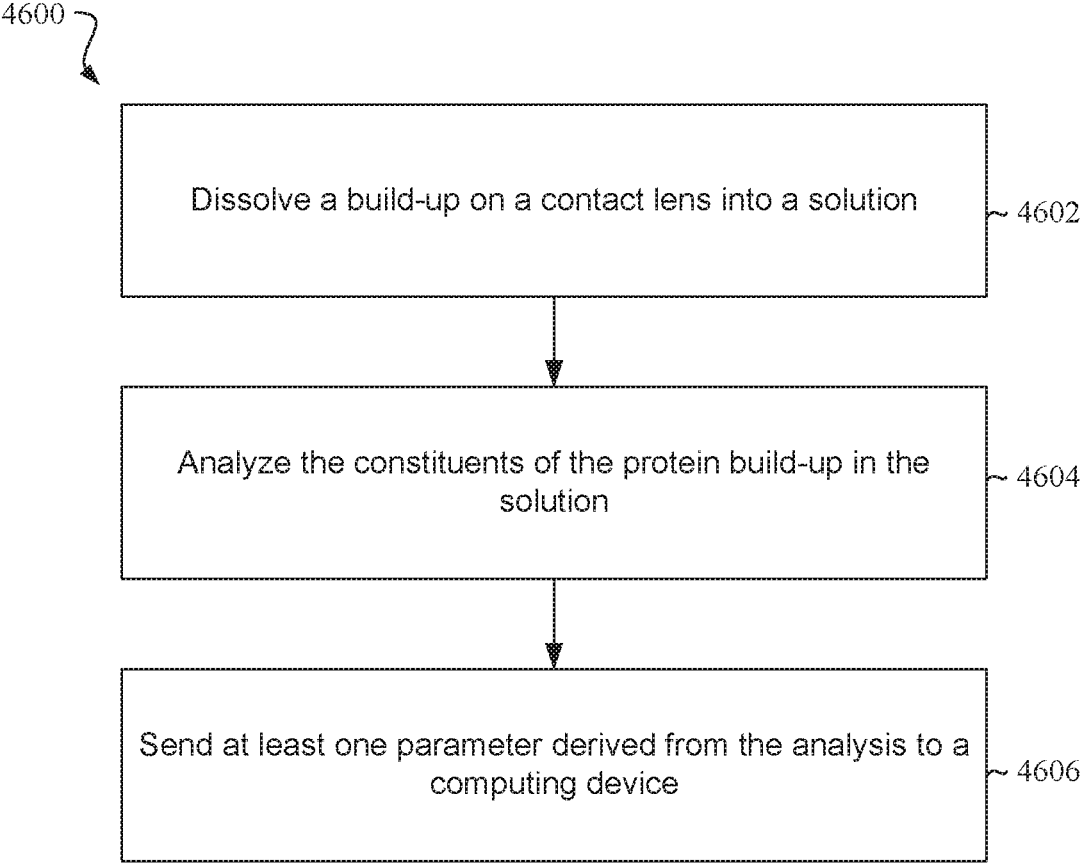
FIG. 46 illustrates a block diagram of a method of an example of determining a health condition, in accordance with the present disclosure.

FIG. 46 illustrates an example of a method 4600 of determining a health condition. In this example, the method 4600 includes dissolving 4602 a build-up on a contact lens into a solution, analyzing 4604 the constituents of the protein build-up in the solution, and sending 4606 at least one parameter derived from the analysis to a computing device. The process blocks 4604 and 4606 can be performed by, for example, the sensing device 4030.

At block 4602, the build-up can be dissolved by placing the contact lens into a contact lens storage solution. Any appropriate type of contact lens solution can be used. For example, the contact lens solution can be a hydrogen peroxide solution, a multiple purpose storage solution, another type of solution, or combinations thereof.

In some examples, the contact lens solution includes hyaluronan, sulfobetaine, poloxamine, boric acid, sodium borate, ascorbic acid, edetate disodium, sodium chloride, hydroxyalkyl phosphate, poloxamer, sodium phosphate buffer, polyoxyethylene polyoxypropylene block copolymer with ethylene diamine, and polyaminopropyl biguanide, or combinations thereof. The contact lens can include a disinfectant, a surfactant, an anti-fungal agent, an anti-bacterial agent, another type of agent, or combinations thereof.

The removal of the biomarkers from the contact lens into the solution can occur over any appropriate time period. In some examples, the biomarkers are in the solution for at least one minute, at least five minutes, at least 20 minutes, at least 45 minutes, at least an hour, at least two hours, at least 5 hours, at least 7 hours, at least one day, at least two days, another appropriate time period, or combinations thereof.

In some examples, the contact lens is free of surface cavities that are constructed to be binding sites for biomarkers or to draw in tear fluid into the contact lens. In some examples, the contact lens is free of surface treatments that target the binding of specific biomarkers to the contact lens.

In some embodiments, the storage solution can includes binding agents configured to facilitate the bonding between a surface of the contact lens and a biomarker from the tear fluid. In other examples, no binding agents are introduced to the contact lens solution. The contact lens can include a surface where the biomarkers are as likely to bind to any surface of the contact lens as any other surface of the contact lens. In some examples, the biomarkers can attach to the optical zone of the contact lens, a peripheral zone of the contact lens, an edge of the contact lens, a posterior side of the contact lens, an anterior side of the contact lens, another area of the contact lens, or combinations thereof.

The dissolved contents can then be analyzed at block 4604, for example according to the process 4302 or 4404 described herein with reference to FIGS. 43 and 44, respectively. At block 4606 at least one parameter derived from the analysis is sent to a computing device, for example as described with reference to FIG. 42.

The principles described in the present disclosure can be applied to other devices that can reside within cavities of the user. For example, a user's mouth guard can be placed in a solution for cleaning when it is removed from the user's mouth after a night's sleep. Proteins, antibodies, lipids, enzymes, electrolytes, and so forth can bind to the mouth guard. These biomarkers can dissociate with the mouth guard into the solution and can be analyzed. The measured biomarker levels can be compared to the correlations contained in a database to determine a dental condition of a user or another type of condition of a user.

In other examples, the device can be a tooth brush, cotton swabs, floss, a q-tip, a head phone, needles, a digestible device, band aids, another type of bandage, removable orthopedic hardware, other types of hardware, chewing gum, other types of device, or combinations thereof.

FIG. 47 depicts an example of a method 4700 for determining a health condition of a user. In this example, the method 4700 includes analyzing 4702 a first characteristic of at least one biomarker from a first contact lens previously worn by a user during a first time period, comparing 4704 the first characteristic with a second characteristic of the at least one biomarker from the user, determining 4706 a change between the first characteristic and the second characteristic, and comparing 4708 the change with a database that correlates the change with the health condition. The process block 4702 can be performed by the same entity (e.g., a processor) as that for the block 4302 in FIG. 43. The process block 4704 through 4708 can be performed by the processor 4015 (specifically, the biomarker and database comparer 4055, for example).

At block 4704, the first characteristic is compared to a second characteristic. The first and second characteristics can be obtained from the same contact lens that is worn at different times. For example, the user can wear the contact lens on a first day and remove the contact lens at the end of the first day when the user has the biomarkers removed from contact lens. An analysis on the biomarkers can be done to obtain the first concentration, such as a first concentration of a first biomarker. On the second day, the user can place the contact lens back into his or her eye and removed the contact lens at the end of the day. The biomarker removal and analysis can also be performed. The second characteristic can be a different concentration of the first biomarker. Thus, the change can be an increased concentration, a decreased concentration, another type of concentration, or combinations thereof. In some embodiments, analysis on the biomarkers can occur once per day for the span of multiple days. In this embodiment, the concentration of biomarkers can be averaged to overcome anomalies associated with a single analysis (e.g., the concentration level of a certain biomarker is found to be uncommonly high or low on one of the days but is at an ordinary concentration level the other days).

In some examples when the same contact lens is used to obtain the second set of biomarkers, the database can include specific correlations. In some examples, not all of the biomarkers can be removed from the contact lens during the first night of cleaning, therefore, the second night when the contact lens is placed in the solution for cleaning more biomarkers can be obtained. In other examples, those biomarkers that remain on the contact lens after the first cleaning can block other biomarkers from attaching to the contact lens such that it is common to obtain fewer biomarkers on the second night.

In other examples, the second set of biomarkers can be obtained from a fresh contact lens. In those situations, lingering biomarkers from the previous cleaning time may not be an issue. The second set of biomarkers (e.g., a second set of biomarker characteristics) can be obtained from a second contact lens that is different than a first contact lens (the contact lens from which the first set of biomarker characteristics were obtained).

At block 4708, the change between the first and second concentrations can be compared to the database where the change is correlated with a health condition. The computing device can, with reference to the database, send, and the user (i.e. the mobile device, hand-held device, sensor, etc.) can receive an indication of the correlated health condition.

In some examples, the first characteristic is obtained at a different time than when the second characteristic is obtained. In other examples, the first and second characteristics can be obtained in about the same time period. For example, a first contact lens can be worn in a first eye and a second contact lens can be worn in a second eye, and the characteristics of the biomarkers can be analyzed. In those situations where the characteristics are different, there can be condition present in one of the eyes that is not in the other eye.

The user can have an account associated with the hand-held device, the mobile device, the database, or associated with another computing device that stores at least some of the characteristics of the user's biomarkers when they are sent to the database. These stored recordings can compile a health history of the user. The health history can be reviewed by the doctor to assist with helping to detect other health conditions, assist in making a treatment plan, assist in making a prevention plan, assist in helping diagnosis health conditions of relatives, determine other types of information, or combinations thereof.

In order to further clarify the specifics of the present disclosure, one embodiment of the present disclosure will be described in detail in reference to FIGS. 48-50. The particular embodiment utilizes an electrode disposed within a contact lens container housing an aqueous solution. The electrode is configured to generate a current at a surface of the electrode. Biomarkers within the aqueous solution can cause the current generated at the surface of the electrode to vary depending on the type, concentration, or other characteristics of the biomarker(s) within the solution. Additionally or alternatively, an impedance can be measured within the aqueous solution. The measured impedance can also vary depending on the type, concentration, or other characteristics of the biomarker(s) within the solution. Deionized water can be used to dilute the aqueous solution to a desired biomarker concentration.

Figure 48:
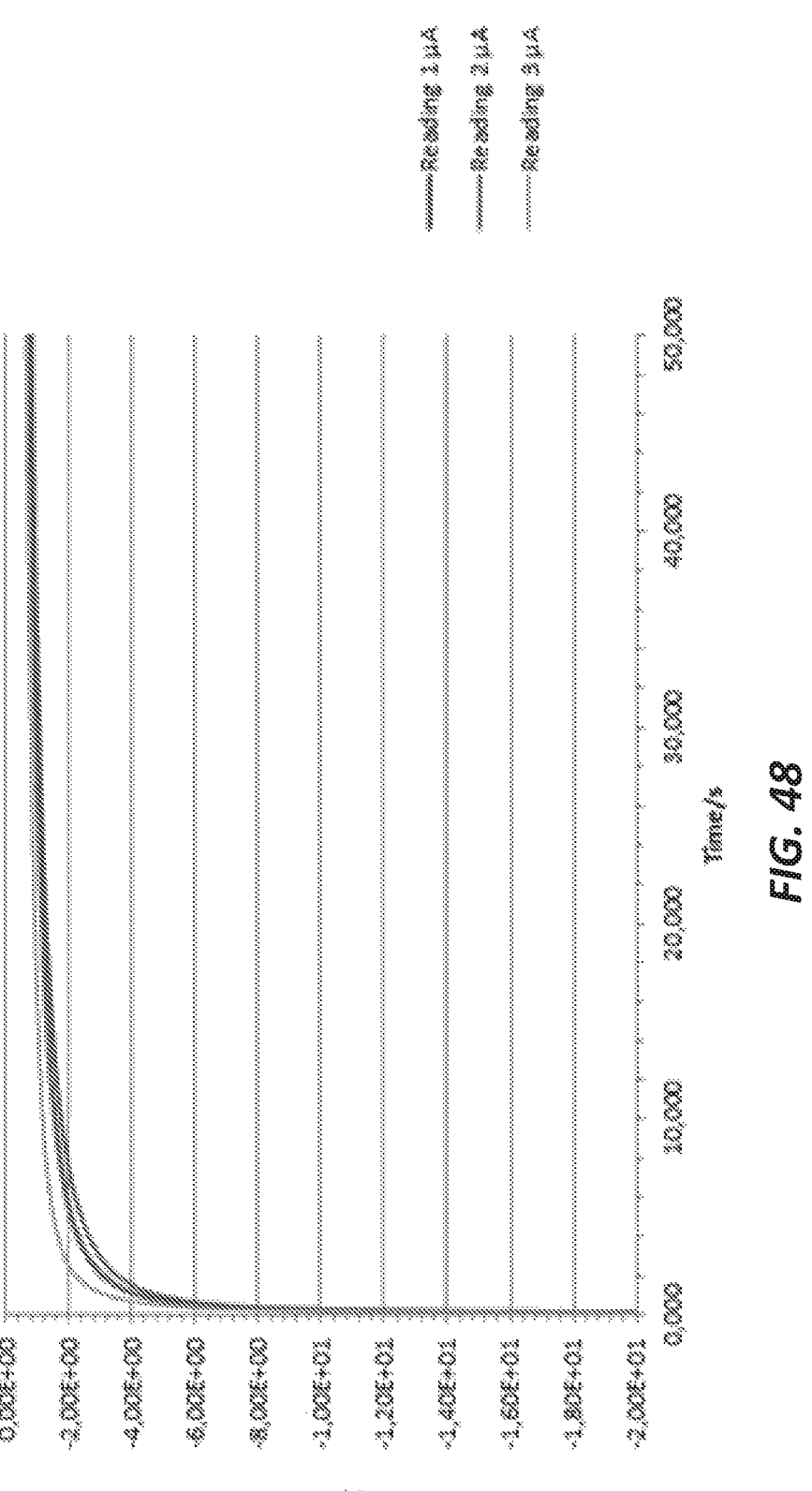
FIG. 48 depicts a graphical representation of measured current at an electrode, in accordance with the present disclosure.

In FIG. 48, a graphical representation of measured current at an electrode positioned within an aqueous solution over a period of time is illustrated. More specifically, chrono-amperometric measurements were taken using the electrode to overlay three sample readings. The three sample readings depicted in FIG. 48 relate to three repeated measurements (i.e., Reading 1, Reading 2, and Reading 3) using three sets of contact lenses which were each deposited into an aqueous solution after being worn for a 12 hour period. The contact lenses were configured to bind immunoglobulin E ("IgE") onto a surface of the contact lens from the wearer's tear fluid. As illustrated by the FIG. 48, each of the readings reached a similar steady-state current of approximately −2 μA at the electrode after 50,000 seconds.

Figure 49:
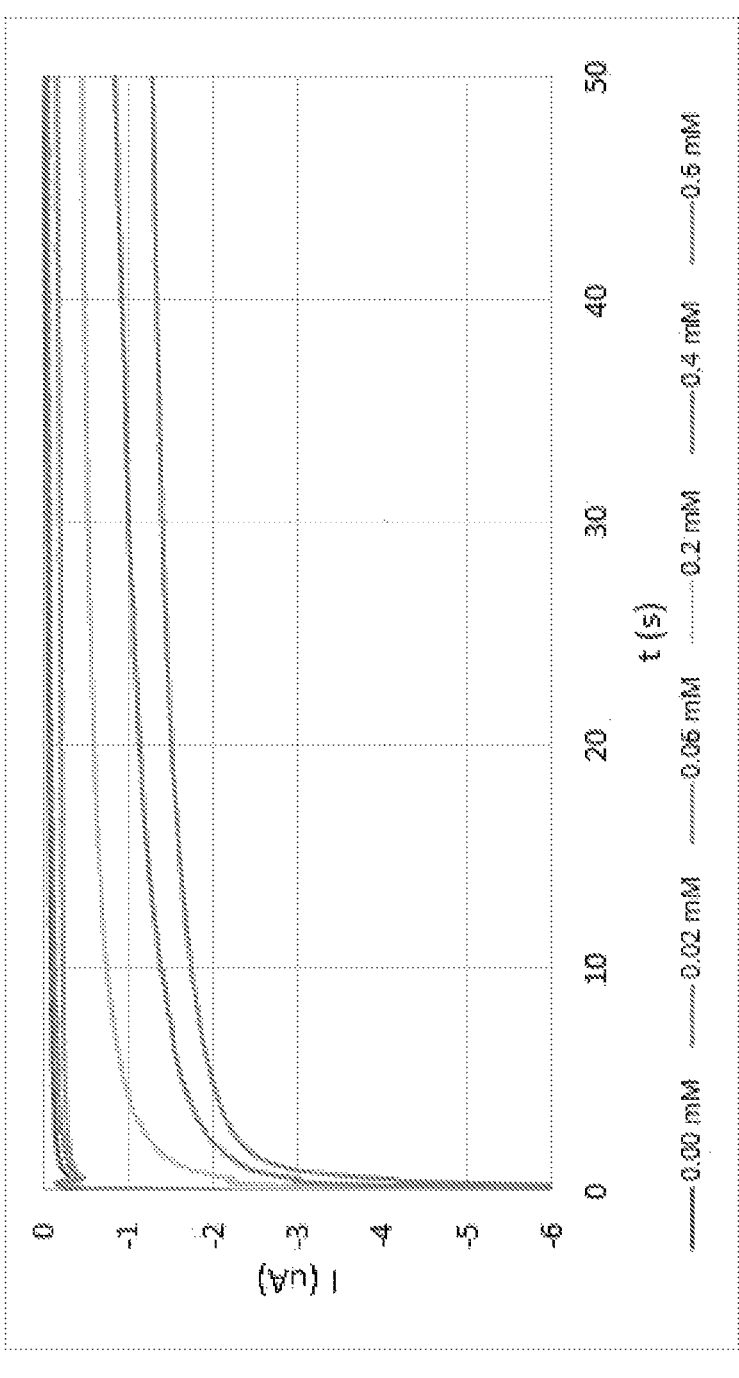
FIG. 49 depicts a graphical representation of measured current intensity at an electrode, in accordance with the present disclosure.

In FIG. 49, a graphical representation of measured current intensity at an electrode within an aqueous solution over a period of time is illustrated. More specifically, chrono-amperometric measurements were taken using a plurality of electrodes, each submerged in a different aqueous solution sample. Each aqueous solution sample contained a different concentration of glucose which ranged between 0.02 mM and 0.6 mM.

When a contact lens is worn, tear fluid containing glucose can adhere to a surface of the contact lens. This tear fluid can dissolve within an aqueous solution and disseminate throughout the aqueous solution when the contact lens is placed within the solution. As illustrated in FIG. 49, the concentration of glucose within a respective aqueous solution can influence the current intensity measured at an electrode over a period time. Thus, an intensity measurement at a given period of time can be used to correlate a concentration of glucose within an aqueous solution.

Current intensity measurements relative to a particular glucose concentration can be stored within a database. Moreover, a particular health condition associated with the particular glucose level can also be stored within the database. Thus, measurements taken at a storage container for contact lenses can be referenced with the information stored on the database to correlate a health condition. In some embodiments, a computing device or processor can be utilized to communicate with the database.

Figure 50:
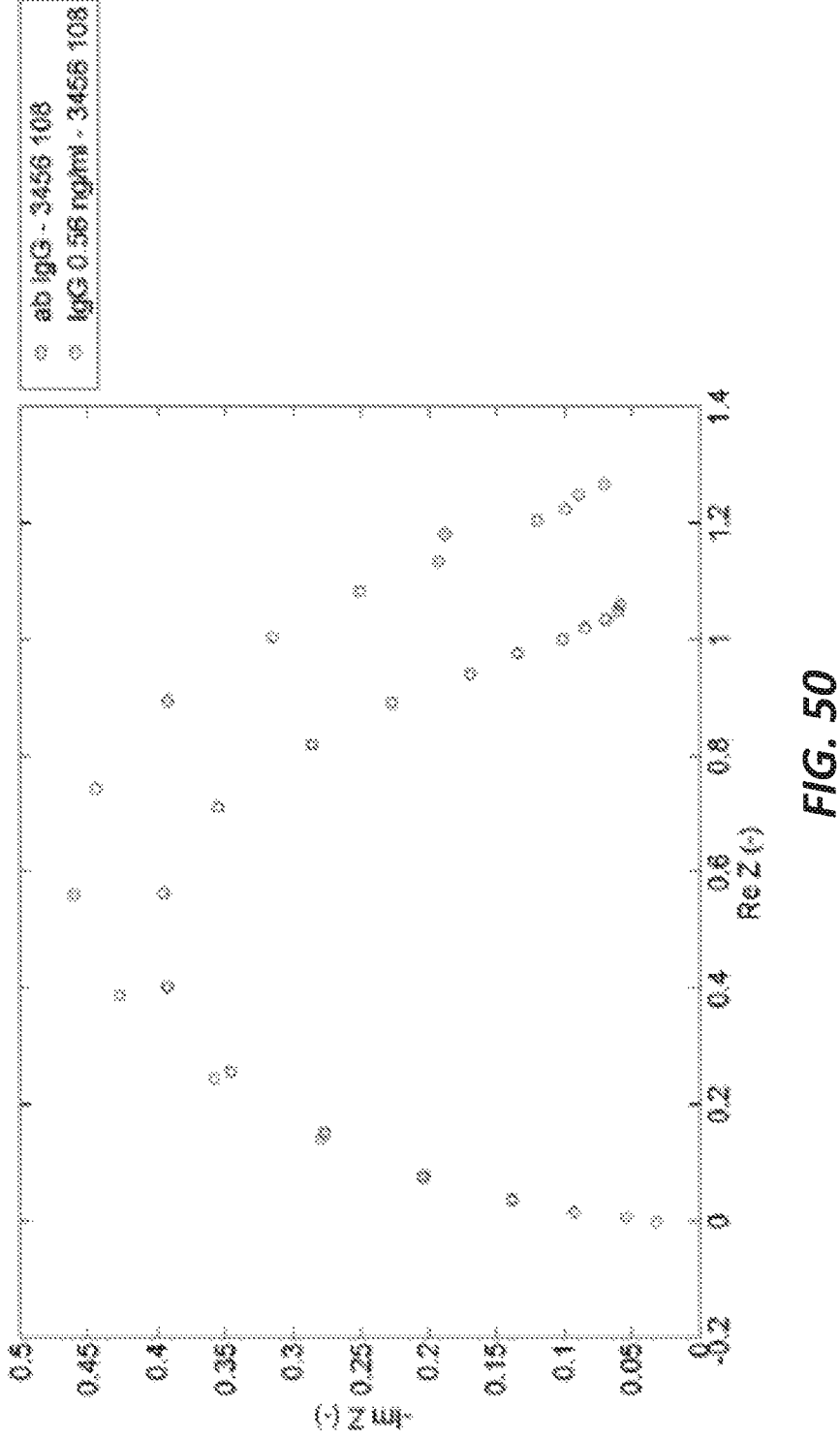
FIG. 50 depicts a graphical representation of the impedance measured at an electrode, in accordance with the present disclosure.

In FIG. 50, a graphical representation of the impedance measured at an electrode is illustrated. More specifically, a Nyquist plot is shown which depicts a change in measured impedance within an aqueous solution as an applied signal at an electrode transitions from a high frequency to a low frequency. Moreover, two aqueous solution samples were utilized. The first sample (i.e., ab IgG) contained no immunoglobulin G ("IgG") in the solution and the second sample (i.e., IgG 0.56 ng/ml) contained a concentration of 0.56 ng/ml of IgG. As illustrated in FIG. 50, the measured impedance does not substantially differ under high frequencies but begins to diverge as the frequency decreases. Thus, the concentration of IgG within an aqueous solution can be determined by measuring impedance within the solution.

Second Embodiment

The principles presented in this disclosure include a method of using the constituents of the tear fluid as biomarkers that can be analyzed to recommend a contact lens for the user, as described in U.S. application Ser. No. 62/642,875 filed 14 Mar. 2018, the disclosure of which is incorporated herein, in its entirety, by this reference. These biomarkers can be collected on a contact lens worn by the user. Any appropriate type of contact lens can be used to collect the biomarkers. However, unaltered commercially available contact lenses from a wide variety of manufacturers for corrective vision are envisioned to be the contact lens that are used to collect the biomarkers. Biomarkers, such as proteins, generally start to bind to the contact lens as soon as the contact lens is placed over the user's eye. Without modifying the contact lens as they are provided by the manufacturers, proteins, electrolytes, and/or other biomarkers in the tear fluid can bind to the contact lens. The number or concertation of proteins adsorbed or otherwise bound to the contact lens can be correlated to the contact lens material and a patient's ocular health status. By collecting, organizing, and referencing biomarker characteristics, a contact lens recommendation can be generated which correlates the biomarker characteristic (e.g., protein concentration) with a patient's ocular health database and proposes a preferential contact lens type for future wear.

Generally, a user removes their contact lenses after wearing them for a period of time. Often, before the user retires to bed, the user removes their contact lens and places the contact lens in a storage example for the night. The storage example can include a storage solution that disinfects the contact lens and also breaks down the build-up on the contact lens. The storage solution can be an aqueous solution that causes the build-up on the contact lens to dissolve into the solution. After a period of time, the storage solution can be replaced with fresh storage solution to reduce the concentration of tear fluid constituents or other contaminants within the solution.

The storage solution can be analyzed to determine the type and/or concentration of biomarkers that dissolved into the solution from the contact lens. In some examples, the solution can be analyzed with the contact lens in the solution. In other examples, the contact lens can be removed from the solution before analyzing the biomarkers.

In some embodiments, a sensor or a sensing device can be used to collect analyte information from the solution. Any appropriate type of sensor can be used to identify the type and/or concentration of the biomarkers within the solution. In some instances, the sensor can be incorporated into the contact lenses' storage container. For example, an optical spectral analyzer can detect or otherwise measure light properties from a light source within the storage container. The spectral analyzer can measure the amount the light's optical transmittance through the storage solution. In some examples, the light source passes light through the storage solution at isolated predetermined wavelengths and the spectral analyzer measures the optical transmittance at each of the predetermined wavelength ranges. Each of the recorded transmittances can correlate to the presence of specific kinds of biomarkers and their concentrations. In one embodiment, the storage container can comprise the sensor, a processor, and a memory. The sensor can be configured to obtain information which indicates a characteristic of at least one biomarker derived from a contact lens used by a user and stored in the storage container. The processor can be configured to send the information to a computing device which generates a contact lens recommendation for the user based on the information.

In other examples, the sensor can be incorporated into a hand-held device. In one example, the sensor can be incorporated into the user's mobile device, such as a smart phone and/or electric tablet. In one of these types of examples, the user can direct a beam of light into the storage solution and measure a reflection.

In some embodiments, the measured values can be augmented with complementary information, such as an amount of time that the user wore the contact lens. For example, the user can interact with a user interface to input how long the user wore the contact lenses. In some examples, the user can be prompted to input the number of hours that the user wore the contact lens. In other examples, the user can be prompted to input the number of days that he or she wore the contact lenses, whether the user removed the contact lenses during the night, the time of when the storage solution was last replaced, other factors that can affect the concentration of biomarkers in the storage solution, or combinations thereof.

In some embodiments, the sensor or other sensing device can record measured values or data to determine a concentration of each of the desired biomarkers. The recorded measurements (i.e., the measured values) can be a numerical value which fall within a predetermined range of numerical values correlated with particular biomarkers. In some examples, the sensor or a sensing device can record solution data in real time. Further, the sensor or sensing device can include local and/or cloud based logic to determine the type concentration, and/or other characteristics of the varying kinds of biomarkers. In some examples, the sensor or a sensing device can use learning algorithms, predictive models, data correlation models, clustering models, artificial intelligence, any other appropriate computational techniques, and combinations thereof. In some examples, the algorithms applied to data collected from the sensor or sensing device can include support vector machines, neural networks, decision trees, Gaussian mixture models, hidden Markov methods, and wavelet analysis. The models used to learn from data can include but are not limited to anomaly detection models, clustering models, classification models, regressions models or summarization models. In some examples, the sensor or sensing device can include a database that stores data used to correlate or compare the identification/concentration of the biomarkers and a contact lens recommendation for the user.

In another embodiment, a sensing device can be used to detect a user's ocular surface parameters related to corneal tribological properties. Such corneal tribological properties can be measured, analyzed, and recorded in the database. For example, a temperature profile of the user's eye can be collected. Such tribological properties can identify the effect a particular contact lens can have on the ocular surface of the wearer's eye. Such tribological properties can include reported patient characteristics, a response to ocular surface stimulation, a functional visual acuity, blinking parameters, tear biomarkers, a contact lens deposition analysis, ocular surface temperature, and ocular surface resistance to movement.

Figure 51A:
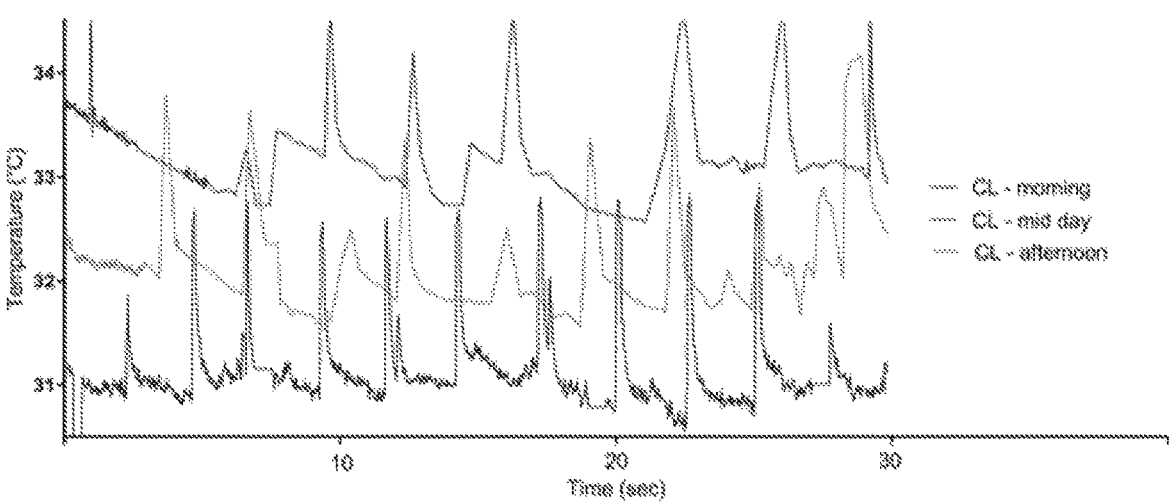
FIG. 51A depicts a graphical representation of measured ocular surface temperature in accordance with the present disclosure.
Figure 51B:
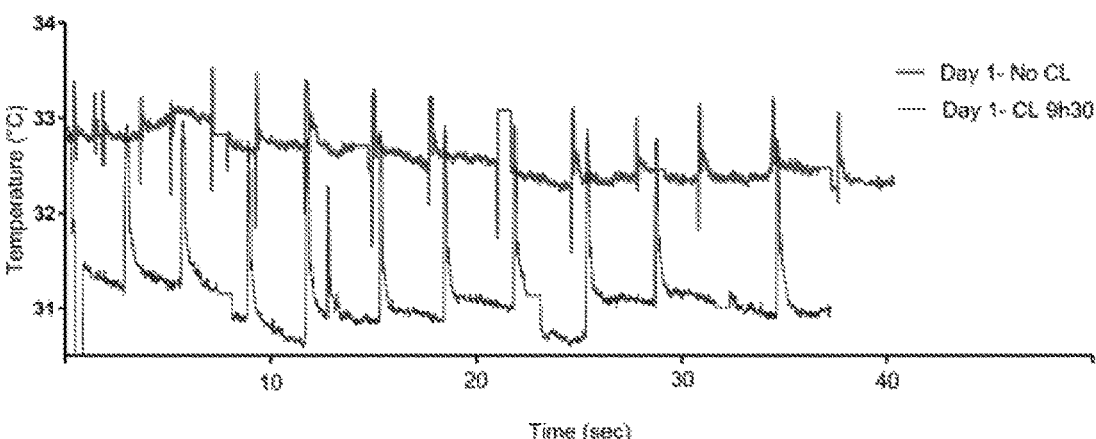
FIG. 51B depicts another graphical representation of measured ocular surface temperature in accordance with the present disclosure.

In some embodiments, a temperature of the ocular surface of a user's eye can be measured over a period of time. For example, FIG. 51A depicts ocular surface temperature measurements over a period of time. Three sets of measurements were collected from a contact lens (CL) wearer and the measurements were collected from the contact lens wearer in the morning, mid-day, and afternoon (i.e., CL-morning, CL-mid-day, and CL-afternoon). Temperature spikes within the data can represent the contact lens wearer blinking. The measurement data depicted in FIG. 51A illustrates that the ocular surface temperature of a contact lens wearer's eye can vary over a given period of time. FIG. 51B also depicts ocular surface temperature measurements collected over a period of time. Two sets of ocular surface temperature measurements were collected in FIG. 51B. First, ocular surface temperature measurements were collected without a contact lens (CL) positioned on the user's eye (i.e., Day 1-No CL). Second, ocular surface temperature measurements were collected with a contact lens positioned on the user's eye (i.e., Day 1-CL 9h30). As illustrated in FIG. 51B, the ocular surface temperature of an eye can vary based on whether the user is wearing a contact lens. Such tribological properties can be measured and recorded within a database.

The measurements can be sent to a computing device that processes the data or other information collected by the sensor. In some examples, at least some computations are performed by the sensor or a sensing device before sending data to a computing device where the computations are finished. In other examples, the sensor sends raw data to the computing device. In this example, all data processing, including data cleaning, data management, data mining, and any application specific issues, is performed remotely away from the sensor. In some examples, information processing can include data preprocessing, for example in order to format or modify the data for use in subsequent processing. In some examples, data preprocessing can include formatting for matrix computations, data normalization, data synchronization and data filtering.

The determinations of the type of biomarkers, the characteristics of biomarkers, such as the concentration of the biomarkers, chemometric data such as ratio kinetics, peak, plateau, time constant, decay, and so forth can be compared to data points stored in a database. The database can be local to the computing device or the computing device can have remote access to the database. The data in the database can correlate the measured biomarker characteristics (e.g., different types and concentrations of biomarkers) with contact lens recommendations or health conditions, such as eye health conditions, allergic conditions, other physiological conditions, or combinations thereof. In some examples, the data in the database can be used as input or training data to implement supervise machine learning techniques, or other statistical learning approaches to solve prediction inference, or other data mining problems related to health conditions, such as eye health conditions, allergic conditions, other physiological conditions, or combinations thereof.

These health conditions can correlate to certain contact lens types that are preferred by or beneficial to users. For example, a first type of contact lens can cause those with certain types of allergies to have discomfort. The allergy type can be detected in the database, and more comfortable types of contact lens can be recommended to the user. In some examples, the database directly correlates the biomarker characteristics directly to recommendations for types of contact lens. The recommendation can include the preferred types of contact lenses from users with similar biomarker characteristics. In some examples, the database is populated with user's preferences for contact lens based on comfort, dry eyes, or other considerations. The database can sort these preferences based on the user's biomarker characteristics.

The database can also store information such as an amount or percentage of correlation between the user's biomarker characteristics and their contact lens preferences. For example, if ninety-five percent of the users with a specific biomarker profile prefer the same type of contact lens, then the correlation rating can be considered high or strong and information regarding this correlation can be stored in the database. In other examples, if just fifty-five percent of the users with a specific biomarker profile have a preferred contact lens type, then the correlation rating can be considered lower, but still high enough to make a recommendation. Correlations with multiple biomarkers can be stored and considered in generating a contact lens recommendation. In those examples, where users with a certain biomarker profile have a plurality of preferred contact lenses, the recommendation can include each of the preferred contact lens, for example in a ranked list. In this situation, the computing device, with reference to the database, can determine which types of contact lenses are not preferred and warn the user against the use of those types of contact lenses. In some examples, the reasons why the contact lenses are preferred or are not recommended can be collected and stored within the database as preference information. This preference information can be shared with other users who have similar biomarker profiles.

In some examples, the database can be in communication with multiple users and data sources. As data relating to a user's biomarker characteristics is collected, this data and data from a plurality of other users can contribute to the information stored within the database. In some examples, data collection can automatically launch a data management system of the database. In some examples, the data management system or another process can incorporate additional data into the database, such as health conditions of each of the users. As a result, the correlations in the database can include reports from the users. The computing device can update the database based on the reports from the users. In some examples, patient data can be used as predictors in a statistical machine learning process. In some examples where the database is built using thousands of users, the database's input can identify correlations between contact lens preferences and specific levels of different types of biomarkers that are unknown to the scientific community. Thus, even before scientific studies can be conducted to find a correlation between a biomarker and a health condition or contact lens recommendation, the computing device can, with reference to the database, send information related to the contact lens recommendation. In some examples, if the user does not have a contact lens preference, no preferences have to be sent. In some situations, those contact lenses that the user does not like can also be sent to the database. As a result, the correlations in the database can also be derived from user reports. In some examples where the database is derived using information from thousands of users, the database's input can identify correlations between user preferences and biomarker profiles.

These principles can allow a vast database to be built that correlates the contact lens preferences of the users with varying parameters of the biomarkers (ie., biomarker characteristics). For example, the database can include supplementary user data such as age, gender, weight, height, and the like.

These principles also allow the user to have a non-invasive procedure to measure the biomarkers and receive a contact lens recommendation. Further, in those examples in which the user is already storing and cleaning his or her contact lens from time to time, the user can incur little to no additional effort in measuring the biomarkers and receive reports on a contact lens recommendation.

The recommendation can include recommending a certain lens material. For example, certain lens materials can react with a user's eye to cause inflammation or make the user's eye prone to infection. In some examples, the contact lens can have a wrong prescription that can cause the eye to react by producing a certain biomarker. In this example, the recommendation can include having the eye prescription checked. In yet other examples, the recommendation can include switching to a different contact lens type, such as daily disposable lens, rigid gas permeable lens, soft contact lens, and so forth. In some examples, the recommendation can include specific brands of contact lenses.

Referring now to the figures, as described above, FIG. 18 depicts an example of a contact lens 1810 situated on the outside of a human eye 1850. The contact lens 1810 spans a portion of the outside surface of the exposed portion of the eye 1850. An upper portion of the contact lens 1810 is adjacent a set of eyelashes 1852 of the upper eye lid. The contact lens 1810 can include a posterior side that is in contact with the cornea of the eye 1850, and an anterior side that is opposite of the posterior side. As the eye lid travels over the eye 1850, the eye lid can move across the anterior side of the contact lens 1810.

A user can wear the contact lens for vision correction purposes. In this type of example, the contact lens can include an optic zone 1820 and a peripheral zone 1822. The optic zone 1820 can include a region that focuses light to the center of the user's retina 1824. The peripheral zone 1822 can contact the eye near or over the sclera. While this example discloses using commercially available contact lenses configured for vision correction to be worn on the eye, other types of contact lenses can be used in accordance with the principles described in the present disclosure. For example, the contact lens may not include a curvature or other features configured to correct vision. Indeed, a physician can prescribe contact lenses for the sole purpose of collecting biomarkers within the patient's tear fluid, in one embodiment.

The contact lens 1810 can be a soft contact lens, rigid gas permeable (RGP) contact lens, orthokeratology contact lens, another type of contact lens, or combinations thereof. The contact lens can be made of any appropriate type of material. A non-exhaustive list of materials that can be used to construct the contact lens can include any appropriate silicone material and/or hydrogel material. Such material can be formed of polymers, such as tefilcon, tetrafilcon A, crofilcon, helfilcon A&B, mafilcon, polymacon, hioxifilcon B, lotrafilcon A, lotrafilcon B, galyfilcon A, senofilcon A, sifilcon A, comfilcon A, enfilcon A, lidofilcon B, surfilcon A, lidofilcon A, alfafilcon A, omafilcon A, vasurfilcon A, hioxifilcon A, hioxifilcon D, nelfilcon A, hilafilcon A, acofilcon A, bufilcon A, deltafilcon A, phemfilcon A, bufilcon A, perfilcon, etafilcon A, focofilcon A, ocufilcon B, ocufilcon C, ocufilcon D ocufilcon E, ocufilcon F, phemfilcon A, methafilcon A, methafilcon B, vilfilcon A, other types of polymers, monomers, or combinations thereof. These materials can include various combinations of monomers, polymers, and other materials to form the material that makes up the contact lens.

In one embodiment, the contact lens material can be made of hydrogel polymers without any silicone. This can be desirable to increase the wettability of the contact lens. In another embodiment, the contact lens material can be made of silicone hydrogel material.

The tear fluid in the ocular cavity can come into contact with the contact lens. In some examples, the entire surface area of the contact lens can come into contact with the tear fluid. The constituents of the tear fluid can include lipids, electrolytes, metabolites, proteins, antibodies, other types of compounds, or combinations thereof. These constituents can be biomarkers that can be indicative of a health condition, a genetic condition, an eye condition, another type of condition, or combinations thereof of the user. These biomarkers can bind to the contact lens.

A non-exhaustive list of biomarkers from the tear fluid that can be of interest includes, but is not limited to, electrolytes, sodium, potassium, chloride, phenylalanine, uric acid, galactose, glucose, cysteine, homocysteine, calcium, ethanol, acetylcholine and acetylcholine analogs, ornithine, blood urea nitrogen, creatinine, metallic elements, iron, copper, magnesium, polypeptide hormones, thyroid stimulating hormone, growth hormone, insulin, luteinizing hormones, chorionogonadotrophic hormone, obesity hormones, leptin, serotonin, medications, dilantin, phenobarbital, propranolol, cocaine, heroin, ketamine, hormones, thyroid hormones, ACTH, estrogen, cortisol, progesterone, histamine, IgE, cytokines, lipids, cholesterol, apolipo protein $A_1$, proteins and enzymes, lactoferrin, lysozyme, tear-specific prealbumin or lipocalin, albumin, complement, coagulation factors, liver function enzymes, heart damage enzymes, ferritin, virus components, immunoglobulins such as IgM, IgG, proteases, protease inhibitors, lactate, ketone bodies, other types of biomarkers, or combinations thereof.

In some embodiments, commercially available contact lenses can have surface properties that allow the biomarkers to bind to the contact lens without any modifications to the contact lens. Conventionally, protein build-ups and other types of build-ups on the surface of a contact lens are considered a problem on a regular contact lens that does not have surface modifications to enhance a biomarker's ability to bind to the contact lens. In other examples, the contact lens can be modified to enhance the binding ability of particular biomarkers or biomarkers in general. In those embodiments in which the surface of the contact lens can be modified to enhance an ability to bind to the biomarkers, the binding enhancements can be made to any appropriate location on the contact lens, including, but not limited to, the peripheral zone, the optical zone, the anterior side of the contact lens, the posterior side of the contact lens, other areas of the contact lens, or combinations thereof. In one example where the contact lens is modified to enhance its ability to collect biomarkers, micro-cavities can be formed in the contact lens material that are shaped and sized to encourage an intake of tear fluid through capillary action.

As previously described, FIG. 19 depicts an example of biomarkers 1914 attached to the posterior surface 1930 of the contact lens. While this example depicts the biomarkers 1914 attached to the posterior surface 1930 of the contact lens, the biomarkers 1914 can be attached to only the anterior surface 1932 or to both the anterior surface 1932 and posterior surface 1930 of the contact lens 1810. In some examples, the biomarkers 1914 can be adsorbed, absorbed, bonded, covalently bonded, ionically bonded, adhered, cohered, or otherwise connected to a surface of the contact lens 1810. In some examples, the biomarkers 1914 are incorporated into the thickness of the contact lens 1810.

When the contact lens 1810 is removed from the user's eye, the biomarkers 1914 can stay with the contact lens 1910 as depicted in FIG. 19. The amount of biomarkers 1914 that are attached to the contact lens 1810 can be related to the amount of time that the contact lens 1810 was on the eye. In some examples, the contact lens 1810 can be worn by the user during that day and removed at night. Under these circumstances, biomarkers 1914 can cover a substantial amount of the contact lens' surface area. However, in other examples, the contact lens 1810 can be worn by the user for a smaller period of time. In one specific instance, a patient can be provided with a contact lens 1810 for a period of minutes in a doctor's office to collect biomarkers 1914 for analysis. In other examples, a patient can be instructed to keep a contact lens 1810 in for a matter of hours or some other duration of time to collect the desired amount of biomarkers 1914.

As previously described, FIG. 20 depicts an example of a contact lens 1810 in a storage container 2040 with an internal cavity 2002. The cavity 2002 can be defined by a first wall 2004 and a second wall 2006 which are connected together bottom surface 2008. A contact lens 1810 and a solution 2012 can also be disposed within the cavity 2002.

The solution 2012 can include a cleansing agent, such as a hydrogen peroxide or another type of agent to clean the contact lens and kill bacteria, fungus, other types of germs, or combinations thereof. The solution 2012 can be an off-the-shelf type of storage solution that hydrates and cleans the contact lens. The storage solution 2012 can cause the biomarkers 1914 to dissolve into the solution 2012 thereby cleaning the contact lens 1810. The contact lens 1810 can remain in the storage solution 2012 until the contact lens 1810 is later retrieved by the user. In some examples, the contact lens 1810 is immersed into the solution for a short period of time, such as a couple of minutes. In other examples, the contact lens 1810 can remain in the solution for multiple hours, such as overnight. With the biomarkers 1914 removed from the contact lens 1810, the biomarkers 1914 can be diluted into the solution 2012 where the biomarker types, their respective concentrations, or other biomarker characteristics can be measured or analyzed.

The biomarkers 1914 can be removed from the contact lens 1810 without adversely affecting the contact lens 1810. In those examples, the contact lens 1810 can be re-worn by the user. In some examples, the contact lens 1810 is removed from the solution 2012 so that the contact lens 1810 is not affected by the testing mechanism performed on the solution 2012. In other examples, the contact lens 1810 can remain in the solution 2012 while the solution 2012 is being measured or analyzed, but the analysis does not adversely affect the contact lens 1810 so that the contact lens 1810 can be re-worn by the user.

In some examples, the biomarkers 1914 can be analyzed in the storage container 1940. In other examples, the solution 2012 can be transferred to another type of device with a sensor for taking the measurements. In yet another example, a hand-held device can incorporate a sensor configured to perform the measurements or analysis on the solution 2012.

One approach of analyzing the solution, as described above, is depicted in FIG. 39A. In some embodiments, an optical spectral analyzer can be incorporated into the storage solution container 1940. In the example depicted in FIG. 39A, a storage container 1940 for a contact lens 1810 includes a cavity 2002 that is defined by at least one wall 2004 that is connected by a floor 2126. In some examples, a single circular wall can define at least a portion of the cavity 2002. In other examples, multiple independent walls are joined together to define the cavity 2002.

A light source 2142 can be incorporated into a first side of the cavity 2002. The light source 2142 can be oriented to direct a beam of light 2144 through the solution 2012 to a light receiver 2146. As the beam of light 2144 is transmitted through the solution 2012, a portion of the light can be absorbed by the solution depending on its contents. A solution 2012 with a different type of biomarker 1914 can cause a different or unique light transmittance through the solution 2012. Further, a solution 2012 with a different concentration of the same biomarker 1914 can also exhibit a different or unique light transmittance.

In some embodiments, the light source 2142 can be configured to transmit a range of isolated wavelengths independently through the solution 2012. The transmittance for each wavelength can be measured. Certain biomarkers in the solution 2012 may not affect the optical transmittance at a first wavelength, but can affect the optical transmittance at a second wavelength. Thus, by transmitting or otherwise emitting light at different wavelengths, a more refined measurement of the solution's composition can be measured and recorded. The measured transmittances at each wavelength can be compared to other solutions wherein the types and concentrations of the biomarkers are known. Thus, the measured transmittance levels can be correlated to the types and concentration of the biomarkers 1914 in the solution 2012.

Other types of spectroscopic methods can be used to identify the types and concentration of the biomarkers in the solution. In some examples, measuring a frequency rather than a wavelength can be performed by the light receiver 2146 (e.g., spectral analyzer). A non-exhaustive list of other types of spectroscopic mechanisms for analyzing the solution can include atomic absorption spectroscopy, attenuated total reflectance spectroscopy, electron paramagnetic spectroscopy, electron spectroscopy, Fourier transform spectroscopy, gamma-ray spectroscopy, infrared spectroscopy, laser spectroscopy, mass spectrometry multiplex or frequency-modulated spectroscopy, Raman spectroscopy, and x-ray spectroscopy. Additionally or alternatively, ultraviolet absorbance at 280 turbidity, and light scattering can be used to analyze the solution for biomarker characteristics. Concerning ultraviolet absorption, the intensity of the ultraviolet absorbance can depend on the tryptophan and tyrosine content of the proteins. Such characteristics can be correlated in a database to a calibration curve with known concentration of proteins. The analysis can be aided or otherwise enhanced by incorporating a colorimetric assay into the solution (e.g., binding a dye to the biomarker or biomarkers).

While the example embodiment of FIG. 39A includes the light source 2142 and the light receiver 2146 on different sides of the cavity walls, the light source 2142 and the light receiver 2146 can be on the same side of the cavity 2002. In such an example, light emitted from the light source 2142 can be reflected within container and the reflection can be recorded or otherwise measured by the light receiver 2146 (e.g., a spectral analyzer).

In some examples, the sensor can be part of the hand-held device 4202 depicted in FIG. 42. In this example, the hand-held device includes a sensor, such as an infrared spectrometer, that can measure a concentration of a biomarker within the solution. For example, the hand-held device can include an end that has an infrared source that sends infrared light into the solution when the user orients the hand-held device to appropriately direct the infrared light and instructs the hand-held device to send the light. The amount of infrared light that is absorbed into the solution can be based at least in part on the constituents within the solution. Thus, the returning amount of the infrared light to the hand-held device can be measured using, for example, an infrared receiver incorporated into the hand-held device.

In other embodiments, a sensor or sensing device within the storage solution container 2040 can be configured to detect a pH level or pH value within the storage solution container 2040, for example, through colorimetric paper-based assay. The pH level or pH value within the storage solution container 2040 can indicate microbial contamination or other biomarker characteristics. In some embodiments, the pH level or pH value is measured without solution 2012 in the storage solution container 2040. In other embodiments, the pH level or pH value is measured with solution 2012 in the storage solution container 2040. The use of a colorimetric paper-based assay can produce a colorimetric output based on ultraviolet absorbance.

In yet other examples, the solution 2012 can be poured into another device for analysis. In one example, the solution 2012 can be poured into an immunodiffusion machine, a centrifuge, another type of device, or combinations thereof for measuring at least one property (e.g., a biomarker characteristic) of the solution 2012.

Another approach of analyzing the solution, as previously described, is depicted in FIG. 39B. In some embodiments, at least one electrode can be incorporated into the storage solution container 2040 to analyze the contents of the storage solution 2012 by chronoamperometry. In the example of FIG. 39B, an electrical potential can be applied to an electrode 3948 over a predetermined time period to elicit a resultant current intensity. The current intensity can vary relative to the properties of the solution 2012. For example, the current intensity measured at the electrode 3948 can vary relative to the concentration of glucose within the solution 2012, in one embodiment. The current intensity of the electrode 3948 can be recorded and compared with a database to determine a health condition of the contact lens user.

The electrode 3948 can be incorporated into the floor 2126 of the container 2040. In some embodiments, a stepped potential or voltage can be applied to the electrode 3948 wherein the voltage applied to the electrode 3948 increases by predetermined steps over a period of time. In other embodiments, the potential or voltage applied to the electrode 3948 can be a constant potential over a period of time. A plurality of electrodes comprising an array of electrodes can be incorporated into the floor 2126 or any other surface of the container 2040. The electrode 3948 can be operably coupled to a power supply (not shown) configured to supply electrical power to the electrode 3948. The electrode 3948 can be operably coupled to a processing unit (not shown) configured to measure operational parameters of the electrode (e.g., voltage, current, time, etc.).

Figure 52:
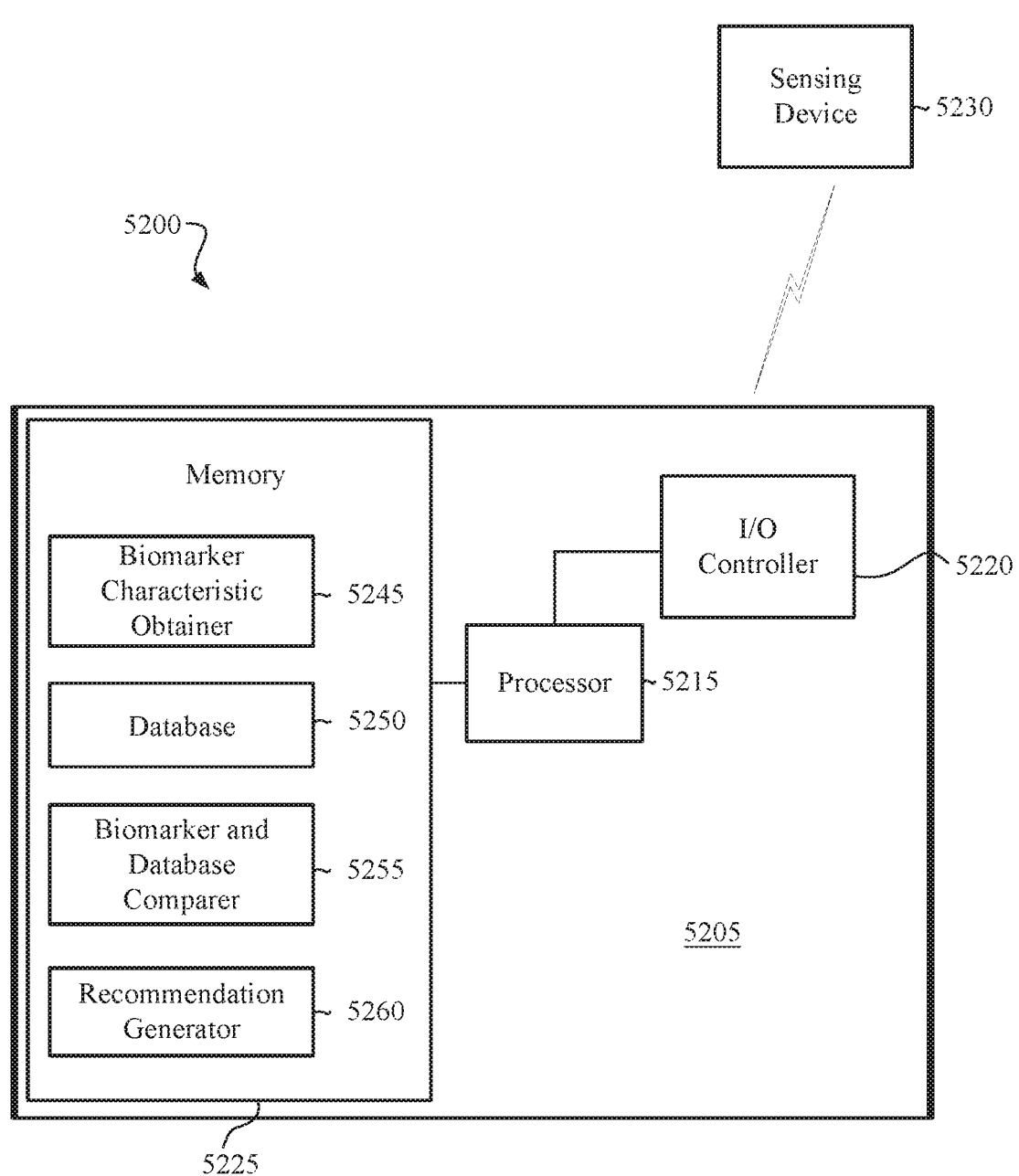
FIG. 52 is a block diagram of an example of a recommendation system in accordance with the present disclosure.

FIG. 52 depicts a diagram of a contact lens recommendation system 5200. The system 5200 includes a base station 5205 having a processor 5215, an input/output (I/O) controller 5220, and memory 5225. In some embodiments, the processor 5215 and the memory 5225 are components or subcomponents of a computing device, for example, the base station 5205 can be a computing device. The I/O controller 5220 can be in communication with a sensing device 5230, for example, through an antenna. In some examples, a sensor of the sensing device 5230 can be incorporated into the contact lens storage example, into a hand-held device, an independent machine configured to analyze the solution, another type of sensor, or combinations thereof. In some examples, the sensing device can include its own processor, memory, and/or I/O controller. The components of the system and the sensing device 5230 can communicate wirelessly, through hard wired connections, or combinations thereof. The memory 5225 of the system can include a biomarker characteristic obtainer 5245, a database 5250, a biomarker and database comparer 5255, and a recommendation generator 5260. In some embodiments, the system 5200 can further include a base station 5205 in communication with the memory 5225, the base station 5205 can be in communication with the processor 5215 and/or the sensing device 5230, for example via an antenna within the I/O controller 5220 or a transponder. In some embodiments, the sensing device 5230 is at least one electrode and/or optical spectral analyzer.

The processor 5215 can include an intelligent hardware device, (e.g., a general-purpose processor, a digital signal processor (DSP), a central processing unit (CPU), a microcontroller, an application-specific integrated circuit (ASIC), a field-programmable gate array (FPGA), a programmable logic device, a discrete gate or transistor logic component, a discrete hardware component, or any combination thereof). In some embodiments, the processor 5215 can be configured to operate a memory array using a memory controller. In other embodiments, a memory controller can be integrated into the processor 5215. The processor 5215 can be configured to execute computer-readable instructions stored in a memory 5225 to perform various functions (e.g., functions or tasks supporting the evaluation of the prescribed optical devices).

The I/O controller 5220 can include a modem, a keyboard, a mouse, a touchscreen, or a similar device. In some examples, the I/O controller 5220 can be implemented as part of the processor 5215. In some examples, a user can interact with the system via the I/O controller 5220 or via hardware components controlled by the I/O controller 5220.

The I/O controller 5220 can be in communication with any input and any output of the system 5200.

The memory 5225 can include random access memory (RAM) and read only memory (ROM). The memory 5225 can store computer-readable, computer-executable software including instructions that, when executed, cause the processor to perform various functions described herein. In some examples, the memory 5225 can include, among other elements, a basic input/output system (BIOS) which can control basic hardware and/or software operation such as the interaction with peripheral components or devices. The memory 5225 storing the software (e.g., a program) can be referred to as a "computer readable recording medium." The recording medium can be a "non-transitory tangible medium" such as, for example, a tape, a disk, a card, a semiconductor memory, a programmable logic circuit, or the like. The program can be supplied to the computer via any transmission medium (such as a communication network or a broadcast wave) that can transmit the program. In some embodiments, aspects of the present disclosure can also be achieved in the form of a computer data signal in which the various programs are embodied via electronic transmission and which is embedded in a carrier wave.

The biomarker characteristic obtainer 5245 can include programmed instructions that cause the processor 5215 to measure or record a biomarker characteristic from the solution. In other words, the processor 5215 can execute the programmed instructions to function as the biomarker characteristic obtainer 5245. The characteristic can include a biomarker identification, a biomarker concentration, another type of characteristic, or combinations thereof. In some examples, the biomarker characteristic obtainer 5245 passively receives a signal containing information about the biomarker characteristic. In other examples, the biomarker characteristic obtainer 5245 actively requests information about the biomarker characteristic.

The database 5250 can include a data structure that holds information relating to the biomarker characteristics. The database 5250 can include information relating to biomarker characteristics that have been recorded or measured in labs, for example, by chemometric methods, obtained from at least one user, or combinations thereof. In some examples, the database can be initially populated with information from users with a history of wearing contact lenses that know certain contact lens types are comfortable for them, caused them discomfort, or had a different experience. These users can submit their biomarker profiles (i.e., personal biomarker information) along with their contact lens history. In some examples, the users have their biomarker profiles analyzed or otherwise correlated with the database to detect a health condition or for another reason other than a contact lens recommendation. In some examples, thousands to millions of biomarker profiles can be collected in the database.

The biomarker and database comparer 5255 can represent or otherwise include programmed instructions that cause the processor 5215 to compare the obtained biomarker characteristic against the information stored in the database 5250. In other words, the processor 5215 can execute the programmed instructions to function as the biomarker and database comparer 5255. In some examples, the programmed instructions can include data mining algorithms to compare biomarker characteristics. The recommendation generator 5260 can represent or otherwise include programmed instructions that cause the processor 5215 to generate a contact lens recommendation based on the user's biomarker profile. In other words, the processor 5215 can execute the programmed instructions to function as the recommendation generator 5260.

In some embodiments, correlations between certain biomarkers and their respective concentrations can be realized with a larger sample size of patient information than the correlations between certain biomarkers that might be realized using only the information provided by an individual patient or user. For example, an analysis can be run on all the biomarker characteristics of users with a specific contact lens preference. Such an analysis can reveal that certain biomarkers that had not previously been linked to that contact lens preference has a statistically significant normal concentration level, a statistically significant low concentration level, a statistically significant high concentration level, another statistically significant concentration level, a statistically insignificant type of concentration level, or combinations thereof that had not previously been observed.

In some embodiments, a recommendation can include a confirmation request to confirm whether or not the user has a good experience with the recommended contact lens. In the examples where a confirmation request is sent and a confirmation message is received, the results of the confirmation test can be sent to a computing device. The results can be used to assist the database 5250 and its associated analytics to improve future recommendations. The confirmation can be conducted by a device that is commonly used by the user (e.g., a mobile phone, laptop, etc.).

FIG. 53 depicts an example of a database 5300 that associates or otherwise correlates a characteristic of the tear chemistry, eye condition (e.g., a health condition), and contact lens recommendation. In this example, the database 5300 can include a first column 5302 that includes the tear chemistry information (e.g., biomarker characteristics), a second column 5304 that includes eye condition information, and a third column 5306 that includes the contact lens recommendation. The database 5300 can include a first row 5308 that includes the correlation for a tear chemistry with a normal first biomarker level and a normal second biomarker level, a second row 5310 that includes the correlation for a tear chemistry with a normal first biomarker level and a high second biomarker level, a third row 5312 that includes the correlation for a tear chemistry with a low first biomarker level and a normal second biomarker level, a fourth row 5314 that includes the correlation for a tear chemistry with a low first biomarker level, a fifth row 5316 that includes the correlation for a tear chemistry with a high first biomarker level, and a sixth row 5318 that includes the correlation for a tear chemistry with a high second biomarker level.

While the example of FIG. 53 depicts an embodiment with correlations of a first and second biomarker, any number of biomarker correlations can be included in the database. In some embodiments, characteristics correlated with a single biomarker can be included as depicted in rows 5314, 5316, 5318. In other embodiments, the characteristics correlated with a specific set of biomarkers can be included. For example, recommendations correlated with two or more characteristics of different types of biomarkers can be included as depicted in rows 5308, 5310, 5312. Any appropriate number of biomarker characteristics can be included. For example, three to hundreds of characteristics can be collectively correlated to a specific type of health condition. In the example shown in FIG. 53, whether a biomarker level is "Normal", "Low", or "High" can be determined by comparing the measurement value of the biomarker with a predetermined threshold.

As previously described, FIG. 42 depicts an embodiment of a system 4200 for detecting a health condition using biomarkers, however, FIG. 42 can also depict a system for recommending a contact lens to a user. In one embodiment, a storage solution (i.e., aqueous solution) can be contained within a contact lens container 2040. A hand-held device 4202 with a sensor can be used to take a measurement of at least one characteristic of the biomarkers in the solution. The hand-held device 4202 can send the recorded levels to a mobile device 4204 (i.e., a computing device) that is in communication with a cloud based data center 4206 that stores the database (FIG. 53, 5300). The mobile device 4204 can relay the recorded levels to the database in the data center 4206, which can send the correlations and contact lens recommendations back to the mobile device 4204. The mobile device 4204 can present the results from the hand-held device 4202 and/or the correlations from the database in a user-interface of the mobile device 4204.

At least some of the processing of the measurement data obtained from the return signals from the storage solution can occur at the hand-held device 4202, the mobile device 4204, and/or the data center 4206. In some examples, the mobile device 4204 includes a program that retrieves the correlations from the database and performs additional tasks. For example, the mobile device 4204 can retrieve information about the recommended contact lens from another source other than the database in response to receiving the recommendation from the database. The mobile device 4204 can also, in response to receiving the contact lens recommendation, retrieve a health professional's contact information that can provide that type of contact lens, consult a user's calendar to set up an appointment with the health professional, schedule an appointment with the health professional, perform another task, purchase that type of contact lens, request samples of that type of contact lens for the user, or combinations thereof.

Figure 54:
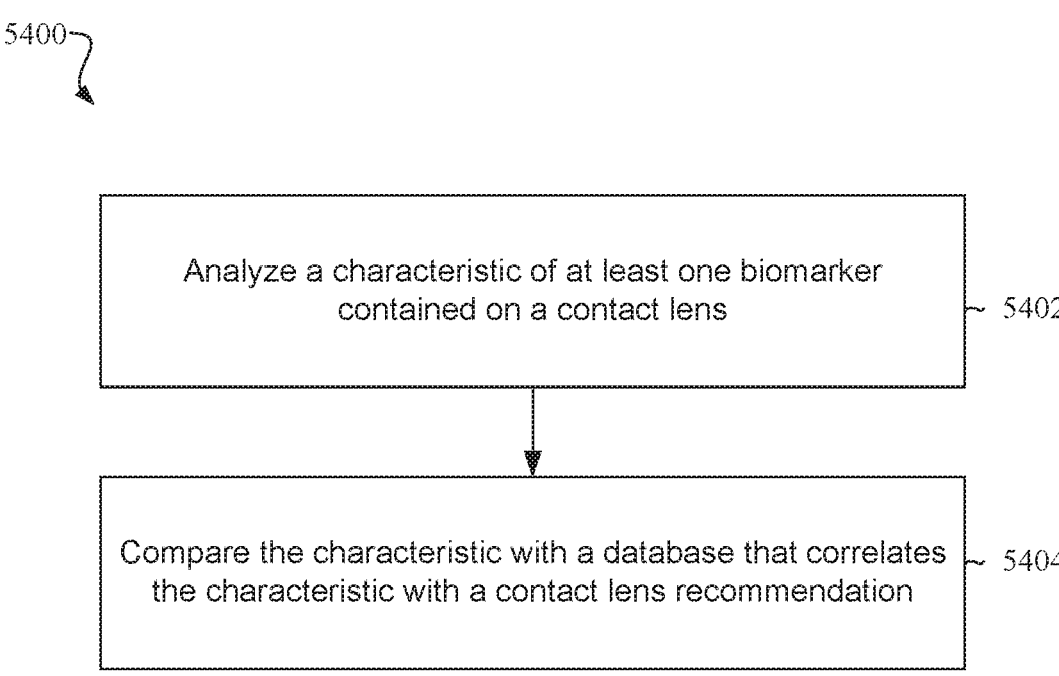
FIG. 54 is a block diagram of an example method for recommending a contact lens in accordance with the present disclosure.

FIG. 54 illustrates an example method 5400 for recommending a contact lens. In one embodiment, the method 5400 can include analyzing 5402 a characteristic of at least one biomarker contained on a contact lens and comparing 5404 the characteristic with a database that correlates the characteristic with a contact lens recommendation.

At block 5402, a characteristic of at least one biomarker is analyzed or otherwise measured. This process can be performed by the sensing device 5230 or by the processor 5215 (e.g., the biomarker characteristic obtainer 5245) after the processor 5215 obtains the measurements taken by the sensor of the sensing device 5230. The biomarkers can be obtained from a contact lens. In some examples, the biomarkers remain on the contact lens when the biomarkers are being analyzed or otherwise measured. In other examples, the biomarkers can be removed from the contact lens before the analysis. The biomarker characteristic can include a type of biomarker, a concentration of biomarker, a location of the biomarker on the contact lens, another type of characteristic, or combinations thereof. The biomarker characteristic can involve a single biomarker. In other examples, the biomarker characteristic includes the collective condition of multiple biomarkers.

At block 5404, the characteristic can be compared to a database (e.g., the database 5250 referenced in FIG. 52) that correlates the characteristic with a contact lens type or recommendation. This process can be performed by the processor 5215 (e.g., the biomarker and database comparer 5255). For example, the database can include the type and concentration of a single biomarker that is correlated with a specific type of contact lens. In one embodiment, the database can correlate a first type of biomarker having a first concentration with a second type of biomarker having a second concentration to recommend a specific type of contact lens.

Figure 55:
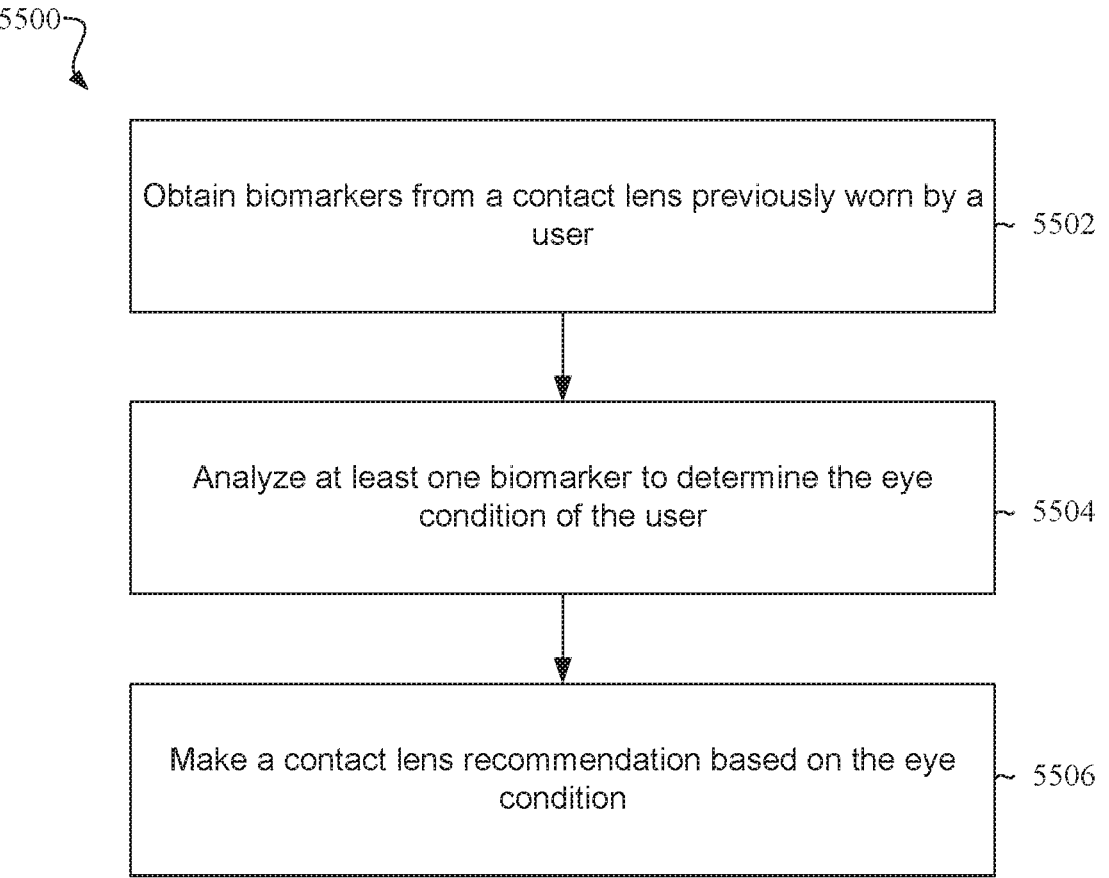
FIG. 55 is a block diagram of another example method for recommending a contact lens in accordance with the present disclosure.

FIG. 55 illustrates an example method 5500 for making a contact lens recommendation. In one embodiment, the method 5500 can include obtaining 5502 biomarkers from a contact lens previously worn by a user, analyzing 5504 at least one biomarker to determine the eye condition of the user, and making 5506 a contact lens recommendation based on the eye condition. The process block 5504 can be performed by the same entity (e.g., a processor) as that of block 5402 in FIG. 54. The process block 5506 can be performed by the processor 5215 (e.g., the recommendation generator 5260).

At block 5502, the biomarkers can be obtained from the contact lens in any appropriate way. In some examples, the biomarkers can dissociate from the contact lens in a multiple purpose contact lens storage solution. In another example, the biomarkers can be obtained from the contact lens by wiping a material across the contact lens' surface. In yet other examples, the biomarkers can be removed from the contact lens by scratching the biomarkers off of the lens's surface. In some examples, obtaining the biomarkers from the contact lens results in a contact lens that can be re-worn by the user. In other examples, obtaining the biomarkers from the contact lens results in modifying the contact lens such that it cannot be re-worn by the user. The biomarker characteristic obtainer 5245 obtains from, for example, the sensing device 5230, information indicating characteristics of the biomarkers obtained as above.

Figure 56:
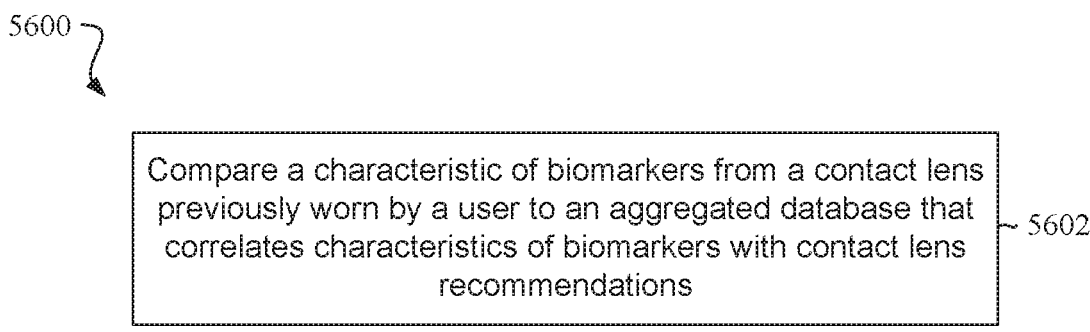
FIG. 56 is a block diagram of yet another example method for recommending a contact lens in accordance with the present disclosure.

FIG. 56 illustrates an example method 5600 for making a contact lens recommendation. In one embodiment, the method 5600 can include comparing 5602 a characteristic of biomarkers from a contact lens previously worn by a user to an aggregated database that correlates characteristics of biomarkers with contact lens recommendations. The process block 5602 can be performed by the same entity as that for the block 5404 in FIG. 54.

The aggregated database can include measurement data or information associated with contact lens recommendations from multiple sources. In one embodiment, doctors, patients, other types of professionals, other types of sources, or combinations thereof can contribute information to the database. In some embodiments, thousands or millions of health conditions and/or contact lens recommendations with their associated biomarker characteristics can be aggregated into the database.

Further, after the contact lens recommendation is sent to the user, the user can have an option to confirm whether the recommendation was accurate or otherwise helpful. For example, a user can place his or her contact lens in the storage example and receive a recommendation indicating that another contact lens can be a better fit for the user. As a result, the user can purchase that type of contact lens. In the event that the user likes the recommended contact lens, the user can send a confirmation message to the computing device to update the database to indicate the user's experience with the contact lens. The confirmation message can increase a confidence level of the correlation between the characteristic of the biomarker and the recommendation. In the event that the user does not have a good experience with the recommended contact lens after trying them, the user can send a confirmation message to the database indicating the poor experience. This confirmation message can cause a decrease in a confidence level of the correlation between the biomarker profile and the recommended contact lens. In the event that the user does not like the recommended contact lens, the database can reassess the correlation drawn and determine whether the correlation drawn is based on proper assumptions.

Figure 57:
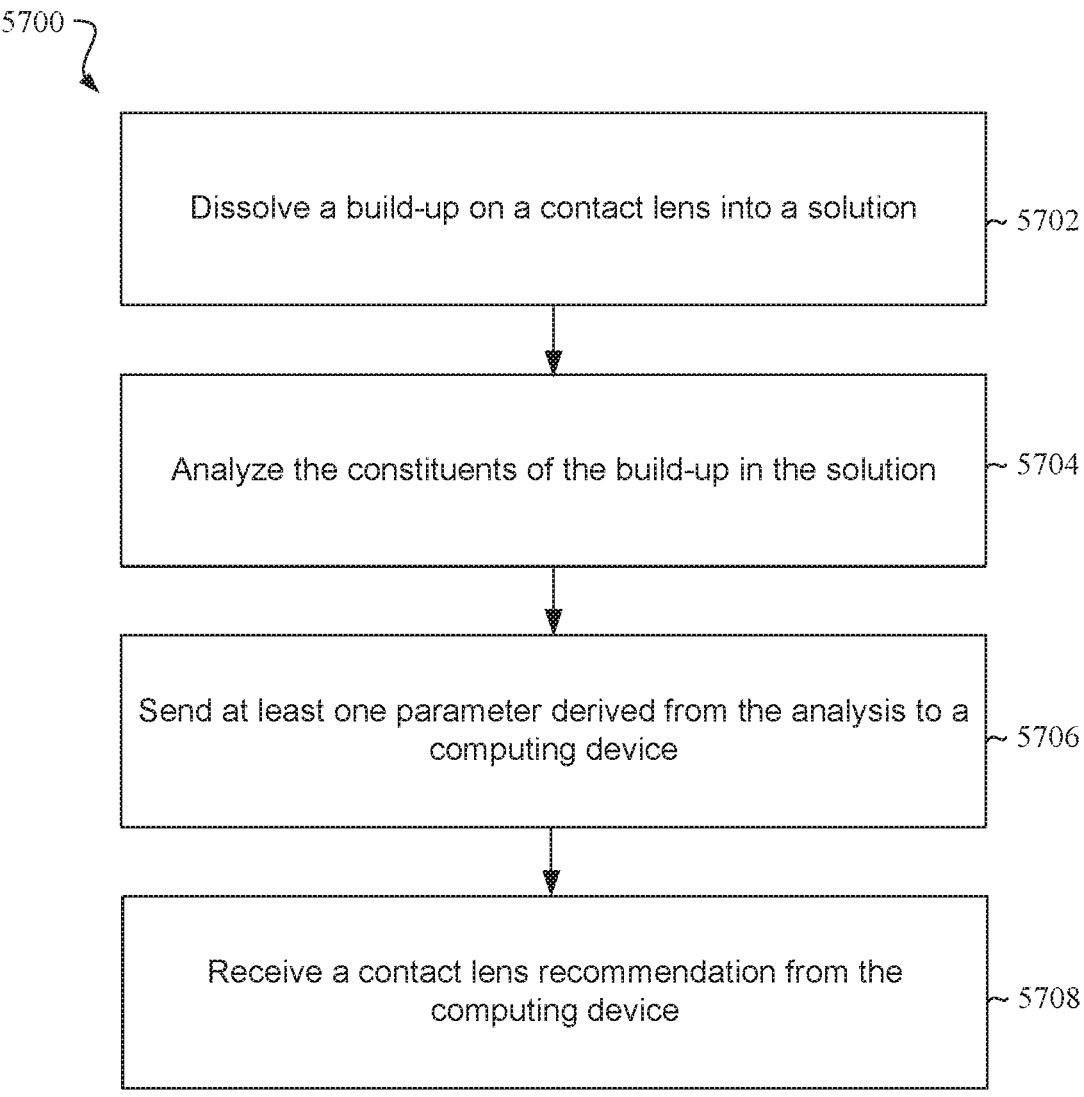
FIG. 57 is a block diagram of another example method for recommending a contact lens in accordance with the present disclosure.

FIG. 57 illustrates an example method 5700 for recommending a contact lens. In one embodiment, the method 5700 includes dissolving 5702 a build-up of biomarkers on a contact lens into a solution, analyzing 5704 the constituents of the build-up in the solution, sending 5706 at least one parameter derived from the analysis to a computing device; and receiving 5708 a contact lens recommendation from the computing device. The process blocks 5704 and 5706 can be performed by, for example, the sensing device 5230. The process block 5708 can be performed by, for example, a mobile device.

At block 5702, the biomarker build-up can be dissolved by placing the contact lens into a contact lens storage solution. Any appropriate type of contact lens solution can be used. For example, the contact lens solution can be a hydrogen peroxide solution, a multiple purpose storage solution, another type of solution, or combinations thereof.

In some examples, the contact lens solution includes hyaluronan, sulfobetaine, poloxamine, boric acid, sodium borate, ascorbic acid, edetate disodium, sodium chloride, hydroxyalkyl phosphate, poloxamer, sodium phosphate buffer, polyoxyethylene polyoxypropylene block copolymer with ethylene diamine, and polyaminopropyl biguanide, or combinations thereof. The contact lens can include a disinfectant, a surfactant, an anti-fungal agent, an anti-bacterial agent, another type of agent, or combinations thereof.

Removal of the biomarkers from the contact lens into the solution can occur over any appropriate time period. In some examples, the biomarkers are in the solution for at least one minute, at least five minutes, at least 20 minutes, at least 45 minutes, at least an hour, at least two hours, at least 5 hours, at least 7 hours, at least one day, at least two days, another appropriate time period, or combinations thereof.

In some examples, the contact lens is free of surface cavities that are constructed to be binding sites for biomarkers or to draw in tear fluid into the contact lens. In some examples, the contact lens is free of surface treatments that target the binding of specific biomarkers to the contact lens.

In some embodiments, the storage solutions includes binding agents that are configured to facilitate the bonding between a surface of the contact lens and a biomarker from the tear fluid. In other examples, no binding agents are introduced to the contact lens solution. The contact lens can include a surface in which the biomarkers are as likely to bind to any surface of the contact lens as any other surface of the contact lens. In some examples, the biomarkers can attach to the optical zone of the contact lens, a peripheral zone of the contact lens, an edge of the contact lens, a posterior side of the contact lens, an anterior side of the contact lens, another area of the contact lens, or combinations thereof.

The dissolved contents can then be analyzed at block 5704, for example according to the process 5402 or 5504 described herein with reference to FIGS. 54 and 55, respectively. At block 5706 at least one parameter derived from the analysis can be sent to a computing device, for example as described with reference to FIG. 42. At block 5708, the user (via a mobile device) can receive a contact lens recommendation from the computing device. In some embodiments, the recommendation can be derived from the at least one parameter sent to the computing device, according to the methods described herein.

FIG. 58 depicts an example method 5800 for determining a contact lens recommendation. In one embodiment, the method 5800 can include analyzing 5802 a first characteristic of at least one biomarker from a first contact lens previously worn by a user during a first time period, comparing 5804 the first characteristic with a second characteristic of the at least one biomarker from the user, determining 5806 a change between the first characteristic and the second characteristic, and comparing 5808 the change with a database that correlates the change with the contact lens recommendation. The process block 5802 can be performed by the same entity (e.g., a processor) as that for the block 5402 in FIG. 54. The process block 5804 through 5808 are performed by the processor 5215 (specifically, the biomarker and database comparer 5255, for example).

At block 5804, the first characteristic can be compared to a second characteristic. The first and second characteristics can be obtained from the same contact lens that is worn at different times. For example, the user can wear the contact lens on a first day and remove the contact lens at the end of the first day when the user has the biomarkers removed from contact lens. An analysis on the biomarkers can be done to obtain the first concentration, such as a first concentration of a first biomarker. On the second day, the user can place the contact lens back into his or her eye and remove the contact lens at the end of the day. The biomarker removal and analysis can also be performed. The second characteristic can be a different concentration of the first biomarker. Thus, the change can be an increased concentration, a decreased concentration, another type of concentration, or combinations thereof.

In some embodiments, wherein the same contact lens is used to obtain the second set of biomarkers, the database can include specific correlations. In some embodiments, not all of the biomarkers can be removed from the contact lens during the first night of cleaning, therefore, the contact lens can be placed in the solution for a second night for cleaning. In other embodiments, biomarkers that remain on the contact lens after the first cleaning can block other biomarkers from attaching to the contact lens such that fewer biomarkers are retained the second night.

In some embodiments, a second set of biomarkers can be obtained using a fresh contact lens to avoid contamination from previous biomarkers. In those situations, lingering biomarkers from the previous cleaning time may not be an issue. The second set of biomarkers (e.g., a second set of biomarker characteristics) can be obtained from a second contact lens that is different than a first contact lens (the contact lens from which the first set of biomarker characteristics were obtained).

At block 5808, the difference between the first and second concentration levels can be compared to the database and correlated with a recommendation of a contact lens, the recommendation being correlated with the health condition of the user. The computing device can, with reference to the database, send, and the user (i.e. the mobile device, hand-held device, sensor, etc.) can receive an indication of the recommendation. The database can include the correlated health condition. In this example, the computing device can send, and the user can receive, an indication of the correlated health condition.

In some embodiments, the first characteristic can be obtained at a different time than the second characteristic. In other embodiments, the first and second characteristics can be obtained within the same time period. For example, a first contact lens can be worn in a first eye and a second contact lens can be worn in a second eye, and the characteristics of the biomarkers can be analyzed and compared. In those situations where the characteristics are different, there can be a condition present in one of the eyes that is not in the other eye.

The user can have an account associated with a hand-held device, a mobile device, a database, or associated with another computing device that stores at least some of the characteristics of the user's biomarkers when data is sent to the database. These stored recordings can compile a health history of the user. The health history can be reviewed by the doctor to help diagnose health conditions, assist in making a treatment plan, assist in making a prevention plan, assist in helping diagnosis health conditions of relatives, determine other types of information, change contact lens recommendation, or combinations thereof. In some embodiments, a user's eye can react to a contact lens by producing a certain biomarker over time. By comparing the user's biomarker profile from earlier sessions of wearing that contact lens, a baseline profile can be obtained that is specific to that user. As the biomarker profile changes over time, the user can discover his or her eye is producing a higher level of a certain biomarker that is high for that user, despite the user's concertation of that biomarker being within a normal concentration level of a significant portion of the population.

As previously described, a holistic system for collecting and utilizing health data is envisioned which allows large quantities of data to be collected and analyzed to provide regular healthcare monitoring to the populace. This system can include detecting health conditions and making healthcare related recommendations based on statistically relevant characteristics of the data. The system can comprise a plurality of elements configured to communicate interchangeably using a cloud computing network.

The data can be collected by smart devices (e.g., a smart contact lens, a smart contact lens container, etc.) or aggregated from other sources (e.g., medical records, state records, family history records, etc.). In some embodiments, data relative to a populace can be stored and organized within a database and data analysis techniques (e.g., data mining) can be used to compare or otherwise correlate aspects of a patient's collected data (e.g., current user health data) relative to the populace's data (e.g., other data or archived user health data). This can be particularly beneficial in areas in which certain diseases are particularly prevalent. Comparisons, correlations, trends, or other characteristics derived from the data can be presented to a physician, patient, or another recipient. For example, a detected or predicted health condition of the patient can be communicated. Additionally or alternatively, a recommendation relative to the patient's healthcare can be communicated, For example, the patient can receive a communication indicating that the system recommends the patient undergo a particular follow-up medical examination.

Unless otherwise indicated, all numbers or expressions, such as those expressing dimensions, physical characteristics, etc., used in the specification (other than the claims) are understood as modified in all instances by the term "approximately." At the very least, and not as an attempt to limit the application of the doctrine of equivalents to the claims, each numerical parameter recited in the specification or claims which is modified by the term "approximately" should at least be construed in light of the number of recited significant digits and by applying ordinary rounding techniques.

In addition, all ranges disclosed herein are to be understood to encompass and provide support for claims that recite any and all subranges or any and all individual values subsumed therein. For example, a stated range of 1 to 10 should be considered to include and provide support for claims that recite any and all subranges or individual values that are between and/or inclusive of the minimum value of 1 and the maximum value of 10; that is, all subranges beginning with a minimum value of 1 or more and ending with a maximum value of 10 or less (e.g., 5.5 to 10, 2.34 to 3.56, and so forth) or any values from 1 to 10 (e.g., 3, 5.8, 9.9994, and so forth).

Various inventions have been described herein with reference to certain specific embodiments and examples. However, they will be recognized by those skilled in the art that many variations are possible without departing from the scope and spirit of the inventions disclosed herein, in that those inventions set forth in the claims below are intended to cover all variations and modifications of the inventions disclosed without departing from the spirit of the inventions. The terms "including:" and "having" come as used in the specification and claims shall have the same meaning as the term "comprising."

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not target to be exhaustive or to limit the embodiments to the precise forms disclosed. It will be apparent that many modifications and variations are possible in view of the above teachings.

We claim:

1. A method of health monitoring, the method being carried out by a processor, the method comprising:

determining, by an optical spectral sensor, biomarker characteristics of a user based analysis of a contact lens worn by the user;

the processor collecting current health data of the user, the current health data of the user comprising the biomarker characteristics of the user received from the optical spectral sensor;

the processor receiving archived health data of the user from a database;

the processor aggregating the current health data with the archived health data;

the processor analyzing the aggregated health data; and the processor correlating the aggregated health data to generate a recommendation, in the correlating, the processor using information that indicates correlation between aggregated biomarker characteristics and aggregated contact lens preferences, to determine a contact lens to be recommended for the user, in accordance with the biomarker characteristics of the user; and the processor notifying the user of the recommendation of the contact lens determined by the processor, wherein:

the information that indicates correlation between the aggregated biomarker characteristics and the aggregated contact lens preferences is a predictor generated by performing machine learning of a contact lens preference of each of a plurality of users that is stored in the database;

the optical spectral sensor comprises a light source and a light receiver incorporated into a contact lens container; and the optical spectral sensor is configured to measure a light transmittance through a solution containing biomarkers within the contact lens container using the light source and the light receiver.

2. The method of claim 1, wherein the recommendation includes recommending at least one of a medical examination and a physician.

3. The method of claim 1, wherein the current user health data includes at least one of age, gender, weight, height, and place of domicile.

4. The method of claim 1, wherein analyzing the aggregated health data comprises at least one of machine learning, artificial intelligence, and data mining.

5. The method of claim 1, wherein:

the contact lens is a smart contact lens; and collecting current user health data comprises using the smart contact lens.

6. The method of claim 5, wherein the smart contact lens is configured to wirelessly communicate with another electronic device.

7. The method of claim 1, wherein:

the contact lens container is a smart contact lens container; and collecting current user health data includes using the smart contact lens container.

8. The method of claim 7, wherein the smart contact lens container is configured to wirelessly communicate with another electronic device.

* * * * *